(12) United States Patent
Pritzker et al.

(10) Patent No.: US 10,731,222 B2
(45) Date of Patent: Aug. 4, 2020

(54) RNA DISRUPTION ASSAY FOR PREDICTING SURVIVAL

(71) Applicant: RNA Diagnostics Inc., Toronto (CA)

(72) Inventors: Kenneth Pritzker, Toronto (CA); Laura Pritzker, Toronto (CA); Amadeo Mark Parissenti, Sudbury (CA); Xiaohui Wang, Waterloo (CA)

(73) Assignee: RNA Diagnostics Inc., Toronto (CA)

( * ) Notice: Subject to any disclaimer, the term of this patent is extended or adjusted under 35 U.S.C. 154(b) by 544 days.

(21) Appl. No.: 15/027,080

(22) PCT Filed: Oct. 6, 2014

(86) PCT No.: PCT/CA2014/000730
§ 371 (c)(1),
(2) Date: Apr. 4, 2016

(87) PCT Pub. No.: WO2015/048887
PCT Pub. Date: Apr. 9, 2015

(65) Prior Publication Data
US 2016/0237506 A1    Aug. 18, 2016

Related U.S. Application Data

(60) Provisional application No. 61/887,054, filed on Oct. 4, 2013.

(51) Int. Cl.
*G01N 33/48* (2006.01)
*C12Q 1/6886* (2018.01)
*G16B 20/00* (2019.01)
*G06G 7/58* (2006.01)

(52) U.S. Cl.
CPC ........... *C12Q 1/6886* (2013.01); *G16B 20/00* (2019.02); *C12Q 2600/106* (2013.01); *C12Q 2600/118* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,251,247 | A | 10/1993 | Sahlin et al. |
| 7,197,401 | B2 | 3/2007 | Hastings |
| 7,504,209 | B2 | 3/2009 | Ingham et al. |
| 7,888,035 | B2 | 2/2011 | Klass et al. |
| 7,968,291 | B2 | 6/2011 | Brees et al. |
| 8,131,473 | B1 | 3/2012 | Coffin et al. |
| 2003/0203408 | A1 | 10/2003 | Williams et al. |
| 2006/0063170 | A1 | 3/2006 | Erlander et al. |
| 2006/0166231 | A1 | 7/2006 | Baker et al. |
| 2006/0246577 | A1 | 11/2006 | Schroeder et al. |
| 2008/0318801 | A1 | 12/2008 | Leung |
| 2010/0057371 | A1 | 3/2010 | Denisov |
| 2010/0317001 | A1 | 12/2010 | Parissenti et al. |
| 2014/0287063 | A1 | 9/2014 | Parissenti et al. |
| 2015/0154350 | A1 | 6/2015 | Pritzker et al. |
| 2015/0315656 | A1 | 11/2015 | Zhu et al. |
| 2016/0077051 | A1 | 3/2016 | Parissenti et al. |

FOREIGN PATENT DOCUMENTS

| | | |
|---|---|---|
| AU | 2008295394 B2 | 3/2009 |
| EP | 1772522 | 4/2007 |
| JP | 5602018 B2 | 12/2010 |
| WO | 2004/090780 A2 | 3/2004 |
| WO | 2009030029 | 12/2009 |
| WO | 2013020201 | 2/2013 |
| WO | 2013/159200 A1 | 10/2013 |

OTHER PUBLICATIONS

Wong et al., "Reduced Plasma RNA Integrity in Nasopharyngealcarcinoma Patients", Clinical Cancer Research, Apr. 15, 2006, 12:2512-2516, 12(8).
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, Abstract No. 107.
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, (Poster).
Parissenti A. M. et al., "Relationship of tumor RNA integrity to clinicopathologic parameters associated with epirubicin/docetaxel chemotherapy", Nov. 2007, Making Connections: A Canadian Cancer Research Conference Celebrating NCIC's 60th Anniversary, 203-204 (Abstract).
Pandey et al., Induction of the Interferon-Inductible RNA-Degrading Enzyme, RNase L, by Stree-Inducing Agents in the Human Cervical Carcinoma Cells, RNA Biology, May/Jun. 2004, pp. 21-27; 1:1.
Parissenti et al., "Reductions in Tumor RNA Integrity Associated with Clinical Response to Epirubicin/Docetaxel Chemotherapy in Breast Cancer Patients", Cancer Research 69 [Suppl 2], 378s, 2008.
Balatsos et al., "Drug action on poly(A) polymerase activity and isoforms during U937 cell apoptosis", Journal of Experimental and Clinical Cancer Research, Jan. 1, 2001, 20(1):63-69.

(Continued)

*Primary Examiner* — Eric S Dejong
(74) *Attorney, Agent, or Firm* — Bereskin & Parr LLP; Carmela De Luca

(57) ABSTRACT

A method for the prediction and/or prognosis of survival time of a patient suffering from cancer, comprising the steps of: a) measuring a RDA score in a tumor tissue sample comprising cellular RNA from said patient after said patient has received one or more doses of a cancer treatment; b) comparing said RDA score to one or more predetermined RNA disruption reference values; and c) providing a favorable prediction and/or prognosis of survival time for said patient when said RDA score is higher than said predetermined RNA disruption reference value; or providing an unfavorable prediction and/or prognosis of survival time for said patient when said RDA score is lower than said predetermined RNA disruption reference value, wherein the RDA score is proportional to the degree of RNA disruption.

16 Claims, 66 Drawing Sheets

(56) References Cited

OTHER PUBLICATIONS

Ogston et al., "A new histological grading system to assess response of breast cancers to primary chemotherapy: Prognostic significance and survival", Breast, Oct. 2003, 12(5):320-327.
Carey et al., "Telomerase activity and prognosis in primary breast cancers", Journal of Clinical Oncology, Oct. 1999, 17(10):3075-3081.
Schroeder et al., "The RIN: an RNA integrity number for assigning integrity values to RNA measurements", BMC Molecular Biology, Biomed Central Ltd., Jan. 31, 2006, 7(1):3.
Imbeaud et al., "Towards standardization of RNA quality assessment using user-independent classifiers of microcapillary electrophoresis traces", Nucleic Acids Research, 2005, 33(6):e56, doi:10.1093/nar/gni054.
Wong et al. "Plasma RNA integrity analysis: methodology and validation", Annals of the New York Academy of Sciences, 2006, 1075:174-178.
Minotti et al., "Anthracyclines: molecular advances and pharmacologic developments in antitumor activity and cardiotoxicity", Pharmacol Rev, 2004, 56:185-229.
Parissenti A. M. et al., "Relationship of tumor RNA integrity to clinicopathologic parameters associated with epirubicin/docetaxel chemotherapy", Internet Citation, Sep. 4, 2007 (Sep. 7, 2007), pp. 1-4.
Strand, Carina et al. RNA quality in frozen breast cancer samples and the influence on gene expression analysis—a comparison of three evaluation methods using microcapillary electrophoreses traces. BMC Molecular Biology 2007, 8:38.
Houge, G., et al. Fine Mapping of 28S rRNA Sites Specifically Cleaved in Cells Undergoing Apoptosis. Molecular and Cellular Biology, Apr. 1995, vol. 15, No. 4, pp. 2051-2062.
Hoat, Trinh X., et al. Specific cleavage of ribosomal RNA and mRNA during victorin-induced apoptotic cell death in bat. The Plant Journal (2006) 46, pp. 922-933.
Marx, Vivien. RNA Quality: Defining the Good, the Bad, & the Ugly. Genomics Proteomics. Retrieved from Internet www.dnaarrays.org/P_GenProMag.pdf May 4, 2005.
King, KL et al. 28S ribosome degradation in lymphoid cell apoptosis: evidence for caspase and Bcl-2 dependent and independent pathways. Cell Death and Differentiation (2000) 7, 994-1001.
Fimognari, Carmela et al. Protective effect of creatine against RNA damage. Mutation Research 670 (2009) 59-67.
Fimognari, Carmela et al. Corrigendum to "Protective effect of creatine against RNA damage". Mutation Research. 670 (2009) 59-67.
Copois, Virginie et al. Impact of RNA degradation on gene expression profiles: Assessment of different methods to reliably determine RNA quality. Journal of Biotechnology 127 (2007) 549-559.
Banerjee et al., "RNase L-independent specific 28S rRNA cleavage in murine coronavirus-infected cells", Journal of Virology, Oct. 2000, pp. 8793-8780, 74(19).
Parissenti et al., "Association of low tumor RNA integrity with response to chemotherapy in breast cancer patients", Breast Cancer Research and Treatment. Jan. 2010, pp. 347-356, 119(2), doi: 10.1007/s10549-009-0531-x.
Kemp et al., "p53 induction and apoptosis in response to radio- and chemotherapy in vivo is tumor-type-dependent", Cancer Research, Jan. 1, 2001, pp. 327-332, 61(1).
Kim et al., "The role of apoptosis in cancer cell survival and therapeutic outcome", Cancer Biology & Therapy, Nov. 2006, pp. 1429-1442, 5:11.
Raman et al., "Quality control in microarray assessment of gene expression in human airway epithelium", BMC Genomics, Oct. 24, 2009, 10:493, doi: 10.1186/1471-2164-10-493.
Samali et al., "The ability to cleave 28S ribosomal RNA during apoptosis is a cell-type dependent trait unrelated to DNA fragmentation", Cell Death and Differentiation, May 1997, pp. 289-293, 4(4).

Gjertsen, Bjorn Tore et al. Multiple apoptotic death types triggered through activation of separate pathways by cAmp and inhibitors of protein phosphatases in one (IPC leukemia) cell line. Journal of Cell Science 107, 3363-3677, 1994.
Greenhalgh D.A. et al. Effect of 5-fluorouracil combination therapy on RNA processing in human colonic carcinoma cells. Br. J. Cancer, 1990, vol. 61, pp. 415-419.
Thadani-Mulero, Maria et al. Androgen Receptor on the Move: Boarding the Microtubule Expressway to the Nucleus. Cancer Research, 72(18), pp. 4611-4615, 2012.
Cheang, Maggie C. U., et al. Ki67 Index, HER2 Status, and Prognosis of Patients With Luminal B Breast Cancer. J. Natl. Cancer Institute, 2009, 101, pp. 736-750.
Goldhirsch A. et al. Strategies for subtypes-dealing with the diversity of breast cancer: highlights of the St Gallen International Expert Consensus on the Primary Therapy of Early Breast Cancer 2011. Annals of Oncology, vol. 22, pp. 1736-1747, 2011.
Narendrula, Rashmi. Quantitative and qualitative changes in cellular RNA in response of chemotherapy. Oral presentation, Apr. 4, 2012.
Johnson G.D. et al. "Cleavage of rRNA ensures translational cessation in sperm at fertilization, Molecular Human Reproduction", Aug. 2011, pp. 721-726, 17(12).
Fimognari et al., "RNA as a new target for toxic and protective agents", Mutation Research, Sep. 2008, pp. 15-22, 648(1-2).
Telli M. et al., "Insight or Confusion: Survival After Response-Guided Neoadjuvant Chemotherapy in Breast Cancer", Journal of Clinical Oncology, Oct. 2013 pp. 3613-3615, 31(29).
Young, L.E. Zeroing in on cancer. Laurentian University Magazine, Winter 2010, p. 5. Retrieved from the internet <URL:http://www.laurentian.ca/NR/rdonlyres/D6249D37-F645-49F1-8CA0-1EA940D81CB4/0/Winter10_English_low.pdf>.
Hannemann J. et al. Changes in Gene Expression Associated With Response to Neoadjuvant Chemotherapy in Breast Cancer, Journal of Clinical Oncology, May 2005, 3331-3342, 23(15).
Sotiriou et al. (200) Gene expression profiles derived from fine needle aspiration correlate with response to chemotherapy in breast cancer Breast Cancer Research. 4:R3 (8 pages).
Thisted. (1998) What is a P-Value? The University of Chicago, p. 1-6.
Fleige et al. (2006) RNA integrity and the effect on the real-time qRT-PCR performance. Molecular Aspects of Medicine, 27:126-139.
Thuerigen et al. (2006). Gene Expression Signature Predicting Pathologic Complete R esponse with Gemcitabine, Epirubicin, and Docetaxel in Primary Breast Cancer, Journal of Clinical Oncology, 24(12):1839-1845.
Degen et al. (2000) Caspase-dependent cleavage of nucleic acids. Cell Death and Differentiation, 7:616-627.
Fulda et al. (2006) Extrinsic versus intrinsic apoptosis pathways in anticancer chemotherapy. Oncogene, 25:4798-4811.
Kaufman et al. (2000) Induction of Apoptosis by Cancer Chemotherapy. Experimental Cell Research, 256:42-49.
Agilent 2100 Bioanalyzer Protocol for RNA 6000 Nano LabChip kit, Jul. 2004 update.
Bulletin 5783 Rev A "Why choose the Experion Automated Eletrophoresis System From Bio-Rad?", Bio-Rad.
Oragene-RNA "Interpreting Bioanalyzer Results for RNA Collected Using Oragene-RNA", 2010 DNA Genotek, PD-WP-017 Issue 1.0.
Benner, "ChIP—Seq Analysis: Finding Peaks (ChIP-enriched Regions), retrieved from Internet: "http://biowhat.ucsd.edu/homer/chipseq/peaks.html, retrieved on Mar. 26, 2012 12:34:41 PM.
Degradometer Version 1.4, Software Manual.
Denisov et al., RNA quality Indicator (RQI)—A New Tool for Assessing RNA Integrity to reliably detect differences in gene expression using qPCR experiments, BIO-RAD, poster.
Freed et al., When ribosomes go bad: diseases of ribosome biogenesis, Mol. BioSyst., 2010, 6, 481-493.
McArthur et al., Targeting Cell Cycle Checkpoints with Specific Inhibitor Drugs, http://www.petermac.org/Research/MolecularOncologyProjects. Accessed Mar. 26, 2012.
Kim et al., A robust peak detection method for RNA structure interference by high-throughput contact mapping, Bioinformatics, vol. 25, No. 9, 2009, pp. 1137-1144.

(56) References Cited

OTHER PUBLICATIONS

Yoon et al., HiTRACE: High-throughput robust analysis for capillary electrophoresis, Bioinformatics, vol. 00, No. 00 2011, pp. 1-13.
Hatzis et al., Effects of Tissue Handling on RNA Integrity and Microarray Measurements from Resected Breast Cancers, Mar. 21, 2012 104 (6), Abstract.
Denisov et al., Development and Validation of RQI: An RNA Quality Indicator for the Experion Automated Eletrophoresis System, Bulletin 5761, 2008 Bio-Rad Laboratories, Inc.
Belin et al., Dysregulation of Ribosome Biogenesis and Translational Capacity is Associated with Tumor Progression of Human Breast Cancer Cells, Sep. 2009, 4(9), e7147.
Agilent RNA 6000 Nano Kit Quick Start Guide, Agilent Technologies, Edition Apr. 2007.
Auer et al., Chipping away at the chip bias: RNA degradation in microarray analysis, Nature Genetics, Dec. 2003, 35(4):292-293.
Weigelt et al., "Gene expression profiles of primary breast tumors maintained in distant metastases", PNAS, Dec. 23, 2003, 100(26):15901-15905.
Hurvitz et al., "Final Analysis of a Phase II, 3-Arm, Randomized Trial of Neoadjuvant Trastuzumab or Lapatinib or the Combination of Trastuzumab and Lapatinib, Followed by 6 cycles of Docetaxel and Carboplatin with Trastuzumab and/or Lapatinib in Patients with HER2+ Breast Cancer (TRIO-US B07)", San Antonio Breast Cancer Symposium Cancer Therapy and Research Center at UT Health Science Center Dec. 10-14, 2013 (poster).
King, KL et al. 28S ribosime degradation in lymphoid cell apoptosis: evidence for caspase and Bcl-2-dependent and -independent pathways. Cell Death and Differentiation, 2000, vol. 7, pp. 994-1001.
Neschadim Anton et al. Relaxin receptor antagonist AT-001 synergizes with docetaxel in androgen-independent prostate xenografts. Endocrine-Related Cancer, 2014, 21(3):459-71.
Martinet et al. Reactive oxygen species induce RNA damage in human atherosclerosis Introduction. European Journal of Clinical Investitgation. vol. 34, Issue 5, Jan. 1, 2004, pp. 323-327.
Tzu-Hsueh Yang et al. Determination of RNA degradation by capillary electrophoresis with cyan light-emited diode-Induced flourescence. Journal of Chromatography. Elsevier Science Puglishers B.V., NL. vol. 1239, Mar. 21, 2012, pp. 78-84.
Best et al. Integrity of Prostatic Tissue for Molecular Analysis After Robotic-Assisted Laparoscopic and Open Prostatectomy. Urology, Belle Mead, NJ, US. vol. 70, No. 2, Aug. 1, 2007, pp. 328-332.
Parissenti et al., Gene Expression Profiles as Biomarkers for the Prediction of Chemotherapy Drug Response in Human Tumor Cells, Anticancer Drugs 18(5) (Jun. 2007) 499-523.
Chang et al., Apoptosis and proliferation as predictors of chemotherapy response in patients with breast carcinoma. Cancer 2000, 89(11): 2145-52.
Archer, et al., Early changes in apoptosis and proliferation following primary chemotherapy for breast cancer. Br J Cancer 2003; 89(6): 1035-41.
Narla, et al. Ribosomopathies: human disorders of ribosome dysfunction. Blood 2010, Apr. 22. 115(16): 3196-205.
Burger, et al. Chemotherapeutic drugs inhibit ribosome biogenesis at various levels. The Journal of Biological chemistry Apr. 16, 2010; 285(16): 12416-25.
Crawford, et al., (1997) 16S mitochondrial ribosomal degradation is associated with apoptosis. Free Rad. Biol. Med. 22(7): 1295-1300.
Swe et al., (2000) zVAD-fmk and DEVD-cho induced late mitotic arrest and apoptotic expressions. Apoptosis 5(1): 29-36.
Cortazar et al. (2014) Pathological complete response and long-term clinical benefit in breast cancer: The CTNeoBC pooled analysis. Lancet vol. 384: 115-116.
Agilent Technologies (Agilent 2100 Bioanalyzer, Expert User's Guide, Copyright 2000, pp. 1-149) (Year: 2000).
Toomey et al., "RE: RNA Disruption Assay as a Biomarker of Pathological Complete Response in Neoadjuvant Trastuzumab-Treated Human Epidermal Growth Factor Receptor 2-Positive Breast Cancer", JNCI, 2016, 108(8): djw111, pp. 1-2.

Trudeau, Maureen, "Response", JNCI J Natl Cancer Inst, 2016, 108(8).
Mueller et al., "RNA Integrity Number (RIN)—Standardization of RNA Quality Control", Agilent Technologies, Inc., 2016, p. 1-7.
Vespucci et al., "Agilent 2100 Bioanalyzer—2100 Expert User's Guide", Agilent Technologies, Inc., 2005, pp. 1-419.
Parissenti et al., "Tumor RNA disruption predicts survival benefit from breast cancer chemotherapy", Breast Cancer Res. Treat., 2015, 153(1): 135-144.
Olinski, R. et al. Epirubicin-induced oxidative DNA damage and evidence for its repair in lymphocytes of cancer patients who are undergoing chemotherapy, Mol.Pharmacol. 52 (1997) 882-885.
Vaishampayan, U. et al. Taxanes: an overview of the pharmacokinetics and pharmacodynamics, Urology 54 (1999) 22-29.
Morse, D.L. et al. Docetaxel induces cell death through mitotic catastrophe in human breast cancer cells, Mol.Cancer Ther. 4 (2005) 1495-1504.
Wieder, T. et al. Activation of caspase-8 in drug-induced apoptosis of B-lymphoid cells is independent of CD95/Fas receptor-ligand interaction and occurs downstream of caspase-3, Blood 97 (2001) 1378-1387.
Mueller, 0. et al. RNA Integrity Number (RIN)—Standardization of RNA Quality Control. (2004).
Ganansia-Leymarie, V. et al. Signal transduction pathways of taxane-induced apoptosis. Curr Med. Chem Antica Ag 2003; 3: 291-306.
Cera, C. et al. Interaction between second generation anthracyclines and DNA in the nucleosomal structure, Nucleic Acids Res. 19 (1991) 2309-2314.
Spadari, S. et al. DNA polymerases and DNA topoisomerases as targets for the development of anticancer drugs, Anticancer Res. 6 (1986) 935-940.
Bachur, N.R. et al. Helicase inhibition by anthracycline anticancer agents, Mol.Pharmacol. 41 (1992) 993-998.
Honaas, Loren et al., A practical examination of RNA isolation methods for European pear (*Pyrus communis*). BMC Research Notes, 10:237, 2017. (DOI 10.1186/s13104-017-2564-2).
Jamshidi, Neema et al., Genomic Adequacy from Solid Tumor Core Needle Biopsies of ex Vivo Tissue and in Vivo Lung Masses: Prospective Study. Radiology, 2016.
Sellin Jeffries, Mario K. et al., A comparison of commercially-available automated and manual extraction kits for the isolation of total RNA from small tissue samples. BMC Biotechnology 2014, 14:94.
Kim, Jin-He et al., Comparison of three different kits for extraction of high-quality RNA from frozen blood. SpringerPlus 2014, 3:76.
Yu, Keke et al., Effect of multiple cycles of freeze-thawing on the RNA quality of lung cancer tissues. Cell Tissue Bank 18:433-440. (2017).
Unger, Conny et al., Ultraviolet C radiation influences the robustness of Rna integrity measurement. Electrophoresis 2015, 36, 2072-208.
Amundson, S.A. et al., Cancer Research, 64, 6368-6371, Sep. 15, 2004.
Shin, S. et al., International Journal of Oncology (2009) 35:81-86.
Burke, H. B. et al., Cancer (1998), 82, pp. 874-877.
Formenti, S. C. et al., Int. J. Radiation Oncology Biol. Phys., vol. 52, No. 2, pp. 397-405, 2002.
Xia, Fen and Powell, Simon N. The molecular basis of radiosensitivity and chemosensitivity in the treatment of breast cancer. Semin Radiat Oncol (2002), 12(4) 296-304. Abstract provided.
Hu, Ze-Ping et al. Metabolomic response of human skin tissue to low dose ionizing radiation. 2012, Mol BioSyst 8; 1979-1986. Abstract provided.
Delic, J. et al., 1993. "Gamma-ray induced transcription and apoptosis-associated loss of 28S rRNA in interphase human lymphocytes". Int J Radiat Biol 64; 39-46. Abstract provided.
Al-Mayah, A.H.J. et al., 2012. "Possible role of exosomes containing RNA in mediating nontargeted effect of ionizing radiation" Radiat Research 177; 539-545. Abstract provided.
Krolak, J.M. et al., 1989. "18S Ribosomal RNA is Degraded during Ribosome Maturation in Irradiated HeLa cells". Radiat Research 118; 330-340. Abstract provided.

(56) References Cited

OTHER PUBLICATIONS

Samkari, A., et al. Tumor RNA disruption as a tool to predict response to neoadjuvant chemotherapy in breast cancer: Optimizing timing of biopsy. (2016) Abstract No. P1-09-19 [abstract]. In: Proceedings of the 2016 San Antonio Breast Cancer Symposium; Dec. 6-10, 2016; San Antonio, TX. Philadelphia (PA): AACR; Cancer Res 2017; 77 (4 suppl): Abstract, 5 pages (Year: 2017).
Pritzker K., et al. RNA Disruption and Drug Response in Breast Cancer Primary Systemic Therapy. Journal of the National Cancer Institute, 2015, 51:76-80.
He, Kaiyu et al. Targets and Intracellular Signaling Mechanisms for Deoxynivalenol-Induced Ribosomal RNA Cleavage Toxicological Sciences, 127(2), 382-390, 2012.
Scholl SM et al. Breast tumours response to primary chemotherapy predicts local and distant control as well as survival. Eur J Ca 1995; 31A: 1969-1995.
Curran W et al. Phase III comparison of sequential versus concurrent chemo-radiation for patients with unresected stage III non-small cell lung cancer (NSCLC): report of Radiation Oncology Group (RTOG) 9410. Lung Ca 2003; 29 (suppl 1): 93, abstract 303.
Bellon JR et al. Concurrent radiation therapy and paclitaxel or docetaxel chemotherapy in high-risk breast cancer. Int J Rad Onc Bio Phys 2000; 48: 393-397.
Chollet P et al. Clinical and pathological response to primary chemotherapy in operable breast cancer. Eur J Ca 1997; 33: 862-866.
Koukourakis MI et al. Weeky docetaxel and concomitant boost radiotherapy for non-small cell lung cancer. A phase I/II dose escalation trial. Eur J Ca 1998; 34: 838-844.
Onishi H et al. Concurrent two-dimensional radiotherapy and weekly docetaxel in the treatment of stage III non-small cell lung cancer: a good local response but no good survival due to radiation pneumonitis. Lung Ca 2003; 40: 79-84.
Adelstein DJ et al. An Intergroup phase III comparison of standard radiation therapy and two schedules of concurrent chemoradiotherapy in patients with unresectable squamous cell head and neck cancer. JCO 2003; 21: 92-98.
Rivera E, Mejia JA, Arun BK, Adinin RB, Walters RS, Brewster A et al. Phase 3 study comparing the use of docetaxel on an every-3-week versus weekly schedule in the treatment of metastatic breast cancer. Cancer 2008; 112 (7):1455-1461.
Bear HD et al. The effect on tumor response of adding sequential preoperative docetaxel to preoperative doxorubicin and cyclophosphamide: preliminary results from National Surgical Adjuvant Breast and Bowel Project protocol B-27. JCO 2003; 21: 4165-4174.
Bissery MC et al. Experimental antitumor activity of Taxotere (RP 56976, NCS 628503) a Taxol analogue. Ca Res 1991; 51: 4845-4852.
Kuerer HM, Newman LA, Smith TL, Ames FC, Hunt KK, Dhingra K et al. Clinical course of breast cancer patients with complete pathologic primary tumor and axillary lymph node response to doxorubicin-based neoadjuvant chemotherapy. J Clin Oncol 1999; 17(2):460-469.
Forastiere AA et al. Concurrent chemotherapy and radiotherapy for organ preservation in advanced laryngeal cancer. NEJM 2003; 349: 2091-2098.
Denis F et al. Final results of the 94-01 French Head and Neck Oncology and Radiotherapy Group randomized trial comparing radiotherapy alone with concomitant radiochemotherapy in advanced-stage oropharynx carcinoma. JCO 2004; 22: 69-76.
Bosset JF et al. Chemotherapy with preoperative radiotherapy in rectal cancer. NEJM 2006; 355: 1114-1123.
Formenti SC, Dunnington G, Uzieli B, Lenz H, Keren-Rosenberg S, Silberman H et al. Original p53 status predicts for pathological response in locally advanced breast cancer patients treated preoperatively with continuous infusion 5-fluorouracil and radiation therapy. Int J Radiat Oncol Biol Phys 1997; 39(5):1059-1068.
Djuzenova CS, et al. Radiosensitivity in breast cancer assessed by the histone γ-H2AX and 53BP1 foci. Radiation Oncology 8:98.
Formenti SC et al. Preoperative twice-weekly paclitaxel with concurrent radiation therapy followed by surgery and postoperative doxorubicin-based chemotherapy in locally advanced breast cancer: a phase I/II trial. JCO 2003; 21: 864-870.
Gazet JC et al. Assessment of the effect of pretreatment with neoadjuvant therapy on primary breast cancer. Br J Ca 1996; 73: 758-762.
Johung et al. A clinical model for identifying radiosensitive tumor genotypes in non-small cell lung cancer 2013 Clin Cancer Res. 19(22).
Martin M et al. Adjuvant docetaxel for node-positive breast cancer. NEJM 2005; 352: 2302-2313.
Mueller, O. et al., A microfluidic system for high-speed reproducible DNA sizing and quantitation. Electrophoresis 21 (2000) 128-134.
Hutcheon AW et al. Improvements in survival in patients receiving primary chemotherapy with docetaxel for breast cancer: a randomized controlled trial. Br Ca Res Tr 2001; 69: 298.
Nabholtz JM et al. Docetaxel and doxorubicin compared with docetaxel and cyclophosphamide as first-line chemotherapy for metastatic breast cancer: results of a randomized, multicenter phase III trial. JCO 2003; 21: 968-975.
Ravdin PM et al. Phase II trial of docetaxel in advanced anthracycline-resistant or anthracenedione-resistant breast cancer. JCO 1995; 13: 2879-2885.
Mauer AM et al. Phase I study of docetaxel with concomitant thoracic radiation therapy. JCO 1998; 16: 159-164.
O'Shaughnessy J et al. Superior survival with capecitabine plus docetaxel combination therapy in anthracycline pretreated patients with advanced breast cancer; phase III trial results. JCO 2002; 20: 2812-2823.
Valero V et al. Phase II trial of docetaxel: a new highly effective antineoplastic agent in the management of patients with anthracycline-resistant metastatic breast cancer. JCO 1995; 13: 2886-2894.
Nature. Comprehensive molecular portraits of human breast tumours. 490:61-70, Oct. 4, 2012.
Chan S et al. Prospective randomized trial of docetaxel versus doxorubicin in patients with metastatic breast cancer. The 303 Study Group. JCO 1999; 17: 2341-2354.
Posner MR et al. Cisplatin and Fluorouracil alone or with docetaxel in head and neck cancer. NEJM 2007; 357: 1705-1715.
Rodel C et al. Prognostic significance of tumor regression after preoperative chemoradiotherapy for rectal cancer. JCO 2005; 23: 8688-8696.
Sauer R et al. Preoperative versus postoperative chemoradiotherapy for rectal cancer. NEJM 2004; 351: 1731-1740.
Ruyck et al. TGFβ1 polymorphisms and late clinical radiosensitivity in patients treated for gynecologic tumors. Int. J. Radiation Oncol.Biol Phys. 2006. 65: 1240.
Roche H et al. Sequential adjuvant epirubicin-based and docetaxel chemotherapy for node-positive breast cancer patients; the FNCLCC PACS 01 trial. JCO 2006; 24: 5664-5671.
Smith IC et al. Neoadjuvant chemotherapy in breast cancer significantly enhanced response with docetaxel. JCO 2002; 20: 1456-1466.
Tabernero J, Climent MA, Lluch A, Albanell J, Vermorken JB, Barnadas A et al. A multicentre, randomised phase II study of weekly or 3-weekly docetaxel in patients with metastatic breast cancer. Ann Oncol 2004; 15(9):1358-1365.
Von Minckwitz G et al. Doxorubicin with cyclophosphamide followed by docetaxel every 21 days compared with doxorubicin and docetaxel every 14 days as preoperative treatment in operable breast cancer: the GEPARDUO study of the German Breast Group. JCO 2005; 23: 2676-2685.
Handbook, Qiagen. Sample & Assay Technologies, "RNeasy® MinElute® Cleanup Handbook: For RNA cleanup and concentration with small elution volumes", Oct. 1, 2010, pp. 1-32.

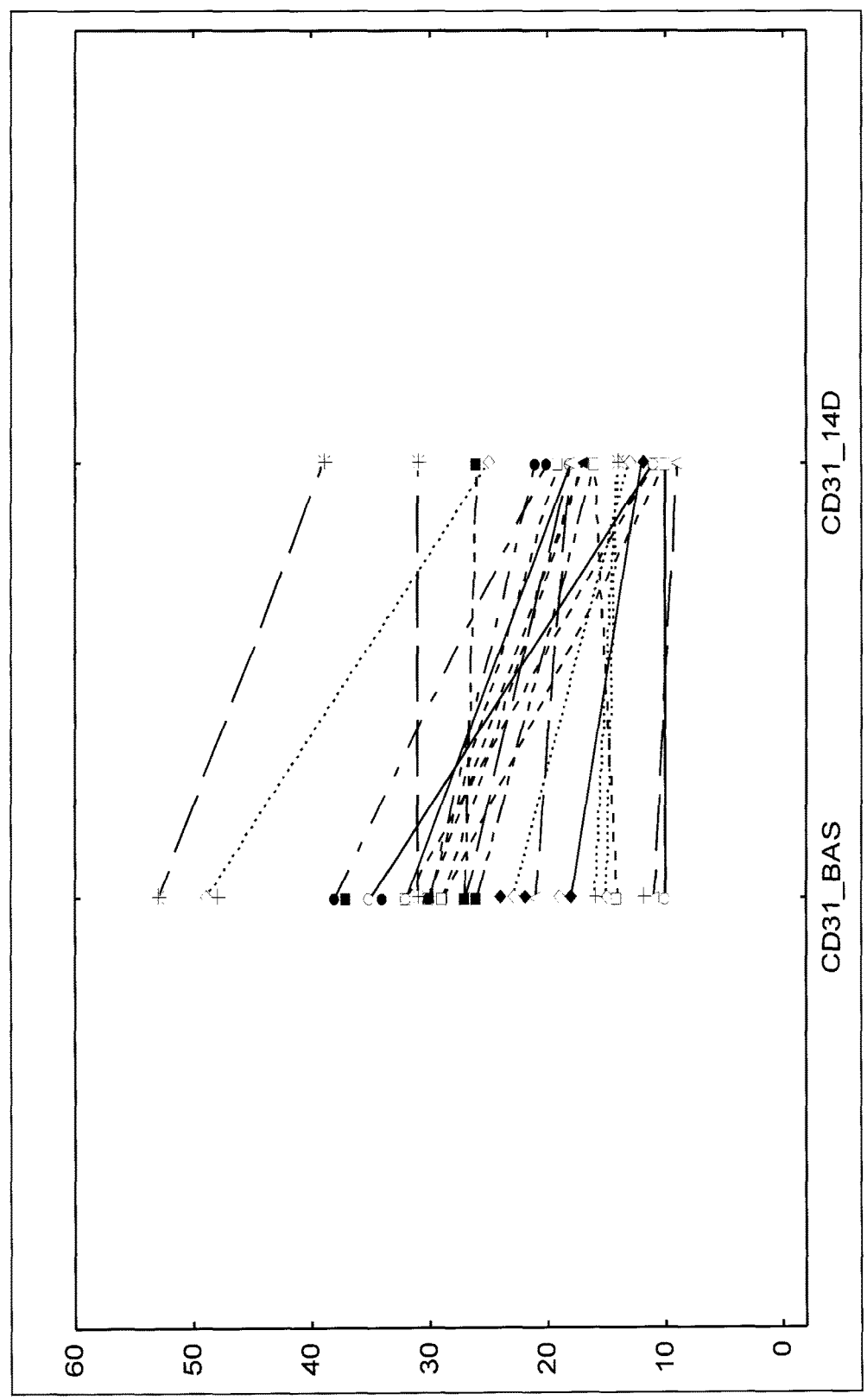
Fig. 10 Cont. B)

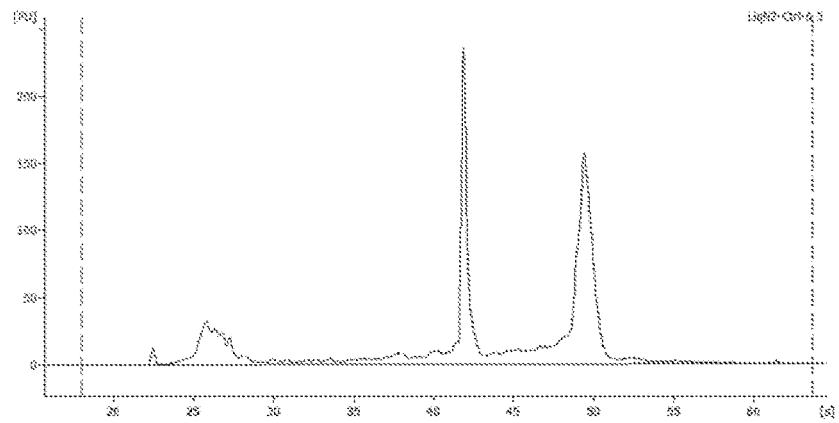

Overall Results
RNA Area: 1,152.7
RNA Concentration: 621 ng/µl
rRNA Ratio [28s / 18s]: 1.6
RNA Integrity Number (RIN): 8.9
Result Flagging Label: RIN: 8.90

Fragment Table

| Name | Start Size [nt] | End Size [nt] | Area | % of total Area |
|---|---|---|---|---|
| 18S | 1,748 | 2,077 | 205.7 | 17.8 |
| 28S | 3,268 | 4,514 | 326.4 | 28.3 |

Figure 23 C

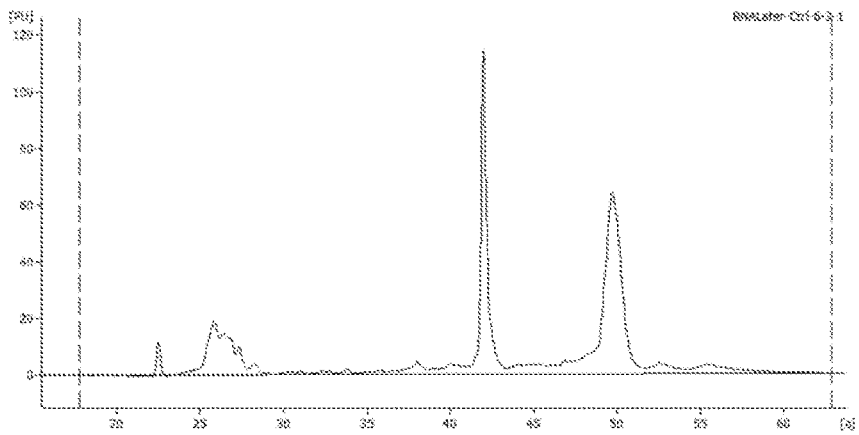

Overall Results
RNA Area: 515.9
RNA Concentration: 278 ng/µl
rRNA Ratio [28s / 18s]: 1.3
RNA Integrity Number (RIN): 9.2
Result Flagging Label: RIN: 9.20

Fragment Table

| Name | Start Size [nt] | End Size [nt] | Area | % of total Area |
|---|---|---|---|---|
| 18S | 1,651 | 2,138 | 108.8 | 21.1 |
| 28S | 3,328 | 4,599 | 138.4 | 26.8 |

Figure 23 D

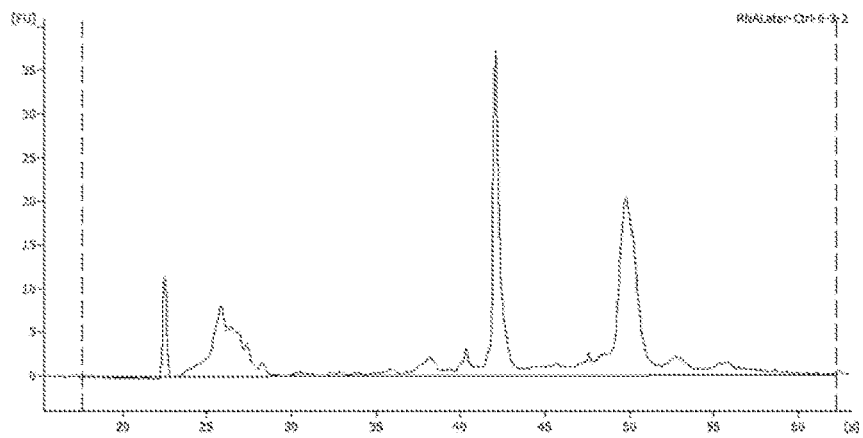

Overall Results
RNA Area: 200.7
RNA Concentration: 108 ng/μl
rRNA Ratio [28s / 18s]: 1.1
RNA Integrity Number (RIN): 8.9
Result Flagging Label: RIN: 8.90

Fragment Table

| Name | Start Size [nt] | End Size [nt] | Area | % of total Area |
|---|---|---|---|---|
| 18S | 1,684 | 2,156 | 37.8 | 18.9 |
| 28S | 3,468 | 4,660 | 43.5 | 21.7 |

Figure 23 E

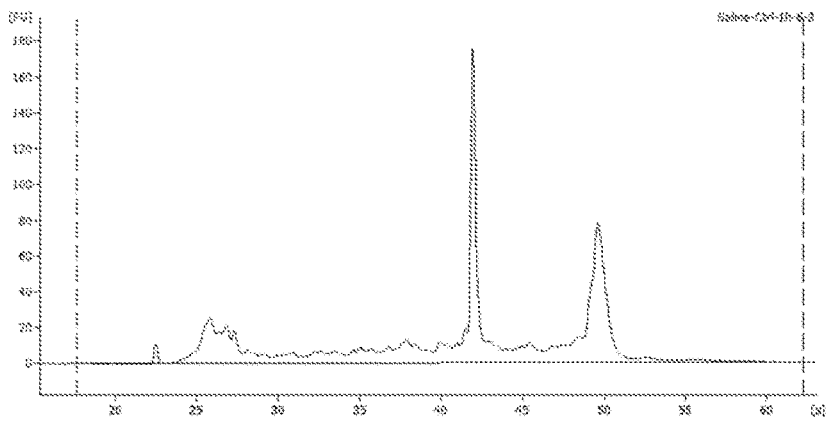

Overall Results:
RNA Area: 932.6
RNA Concentration: 502 ng/μl
rRNA Ratio [28s / 18s]: 0.9
RNA Integrity Number (RIN): 7.3
Result Flagging Label: RIN: 7.30

Fragment Table

| Name | Start Size [nt] | End Size [nt] | Area | % of total Area |
|---|---|---|---|---|
| 18S | 1,676 | 1,997 | 142.1 | 15.2 |
| 28S | 3,709 | 4,459 | 123.2 | 13.2 |

Figure 23 F

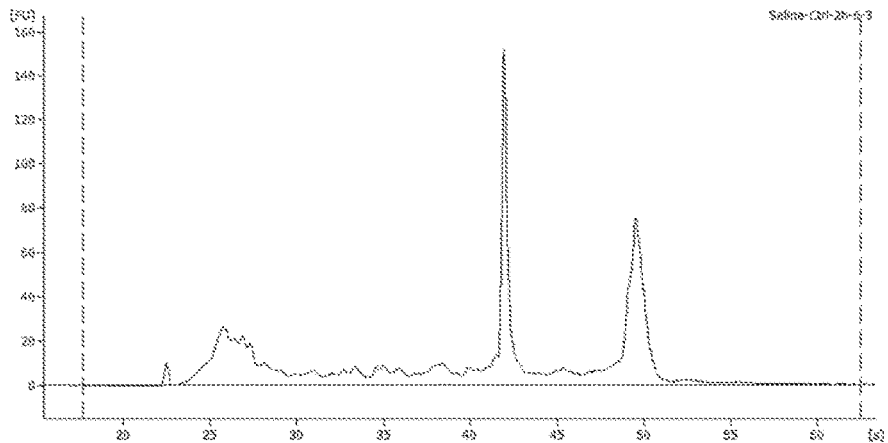

Overall Results:
RNA Area: 887.9
RNA Concentration: 478 ng/µl
rRNA Ratio [28s / 18s]: 1.0
RNA Integrity Number (RIN): 7.7
Result Flagging Label: RIN: 7.70

Fragment Table

| Name | Start Size [nt] | End Size [nt] | Area | % of total Area |
|---|---|---|---|---|
| 18S | 1,586 | 2,249 | 140.8 | 15.9 |
| 28S | 3,391 | 4,561 | 147.8 | 16.6 |

Figure 23 G

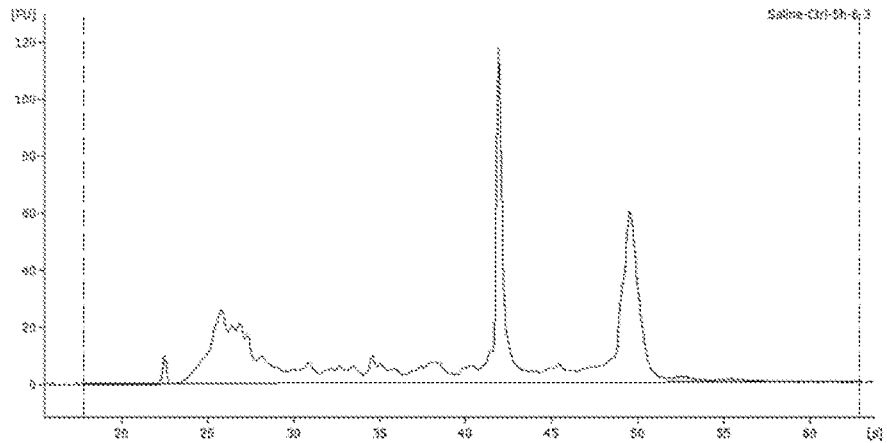

Overall Results:
RNA Area: 774.6
RNA Concentration: 417 ng/µl
rRNA Ratio [28s / 18s]: 1.0
RNA Integrity Number (RIN): 7.6
Result Flagging Label: RIN: 7.60

Fragment Table

| Name | Start Size [nt] | End Size [nt] | Area | % of total Area |
|---|---|---|---|---|
| 18S | 1,589 | 2,436 | 115.6 | 14.9 |
| 28S | 3,477 | 4,572 | 117.0 | 15.1 |

Figure 23 H

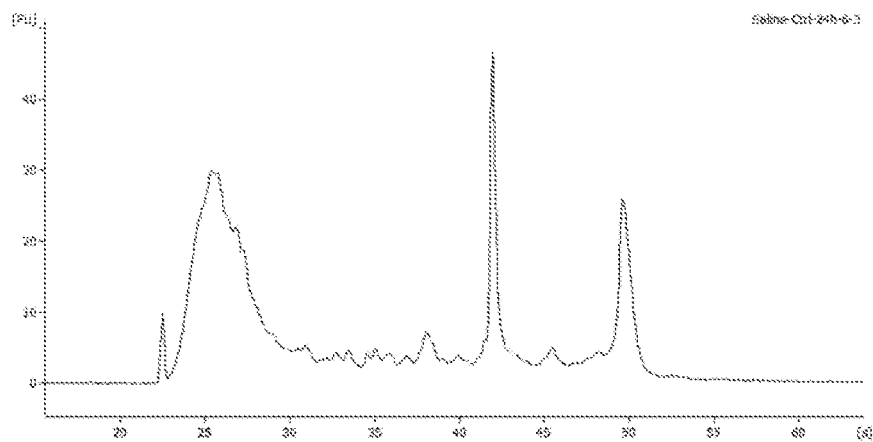

Overall Results:
RNA Area: 682.2
RNA Concentration: 367 ng/μl
rRNA Ratio [28s / 18s]: 0.9
RNA Integrity Number (RIN): N/A
Result Flagging Label: RIN N/A Fragment Table

| Name | Start Size [nt] | End Size [nt] | Area | % of total Area |
|---|---|---|---|---|
| 18S | 1,588 | 2,476 | 50.5 | 7.4 |
| 28S | 3,289 | 4,617 | 47.6 | 7.0 |

Figure 23 I

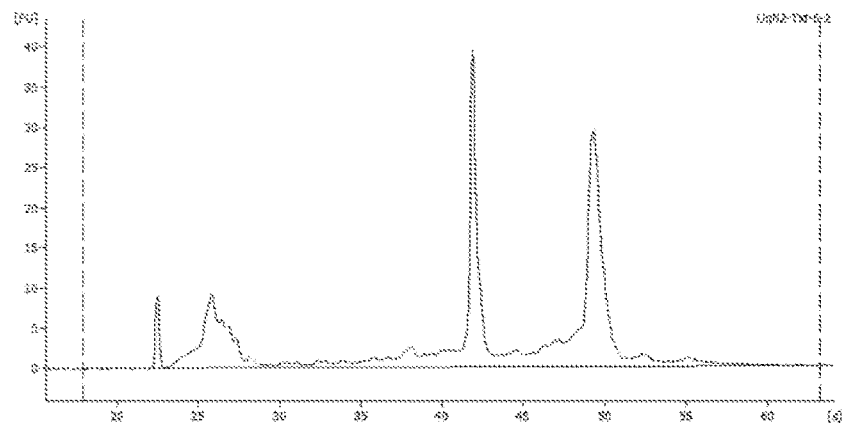

Overall Results:
RNA Area: 250.5
RNA Concentration: 135 ng/μl
rRNA Ratio [28s / 18s]: 1.2
RNA Integrity Number (RIN): 9.1
Result Flagging Label: RIN: 9.10

Fragment Table

| Name | Start Size [nt] | End Size [nt] | Area | % of total Area |
|---|---|---|---|---|
| 18S | 1,196 | 2,162 | 46.1 | 18.4 |
| 28S | 3,373 | 4,462 | 54.6 | 21.8 |

Figure 23 J

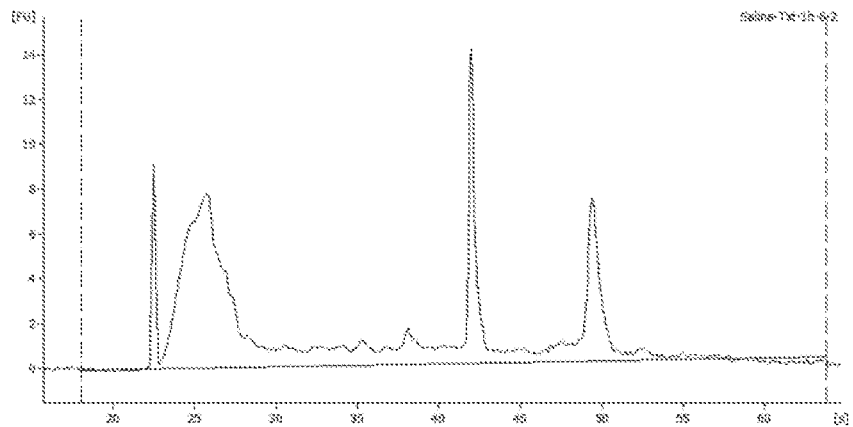

Overall Results:
RNA Area: 158.4
RNA Concentration: 85 ng/µl
rRNA Ratio [28s / 18s]: 0.8
RNA Integrity Number (RIN): N/A
Result Flagging Label: RIN N/A

Fragment Table

| Name | Start Size [nt] | End Size [nt] | Area | % of total Area |
|---|---|---|---|---|
| 18S | 1,711 | 2,145 | 13.2 | 8.3 |
| 28S | 3,736 | 4,477 | 10.2 | 6.4 |

Figure 23 K

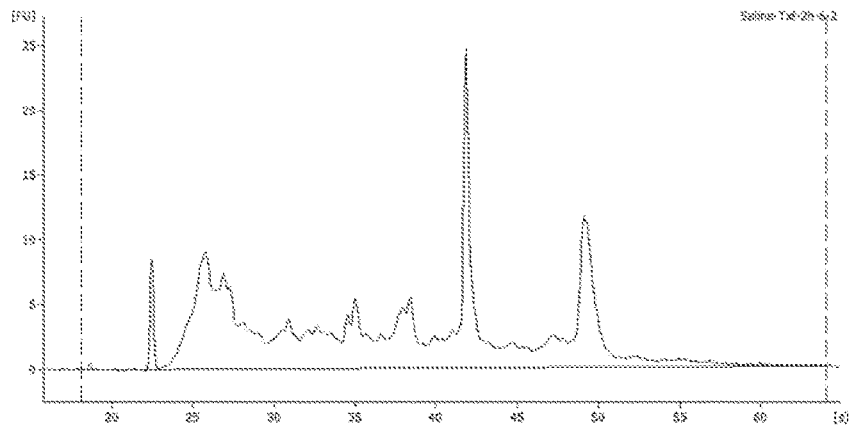

Overall Results:
RNA Area: 278.5
RNA Concentration: 150 ng/µl
rRNA Ratio [28s / 18s]: 0.7
RNA Integrity Number (RIN): 6.5
Result Flagging Label: RIN: 6.50

Fragment Table

| Name | Start Size [nt] | End Size [nt] | Area | % of total Area |
|---|---|---|---|---|
| 18S | 1,351 | 2,253 | 27.3 | 9.8 |
| 28S | 3,575 | 4,415 | 18.5 | 6.6 |

Figure 23 L

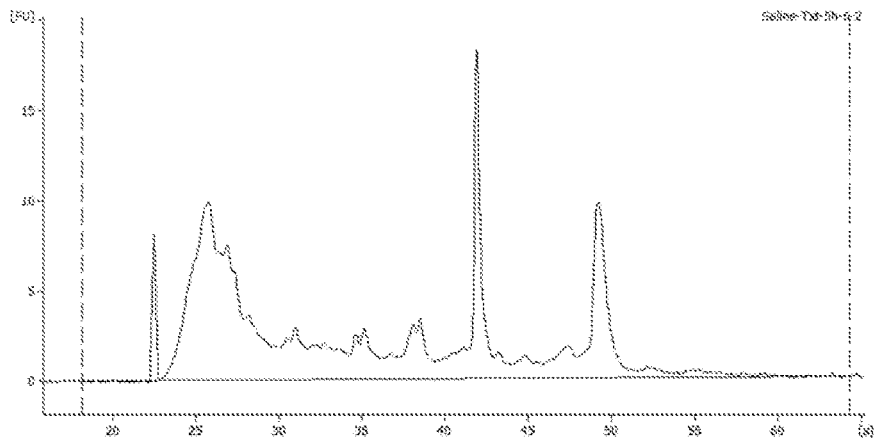

Overall Results:
RNA Area: 235.3
RNA Concentration: 127 ng/µl
rRNA Ratio [28s / 18s]: 1.0
RNA Integrity Number (RIN): N/A
Result Flagging Label: RIN N/A Fragment Table

| Name | Start Size [nt] | End Size [nt] | Area | % of total Area |
|------|-----------------|---------------|------|-----------------|
| 18S  | 1,696           | 2,016         | 15.4 | 6.5             |
| 28S  | 3,496           | 4,436         | 15.4 | 6.6             |

Figure 23 M

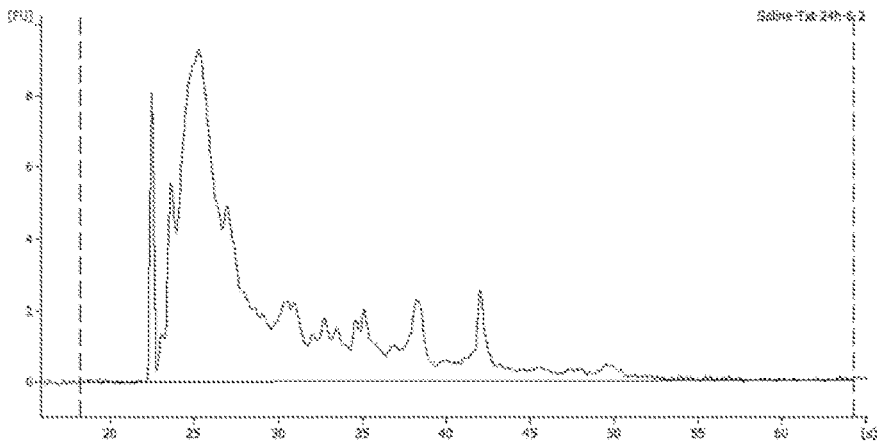

Overall Results:
RNA Area: 168.9
RNA Concentration: 91 ng/µl
rRNA Ratio [28s / 18s]: 0.0
RNA Integrity Number (RIN): 2.7
Result Flagging Label: RIN: 2.70

Fragment Table

| Name | Start Size [nt] | End Size [nt] | Area | % of total Area |
|------|-----------------|---------------|------|-----------------|
| 18S  | 1,777           | 2,016         | 1.9  | 1.1             | i)

ii)

iii)

iv)

v)

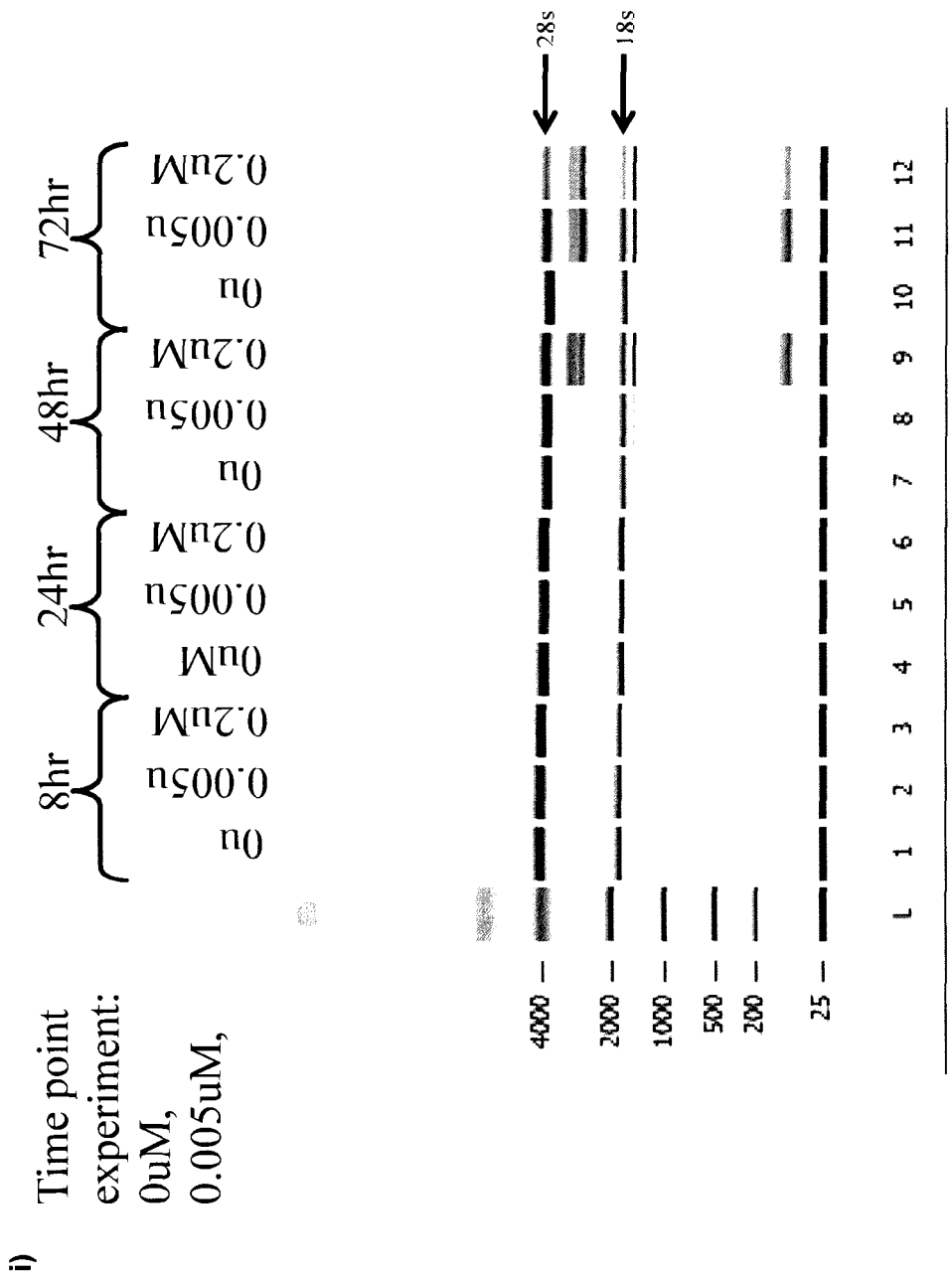

ii)

Effect of Radiation on RNA Disruption in A2780 Cells

RNA DISRUPTION ASSAY FOR PREDICTING SURVIVAL

FIELD

The disclosure pertains to methods of predicting and/or prognosing survival time and more particularly to methods comprising measuring RNA disruption for predicting and/or prognosing survival times.

BACKGROUND

Complete pathological response (pCR) is well recognized as the best intermediate endpoint to predict disease free survival. However, pCR has limitations which limit its utility for example for response guided therapy, including its availability only after therapy, and pCR response in <10% of ER+ve patients.

Despite their ability to reduce tumor size as assessed by palpation and imaging techniques [30], it is becoming increasingly apparent that by pCR criteria, primary systemic therapy with cytotoxic drugs increases disease free and overall survival in only a small a minority of breast cancer patients [31-33]. Since most breast cancer patients experience severe short-term and long-term side effects from chemotherapy [33-35] (whether or not treatment enhances survival benefit), there has long been a search for an effective intermediate endpoint for assessing chemotherapy response prior to or during treatment of breast cancer [36-38]. Given current evidence that switching regimens in nonresponders early in therapy can increase pCR rates and survival [39;40], the need for a test to reliably identify nonresponders to chemotherapy is becoming increasingly urgent. If this test (or another) can also accurately identify patients with chemotherapy-responsive tumors, then this would provide reassurance to patients with such tumors that the chosen treatment regimen is working.

Ribonucleic acids (RNA) are biopolymers which encode genetic information and play various roles in a cell, including encoding proteins. RNA preparations are employed in the investigation of gene expression, for example, by microarray experiments, RT-PCR and many other methods. The results of experiments employing RNA preparations and the significance of results obtained by such experiments, is largely dependent upon the integrity of the RNA employed. Different methods are available to measure RNA integrity of a sample. Typically the methods compare heat degraded or RNAse degraded samples to samples with intact RNA with regard to the capacity of the RNA at a particular degradation level to be sufficiently intact to permit PCR amplification of specific mRNAs such as "housekeeping" genes.

For example, Schroeder, A., O. Mueller, et al. (2006) [43] describes a method that automatically selects features from signal measurements and constructs regression models based on a Bayesian learning technique. Feature spaces of different dimensionality are compared in the Bayesian framework, which allows selecting a final feature combination corresponding to models with high posterior probability. The approach was applied to a large collection of electrophoretic RNA measurements recorded with an Agilent 2100 bioanalyzer to develop an algorithm that describes RNA integrity. The resulting algorithm is a user-independent, automated and reliable procedure for standardization of RNA quality control that allows the calculation of an RNA integrity number (RIN) under certain conditions and/or for certain samples.

A method of using tumour RNA integrity to measure response to chemotherapy in cancer patients is disclosed in PCT/CA2008/001561 filed Sep. 5, 2008.

SUMMARY

An aspect includes a method for predicting and/or prognosing survival time of a patient suffering from cancer, comprising the steps of: a) measuring RNA disruption by determining an RNA disruption assay (RDA) score in a tumor tissue sample comprising cellular RNA from said patient after said patient has received one or more doses of a cancer treatment; b) comparing said RDA score to one or more predetermined RNA disruption reference values; and c) providing a favorable prediction and/or prognosis of survival time for said patient when said RDA score is higher than said predetermined RNA disruption reference value; or providing an unfavorable prognosis of survival time for said patient when said RDA score is lower than said predetermined RNA disruption reference value, wherein the RDA score is proportional to the degree of RNA disruption.

In an embodiment, the RDA score is a RNA disruption index (RDI) value, which is proportional to the degree of RNA disruption.

In an embodiment, the RDA score, optionally an RDI value, is determined by a RNA disruption assay, the RNA disruption assay comprising obtaining at least one electropherogram dataset corresponding to a tumour tissue sample comprising cellular RNA from said patient after said patient has received one or more doses of a cancer treatment; determining values for features from the at least one electropherogram dataset by using two identifying ranges to accommodate possible shifting of 18S and 28S peaks (e.g. 18S and 28S rRNA peaks), detecting the 18S and 28S peaks, and calculating the features derived at least in part based on the located 18S and 28S peaks; determining an RDA score based on a combination of the values of the features.

In an embodiment, the tumor tissue sample is obtained from the patient about midtreatment.

In an embodiment, the RDI value associated with a favourable survival prediction and/or prognosis is at least 10, at least 15, at least 20, at least 35, at least 40, at least 50, at least 60, at least 70, at least 80, at least 90, at least 100, at least 110, at least 120, at least 130, at least 140, at least 150, at least 160, or at least 170.

In an embodiment, when a sample is taken after a single cycle and/or dose, the RDI value associated with a favourablel survival prediction and/or prognosis, is at least 3, at least 3.5, at least 4, at least 4.5, or at least 5.

In an embodiment, the RDI value is increased compared to a pretreatment RNA disruption reference value by at least 2 fold, at least 2.5 fold, at least 3 fold, at least 3.5 fold, at least 4 fold, at least 4.5 fold, at least 5 fold, at least 5.5 fold or at least 5.8 fold.

In an embodiment, two RNA disruption reference values are used to stratify patients into 3 zones, wherein zone 3 identifies patients having a favorable prognosis of survival time for said patient when said RDA score is higher than said predetermined RNA disruption reference value; zone 1 identifies patients with unfavorable prediction and/or prognosis of survival time for said patient when said RDA score is lower than said predetermined RNA disruption reference value; and zone 2 identifies patients with insufficient response and/or mixed survival prognosis.

In an embodiment, the method further comprises measuring RNA concentration of the sample.

In an embodiment, the cancer is breast cancer.

In an embodiment, the breast cancer is locally advanced breast cancer.

In an embodiment, the breast cancer is ER+/−, HER2+/−, and/or PR+/−.

In an embodiment, the breast cancer is ER+.

In an embodiment, the survival time is disease-free survival (DFS) or overall survival.

In an embodiment, the DFS is increased by at least 5 months, at least 10 months, at least 15 months, at least 20 months, at least 25 months, at least 30 months, at least 35 months or at least at least 40 months.

Another aspect includes a method for determining/predicting if a subject is responding to a cancer treatment comprising: assaying a tissue tumour sample obtained from the subject before, during and/or after the subject has received a dose treatment for the quantity of RNA disruption using an RNA Disruption Assay (RDA), wherein the subject is identified as responding to the treatment if the quantity of RNA disruption is increased relative to the threshold or reference value, wherein the cancer treatment comprises a bisphosphonate, a monoclonal antibody that targets HER2/neu receptor, aromatase inhibitor and/or a TKI and/or wherein the sample is obtained from the patient after 2 days, 5 days, 10 days or 15 days after administration of a dose of a cancer treatment.

In an embodiment, the cancer treatment comprises a bisphosphonate.

In an embodiment, the bisphosphonate is zoledronic acid.

In an embodiment, the cancer treatment comprises a monoclonal antibody that targets HER2/neu receptor.

In an embodiment, the monoclonal antibody is trastuzumab.

In an embodiment, the cancer treatment comprises an aromatase inhibitor.

In an embodiment, the aromatase inhibitor is letrozole.

In an embodiment, the cancer treatment comprises a tyrosine kinase inhibitor (TKI).

In an embodiment, the TKI is sorafenib.

In an embodiment, the cancer treatment comprises an aromatase inhibitor, optionally letrozole, in combination with cyclosphosphamide and/or sorafenib.

In an embodiment, the tumour tissue sample is obtained after administration of a dose of a cancer treatment.

In an embodiment, the biological sample optionally a tumour tissue sample is obtained from the patient after 2 days, 5 days, 10 days or 15 days after administration of a dose of a cancer treatment.

A further aspect includes a method for response guided primary systemic therapy of breast cancer, the method comprising: determining according to a method described herein if the subject is predicted to have: i) a favourable prediction and/or prognosis of survival time or ii) an unfavourable prediction and/or prognosis of survival time according to a method described herein; and for patients identified as having a favourable prediction and/or prognosis of survival time, discontinuing said cancer treatment and/or continuing with said cancer treatment and for patients identified as having an unfavourable prediction and/or prognosis of survival time, discontinuing said cancer treatment and/or switching treatments.

In an embodiment, the method further comprises measuring in the tumour tissue sample Annexin V-FITC binding, sub-G1 level of DNA content, cleavage of poly ADP ribose polymerase (PARP) and/or caspase activity.

In an embodiment, the RDA assay comprises:
obtaining at least one electropherogram dataset corresponding to a unique biological sample comprising cellular RNA optionally at a time point before, during or after the treatment;
determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and
optionally determining an RDA score based on a combination of the values of the features.

In an embodiment, the features comprise intermediate area, low C area, 28S area and 18S area, optionally (intermediate area+low C)/(28S+18S).

Yet a further aspect includes an in vitro model system for RNA disruption comprising for example A2780 ovarian tumour cell line, and one or more of a reference anti-cancer agent and a test agent. The model can be comprised in a kit with one or more drugs and/or instructions for use. Other cells that can be used include CaOV3 ovarian tumour cell line and Jurkat leukemia cell line, Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and in which:

FIG. 23B is an illustration of an electropherogram trace of lane 1 of the gel of FIG. 23A;

FIG. 23C is an illustration of an electropherogram trace corresponding to lane 2 of the gel of FIG. 23A;

FIG. 23D is an illustration of an electropherogram trace corresponding to lane 3 of the gel of FIG. 23A;

FIG. 23E is an illustration of an electropherogram trace corresponding to lane 4 of the gel of FIG. 23A;

FIG. 23F is an illustration of an electropherogram trace corresponding to lane 5 of the gel of FIG. 23A;

FIG. 23G is an illustration of an electropherogram trace corresponding to lane 6 of the gel of FIG. 23A;

FIG. 23H is an illustration of an electropherogram trace corresponding to lane 7 of the gel of FIG. 23A;

FIG. 23I is an illustration of an electropherogram trace corresponding to lane 8 of the gel of FIG. 23A;

FIG. 23J is an illustration of an electropherogram trace corresponding to lane 9 of the gel of FIG. 23A;

FIG. 23K is an illustration of an electropherogram trace corresponding to lane 10 of the gel of FIG. 23A;

FIG. 23L is an illustration of an electropherogram trace corresponding to lane 11 of the gel of FIG. 23A; and FIG. 23M is an illustration of an electropherogram trace corresponding to lane 12 of the gel of FIG. 23A;

DETAILED DESCRIPTION OF THE DISCLOSURE

Figure 1:
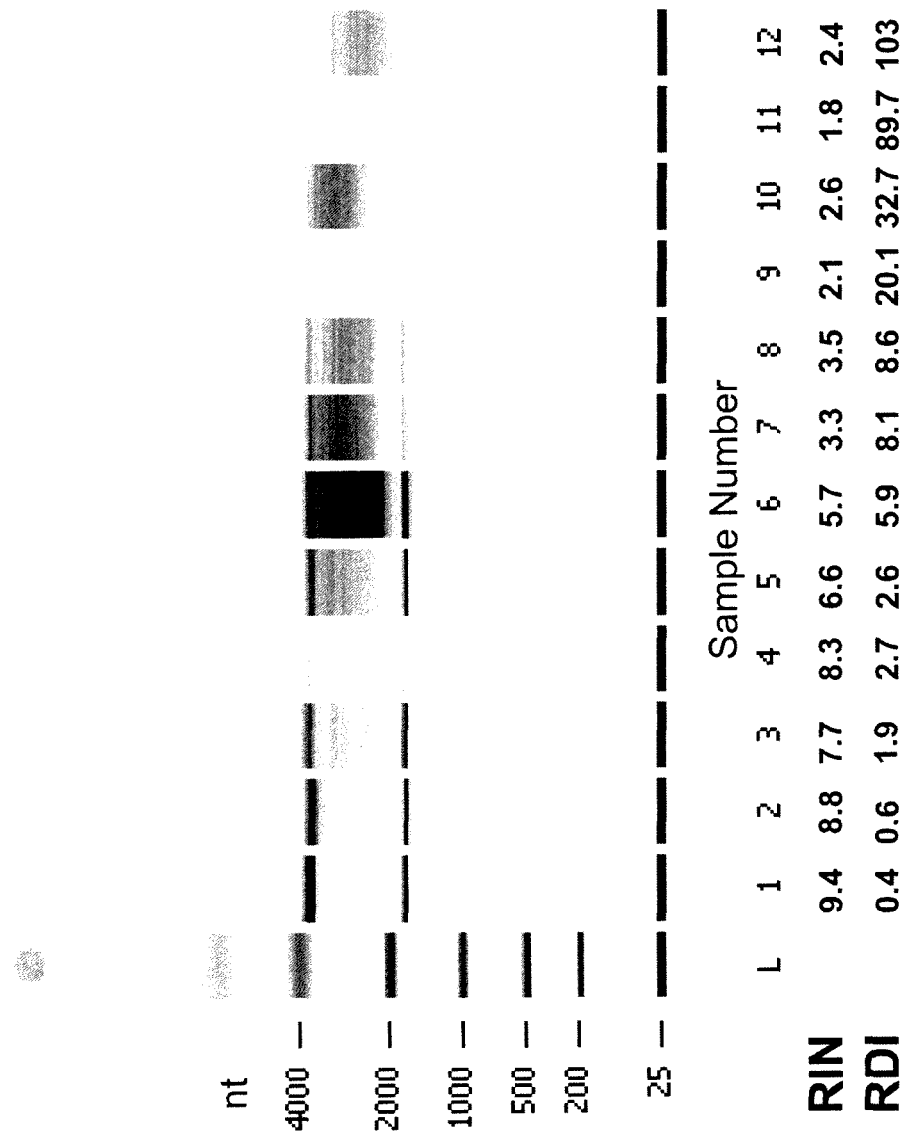
FIG. 1 is is an image of a gel of electrophoretically separated RNA samples and RNA disruption index (RDI) for selected RNA samples from MA.22 tumour core biopsies exhibiting various levels of RNA degradation as depicted by resolving the component RNAs in the various samples by capillary electrophoresis on an Agilent 2100 Bioanalyzer. The positions of several reference RNAs of various lengths of nucleotides (nt) are noted.

Various assays, methods or apparatuses will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

I. Definitions

The term "coupled" used herein indicates that two elements can be directly coupled to one another or coupled to one another through one or more intermediate elements.

The term "autolytic RNA degradation" as used herein refers to RNA degradation taking place during autolytic cell destruction. Autolysis is initiated, for example, by the cells' lysosomes releasing digestive enzymes into the cytoplasm due to the cessation of active processes in the cell, and not due to an active physiologic or pathophysiologic process. Autolytic RNA degradation in a sample can be induced by removal of cells from an environment necessary to sustain cell or tissue viability for extended period of time (e.g. incubation in saline at room temperature) with or without specific stressors e.g. heat treatment.

The term "RNA disruption" as used herein refers to discretely fragmented and/or degraded RNA that is signal induced in response to a cytotoxic treatment such as a drug treatment, e.g. chemotherapy, radiation treatment, and/or cytotoxic antibody treatment (e.g. Trastuzumab). Cytotoxic signal induced RNA disruption can include RNA degradation that has some features that resemble autolytic degradation, particularly for example during later stages. RNA disruption may also include a reduction in the content of RNA in tumour tissues in response to a cytotoxic treatment.

The term "subject" as used herein refers to any member of the animal kingdom, preferably a human being including, for example, a subject that has or is suspected of having a proliferative disorder such as cancer.

The term "control" as used herein refers to a comparator such as intact RNA, a pretreatment sample(s) from a subject or group of individuals with a known outcome and/or a value corresponding to or derived from such samples. With respect to methods for assessing treatment outcome, the control can be a reference value such as a baseline amount or a median or average pretreatment amount of RNA disruption for a particular cell or cancerous tumour (e.g. referred to for example as an RNA disruption reference value). The control can be a sample from a subject or subjects who are known as responding or not responding to a cytotoxic treatment such as a cancer treatment e.g. chemotherapeutic and/or radiation treatment or a value determinable from such samples, such as one or more threshold values above which or below which (depending on how the threshold or measurement is defined) identifies the likelihood that a sample has disrupted RNA, or that a subject or disease is responsive to the cytotoxic treatment e.g. that the tumour is responsive to a chemotherapeutic treatment. The control can also be more than one control, such as a series of threshold values that define clinical zones for a known outcome group of subjects, wherein each zone is associated with a likely response. Untreated cells (e.g. cells pretreatment) from many cells types or, for example, from pretreated tumour samples can have a high RNA integrity. Accordingly, the control can, for example, be a pretreatment value derived from one or more pretreatment samples. As described below, subjects in the MA22 study with mid-treatment tumour values above a threshold (e.g. which exhibited increased degradation) correlated with a pathologic complete response within the breast and axilla post-treatment.

The term "internal standard" as used herein means an RNA sample that is used as a normalizer for a particular assay. For example, when the assay comprises using an RNA chip, the internal standard can be the sample that is determined as having the smallest value for the measure: (intermediate area+low B area+low C area)/(28S area+18S area). The internal standard can be used to identify which samples are adjusted. The internal standard can be a subject sample and/or a control sample (eg. untreated control).

The term "baseline amount" as used herein refers to an amount of RNA degradation (e.g. RNA disruption and/or autocatalytic RNA degradation) in a sample such as a pretreatment sample that is used for comparison to a test sample (e.g. comparison to a cell population and/or tumour) taken at a later time point, for example during or after treatment e.g. during or after a treatment regimen comprising chemotherapy, cytotoxic antibody and/or radiation treatment. For example, in methods related to monitoring response to treatment, "base-line amount" can refer to a level of RNA degradation in a sample taken prior to a subsequent sample, e.g. a base-line sample is taken before treatment, the comparison to which provides an indication of response to treatment.

The term "amount" as used herein with respect to RNA degradation or disruption refers to an amount (e.g. relative amount or absolute amount) of RNA degradation/disruption that is detectable or measurable in RNA isolated from a sample, for example, using an RDA assay described herein. For example, the amount can be expressed using an absolute value (e.g. an RDI value) or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5, 6, 7, 8, 9, 10, 15, 20, 25, 30, 40, 60, 80 and/or 100 times a control amount, where for example, the control amount is, for example, a pretreatment amount or, for example, a reference value corresponding to the average or median level in untreated or pretreatment samples. The amount can be compared to a threshold value which identifies subjects with a likelihood of responding to the treatment.

The term "threshold" with respect to discriminating subject outcome also referred to as "cut-off" or "cut-off value" as used herein refers to a value or curve which is derived from a population of samples with known outcomes and identifies a clinical zone boundary (e.g. RDA zone) for a selected specificity and/or sensitivity. Multiple threshold values defining multiple clinical zone boundaries can be employed. The zone boundaries define clinical zones and subjects having an RDA score (e.g. an RDI) falling within a RDA zone are identified as having an increased likelihood of responding or not responding to a particular cytotoxic treatment e.g. chemotherapeutic and/or radiation treatment, defined by the zone. For example, the threshold value can be the highest value associated with a panel of known outcome patients (e.g. 100% specificity) or a median level or other selected level, for example, as calculated according to one of the Examples described herein. A subject with an RDI score above the threshold value or falling within a zone specified as being below one threshold value or between two threshold values or above a second threshold value is predicted for example to be likely responding to the treatment, indeterminate or likely not responding to the treatment. The threshold value can be derived, for example, from a database of a plurality of samples.

The terms "18S" and "28S" generally refer to the 18S peak area (also referred to as 18S rRNA peak area) and the 28S peak area (also referred to as 28S rRNA peak area), respectively, unless these terms are modified by other words such as peak or width or band (which can refer to the 18S and 28S bands separated on a gel). Accordingly, the terms "18S peak" and "28S peak" represent the heights of the 18S and 28S peaks respectively. Furthermore, the terms 18S width and 28S width represent the widths of the 18S and 28S peaks respectively. Once a peak is located, the peak width and the peak height are determined according to certain methods described herein. For example, the peak width may be defined by the subtraction of the starting time of the peak from the ending time of the peak. Another example is that the peak height may be defined as the absolute value of the highest point in a peak region or band.

The term "specificity" as used herein refers to the percentage of subjects that are responding to a treatment that are identified as not responding to the treatment based on a RNA disruption score that is, for example, at or below a control level and/or a cut-off level.

The term "sensitivity" as used herein refers to the percentage of subjects that are responsive that are identified as responding to the treatment based on a RNA disruption assay score, that is, for example, above a control amount and/or threshold value.

The term "sample" as used herein refers to 1) any biological fluid, cell or tissue sample from a subject (e.g. test subject) or cell line that comprises cellular RNA, optionally tumour tissue/cells and/or 2) RNA derived from such a sample. For example, the sample can be a tumour tissue sample obtained by a biopsy, including a needle aspirate, such as a fine needle aspirate, a core biopsy, a brush biopsy and/or a laparoscopic biopsy, as well as pieces or slices of tissue that have been removed including following a surgical tumor resection. The tumor tissue sample can be subjected to a variety of well-known post-collection preparative and storage techniques suitable for preserving RNA integrity (e.g., fixation in a suitable RNAse inhibitor solution, storage, freezing, etc.) prior to measuring RNA disruption. The sample can, for example, be a "post-treatment" sample wherein the sample is obtained after one or more cytotoxic, e.g. cancer treatments, or a "base-line sample" which is optionally pre-treatment or taken at an earlier time-point than the post-treatment sample, and is for example, used as a base line for assessing or monitoring response to a cytotoxic treatment. The tumour tissue/cells can be any tissue or cells, for example cancerous tissue or cells, for example ovarian cancer, prostate cancer, lung cancer, sarcomas, leukemia, lymphoma or multiple myeloma or colon cancer and/or any cancer for example cancers treatable by an anthracycline and/or taxane, including any subtype thereof including, for example, HER2+/−, ER+/−, PR+/−, topoisomerase+/− or triple negative breast cancer.

The term "RNA disruption assay score" or "RDA score" as used herein is a score or measure indicative of the extent of RNA disruption and/or likelihood of response to treatment, assessed on the basis of an RNA disruption assay described herein. The RDA score can for example be the output of a calculation based on electropherogram features described herein, for example represented as an RNA Disruption Index (RDI) value, which is described below, or can be a transformed scale, defined by clinical RDA zones based on cut-offs or thresholds, wherein each score or RDA zone is associated with a likelihood of a response for example associated with a likelihood of responsive to a treatment, for example defined by NPV and/or PPV. In an embodiment, a high or increased RNA disruption assay score (for example compared to a baseline sample or control) is indicative of high or increased RNA disruption. For example in such an embodiment, the higher the RNA disruption score, the greater the RNA disruption (and a decrease in RNA integrity). Any scale can be employed, for example 3, 10, or 600. A person skilled in the art would recognize that the scale could also be inverted (for example, by dividing the score into 1, e.g. 1/RNA score) such that the lower the RNA disruption score, the greater the RNA disruption.

The term "RDA zones" as used herein refers to clinical zones associated with treatment response outcome comprising a range of RNA disruption scores, for example RDI values. Each RDA zone is defined by one or two boundaries each boundary corresponding to a selected threshold (e.g. corresponding to a desired NPV or PPV). Subject RDA scores (optionally RDI values) that fall within the clinical zones that are associated with or are predictive of treatment response, for example pCR and/or survival including DFS. In the Examples, 3 RNA disruption assay zones are used, RDA zone 1, RDA zone 2 and RDA zone 3, defined by selected NPV and/or PPVs. A person skilled in the art would readily realize that any number of zones can be used each with different selected thresholds.

The term RNA Disruption Index "RDI" as used herein is a value generated using RDA and can be a ratio of features defined herein of the output of linear discriminant analysis (LDA) or quadratic discriminant analysis of features described herein. The RDI values determined from a group of known response outcome patients (e.g. that are determined to be associated with a particular NPV or PPV) can be used to define the thresholds boundary for RDA zones.

The term "RDA zone 1" as used herein refers to a range of RDA scores (e.g. RDI values) that have a negative predictive value (NPV) of at least 0.8, at least 0.85, at least 0.9, at least 0.95, at least 0.96, at least 0.97, at least 0.98 or greater. These numbers and the associated thresholds, are for example based on the pCR in the MA.22 data set and RDA measurement at third cycle used in the Examples. In an example embodiment, RDA Zone 1 is equal to an RDI of equal or less than 10 calculated using the feature Intermediate Area/(28S+18S Areas). In other embodiments, other features or combination of features can be used. The "RDA zone 1" can be defined to include any set of scores by selecting the desired NPV.

The term "RDA zone 2" as used herein refers to a range of RDA scores (e.g. RDI values) falling between RDA zone 1 and 3, and can be considered an intermediate or indeterminate zone.

The term "RDA zone 3" as used herein refers to a range of RDA scores (e.g. RDI values) that have a positive predictive value (PPV) of at least 0.15, at least 0.16, at least 0.17, at least 0.18, at least 0.19, at least 0.2 or greater. These numbers and the associated thresholds are for example based on the pCR in the MA.22 data set and RDA measurement at third cycle used in the Examples. The "RDA zone 3" can be defined to include any set of scores by selecting the desired PPV.

The term "response", "responding" or "responsive" as used herein refers to a cell such as a cancerous cell or tumor response to a cytotoxic treatment such as a chemotherapeutic and/or radiation treatment, where the cells for example cancer cells or a subset of cancer cells within a tumour respond to the treatment in terms of RNA disruption—e.g. in the context of a subject, the cells show significant treatment induced RNA degradation, and the subject has a positive treatment outcome, for example, reduction of tumour burden, disease stabilization, improved survival such as disease free survival and/or pathological complete response. In an embodiment, a subject who responds to a cytotoxic treatment with for example, one or more of a reduction of tumour burden, disease stabilization, improved survival such as disease free survival and/or pathological complete response, is considered, a "Responder" and/or a subject who does not for example, exhibit reduction in one or more of tumour burden, disease stabilization, improved survival such as disease free survival and/or pathological complete response is considered a "Non-Responder".

The term "resistant" as used herein in reference to a cell such as a cancerous cell or tumour, refers to a cell or tumour response to a cytotoxic treatment, where the cells, e.g. cancer cells or subset of cancer cells within the tumour show no or little response (response as described above), for example disease progression and/or a lack of treatment benefit for the subject having the cancerous tumour.

The term "decreased RNA concentration" as used herein means an RNA concentration that is at least 20%, at least 25%, at least 30%, at least 40%, at least 50%, at least 60%, at least 70%, at least 80% or at least 90% less than a control or corresponding reference value for example a pretreatment sample. The reference value can also be a maximal value or a mean RNA value determined from tumour RNA concentration during treatment for a population of patients. For example RNA concentration values of a patient's tumour during treatment can be decreased relative to a reference value such that RNA concentrations values for example below 100 ng/ul, below 80 ng/ul, below 60 ng/ul, or below 40 ng/ul are associated with increased survival. It was found for example in MA.22 that the mean RNA concentration mid-treatment for all patients was about 94 ng/ul and for pCR recipients about 83 ng/ul. Optionally, the decrease in RNA concentration is relative to a pretreatment sample or value derived therefrom and decreases in RNA concentration of greater than about about 1.2 fold, about 1.4 fold, about 1.6 fold, about 1.8 fold, about 2-fold (e.g. pretreatment RNA concentration is assigned a value of 100 and a two fold decrease would be 50), about 2.2 fold, about 2.5 fold, about 2.7 fold, or about 3-fold. In the MA.22 cohort, the decrease in RNA concentration for all patients was about 2.1-fold, and for pCR patients about 2.7 fold.

RNA concentration can be determined by a number of methods including for example microcapillary electrophoresis, for example using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. The RNA concentration can be based on UV absorbance, for example by assessing UV absorbance at 260 nm.

The term "low risk" as used in relation to progression refers to risk sufficiently less than average risk (e.g. decreased probability) calculated for a group of patients for example with the same cancer, treated similarly such that the patients would have high probability of survival with conservative therapy; and high risk of progression means greater than average risk (e.g. increased probability) compared to the low risk group of patients.

The term "stable RNA integrity" or "lack of RNA disruption" as used herein means RNA that is not degraded appreciably, for example as compared to an appropriate comparator sample or the expected RNA integrity for the cell type of tissue, for example, less than a 10% decrease in integrity or less than a 15% decrease in integrity.

The term "RNA isolating or stabilizing composition" as used herein refers to any composition that inhibits RNAse activity sufficiently and/or stabilizes RNA preventing RNA degradation.

The term "RNA integrity" as used herein means the degree of intactness of the RNA following extraction or isolation from the cell or tissue e.g. whether the isolated RNA is degraded (e.g. disrupted and/or autolytically degraded). High RNA integrity is commonly taken as meaning little to no degradation, for example less than a 30%, less than 25%, less than 20% or less than 10% decrease from a maximal RNA integrity and/or control sample or the retention of capacity to amplify mRNAs of interest following extraction or isolation. Low integrity RNA is, for example, RNA that exhibits greater than 20%, greater than 25%, greater than 30%, greater than 35%, greater than 40%, greater than 45%, greater than 50%, greater than 55%, greater than 60%, greater than 65%, greater than 70%, or greater than 75% decrease from maximal and/or a control sample or decreased capacity to amplify mRNAs of interest when they are known to be present in controls in RNA following extraction or isolation. RNA integrity can also be represented as an absolute number. For example, one RNA integrity scale assigns a number from 1 to 600 wherein an increasing score is associated with greater RNA disruption/degradation. For example, a sample that comprises a score of 500 comprises more RNA degradation than a sample scoring 400. Another example of a RNA integrity scale assigns a number from 1 to 1500, or 1 to 2000 wherein an increasing score is associated with greater RNA disruption.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, reversal of disease, amelioration or palliation of the disease state, and remission (whether partial or total), whether detectable or undetectable. "Treatment" can also mean prolonging survival as compared to expected survival if not receiving treatment.

The term "cancer treatment" as used herein means any agent or radiation that can induce cell death that is used in the treatment of e cancer, including for example, traditional and non-traditional chemotherapy (e.g. targeted therapies), radiation treatment, hormonal treatment (e.g. for responsive cancers) and combinations thereof. Such agents include but are not limited to microtubule stabilizing agents such as Docetaxel and paclitaxel, DNA synthesis inhibitors such Epirubicin, inhibitors of Her2 Receptor such as Trastuzumab, DNA cross-linking agents such as Mafosfamide, carboplatin and cisplatin, VEGFA inhibitors such as Bevacizumab, Receptor Tyrosine Kinase inhibitors such as sorafenib, Sunitinib and Toceranib, Bisphosphonates such as Zoledronic acid, Thymidylate synthase inhibitors such as 5-fluorouracil and aromatase inhibitors such as letrozole, optionally in combination with cyclophosphamide and/or sorafenib.

The term "radiation" in relation to a treatment means any energy, photon or particle, applied to a tumour, including for example ionizing radiation.

The term "dose" as used herein in reference to radiation refers to an individual radiation exposure either administered at each time within a schedule or the total amount of radiation exposure within a schedule. With respect to a chemotherapy treatment, a dose means an amount of an individual drug either administered at each time within a schedule or the total amount of each drug administered within a schedule or the total amount of drug administered during a course of chemotherapy.

The term "changing cancer treatment" or "altering cancer treatment" as used herein includes for example one or more of changing the dosage level of the radiation, discontinuing the treatment, adding a chemotherapeutic agent(s) to the treatment or changing to an alternate cancer treatment such as a drug therapy or surgery.

The term "favourable survival time" as used herein means to have a greater likelihood of remaining disease free for a longer period of time compared to the average of patients with the same type of cancer e.g. breast cancer. For example, a favourable survival time for breast cancer can be more likely to be disease free for at least 3 years, at least 3.5 years, at least 4 years, at least 4.5 years or at least 5 years.

The term "unfavourable survival time" as used herein means to have a greater likelihood of earlier relapse time compared to the average of patients with the same type of cancer e.g. breast cancer. For example, an unfavourable survival time for breast cancer can be more likely to be relapse within 2 years, 2.5 years, 3 years, or 3.5 years.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

In understanding the scope of the present disclosure, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Assays, Methods and Products

It is demonstrated herein, that high tumor RNA disruption is associated with increased survival in patients with breast cancer. As described in Example 1 below, it was recently reported that epirubicin/docetaxel treatment of locally advanced breast cancer patients in the MA.22 clinical trial reduced tumor RNA integrity and that low mid-treatment tumor RNA integrity was associated with a pathologic complete response (pCR) post-treatment [*Breast Cancer Res. Treat.* 119:347-356 WO2009/03029, filed Sep. 5, 2008 herein incorporated by reference in its entirety].

The MA22 RNA electropherogram data was examined to determine components of the electropherogram correlating with clinical response. It became evident that the Agilent Bioanalyzer software misidentified either the 28S peak or the 18S peak on electropherograms in >20% of the samples. For example, in at least some of these samples, a small portion of the tip of a peak was identified as the whole peak. However, The Agilent 2100 Bioanalyzer software (Agilent Expert) (Mueller 2004; Vespucci 2005) was able to correctly identify the 28S and 18S peaks on electropherograms of intact RNA which are identifiable by eye. However, in samples with disrupted RNA, electropherogram peaks were misidentified by Agilent RIN software although the correct peaks remained in appropriate locations visually on the electropherogram. The Agilent method which generates RIN values, hereafter referred to as the RIN algorithm, was based on RNA samples which were either intact or had undergone complete autolytic degradation and had few "partially degraded" samples (Schroeder, Mueller et al. 2006). Methods such as the Agilent method are generally for the purpose of assessing autolytic degradation.

Importantly, the current RIN algorithm's misidentification of the 28S and 18S peaks resulted in aberrant 28S:18S ratios (often having a "0" value) or RIN values that were designated N/A. It was found for example that RIN values were N/A when an aberrant RNA banding pattern was present and/or the RNA concentration fell below for example 20 ng/ul.

A method for detection of chemotherapy-dependent loss of RNA integrity, the RNA disruption assay (RDA), has been developed described herein and in PCT/CA2013/000408 filed Apr. 24, 2013, ASSAYS, METHODS AND APPARATUS FOR ASSESSING RNA DISRUPTION herein incorporated by reference in its entirety, which can stratify RNA disruption.

Complete pathological response (pCR) is well recognized as the best intermediate endpoint to predict disease free survival. However, pCR has limitations which limit its utility for example for response guided therapy, including its availability only after therapy, and pCR response in <10% of ER+ve patients (116). According to the author, it is unclear if pCR can be leveraged to de-escalate treatment.

It is demonstrated herein that measuring RNA disruption can be used to predict survival times and identify breast cancer patients that have an increased likelihood of experiencing pCR as well as additional patients likely to experience similar disease free survival (DFS) as patients that meet the criteria of pCR even though those criteria are not met. Further, it is demonstrated herein that measuring RNA disruption using the RNA disruption assay identifies patients who have increased DFS irrespective of breast cancer subtype, including ER+ breast cancer.

The findings described herein suggest that tumor RNA disruption measurements during treatment can predict response and survival for cancer patients including locally advanced breast cancer patients. For example, data demonstrates that non-responding patients (RDA zone 1) have considerably reduced DFS with very little chance of achieving a pCR. Such patients may be spared the toxicities associated with continuing an ineffective regimen and could be considered for alternate treatments, including surgery, radiation therapy, or other anti-cancer drugs.

Accordingly an aspect includes a method for the prediction and/or prognosis of survival time of a patient suffering from cancer, comprising the steps of: measuring RNA disruption by determining an RNA disruption assay (RDA) score in a tumor tissue sample comprising cellular RNA from said patient after said patient has received one or more doses of a cancer treatment; b) comparing said RDA score to one or more predetermined RNA disruption reference values; and c) providing a favorable prediction and/or prognosis of survival time for said patient when said RDA score is higher than said predetermined RNA disruption reference value; or providing an unfavorable prediction and/or prognosis of survival time for said patient when said RDA score is lower than said predetermined RNA disruption reference value, wherein the RDA score is proportional to the degree of RNA disruption.

A person skilled in the art would recognize that a RDA score that is inverse to the degree of RNA disruption would result in an inverse relationship e.g. providing a favourable prediction and/or prognosis of survival time for said patient when said RDA score is lower than said predetermined RNA disruption reference value; or providing an unfavourable prediction and/or prognosis of survival time for said patient when said RDA score is higher than said predetermined RNA disruption reference value, wherein the RDA score is inverse proportional to the degree of RNA disruption.

In an embodiment, the prediction and/or prognosis is provided by communicating the prediction and/or prognosis, optionally transmitted electronically, orally or by written communication.

In an embodiment, the RDA score is a RNA disruption index (RDI) value, which is proportional to the degree of RNA disruption.

The method wherein the RNA disruption index value is determined by a RNA disruption assay described herein. In an embodiment the RNA disruption assay comprises obtaining at least one electropherogram dataset corresponding to a tumour tissue sample comprising cellular RNA from said patient after said patient has received one or more doses of a cancer treatment; determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; determining a RDA score based on a combination of the values of the features, optionally an RDI value and RDA zone.

Where the RDA score is provided as an RDA zone which comprises a range of RDI values, the patient is provided with a favorable prediction and/or prognosis of survival time when said patient is determined to fall within the RDA zone comprising RDIs higher than said predetermined RNA disruption reference value; or the patient is provided with an unfavorable prediction and/or prognosis of survival time when said patient is determined to fall within the RDA zone comprising RDIs that are lower than said predetermined RNA disruption reference value.

It is demonstrated herein that mean mid-treatment maximum RDI values were substantially different between pCR responders and non-responders, with mean RDI values of 176±59.9 and 79.0±20.0, respectively (85 patients assessed; p=0.0049 by Mann Whitney Wilcoxon (MWW) test).

In an embodiment, the RDI value associated with a favourable prediction and/or prognosis (e.g. favourable survival prognosis) is at least 10, at least 15, at least 20, at least 35, at least 40, at least 50, at least 60, at least 70, at least 80, at least 90, at least 100, at least 110, at least 120, at least 130, at least 140, at least 150, at least 160, or at least 170.

In an embodiment, wherein the sample is obtained after the subject has received one or more doses of chemotherapeutic (e.g. prior to completion of a $1^{st}$ or $2^{nd}$ cycle of chemotherapy) and the sample obtained is a fine needle aspirate, the RDI value associated with a favourable prediction and/or prognosis is, at least 3, at least 3.5. at least 4, at least 5, at least 6, at least 7, at least 8, at least 9, least 10, at least 15, at least 20, at least 35, at least 40, at least 50, at least 60, at least 70, at least 80, at least 90, at least 100, at least 110, at least 120, at least 130, at least 140, at least 150, at least 160, or at least 170.

In an embodiment, the value selected is selected according to the particular drug and dose being tested, and the timing of taking the sample. For example the value selected can be determined empirically in vivo.

In an embodiment, wherein the sample is obtained after the subject has received at least 2 cycles of chemotherapy, optionally wherein the sample is obtained mid-treatment and the sample is a core biopsy, the RDI value is 35, at least 40, at least 50, at least 60, at least 70, at least 80, at least 90, at least 100, at least 110, at least 120, at least 130, at least 140, at least 150, at least 160, or at least 170.

In an embodiment, the RDI value is increased compared to a pretreatment RNA disruption reference value by at least 2 fold, at least 2.5 fold, at least 3 fold, at least 3.5 fold, at least 4 fold, at least 4.5 fold, at least 5 fold, at least 5.5 fold or at least 5.8 fold.

One or more RNA disruption reference values, optionally reference RDI values, can be used to stratify the patients. For example, a zone 1 cut-off can be selected, below which identifies a patient with an unfavourable prediction and/or prognosis of survival time, and a zone 3 cut-off can be selected, above which identifies a patient with a favourable prediction and/or prognosis of survival time. Patients having a RDI value falling within a zone 1 cut-off is referred to as RDA zone 1, falling above a zone 3 cut-off is referred to as RDA zone 3 and falling between the cut-off s for RDA zone 1 and 3, as RDA zone 2.

For example the RDA zone 1 cut off can be a RDI value of ≤10 and RDA zone 3 can be an RDI value of >35. The RDA zone cut offs provide for ranges for example where RDA zone 1: ≥0 and ≤10; RDA zone 2: >10 and ≤35; RDA zone 3: >35.

Figure 7:
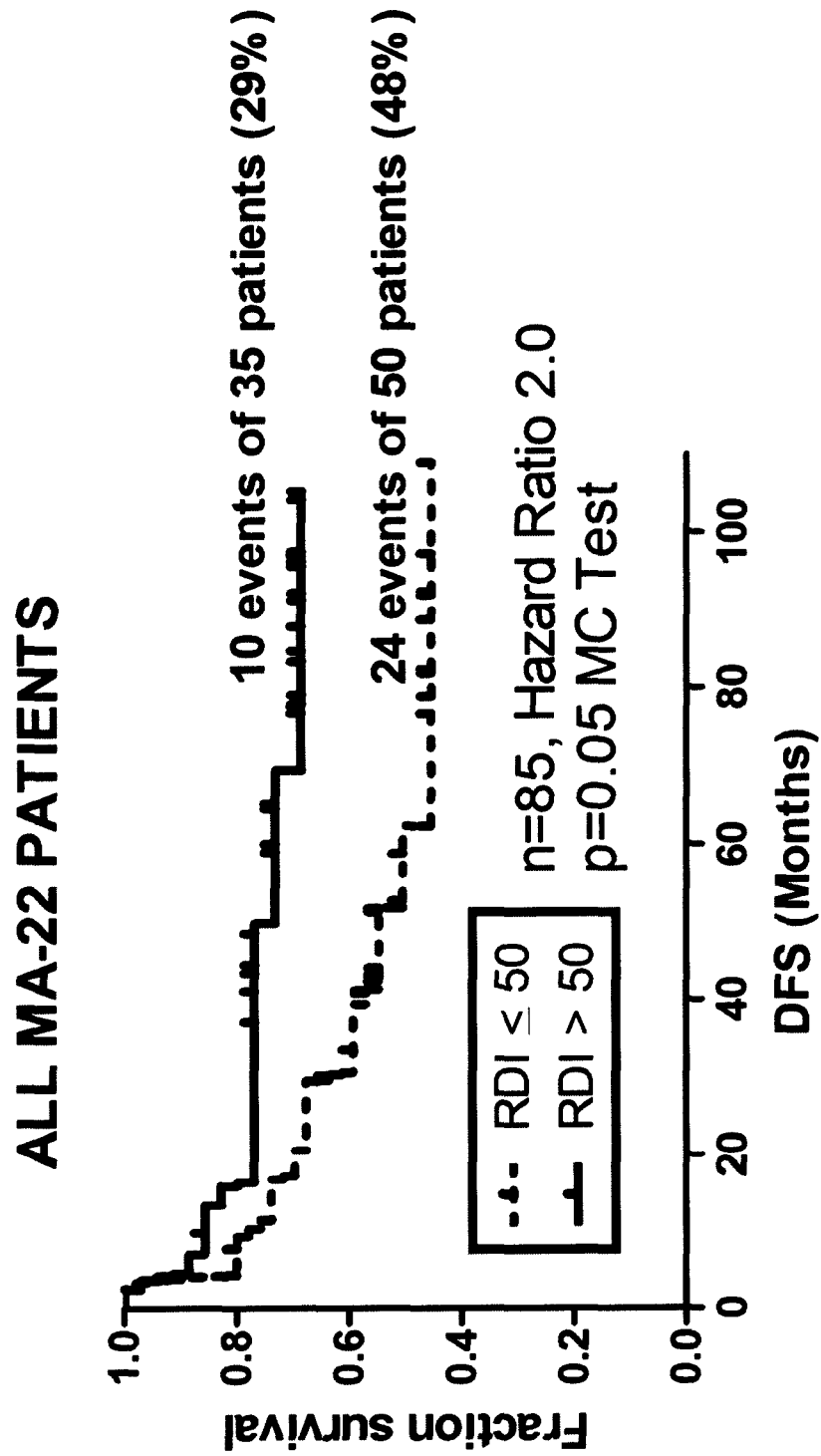
FIG. 7 is a Kaplan Meier Survival curve for patients where disease-free survival is plotted against fraction survival for patients at or below versus above tumour RDI values of 50.

In another example the RDA zone 1 cut off can be a RDI value of ≤10 and RDA zone 3 can be an RDI value of >50 or greater than 100, for example where RDA zone 1: ≥0 and ≤10; RDA zone 2: >10 and ≤50; RDA zone 3: >50 or where RDA zone 1: ≥0 and ≤10; RDA zone 2: >10 and ≤100; RDA zone 3: >100. As shown in FIG. 7, breast cancer patients with a RDI of greater than 50 and/or greater than 100 (e.g. calculated using features (intermediate area+low C)/(28S+18S) have statistically significant improved survival.

In an embodiment, two RNA disruption reference values are used to stratify patients into 3 RDA zones, wherein RDA zone 3 identifies patients having a favorable prediction and/or prognosis of survival time for said patient when said RDA score is higher than said predetermined RNA disruption reference value; RDA zone 1 identifies patients with unfavorable prediction and/or prognosis of survival time for said patient when said RDA score is lower than said predetermined RNA disruption reference value; and RDA zone 2 identifies patients with insufficient response and/or mixed survival time prognosis.

In an embodiment RIN and/or other RNA degradation method is used instead of RDA in a method described herein.

In an embodiment, the method further comprises measuring RNA concentration of the sample. A decrease in RNA concentration compared to a control can be a further indication for stratifying the patient.

In an embodiment, the RDA score is measured in a tumor tissue sample comprising cellular RNA obtained from said patient about mid-treatment.

In an embodiment, the survival time is disease-free survival (DFS) or overall survival (OS).

The methods described are suitable for predicting (prognosing) the duration of the overall survival (OS) and/or the disease-free survival (DFS) of the cancer patient. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they've become cancer-free (achieved remission). DSF gives more specific information and is the number of people with a particular cancer who achieve remission. DFS is the length of time the patient has survived disease free.

In an embodiment, the DFS is increased by by at least 5 months, at least 10 months, at least 15 months, at least 20 months, at least 25 months, at least 30 months, at least 35 months or at least at least 40 months.

In an embodiment, the patient has breast cancer.

In an embodiment, the patient has locally advanced breast cancer.

In an embodiment, the breast cancer is ER+/−, HER2+/−, and/or PR+/−.

It is demonstrated herein that RDA, in contrast to pCR, is able to identify patients with ER+ cancer who benefit from treatment. Accordingly in an embodiment, the patient has an ER+ breast cancer.

As mentioned above the current RIN algorithm's misidentification of the 28S and 18S peaks resulted in aberrant 28S:18S ratios (often having a "0" value) or RIN values that were designated N/A (see for example FIGS. 33A-33F).

Figure 16:
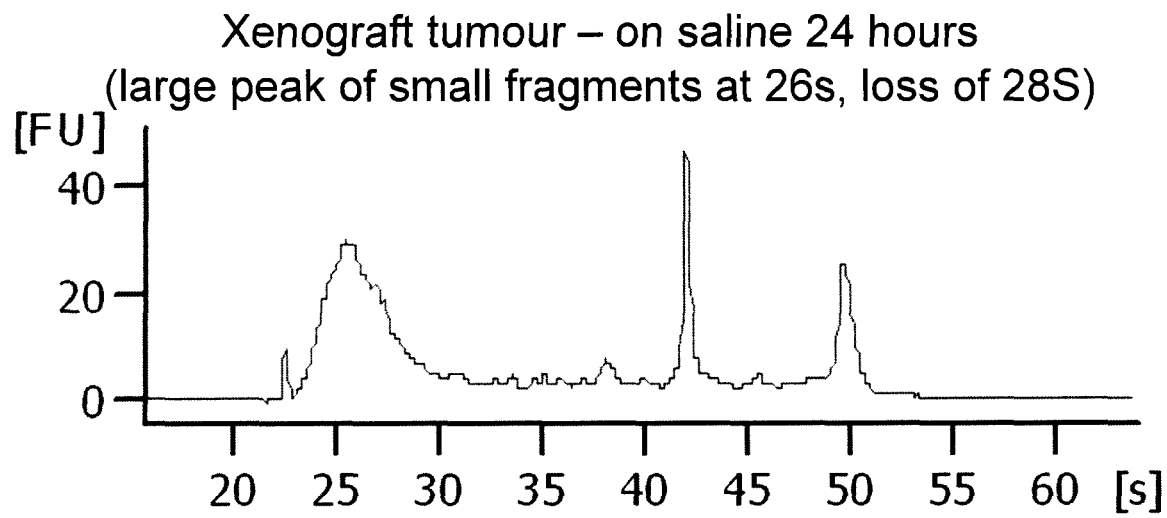
FIG. 16 is an illustration of an electropherogram trace of RNA isolated from a punch biopsy of a MCF-7 tumour xenograft that has been kept at room temperature in saline for 24 hours where autolytic degradation takes place.

Cytotoxic cancer treatment such as chemotherapy and/or radiation therapy induced RNA disruption comprises different profile features from autolytically degraded RNA. For example, FIG. 16 shows an electropherogram trace of a tumour sample in saline soaked gauze for 24 hours where autolytic degradation takes place. A large peak of small fragments is visible at approximately the 26 second mark of the trace. There is also a loss of the 28S peak.

Figure 17:
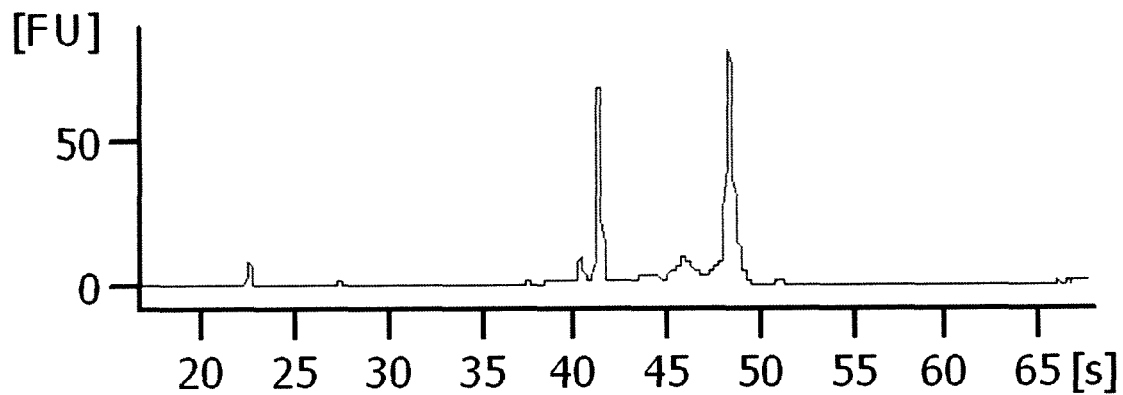
FIG. 17 is an illustration of an electropherogram trace of RNA isolated from human A2780 ovarian cancer cells that have been treated for 24 hours at 37° C. with the chemotherapeutic agent docetaxel (10 μM in medium diluted 1 in 2 with phosphate buffered saline (50% media)
Figure 18:
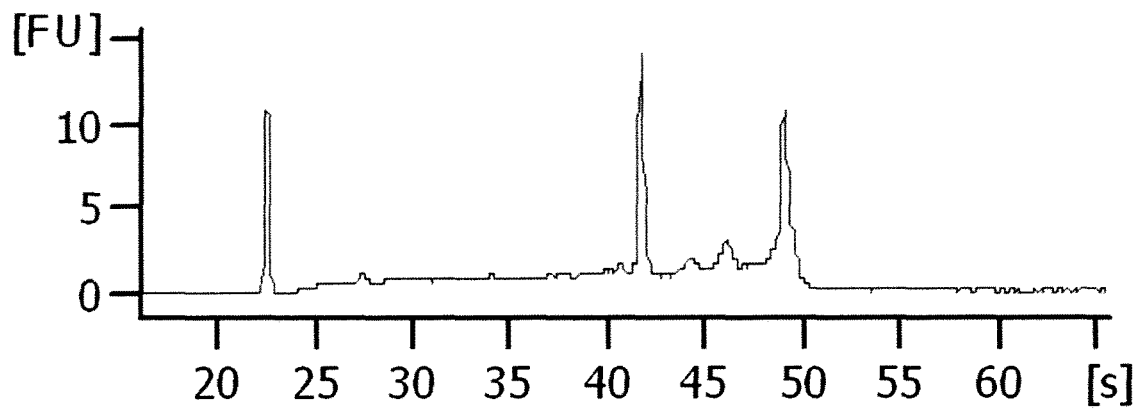
FIG. 18 is an illustration of an electropherogram trace of RNA isolated from A2780 cells treated for 24 hours at 37° C. with the chemotherapic epirubicin (20 μM in 50% media)
Figure 24A:
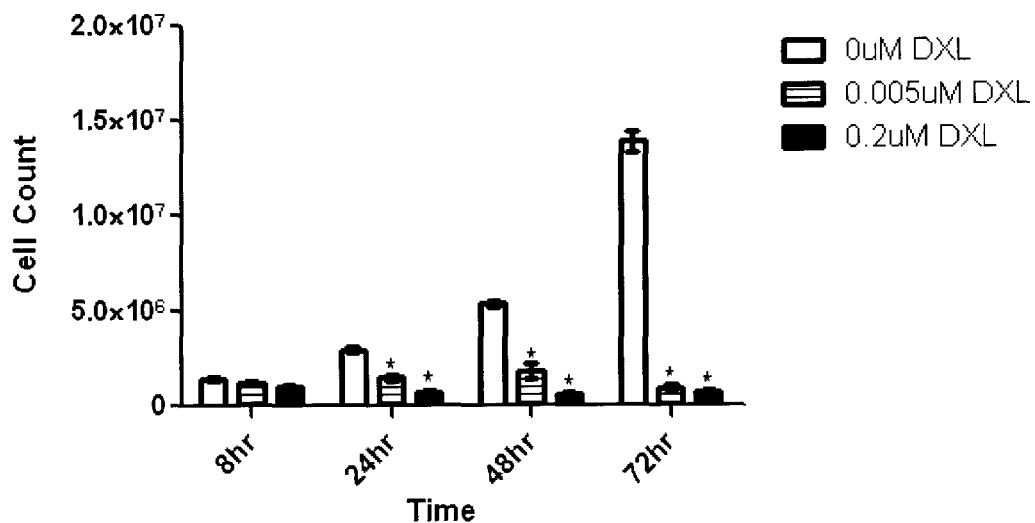
FIG. 24A is a graph demonstrating the number of A2780 ovarian cancer cells in culture after treatment with different concentrations of docetaxel for different time periods.
Figure 24B:
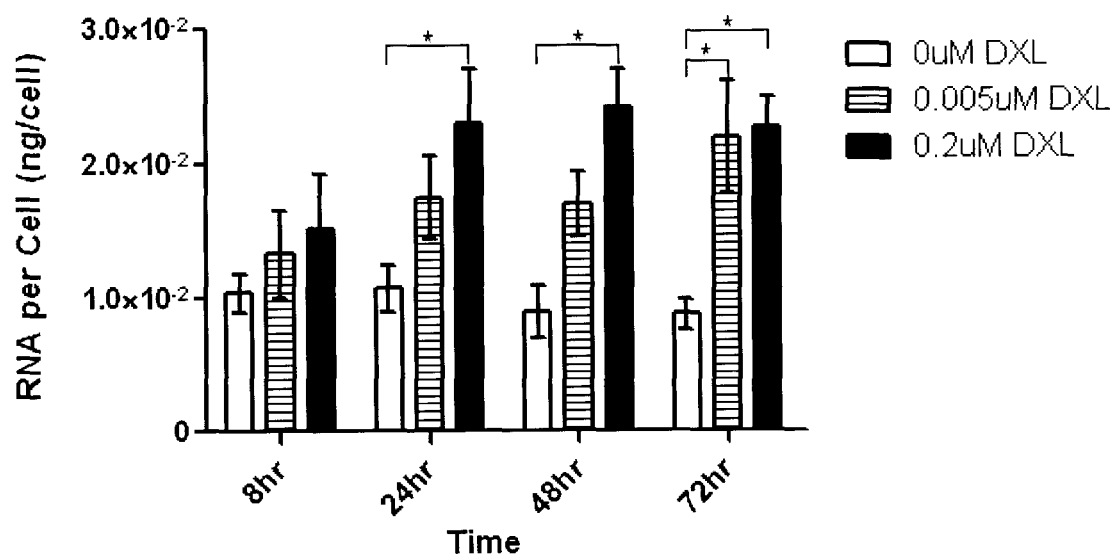
FIG. 24B is a graph of the amount of RNA per cell for A2780 ovarian cancer cells treated with different concentrations of docetaxel for different time periods.
Figure 24C:
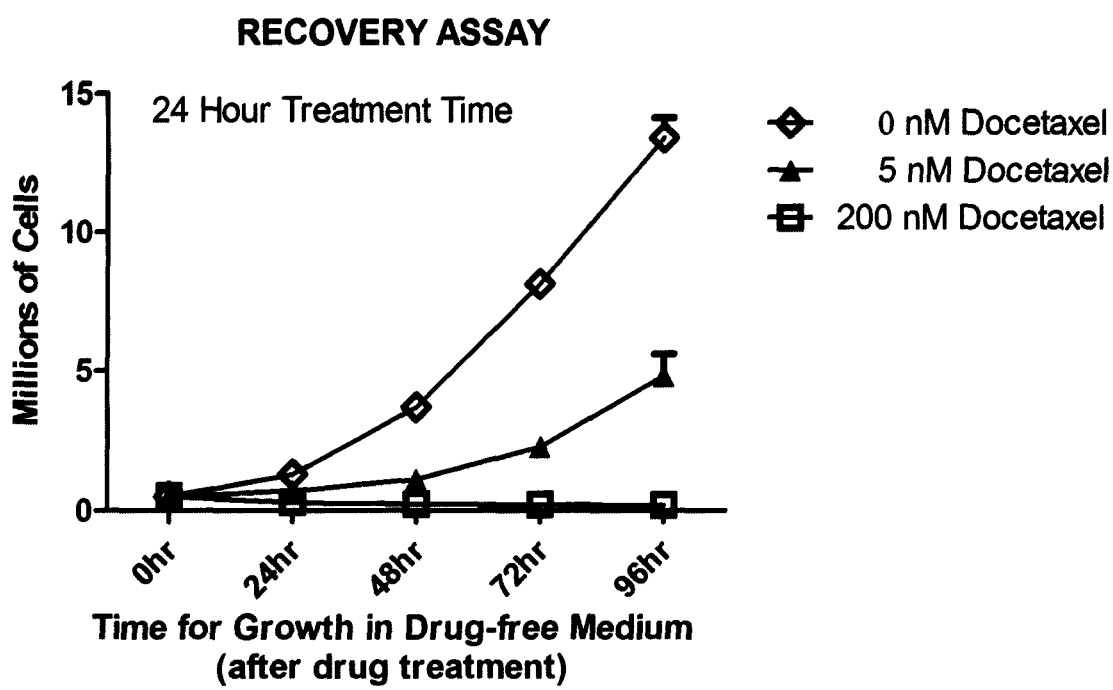
FIG. 24C is a series of graphs plotting cell counts for cells treated with 5 nM or 0.2 micromolar docetaxel at different time points (i, ii and iii), plotting RDI (iv and v)
Figure 24C:
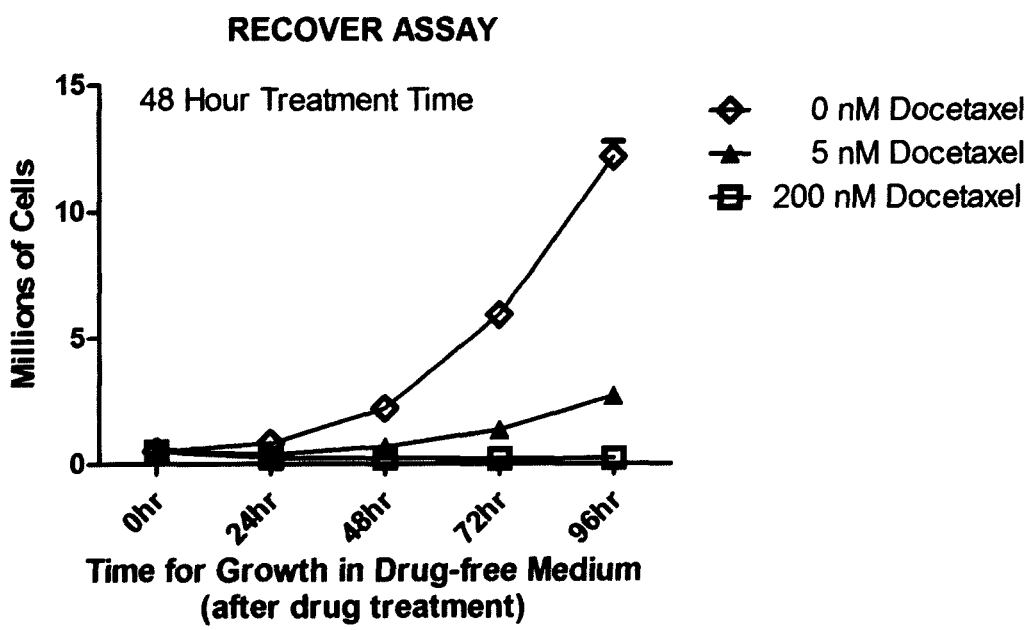
Figure 24C:
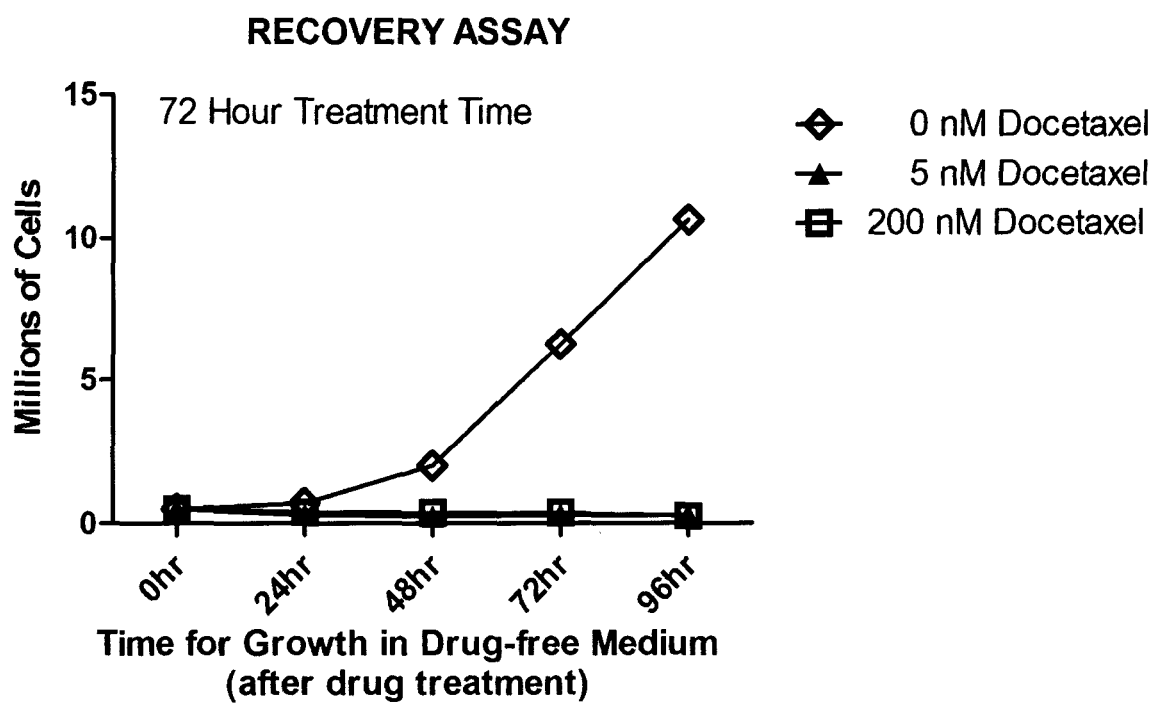
Figure 24C:
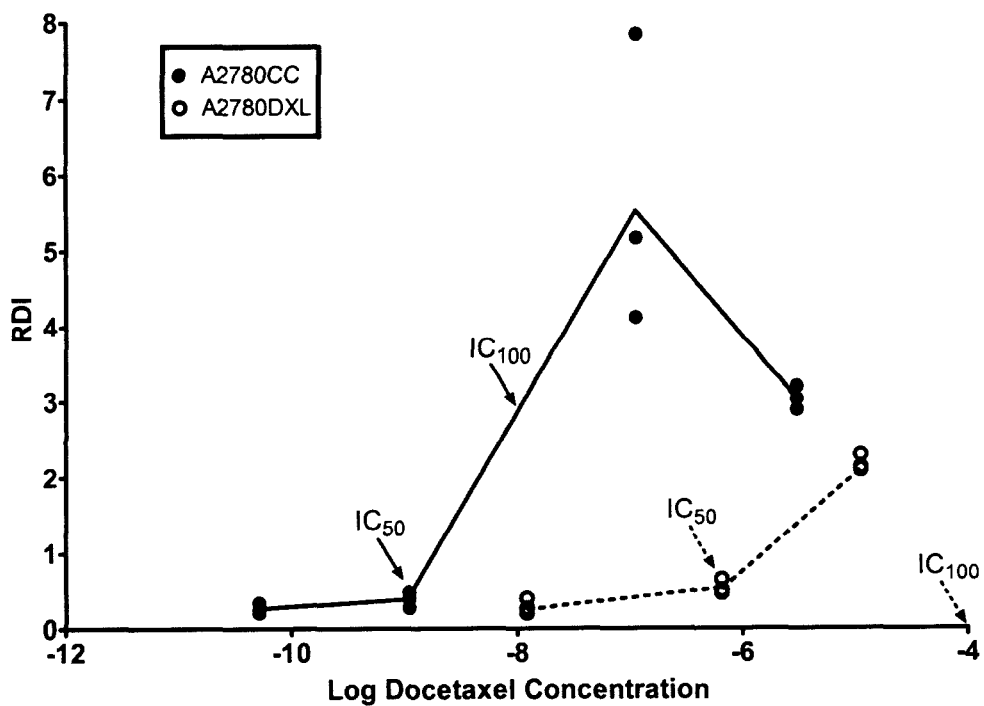
Figure 24C:
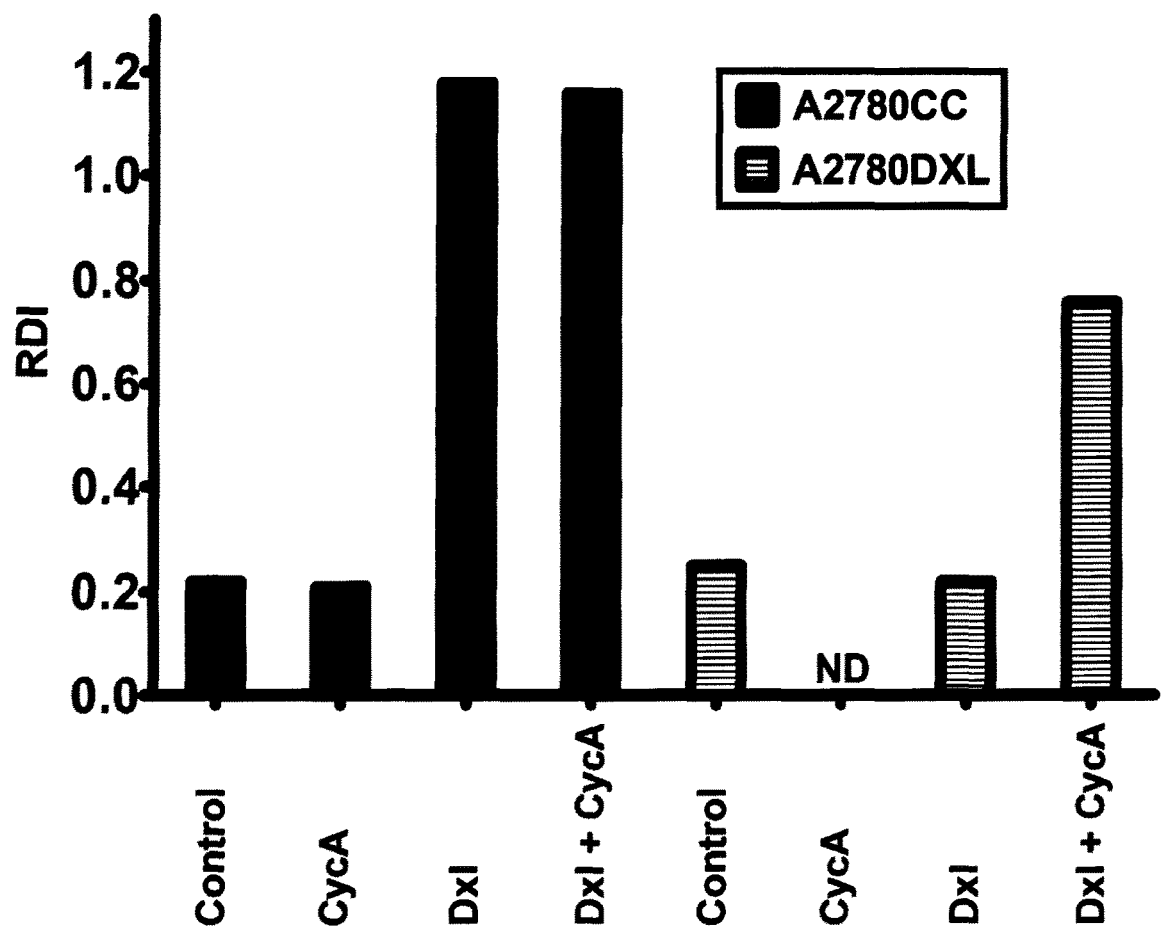
Figure 24D:
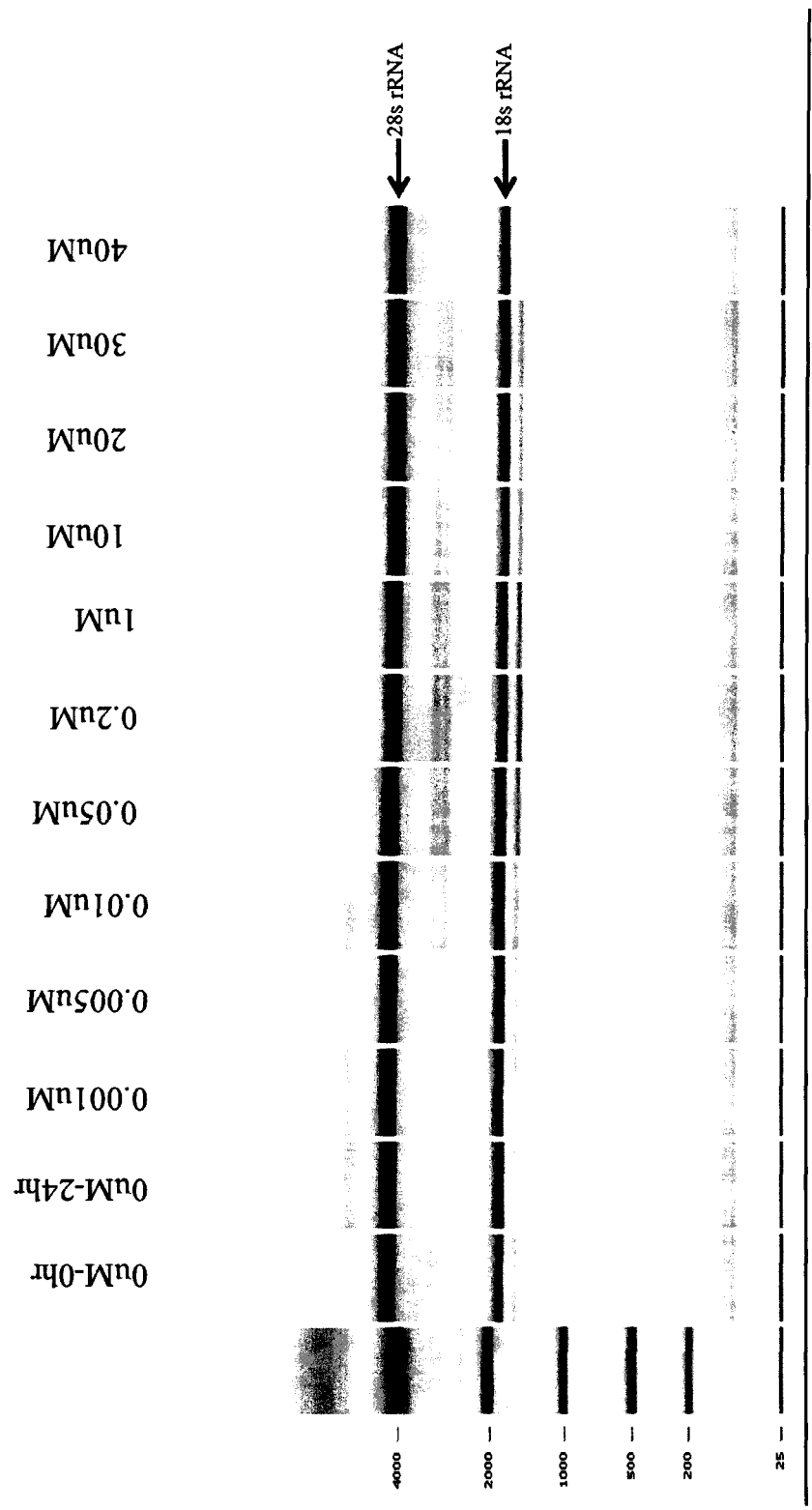
FIG. 24D is an image of a gel of electrophoretically separated A2780 ovarian cancer cell RNA samples treated with different concentrations of docetaxel for 24 hours.
Figure 24E:
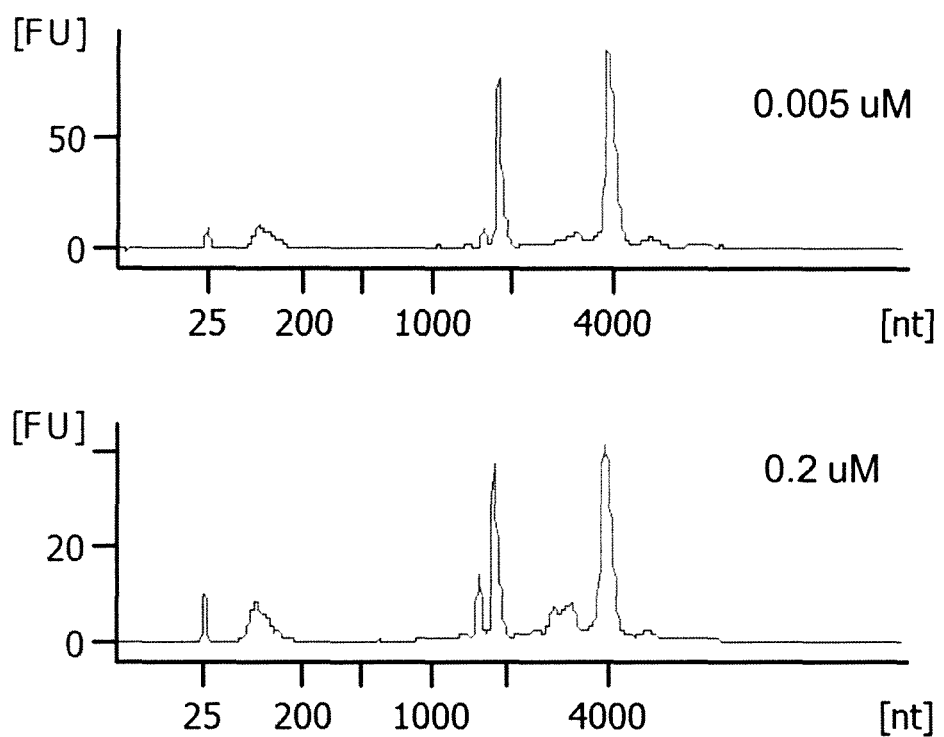
FIG. 24E is an illustration of an electropherogram trace corresponding to 0.005 micromolar and 0.2 micromolar lanes of FIG. 24D.

Cancer cells treated with chemotherapeutic drugs show a different pattern of RNA disruption. For example, FIG. 17 shows human ovarian cancer cell line A2780 treated with chemotherapeutic docetaxel and shows an intermediate peak and a peak adjacent to the 18S peak. FIG. 18 shows A2780 cells treated with chemotherapeutic epirubicin. The electropherogram shows intermediate bands between the 18S and 28S peaks. FIG. 24D shows an image of a gel of RNA from A2780 cells treated with increasing concentrations of chemotherapeutic docetaxel. Additional bands are visible in cells treated with 0.05 uM docetaxel. FIG. 24E shown an electropherogram of the 0.005 and 0.2 uM time-points with the x axis being the size of the nucleotides. The electropherogram of the 0.2 uM time-point shows intermediate bands between the 18S and 28S peaks. In addition, the 28S and 18S peaks are shifted relative to those of FIG. 16 which shows autolytic RNA degradation.

It was also identified that the peaks misidentified using the RIN algorithm were found in RNA samples which had large "intermediate banding" peaks located between the 28S peak and 18S peak (see the examples in FIGS. 33A-F and FIG. 1B).

A similar pattern is seen with radiation treatment. Additional bands are also visible in cells treated with radiation.

Accordingly, an aspect of the disclosure includes assays, methods and apparatuses for determining if a cancer patient is responding favourably or unfavourably, optionally in terms of survival time and/or pCR to a cancer treatment, optionally a cancer treatment described herein. Generally, the method comprises determining features that are obtained from at least two of four different shifted regions of the electropherogram due to cancer treatment: the shifted 28S peak, the shifted 18S peak, at least one peak in the "intermediate banding" region where the intermediate banding region is between the shifted 18S peak and the shifted 28S peak, and at least one peak in the "low banding" region where the low banding region is below the shifted 18S peak. For example, a scale of 0 to 100 units (the scale is described in more detail with regards to FIG. 20B) may be selected which includes all RNA migrating between 9.5 and 42.8 seconds under the condition of a Caliper Nano chip run on an Agilent 2100 Bioanalyzer.

Figure 19:
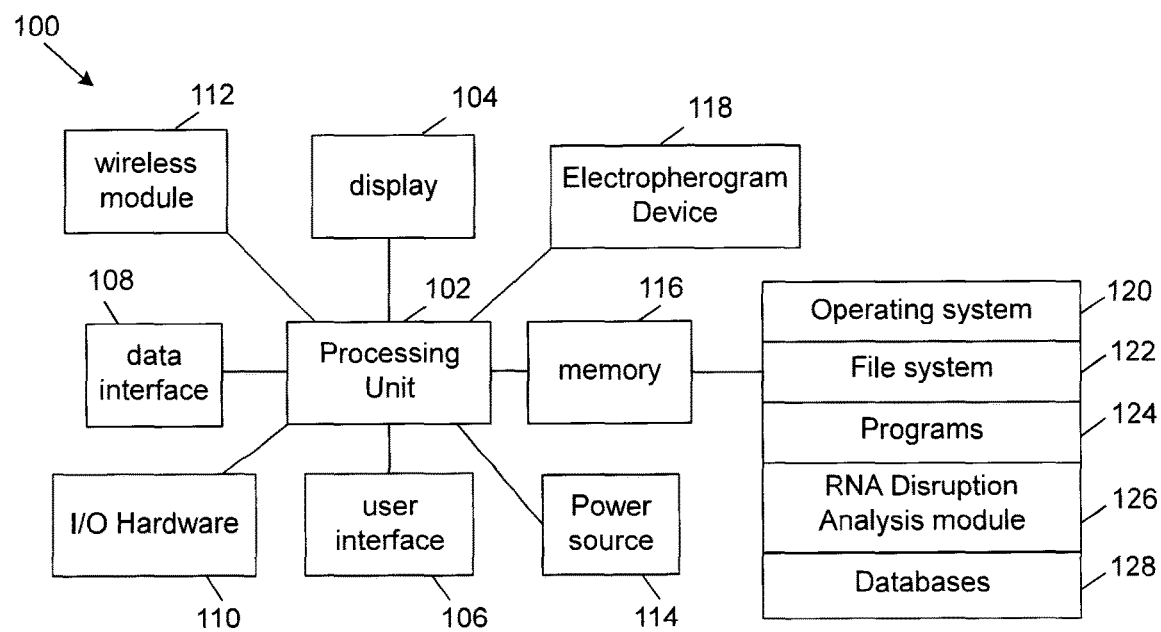
FIG. 19 is a block diagram of an example embodiment of an apparatus that can be used to assess RNA disruption.

Referring now to FIG. 19, shown therein is a block diagram of an example embodiment of an apparatus 100 that can be used to assess RNA disruption in a tumour tissus sample. The apparatus 100 is configured to perform a method to assess the electropherogram of tumour RNA samples s after the cancer samples have been subjected to a cancer treatment. The assessment results in a RNA Disruption Index value and/or RNA Disruption Assay (RDA) score that incorporates various features based on the electropherogram data as described herein. A high RDI value and/or RDA score is associated, for example, with positive treatment response such as increased disease free survival, overall survival and/or pCR, while a low RDI value and/or RDA score indicates that patients are unlikely to receive long term chemotherapy and/or radiation benefit. The methods described herein detect peaks and abnormal peaks in the electropherogram with increased resolution and increased robustness to help assess the effectiveness of the cancer treatment. Accordingly, the application of the method described herein depends on accurate recording of fluorescent intensities during the separation of RNA molecules but is independent of commercial software used to analyze peaks in the electropherogram data.

In general, the apparatus 100 comprises at least one processing unit 102, a display 104, a user interface 106, data interface 108, Input/Output (I/O) hardware 110, a wireless module 112, a power source 114, a memory 116, and an electropherogram device 118. The memory 116 comprises software code for implementing an operating system 120, a file system 122, various programs 124 including an RNA disruption analysis module 126 and at least one database 128. The apparatus 10 can be a standalone device or can incorporate a desktop computer, a laptop, a mobile device, a smart phone, a cell phone, a tablet, a personal digital assistant, and the like.

There can be various alternative embodiments for the apparatus 100 in which one or more of the components are not used. For example, in some embodiments the wireless module 112 is optional. Some embodiments may use either the wireless module 112 or the data interface 108. Furthermore, in some embodiments, the electropherogram device 118 is not included as the electropherogram data may be obtained and sent, for example, via a data communication network or wireless communication, or otherwise provided to the apparatus 100, for example, via a CD, a USB drive, a USB key and the like. In these cases, the electropherogram data is typically available in a data file that can be in a spreadsheet format or other numeric format that provides a time series of fluorescence intensity for one or more samples. In these cases, a medical professional, medical institution or a research institution can obtain the electropherogram data and provide this data for analysis by the apparatus 100. For example, there can be situations in which a second institution has the apparatus 100, receives the electropherogram data, analyzes the electropherogram data using the apparatus 100 and then sends the results to the entity which originally provided the electropherogram data.

The processing unit 102 controls the operation of the apparatus 100 and can be any suitable processor depending on the configuration of the apparatus 100 as is known by those skilled in the art. In some embodiments, the processing unit 102 can be implemented using an Application Specific Integrated Circuit (ASIC), a programmable logic array, or a collection of discrete analog and discrete circuits.

The display 104 can be any suitable display that provides visual information depending on the configuration of the apparatus 100. For instance, the display 104 can be a cathode ray tube, flat-screen monitor and the like if the apparatus 100 is a computer. In other cases, the display 104 can be a display suitable for a laptop, tablet or handheld device such as an LCD-based display and the like.

The user interface 106 can include at least one of a graphical user interface, a mouse, a keyboard, a touch screen, a thumbwheel, a track-pad, a track-ball, a cardreader, voice recognition software and the like again depending on the particular implementation of the apparatus 100. In some cases, some of these components can be integrated with one another.

The data interface 108 can be any interface that allows the apparatus 100 to communicate with other devices or computers. In some cases, the data interface 108 can include at least one of a serial port, a parallel port, or a USB port that provides USB connectivity. The data interface 108 can also include at least one of an Internet or local area network connection through Ethernet, Firewire or modem connections or through a digital subscriber line. Various combinations of these elements can be incorporated within the data interface 108.

The I/O hardware 110 can include at least one of a microphone, a CD-ROM drive, a CD-ROM read/write drive, a speaker and a printer. The wireless module 112 can be a radio that communicates utilizing CDMA, GSM, GPRS or Bluetooth protocol according to appropriate standards such as IEEE 802.11a, 802.11b, or 802.11g. The power source 114 can be any suitable power source that provides power to the apparatus 100 such as a power adaptor or a rechargeable battery pack depending on the implementation of the apparatus 100 as is known by those skilled in the art.

The memory 116 can include RAM and flash memory elements as well as other storage elements such as disk drives and hard drives. The memory 116 is used to store an operating system 120, a file system 122 and programs 124 as is commonly known by those skilled in the art. For instance, the operating system 120 and the file system 122 provide various basic operational processes for the apparatus 100. The programs 124 include various user programs so that a user can interact with the apparatus 100 including viewing, analyzing and reporting data as well as possibly sending and receiving messages depending on the implementation of the apparatus 100.

The memory 116 also stores an RNA Disruption analysis module 126 and one or more databases 128. The RNA Disruption analysis module 126 can determine RNA Disruption values for samples obtained from a patient that is receiving a form of chemotherapy and/or radiation according to various features and methods that are described in more detail with respect to FIGS. 20A, and 20B or 27A. In some embodiments, the RNA Disruption analysis module 126 can be implemented generally by the processing unit 102 which can be a processor that is programmed with firmware or that runs executable code, or is implemented by discrete circuit components, depending on the implementation of the apparatus 100.

In general, the processing unit 102 is configured to determine values for features from at least two shifted regions of the at least one electropherogram dataset and to determine an RDI value and/or an RDA score based on a combination of the values of the features. Accordingly, the processing unit 102, in its various alternative implementations, can acts as means for determining values for features from at least two shifted regions of the at least one electropherogram dataset and means for determining an RDI value and/or an RDA score based on a combination of the values of the features. The shifting is due to the treatment by the cytotoxic cancer treatment e.g. chemotherapy and/or radiation.

The processing unit 102 is coupled to a data input to receive at least one electropherogram dataset corresponding to a unique biological sample comprising cellular RNA, such as cancerous tumour RNA, at various time points including at least one of during or after the treatment. In some cases, the electropherogram dataset can correspond to (i.e. is derived from) a unique biological sample that has not undergone treatment. In some embodiments, at least one of the electropherogram device 18, the data interface 108, the wireless module 112, the I/O hardware 110, the memory 116 and other suitable devices can acts as the data input or as means for obtaining at least one electropherogram dataset. The processing unit 102 is also coupled to a data output to convey an indication of the RDA score such as an RDI score, an RDA zone, or any other relevant analytical RNA data for at least one subject. In some embodiments, at least one of the display 104, wireless module 112, data interface 108, memory 116, and other suitable devices can act as the data output.

The databases 128 can be used to store data for samples that are assessed with the RNA Disruption analysis module 126. The databases 128 can also store other information required for the operation of the programs 124 or the operating system 120 such as dynamically linked libraries and the like.

The electropherogram device 118 is configured to produce an electropherogram of a sample. In general, the electropherogram device 118 employs a gel having a certain porosity in order to fractionate the RNA of the sample by size and charge of the particles. Fluorescence information related to the fractionated RNA is then obtained to produce an electropherogram trace for the sample. The electropherogram trace is then digitized to form an electropherogram dataset. The electropherogram device 118 can be implemented in a variety of ways. For example, in some embodiments, the electropherogram device 118 is an Agilent 2100 BioAnalyzer that employs Agilent RNA 6000 Nano kits and Caliper Technology's RNA Nanochips.

The apparatus 100 comprises at least one user interface and the processing unit 102 communicates with at least one of these user interfaces to receive electropherogram data as well as other information such as information on the individual from which the electropherogram was derived. This data can be received through the data interface 108, the I/O hardware 110, the wireless module 112, the memory 116 or the electropherogram device 118 depending on the particular implementation of the apparatus 100 and the type of data. The processing unit 102 can communicate with either one of these elements as well as the display 104 or the I/O hardware 110 in order to output the RDA score. For instance, the apparatus 100 can output the RDA score to a user of the apparatus 100. In addition, users of the apparatus 100 can communicate the resulting RDA score via a network connection to a remote system for storage and/or further analysis by other medical personnel. This communication can also include email communication in some embodiments.

In an alternative embodiment, the apparatus 100 can be a computer that acts as a web server and provides content for a web site. One of the webpages on the website can be a webpage that provides one or more RDA scores from samples as described herein. In this case, a user can interact with the webpage to provide the electropherogram data (e.g. by uploading the data) and the apparatus 100 can analyze the electropherogram data and display the RDA score on the web page and/or email the RDA score to the user and/or provide the RDA score for download by the user. Alternatively, the electropherogram data can be sent to the web server in an email communication, and the web server can analyze the electropherogram data to determine the RDA score and then send this information to a predefined destination, via email communication.

Figure 20A:
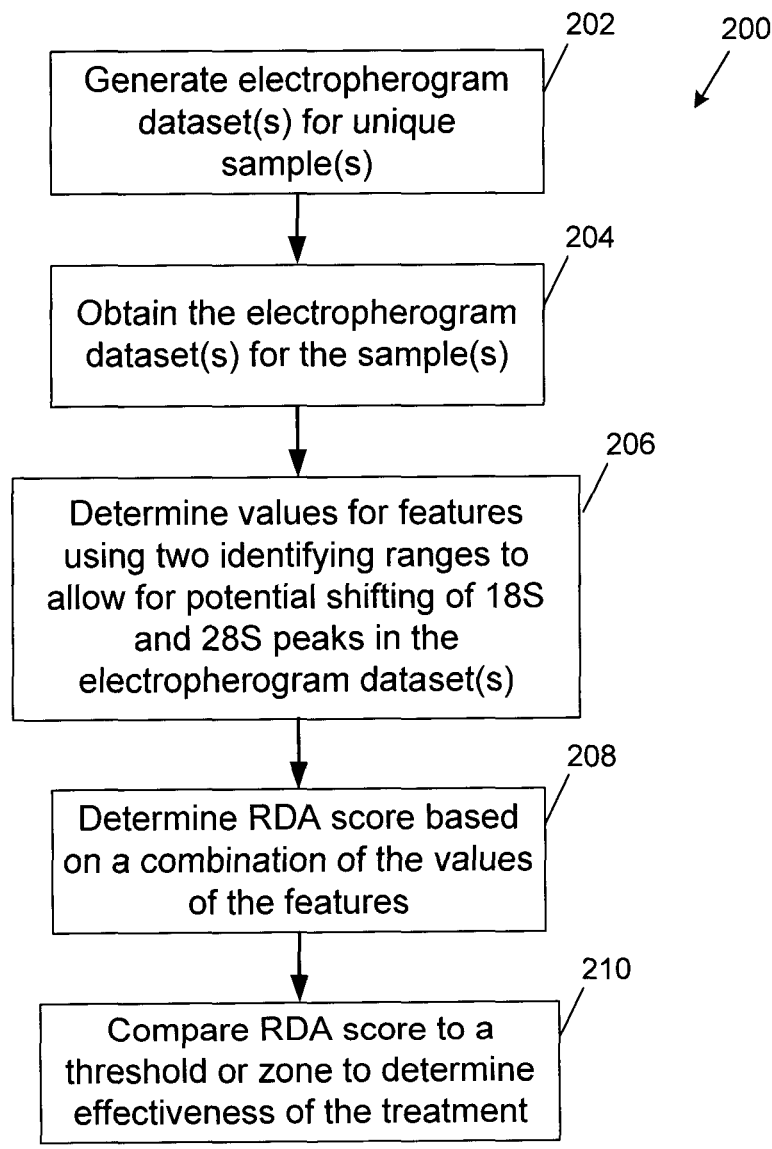
FIG. 20A is a flowchart of an example embodiment of a method that can be employed to assess RNA disruption.

Referring now to FIG. 20A, shown therein is a flowchart of an example embodiment of a method 200 that can be employed to assess RNA disruption. The method 200 is generally performed by the processing unit 102 in concert with additional elements of the apparatus 100, when required, in order to determine an RNA disruption assay score for electropherogram data that has been obtained from at least one sample at the same point in time.

Accordingly, in the methods described herein RNA disruption can be measured using an RNA Disruption Assay (RDA), wherein the method comprises:

obtaining at least one electropherogram dataset corresponding to a unique biological sample (e.g. a tumour tissue sample) comprising cellular RNA at a time point, during the course of treatment or after completion of the treatment;

determining values for features from at least two shifted regions of the at least one electropherogram dataset, the shifting being due to the treatment; and determining an RDA score based on a combination of the values of the features.

At 202, electropherogram data is generated for a sample. This may include generating several electropherogram datasets each from a unique biological sample that is taken from a patient or test subject (or if in vitro harvested) at a certain point in time, such as during or after cytotoxic treatment, for example, which may also be referred to as pre-therapy, mid-therapy and post-therapy respectively (also pre-treatment, mid-treatment and post-treatment) where therapy is defined as a series of chemotherapeutic and/or radiation administrations (e.g. injections, exposures) that are performed over a certain period of time such as minutes, days or weeks. In general, an electropherogram dataset is a digitized version of electropherogram traces that are generated for a sample. The electropherogram dataset is an array of numbers that are processed to generate an RDA score. In some embodiments, the electropherogram dataset can be in a spreadsheet format such as a Comma Value Separated (CVS) data file or an EXCEL data file format. In some embodiments, 202 of method 200 can be optional if the electropherogram data is produced by another entity and is then sent to another location for analysis at which case the method 200 starts at 204.

At 204, at least one electropherogram dataset(s) is obtained for a unique biological sample. The number of dataset(s) that are obtained depend on the features that are used to determine the RDA score. For example, some features can be used to determine the RDA score that require values from only one electropherogram dataset generated from one sample. However, some features can be used to determine the RDA score that require several electropherogram datasets generated from several unique biological samples, such as two or three datasets obtained from two or three unique biological samples, for example. In either case, the electropherogram dataset is typically obtained from a storage device such as a memory element 116, a CD-ROM, a USB key, a portable hard drive, from a database, from a network element, or from data that is uploaded over the Internet.

Figure 27A:
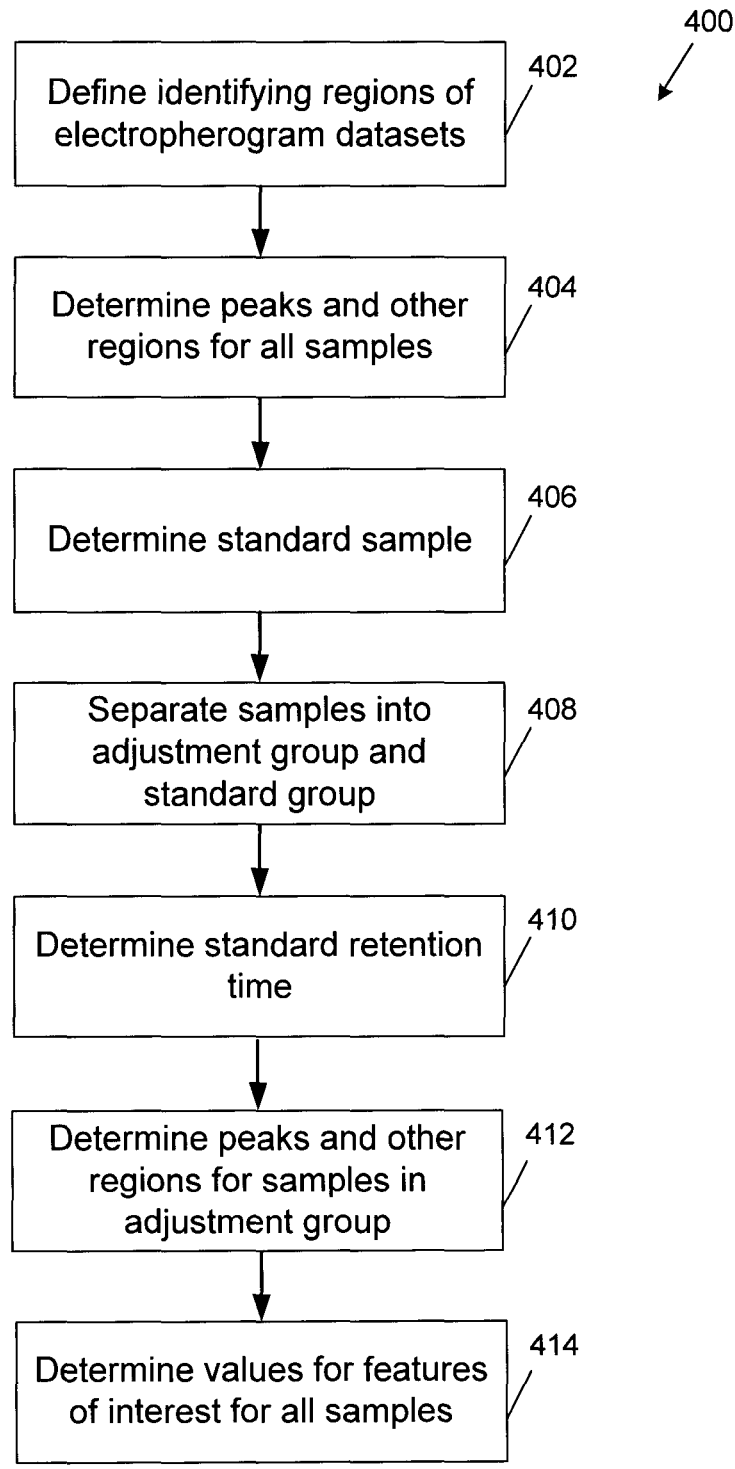
FIG. 27A is a flowchart of another example embodiment of a method that can be employed to determine features related to the 18S peak and the 28S peak in the 18S and 28S shifted regions respectively.

At 206, values are determined for features using two identifying ranges to allow for potential shifting of at least one of the 18S peak and 28S peak in the electropherogram dataset(s). For example, the identifying regions may be at least two shifted regions of the electropherogram dataset(s). The shifted regions that are analyzed in order to determine the values for the features include at least two of a shifted 18S region, a shifted 28S region, an intermediate banding region and a low banding region. The intermediate banding region is defined as the region between the 28S and 18S peaks. The low banding region includes all banding below the 18S peak but does not include the marker region. FIG. 20C is an example electropherogram in which these various peaks and regions are illustrated. The 28S and 18S peaks are defined to be within specific x axis (i.e. the time axis) ranges and can contain multiple maxima. However, an alternative method can be used for the identification of the 18S and 28S peaks and is described below in more detail with respect to FIG. 27A. In this case, the identifying ranges are two broad regions that are defined (e.g. having a certain size) in order to locate the 18S and 28S peaks regardless of whether these peaks are shifted or otherwise distributed in the electropherogram dataset(s). Regardless of whether the method of FIG. 20B or the method of FIG. 27A is used, various features can be defined based on these regions and/or peaks. For example, the features can include one or more of the area of an 18S peak, the area of a 28S peak, the area of an intermediate banding region, the area of a low banding region, the area of one or more band sub-regions, and the total area. The total area is the sum of the area of the 18S peak, the 28S peak, the intermediate banding region and the low banding region. Other features can include one or more of the width of the 18S peak and the width of the 28S peak. The area of these peaks and regions can be calculated in general using well-known mathematical techniques such as the trapezoidal rule for numerical integration (Atkinson, 1989). However, the starting points of these peaks and regions are different due to the chemotherapeutic effect on the samples. Accordingly, in some cases, additional rules have to be used, in order to correctly determine the values of these features.

Another example embodiment of an improved method for the identification of the 18S and 28S peaks and the calculation of certain features associated with these peaks or neighboring regions that can be used in act 206 of method 200 is described with respect to FIG. 27A. The low banding region can also be divided into the "low C", "low B" and "low A" sub-regions or banding regions as demonstrated in FIG. 27B for use in some methods described herein. It has been found that the low A banding region may contain RNA due to autolytic degradation as well as due to other effects and that the low C banding region is an important region in assessing the effect on RNA due to various external stimuli such as cytotoxic treatments, for example. It has also been found that in response to certain drugs, the RNA starts to spread to the low C banding region, then to the low B banding region and then to the low A banding region.

At 208, an RDA score is determined based on a combination of the values for various features. These combinations can include the ratios of some of these features. In some cases, only one electropherogram dataset from one sample is used to determine an RDA score. In other cases, several electropherogram datasets from several unique biological samples obtained at the same time are used to determine an RDA score. In these latter cases, the values can be combined using a mathematical function such as the minimum function or the maximum function.

Features can also be based on other components of the shifted regions of the electropherogram such as one or more of a peak height, a peak width and a peak position. For example, in one embodiment, it may be possible for the combination of features to be based on the 18S and 28S peak widths to discriminate between Responders with favourable survival time and Non-Responders with unfavourable survival time.

In one embodiment, the combination of features comprises a ratio of the 28S peak area in the shifted 28S region to the 18S peak area in the shifted 18S region, which can be represented by the expressions "28S/18S" or "28S:18S".

In one embodiment, the combination of features comprises a ratio of the 28S peak area in the shifted 28S region to the total area, which can be represented by the expression "28S/total area".

In one embodiment, the combination of features comprises a ratio of the 18S peak area in the shifted 18S region to the total area, which can be represented by the expression "18S/total area".

In one embodiment, the combination of features comprises a ratio of the intermediate banding region area to the total area, which can be represented by the expression "intermediate area/total area".

In one embodiment, the combination of features comprises a ratio of the low banding region area to total area, which can be represented by the expression "low banding area/total area".

In one embodiment, the combination of features comprises a ratio of the intermediate banding region area to the addition of the 18S peak area in the shifted 18S region and the 28S peak area in the shifted 28S region, which can be represented by the expression "intermediate banding area/(18S+28S)".

In one embodiment, the combination of features comprises a ratio of the low banding region area to the addition of the 18S peak area in the shifted 18S region and the 28S peak area in the shifted 28S region, which can be represented by the expression "low banding area/(18S+28S)".

In one embodiment, the combination of features comprises a ratio of the low C banding region area to the sum of the 18S peak area in the shifted 18S region and the 28S peak area in the shifted 28S region, which can be represented by the expression "low C/(18S+28S)". It should be noted that 18S and 28S can be reversed in any of these expression such as 28S+18S and it would not change the meaning of the expression.

In one embodiment, the combination of features comprises a ratio of the intermediate banding region area to the 18S peak area in the shifted 18S region, which can be represented by the expression "intermediate banding area/18S".

In one embodiment, the combination of features comprises a ratio of the low banding region area to the 18S peak area in the shifted 18S region, which can be represented by the expression "low banding area/18S".

In one embodiment, the combination of features comprises a ratio of the intermediate banding region area to the 28S peak area in the shifted 28S region, which can be represented by the expression "intermediate banding area/28S".

In one embodiment, the combination of features comprises a ratio of the low banding region area to the 28S peak area in the shifted 28S region, which can be represented by the expression "low banding area/28S".

In one embodiment, the combination of features comprises a ratio of the addition of low banding region area and intermediate banding region area to the addition of the 18S peak area in the shifted 18S region and the 28S peak area in the shifted 28S region, which can be represented by the expression "(low banding area+intermediate banding area)/(18S+28S)".

In one embodiment, the combination of features comprises a maximum ratio determined from at least two electropherogram datasets. The ratio is defined as the intermediate banding region area divided by a sum of the 18S peak area in the shifted 18S region and the 28S peak area in the shifted 28S region. This can be represented by the expression "maximum intermediate banding area/(18S+28S)". In this case, as with other calculations that use the maximum function with particular features that follow below, the ratios of intermediate banding area/(18S+28S) are calculated for two or more electropherogram datasets (derived from two or more unique biological samples at the same time point), the maximum of these ratios is calculated and then the logarithm is calculated. For example, two or more electropherogram datasets can be derived from two or more biopsies taken at a time point and/or a biopsy that is divided into two or more samples.

In one embodiment, the combination of features comprises a minimum ratio determined from at least two electropherogram datasets. The ratio is defined as the intermediate banding region area divided by a sum of the 18S peak area in the shifted 18S region and the 28S peak area in the shifted 28S region. This can be represented by the expression "minimum intermediate banding area/(18S+28S)". In this case, as with other calculations that use the minimum function with particular features that follow below, the ratios of intermediate banding area/(18S+28S) are calculated for two or more electropherogram datasets (derived from two or more unique biological samples at the same time point) and the minimum of these ratios are is calculated.

In one embodiment, the combination of features comprises a maximum ratio determined from at least two electropherogram datasets. The ratio is defined as the intermediate banding region area divided by the total area. This can be represented by the expression "maximum intermediate banding area/total area".

In one embodiment, the combination of features comprises a minimum ratio determined from at least two electropherogram datasets. The ratio is defined as the low banding region area divided by the total area. This can be represented by the expression "minimum low banding area/total area".

In one embodiment, the combination of features comprises a ratio of low banding region area divided by the total area and a maximum of a second ratio determined from at least two electropherogram datasets, the second ratio being the intermediate banding area divided by the total area. These combinations of features can be represented by the expressions "low banding area/total area" and "maximum intermediate banding area/total area", respectively.

In one embodiment, the combination of features comprises a maximum ratio determined from at least two electropherogram datasets. The ratio is defined as the 28S peak area divided by the total area. This can be represented by the expression "maximum 28S/total area".

In one embodiment, the combination of features comprises a minimum ratio determined from at least two electropherogram datasets. The ratio is defined as the 28S peak area divided by the total area. This can be represented by the expression "minimum 28S/total area".

In one embodiment, the combination of features comprises a maximum ratio determined from at least two electropherogram datasets. The ratio is defined as the 18S peak area divided by the total area. This can be represented by the expression "maximum 18S/total area".

In one embodiment, the combination of features comprises a minimum ratio determined from at least two electropherogram datasets. The ratio is defined as the 18S peak area divided by the total area. This can be represented by the expression "minimum 18S/total area".

In one embodiment, the combination of features comprises a maximum ratio determined from at least two electropherogram datasets. The ratio is defined as the intermediate area divided by the 28S peak area in the shifted 28S region. This can be represented by the expression "maximum intermediate/28S".

In one embodiment, the combination of features comprises a minimum ratio determined from at least two electropherogram datasets. The ratio is defined as the intermediate area divided by the 28S peak area in the shifted 28S region. This can be represented by the expression "minimum intermediate/28S area".

It should be noted that in each of these feature combinations described above, either method 300 or method 400 (described in FIG. 27A) can be used to define the 18S and 28S peaks and the other regions. If method 400 is used than rather than using shifted regions, broader regions are used to locate the 18S and 28S peaks.

At 210, the RDA score can be compared to a threshold to determine the effectiveness of the treatment. The threshold can be a scalar value determined based on conducting ROC analysis on a database of various experimental results to identify responders which can be done by selecting a threshold value to accomplish a high Positive Predictive Value (PPV) and a low false positive rate. The analysis can also be conducted to identify non-responders by selecting a threshold value so that the non-responders can be identified with a high Negative Predictive Value (NPV) and a low false negative rate. Accordingly, the goal is to have a threshold for high PPV and a threshold with high NPV and to minimize the distance between the PPV and NPV threshold values. In some embodiments, several thresholds can be used to define several RDA zones which relate to different types of expected treatment results such as increased likelihood of a complete response, a partial response and no response (see FIG. 22A and/or FIG. 29A for examples of the RDA zones).

Predetermined reference values and/or cut-off values can be selected as described herein. For example, such a value can be determined a) providing or obtaining a collection or plurality of tumor tissue samples from a plurality of cancer patients;

b) providing, for each tumor tissue sample provided at step a), information relating to the actual clinical outcome for the corresponding cancer patient (i.e. the duration of the disease-free survival (DFS) and/or the overall survival (OS));

c) providing a scale comprising a series of arbitrary quantification values;

d) determining the RNA disruption assay score for each tumor tissue sample contained in the collection provided at step a);

e) classifying the tumor tissue samples into three groups according to selected specific arbitrary quantification values provided at step c), respectively, as follows: (i) a RDA zone 1 group comprising tissue tumor samples that exhibit a RNA disruption assay score that is lower than the specific arbitrary quantification value (e.g. less than or equal to 10) that is selected from the series of arbitrary quantification values; (ii) a RDA zone 3 group comprising tumor tissue samples each of which exhibit an RNA disruption assay score that is higher than the specific arbitrary quantification value (e.g. greater than 35) selected from the series of quantification values; and (iii) a RDA zone 2 group comprising tumour tissue samples each of which exhibit a RNA disruption assay score that is between RDA zone 1 and RDA zone 3;

f) calculating the statistical significance between (i) the RDA score obtained at step e) and (ii) the actual clinical outcome of the patients from which tumor tissue samples contained in one or more of the groups;

g) reiterating steps f) and g) until every arbitrary quantification value provided at step d) is tested (i.e. performing steps f) and g) for a second, third, fourth etc. selected arbitrary quantification values up to and including the nth arbitrary quantification value of the set;

h) setting the predetermined reference value ("cut-off" value) as consisting of the specific arbitrary quantification value for which the highest statistical significance (most significant) is calculated at step g).

In an alternative embodiment, rather than comparing the RDA score to a threshold value, the RDA score may be compared to a threshold curve which may be linear or non-linear or a threshold three dimensional region. In this case, the threshold line, threshold curve or threshold plane can be determined using LDA or QDA as is described with respect to FIGS. 30B-30D.

Figure 20B:
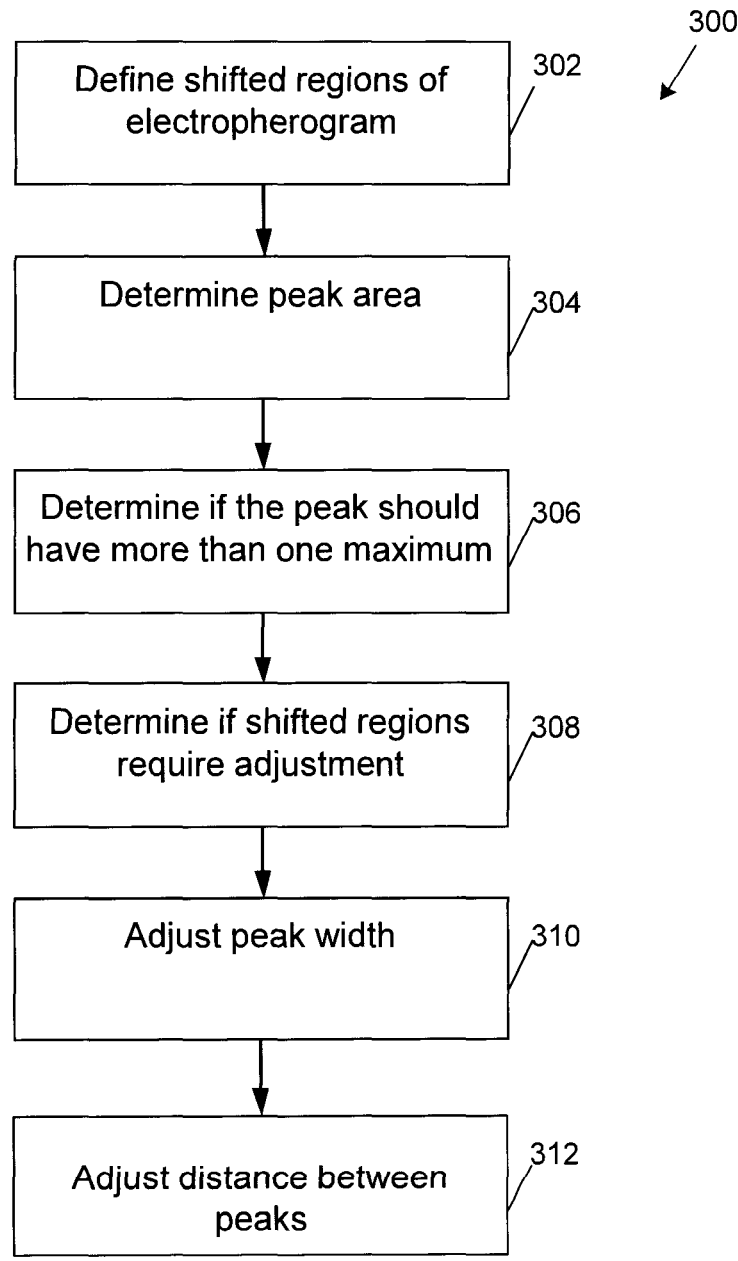
FIG. 20B is a flowchart of an example embodiment of a method that can be employed to determine features related to 18S and 28S peaks in the 18S and 28S shifted regions respectively.
Figure 20C:
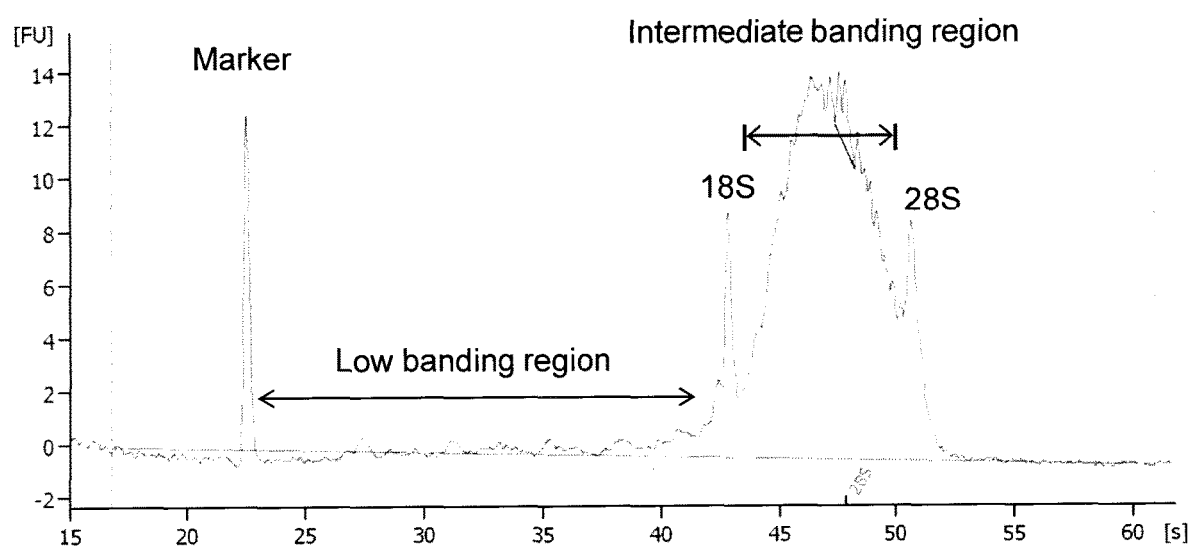
FIG. 20C is a graph of an example electropherogram that defines the 18S peak, 28S peak, intermediate banding region, low banding region and the marker region.

Referring now to FIG. 20B, shown therein is a flowchart of an example embodiment of a method 300 that can be employed to determine features related to 18S and 28S peaks in the 18S and 28S shifted regions respectively (another method is described with respect to FIG. 27A). While these peaks are distinguishable from other peaks and have certain sizes, one or more rules can be used to increase the accuracy of the determination of these peaks and their resulting areas. However, not all of the following rules need to be applied. For example, when there are strong 18S and 28S peaks and little or no intermediate banding, then steps 310 and 312 may not have to be performed.

At 302, boundaries for the shifted regions of the electropherogram are defined due to the effects of chemotherapy, or some other cancer treatment regimen or effect, on the sample in order to properly determine the 18S and 28S peaks. After iterating through a number of experimental results, about 95% of the 18S peaks were found in the range of 39.5 to 43.5 seconds (i.e. shifted 18S region) and those of the 28S peaks were in the range of 47.5 to 53.5 seconds (i.e. shifted 28S region); this analysis can be repeated for other treatment regimens. Accordingly, the boundary conditions for the shifted 18S and 28S regions were changed from the range of 38.5 to 46.5 seconds and the range of 43 to 53.5 seconds to the range of 39.5 to 43.5 seconds and the range of 47.5 to 53.5 seconds respectively. It should be noted that these ranges can change depending on different processing techniques such as that described with respect to FIG. 27A, for example. If the time axis (e.g. x axis) of the electropherogram datasets is converted to a scale of 0 to 100 units, then the boundary conditions for the shifted 18S region become 40.9 to 50.4 and the boundary conditions for the shifted 28S region become 58.1 to 69.5. The conversion includes mapping the end of the marker region as the 0 unit and a time point in the area of about 60 to 65 seconds, such as 63 seconds, for example, as the 100 unit. This resulted in 18S and 28S peaks being defined by more stringent conditions.

Most peaks were identified correctly using these shifted 18S and 28S regions. This may involve searching for all of the peak candidates first, and then choosing the one with largest area as the 18S peak or the 28S peak. Candidate peaks whose width is not within about 0.6 to 7.6 units for the 18S peak and not within about 0.8 to 10.5 units for the 28S peak, respectively, may be excluded from the candidate peak set, so that they will not be chosen as the 18S peak or the 28S peak. It has been found that the probability of misidentifying the 28S peak is much larger than that of misidentifying the 18S peak. Accordingly, one may determine the 18S peak first. Also, when identifying the 28S peaks, those 28S peak candidates whose distance to the 18S peak is greater than a distance threshold will be excluded from the peak candidates set so that they will not be chosen as the 28S peak.

At 304, the peak area is determined for a peak, such as the 18S and the 28S peaks, for example. To make this determination, the idea of a local minimum (Stewart, 2008) can be used to define the peak area. The local minimum of a function is the smallest value that the function takes at a point within a given neighborhood. Once the peak of 18S or 28S is known, the two local minimums closest to the peak can be found. The point corresponding to the local minimum on the left side of the peak (within the shifted region) can be defined as the starting position of the peak, and the point corresponding to the local minimum on the right side of the peak (within the shifted region) can be defined as the ending position of the peak. The peak area is defined as the area between these two local minimums. Accordingly, a peak area for a given peak is defined by an area between two local minimum values on either side of the peak in the given shifted region where the peak has one maximum value.

However, the peak can also be defined to have more than one maximum value in certain cases as is described below. At 306, it is determined if the peak should have more than one maximum value (i.e. more than one peak) depending on the area of the peak. This adjustment is used since many of the errors which were found with the RIN method were due to multiple maxima within the 28S and 18S peaks (see FIG. 33). The existence of multiple peaks or multiple values in a peak can be determined in several ways. By analyzing experimental data, if it was found that the value of a peak area was smaller than a threshold value, then the peak was allowed to comprise more than one maximum value. In other words, if the calculated area doesn't match the corresponding peak, i.e. the peak area is very small when the peak is actually large, then the peak is defined to be multi-peaked. For example, the peak could have two maximum values. In one example embodiment, the threshold is 0.2 FU·seconds. This condition successfully corrected for most of the previously improperly detected examples of the RIN method.

At 308, boundaries of the shifted 18S and 28S regions are adjusted if needed depending on the areas of these peaks with respect to each other. For example, if an 18S peak area in the shifted 18S region divided by total area multiplied by 100 (which is represented by 18S %) is less than about 8 times the 28S peak area in the shifted 28S region divided by total area multiplied by 100 (which is represented by 28S %), the shifted 18S region is defined to be the range of 42.8 to 51.4 units (where the time axis is converted to a scale of 0 to 100), i.e. the bounds of the shifted 18S region were extended from 42.8 to 50.4 units to about 42.8 to 51.4 units. In a similar fashion, if the 28S peak area in the shifted 28S region divided by total area multiplied by 100 (i.e. 28S %) is less than about 8 times an 18S peak area in the shifted 18S region divided by total area multiplied by 100 (i.e. 18S %), the shifted 28S region is defined to be the range of about 52.3 to 69.5 units (where the time axis is converted to a scale of 0 to 100), i.e. the bounds of the shifted 28S region were extended from about 58.1 to 69.5 units to about 52.3 to 69.5 units.

At 310, the peak widths are adjusted if needed, i.e. if the widths are defined to be too large based on the position of the starting and ending position of a peak and a study of experimental results. Accordingly, after the peak widths of 18S and 28S were calculated they were subsequently adjusted if the width was outside a width range such that the width of the 18S peak should be within 0.6 to 7.6 units and the width of the 28S should be within 0.8 to 10.5 units when the time axis is converted to a scale of 0 to 100.

At 312, the distance between the peaks is adjusted if they are calculated such that they are too far apart to enhance the definition of the 18S and 28S peaks. Accordingly, a location of at least one of the 18S and 28S peaks is adjusted by picking a different candidate peak if the distance between the 18S and 28S peaks is greater than a distance threshold. For example, in some embodiments, the distance between an ending position of an 18S peak and a starting position of a 28S peak is defined to be less than about 17.1 units apart.

In an embodiment method for performing an RNA Disruption Assay (RDA) comprises: obtaining at least one electropherogram dataset corresponding to a unique biological sample comprising the cellular RNA at a time point; defining an 18S peak and a 28S peak from the at least one electropherogram dataset; determining at least one parameter value for both the 18S peak and the 28S peak; and redefining at least one of the 18S peak and the 28S peak when required according to one or more rules applied to the at least one parameter value. In at least some cases, the method can further include determining an 18S peak area and a 28S peak area; and determining an RDA score based on at least one of the 18S peak area and the 28S peak area.

In some embodiments, the at least one parameter value comprises at least one of a peak area, a peak width and a peak location.

The one or more rules comprises at least one of determining if at least one of the 18S peak and the 28S peak have more than one maximum value based on peak area, determining if boundaries where the 18S peak and the 28S peak are located require adjustment depending on comparing the areas of the 28S peak and 18S peak to one another, adjusting widths of the 18S peak and the 28S peak to be in a certain width range, and adjusting a location of at least one of the 18S peak and the 28S peak if a distance between the 18S peak and 28S peak is greater than a distance threshold. In some cases, the two rules of adjusting widths of the 18S peak and the 28S peak to be in a certain width range, and adjusting a location of at least one of the 18S peak and the 28S peak if a distance between the 18S peak and 28S peak is greater than a distance threshold are optional.

Once the 18S and 28S peaks are defined according to the method 200, other values can be determined such as the intermediate area, low banding area, etc.

It should be noted that in each of these feature combinations described below, either method 300 or method 400 (described in FIG. 27A) can be used to define the 18S and 28S peaks and the other regions. If method 400 is used than rather than using shifted regions, broader regions are used to locate the 18S and 28S peaks.

In one embodiment, the combination of features comprises a ratio of the intermediate area to the sum of the 28S peak area in the shifted 28S region and the 18S peak area in the shifted 18S region, which can be represented by the expression "Intermediate/(28S+18S)".

In one embodiment, the combination of features comprises a ratio of the sum of the low C banding region area and intermediate area to the sum of the 28S peak area in the shifted 28S region and the 18S peak area in the shifted 18S region, which can be represented by the expression "Intermediate+low C/(28S+18S)".

In one embodiment, the combination of features comprises a ratio of the sum of the low C banding region area and the intermediate area to the sum of the 28S peak area in the shifted 28S region and the 18S peak area in the shifted 18S peak region, which can be represented by the expression "(low C+Intermediate)/(28S+18S)".

In one embodiment, the combination of features comprises a maximum ratio determined from at least two electropherogram datasets. The ratio is defined as the intermediate area divided by the sum of the 18S and 28S peak areas in the shifted 18S and 28S regions respectively. This can be represented by the expression "maximum intermediate/(28S+18S)".

In some embodiments, the apparatus 100 and the computer readable medium can be configured to implement methods 200 and 300 or methods 200 and 400 or methods 200, 300 and 400 where method 400 is described with respect to FIG. 27A.

The step of obtaining the at least one electropherogram dataset comprises in an embodiment: separating the cellular RNA by electrophoresis; detecting one or more species of the separated cellular RNA; plotting the electropherogram and obtaining the at least one electropherogram dataset from the electropherogram plot.

Electrophoresis for separating RNA is a commonly used technique. For example, gels containing fluorescent dyes can be employed to detect separated RNA species. Automated microfluidics based electrophoresis methods and systems such as the Experion automated electrophoresis system (Bio Rad Laboratories, Inc.) and the Agilent 2100 Bioanalyzer (Agilent Technologic, Inc.) have been developed which can be used to separate RNA species. These systems use very small amounts of RNA and conduct microcapillary electrophoresis in channels of microchips.

Accordingly, in an embodiment the gel electrophoresis is microcapillary electrophoresis. In another embodiment, the microcapillary electrophoresis comprises using an RNA chip for electrophoretically separating the RNA.

Detection of the separated cellular RNA is performed, for example, using RNA dyes such as fluorescent dyes which bind the RNA. The RNA dyes can be added to the electrophoresis gel permitting detection of the RNA by detecting the dye signal.

Cellular RNA for use in the assay can be, for example, isolated from a tumour tissues or any biological sample comprising cancer cells including for example a sample comprising cells of a cell line, human tissue or animal tissue) using techniques known in the art. For example, cells and/or a biopsy can be re-suspended/lysed in a RNA isolating or stabilizing solution such as RNAzol™ (Sigmal/Aldrich Co.), RNAlater™ (Qiagen Laboratories), RNA Stable™ (Biomatrica Co.), RNA Protect Cell Reagent™ (Qiagen Laboratories) and RNA isolated using one or more commercially available kits (according to manufacturer's directions), including, but not limited to, RNeasy™ (Qiagen Laboratories), miRNeasy™. (Qiagen Laboratories), RNAzol™ (Sigmal/Aldrich Co.), Total RNA Isolation Kit (Norgen Biotek Co. and Agilent Technologies, Inc.), Purelink™ (Invitrogen Labs), 5 PRIME PerfectPure™, and GeneJET (Thermo Scientific) kits.

Figure 6:
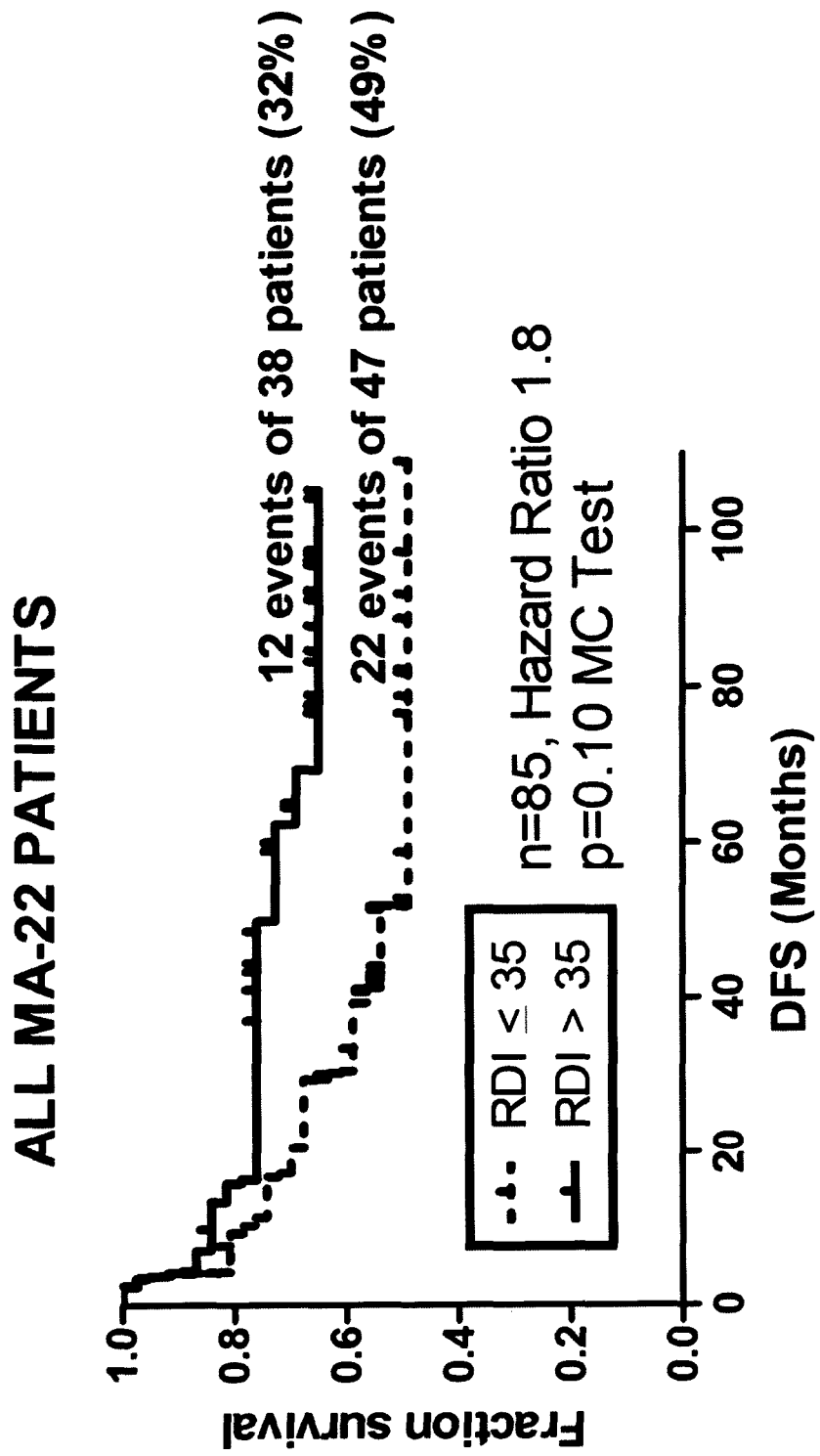
FIG. 6 is a Kaplan Meier Survival curves for patients where disease-free survival is plotted against fraction survival for patients at or below versus above tumour RDI value of 35.
Figure 8:
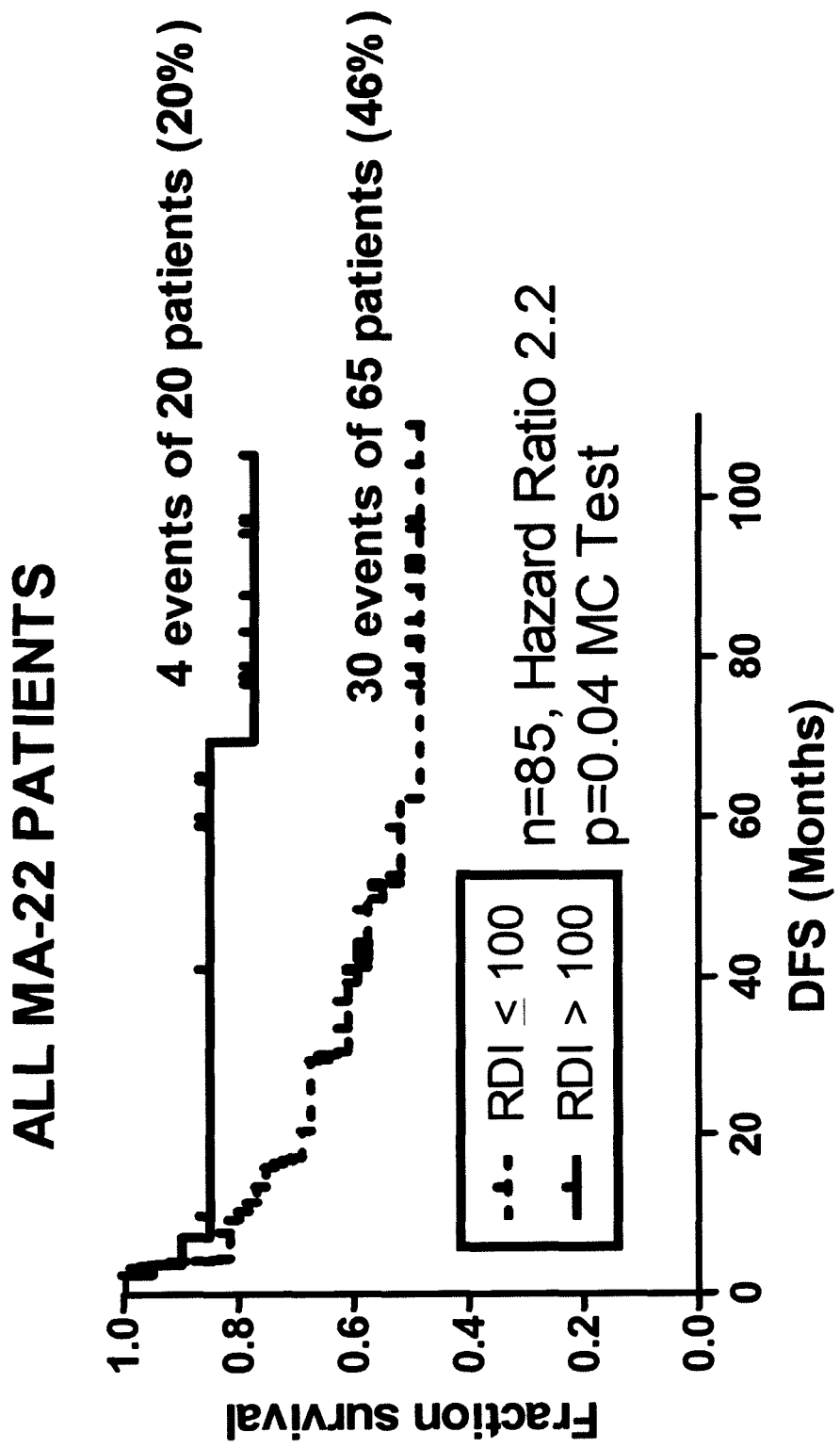
FIG. 8 is a Kaplan Meier Survival curve for patients where disease-free survival is plotted against fraction survival for patients at or below versus above tumour RDI value of 100.

As mentioned, changes in RNA disruption can be used to monitor response to cytotoxic cancer treatment. For example, FIGS. 21A-21K, 28, 29A-D, 30A-30D and others demonstrate that RDA can be used to discriminate subjects receiving chemotherapy with an increased likelihood of pCR from non-responders (i.e. non-pCR responders) and Tables 5 and 6 for example show that RDA can also be used to discriminate subjects receiving chemotherapy with an increased likelihood of favourable or unfavourable survival, including DFS as well identify patients in an intermediate RDA zone. For example, the Kaplan Meier plots demonstrate that there are distinct survival curves between patients with tumour RDI values above or below 35, 50, and 100 (see for example FIGS. 6-8). RDI cut points of 50 and 100 yielded statistically significant differences shown by the Kaplan Meier survival curves (FIGS. 7 and 8).

Figure 25A:
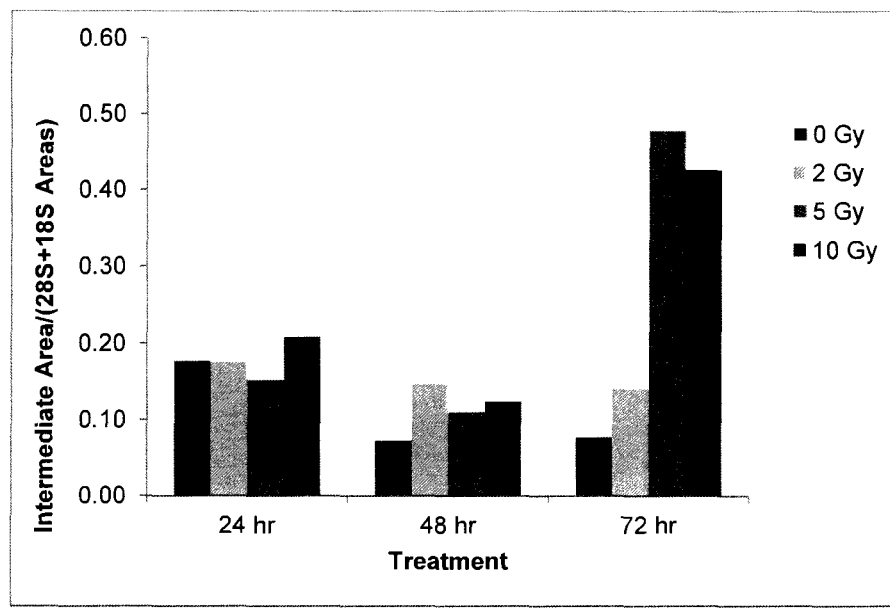
FIG. 25A is a graph of the intermediate area/(28S+18S) calculated for A2780 ovarian cancer cells treated with radiation for different time periods.
Figure 25B:
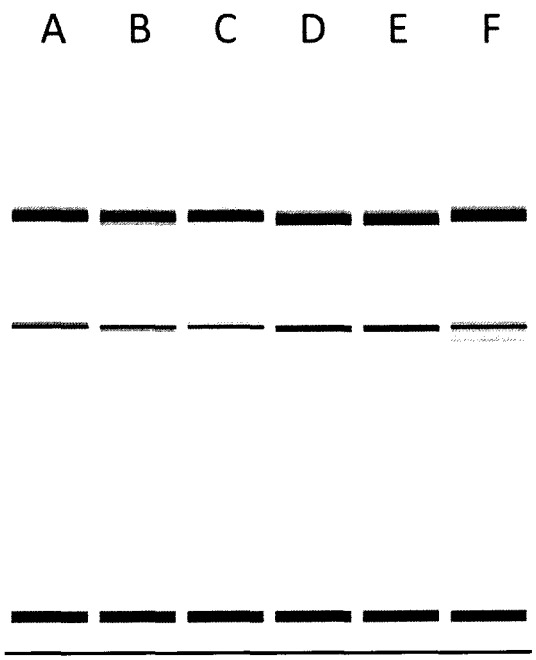
FIG. 25B is an image of a gel of electrophoretically separated A2780 ovarian cancer cell RNA samples of cells treated with radiation for different doses and time periods.
Figure 26A:
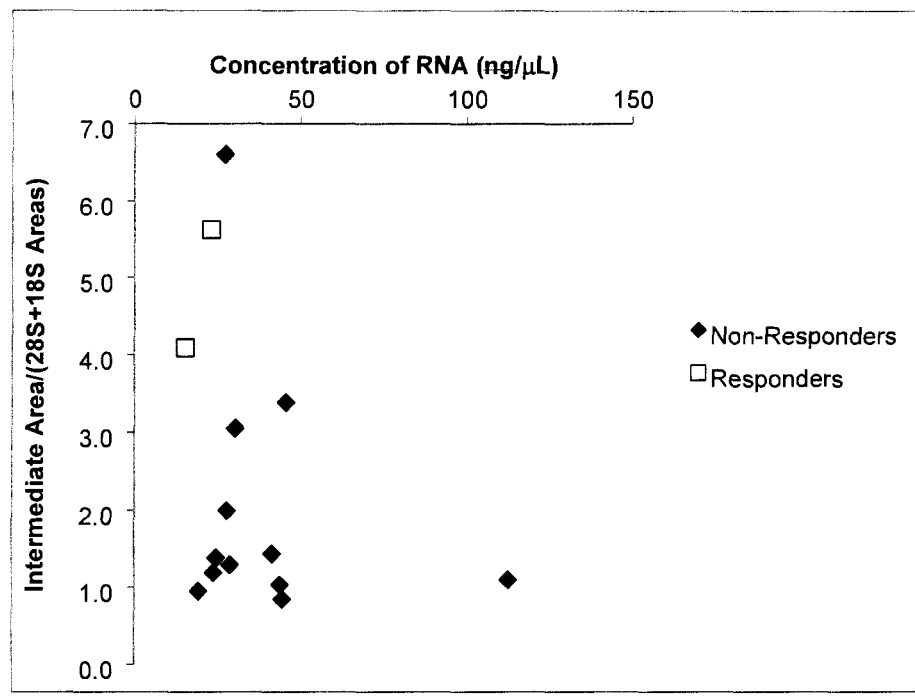
FIG. 26A is a graph of the intermediate area/(28S+18S) versus concentration calculated for patients treated with FEC, radiation and docetaxel.
Figure 26B:
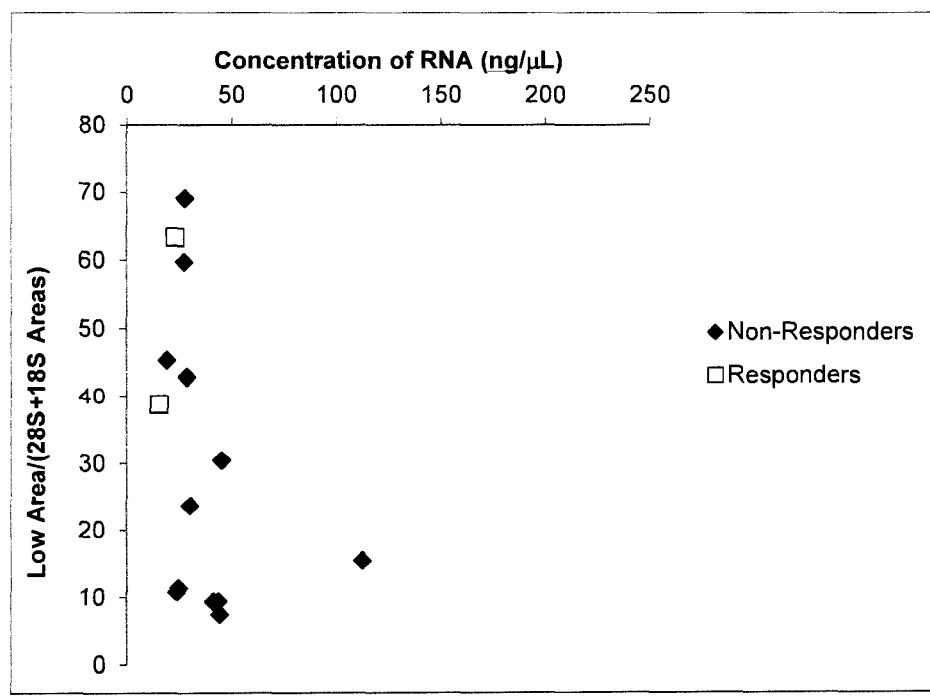
FIG. 26B is a graph of the low Area/(28S+18S) for patients treated with FEC, radiation and docetaxel.

Changes in RNA disruption are also seen with radiation (e.g. see FIGS. 25, 26A and 26B). Without wishing to be bound by theory, RNA disruption in a tumour cell may take place before cell death and/or before changes in cellularity, particularly during early stages of treatment. Accordingly, the RDA is suitable for assessing subject response to a cytotoxic treatment, such as a chemotherapy treatment.

In an embodiment, the RDA comprises:

quantifying the amount of RNA disruption in a biological sample comprising cellular tumour RNA at a time point during or after cytotoxic treatment such as, but not limited to, chemotherapeutic treatment, radiation treatment, and cytotoxic adjuvant treatment, for example, using an RNA disruption assay (RDA) as described herein to determine an RDA score; and determining if the amount of RNA disruption of the cellular RNA is increased or not increased.

As mentioned this can involve determining whether a subject falls within an RDA zone. For example, FIGS. 22A and 29A, which are log-log plots, show that responders and non-responders can be separated by RDA zones.

In an embodiment, the RDA zone information may be transmitted to the subject, optionally through a medical professional.

The tumour cell RNA can be from, for example, a tumour cell line, or can be from a tumour tissue/cell sample from a subject such as a biopsy.

In one embodiment, the tumour cell RNA assessed is from an untreated sample (e.g. untreated tumour cells in vitro) or is from a subject at a time point before treatment (e.g. pre-therapy).

Reports of tumour samples showing aberrant 28S/18S ratios have been reported.

For example, abnormal 28S:18S ratios have been reported in untreated tumour tissue (Skrypina, et al. 2003). It has been suggested that this loss in 28S is due to preferential cleavage within GC-rich regions (Johnson, Sendler, Lalancette, Hauser, Diamond, & Krawetz, 2011).

In one embodiment, the determining step comprises comparing the quantified amount of RNA disruption in the tumour tissue sample with a control such as a threshold or reference value. In an embodiment, the reference value corresponds to a pretreatment value.

In an embodiment, the increase is relative to a control or an expected or reference pretreatment score or value.

A pretreatment sample comprising for example cancerous tumour cell RNA can comprise relatively little or no RNA disruption. For example, the RNA integrity will be stable. For example, untreated breast cancer tumour biopsies assessed for RNA disruption using the methods described herein are typically identified as falling within zone 1. RNA degradation can be scored in some embodiments without relation to a comparator (e.g. using an absolute scale). In some embodiments, threshold values can be used. Thresholds values for example, which define a zone can be used to classify the subject. Accordingly a determination of an RDA score that falls for example within RDA zone 2 or RDA zone 3 is indicative that the sample contained disrupted RNA even in the absence of a comparator sample on the basis of the expected untreated amount of RNA disruption. Accordingly, the determining step can comprise comparing to a priori determined value or an expected value for the tumour type.

Assays employing the RDA can be used to identify or predict which subjects and/or tumours respond for example by pCR and/or with a favourable or unfavourable survival prediction and/or prognosis to a chemotherapy and/or radiation treatment.

Accordingly in another embodiment, the assay further comprises identifying whether the patient is responding and/or having a favourable or unfavourable survival time to a cancer treatment, optionally a chemotherapeutic and/or radiation treatment, if the amount of RNA disruption (e.g. the RDA score) is increased relative to the reference or threshold value.

FIG. 9I shows that sensitive A2780 cells show RNA disruption whereas resistant A2780 cells do not.

In one embodiment, the RNA disruption is expressed as an RDA score. The RDA score is reflection of the amount of RNA disruption in the sample, with increased RDA score reflecting increased RNA disruption.

As mentioned, the assays can be used to determine the likelihood that a subject will or is responding to a cancer treatment and/or their survival prediction and/or prognosis and/or risk of progression.

Accordingly a further embodiment comprises an assay for determining if a subject is responding to a cancer treatment comprising: assaying a biological sample obtained from the subject during and/or after the subject has received a cancer treatment, optionally chemotherapy and/or radiation therapy for the quantity of RNA disruption using an RNA Disruption Assay (RDA) performed according to a method described herein, wherein the subject is identified as having a favourable survival time and/or response to the treatment if the amount of RNA disruption (e.g. the RDA score) is increased relative to the threshold or reference value.

In one embodiment, the responsiveness is indicative of treatment outcome, and an increased amount of RNA disruption relative to a threshold or reference value (indicative of increased chemotherapy induced RNA disruption) is predictive of a positive treatment outcome and a lack of RNA disruption relative to a threshold or reference value (e.g. indicative of little or no chemotherapy induced disruption) is predictive of negative treatment response (e.g. lack of long-term benefit).

In another embodiment, the positive treatment outcome is pathologic complete response following treatment, partial response, reduced risk of disease progression, increased disease free survival or increased overall survival. Conversely negative treatment outcome can be lack of pCR, lack of increase in disease free survival or lack of increase in overall survival compared to a threshold for example the average of a group of patients or the average of a subset of patients (e.g RDA zone 1 patients).

In one embodiment, the cancerous tumour sample assessed is obtained from a subject during and/or after the treatment, and/or the time point is, during and/or after the treatment.

In one embodiment, the methods or assays described herein are used to monitor treatment response. For example, a subsequent sample is compared to a previous sample such as a baseline sample or value. In another embodiment, the assay and methods described herein are employed in a clinical trial to assess and/or monitor which subjects are responding to the treatment. For example, subjects can be assigned treatments optionally based on expression analysis.

Biopsies can be taken, during and/or post treatment, and the RDA can be used to predict response, such as, for example, to predict if a subject is likely to benefit from remaining on a treatment (e.g. is a responder) or is likely to benefit from switching treatments thereby monitoring treatment response, adequate dosage etc. For subjects not responding according to the RDA, a subset can be switched to a new treatment. The outcome of patients that were switched can be compared to those that remained on the treatment predicted to be ineffective according to RDA score.

Accordingly in an embodiment, the method or assay further comprises selecting non-responders and randomizing participation in two or more arms of a clinical trial.

In yet another embodiment, the method or assay further comprises selecting responders and randomizing participation in two or more arms of a clinical trial.

In another aspect, the disclosure includes a method for selecting subjects for a multi-arm clinical trial, the method comprising:
- predicting if the subject receiving a cancer treatment such as chemotherapeutic and/or radiation treatment is responding or not responding and/or predicted to have a favourable or unfavourable survival time to the treatment according to a method for determining an RDA score described herein;
- randomizing non-responders and/or patients predicted to have unfavourable survival time to two or more treatment arms; and
- optionally randomizing responders and/or patients predicted to have favorable survival time to two or more treatment arms.

In an embodiment, the clinical trail is an adaptive clinical trial. For example, patients that are not predicted to have a survival benefit receive an altered treatment.

A further aspect includes a method for predicting the efficacy of a cancer treatment, such as a chemotherapy and/or radiation treatment, comprising:
- stratifying a subject group into at least 2 subgroups;
- treating the subjects of each subgroup with the chemotherapy treatment for a suitable time;
- determining an RDA score for each subject according to the method described herein; and
- predicting the treatment to be efficacious in terms of survival time if the subjects have an RDA score above a threshold or reference value and predicting the treatment not to be efficacious in terms of survival time if the subjects have an RDA score below a threshold or reference value.

The threshold or reference value is for example a value associated with differentiating patients with a survival time benefit from patients without a survival time benefit.

Also provided is a method for predicting the efficacy of a chemotherapy treatment for a subject, comprising:
- treating the subject with chemotherapy treatment for a suitable time; and
- determining an RDA score according to the method described herein;

wherein a treatment is predicted to be efficacious for the subject if the subject has an RDA score above a threshold or reference value and predicted not to be efficacious for the subject if the subject has an RDA score below a threshold or reference value.

If a subject is identified as not responding to a cancer treatment, the subject's treatment can be altered or changed. For example, the treatment dose administered can be increased, radiation and/or a chemotherapeutic agent can be added to the regimen or the treatment can be discontinued and/or a different cytotherapy regimen initiated. The methods and assays can also be used to monitor response to the altered treatment. Other treatment modalities can also be employed if a subject is not responding to a cytotoxic, e.g. chemotherapy treatment such as radiation treatment or surgery.

Cancer treatments such as chemotherapy and radiation are often administered in cycles wherein the cycle can comprise administration of 1, 2 or more doses per period, for example, per day, per week, per two week period. Protocols have been established for different drugs and different cancers. A treatment regimen can consist of 1, 2, 3, 4, 5, 6 or more cycles. Accordingly, in an embodiment, the RNA sample is at a time point after a first cycle. In another embodiment, the RNA sample that is assessed is obtained from a subject mid-treatment, and/or the time point is mid-treatment (e.g. for a 6 cycle treatment regimen, the RNA sample assessed is obtained from a subject and/or the time point is after 2, 3, or 4 cycles).

In one embodiment, the biological sample is obtained after the subject has received a first cycle of cancer treatment for example a first cycle of a chemotherapeutic or radiation treatment. In another embodiment, the biological sample is obtained from the subject after the subject has received 2, 3, 4 or more cycles of the treatment. In yet another embodiment, the biological sample is obtained from the subject after completion of the treatment regimen.

In an embodiment, the biological sample is a biopsy such as a fine needle aspirate or a core biopsy. In another embodiment the biological sample comprises a population of cancer cells or tissue obtained from the subject.

More than one biological sample can be assessed. For example, where multiple samples are taken at a time point and/or at the same time, for example, 2 or more fine needle aspirate biopsies, each sample can be assessed separately and the congruity of the samples can be assessed to determine any heterogeneity in treatment response.

In an embodiment, the RDA score indicative of responsiveness and/or positive treatment outcome (e.g. increased survival, such as DFS) correlates to a decrease in RNA disruption of at least by 20%, at least 30%, at least 40%, at least 50%, at least 60%, at least 70%, at least 80% or at least 90%.

In an embodiment, the peaks are not shifted. However, the method is still applied according to the methods described herein.

The assays can be applied to any tumour type and/or subtype. For example, the cancerous tumour can be a breast cancer, lung cancer, a sarcoma, prostate cancer, colon cancer or ovarian cancer including any subtype thereof. In certain embodiments, the methods and assays are applied to blood cancers such as leukemias, multiple myeloma or lymphomas. In an embodiment, the cancer is a cancer treatable by an anthracycline and/or a taxane and/or radiation. For example, prostate cancer is a cancer that can be treated by docetaxel and lung cancer and sarcomas can also be treated by anthracyclines and/or taxanes. Anthracyclines include for example doxorubicin, daunorubicin, epirubicin, idarubicin, valrubicin and mitoxantrone. Taxanes for example include paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

As demonstrated for example in FIG. 25, cancer cells demonstrate RNA disruption in response to radiation treatment. FIGS. 26A and 26B provide a description of analyses where patients received chemotherapy and radiation therapy.

In an embodiment, the subject or cells have received 1, 2, 3, 4, 5, 6 or more doses of radiation. In an embodiment, the cells and/or subject are treated with a dose of a chemotherapeutic agent prior to or concurrent with radiation treatment.

The MA22 dataset for example, included samples with differing ER, PR, Her2, topoisomerase status. As demonstrated in the Examples section, the method and assays described herein are applicable independent of ER, PR, Her2, topoisomerase status. The methods have been used to assess breast cancer samples that vary in ER, PR and Her2 status including triple negative samples. Further, RDA is effective for ER+ breast cancer. pCR as a prognosis marker is less effective for ER+ breast cancer.

In one embodiment, the cancerous tumour is selected from breast cancer, prostate cancer, colon cancer and ovarian cancer or any subtype thereof.

In an embodiment, the cancerous tumour is selected from leukemia, lymphoma or multiple myeloma and/or any cancer treatable by an anthracycline and/or taxane.

In one embodiment, the cancerous tumour is breast cancer.

In another embodiment, the breast cancer is HER2+ positive breast cancer.

In yet another embodiment, the breast cancer is locally advanced breast cancer. In another embodiment, the breast cancer is metastatic, optionally with bone metastases.

A further aspect includes a method of treating a subject with cancer in need thereof comprising:
administering a cancer treatment optionally a chemotherapeutic and/or radiation treatment;
determining if the subject is responding to the treatment according to a method disclosed herein; and
continuing administration of the treatment if the subject is responding and/or discontinuing administration of the treatment is the subject is not responding.

In an embodiment, the cancer treatment/chemotherapeutic dose, is increased, for example wherein a subject sample includes an intermediate level of RNA disruption, for example RDA zone 2. As subjects who fall within RDA zone 3, are more likely to be pathological complete responders and/or exhibit survival benefit, a subject whose RDA score does not fall within said RDA zone may benefit from increased treatment dose.

In an embodiment, the cancer/chemotherapeutic treatment is selected from microtubule stabilizing agents such as Docetaxel and paclitaxel, DNA synthesis inhibitors such Epirubicin, inhibitors of Her2 Receptor such as Trastuzumab, DNA cross-linking agents such as Mafosfamide, carboplatin and cisplatin, VEGFA inhibitors such as Bevacizumab, Receptor Tyrosine Kinase inhibitors such as Sunitinib and Toceranib, Bisphosphonates such as Zoledronic acid, and Thymidylate synthase inhibitors such as 5-fluorouracil.

In one embodiment, the cancer/chemotherapeutic treatment is selected from taxanes, anthracyclines, and vinca alkaloids such as vinblastine, alkylating agents such as cisplatin and nucleoside analogs such as 5-FU and combinations thereof. In an embodiment, the chemotherapeutic treatment comprises a drug selected from docetaxel, paclitaxel, epirubicin, doxorubicin, vinblastine and cisplatin and/or combinations thereof. In an embodiment, the taxane is selected from paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

Breast cancer can be treated, for example, with taxanes, anthracyclines or, for example, paclitaxel, docetaxel, docetaxel and epirubicin and combinations thereof. Breast cancer can also be treated with bisphosphonates such as zoledronic acid, aromatase inhibitors such as letrozole, TKIs such as sorafenib and monoclonal antibodies such as trastuzumab Ovarian cancer can be treated, for example, with taxanes, anthracyclines, and vinca alkaloids such as vinblastine, alkylating agents such as cisplatin and nucleoside analogs such as 5-FU and combinations thereof.

In an embodiment, the RNA integrity is determined for total RNA. In another embodiment, the RNA integrity is determined for ribosomal RNA. Ribosomal RNA includes, for example, 28S, 18S, 5.8S and 5S rRNA.

At least some of the elements of the methods that are described herein that are implemented via software may be written in a high-level procedural language such as object oriented programming or a scripting language. Accordingly, the program code may be written in C, C$^{++}$, SQL or any other suitable programming language and may comprise modules or classes, as is known to those skilled in object oriented programming. At least some of the elements of the methods described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Yet a further aspect includes an in vitro model system for RNA disruption comprising A2780 ovarian tumour cell line cells, optionally propagatable or treated, and optionally one or more of a reference anti-cancer agent, instructions for use and a test agent. In another embodiment, the in vitro model system for RNA disruption comprises a The model can be comprised in a kit with one or more drugs and/or instructions for use. Alternatively in another embodiment, the in vitro system comprises CaOV3 ovarian tumour cell line cells and/or Jurkat leukemia cell line cells. In an embodiment, a cell line that shows an at least 2 fold, at least 3 fold or at least 4 fold increase in RDI after incubation with a known chemotherapeutic drug for 72 compared to untreated cells, can be used as an in vitro model. In an embodiment, the in vitro model further comprises a related drug resistant cell line for example docetaxel resistant A2780 cells which can be used for screening for test agents that reverse resistance.

In an embodiment, the cell line cells have been treated with a RNA disruption inducing agent to produce a reference sample, optionally the cells and/or a RNA comprising preparation therefrom, optionally the cell line cells in a RNA isolating or stabilizing solution. In an embodiment, the in vitro model system comprises one or more reference samples comprising cell line cells treated with the RNA disruption inducing agent and/or an RNA comprising preparation therefrom in a sterile vial. For example the cell line can be treated with a chemotherapy drug, optionally at one or more doses to induce a reference amount of RNA disruption. In an embodiment the RNA preparation is isolated RNA. In an embodiment, the in vitro model system includes instructions on how to perform the assay using the reference samples. In an embodiment, the cells are treated with an RNA inducing agent to provide a reference sample having a RDI of about 1, about 2, about 3, about 4, about 5, about 6, about 10, about 15, about 35, about 50 and/or any RDI between 1 and 2000 using a method described herein.

In an embodiment, the kit further comprises a drug resistant control such as A2780 docetaxel resistant cells.

In an embodiment, the in vitro model is used for testing a candidate drug. Accordingly another aspect is a high throughput screen for identifying chemotherapy agents and/or potentiators; the method comprising contacting a model cell line cultured in a multiwell vessel with or without a test agent and optionally in combination with a known chemotherapeutic agent; incubating the cells for a selected period of time with the drug, optionally 24, 48 or 72 hours, optionally culturing the cells in the absence of drug for 24, 48, or 72 hrs; lysing cells; measuring RNA disruption, optionally using RDI or a method described herein; comparing to a control and identifying the test agent that show a preselected level of RNA disruption or increase in RNA disruption as a candidate chemotherapy drug and/or potentiator thereof.

In an embodiment, a plurality of test agents are tested, for example a library of different or related compounds.

In an embodiment, the cell line is resistant to a drug and a combination of the resistant drug and a test agent are incubated with the cell line.

In an embodiment, the level of RNA disruption is a RDI of at least 1, at least 1.5, at least 2, at least 3, at least 3.5, at least 4, at least 4.5 or at least 5.

In an embodiment, RDA is used as a primary or secondary screen. In an embodiment, RDA is used to screen for agents that act in concert with known drugs or treatments to augment their cytotoxicity (chemosensitizers). In another embodiment, RDA is used to test a variety of related structures to identify those structures that maximize RNA disruption.

Furthermore, at least some of the methods described herein are capable of beaing distributed in a computer program product comprising a computer readable medium that bears computer usable instructions for one or more processors. The computer readable medium may be provided in various non-transitory forms and other forms such as, but not limited to, one or more diskettes, compact disks, tapes, chips, USB keys, external hard drives, wire-line transmissions, satellite transmissions, Internet transmissions or downloads, magnetic and electronic storage media, digital and analog signals, and the like. The computer-useable instructions may also be in various forms, including compiled and non-compiled code.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Breast cancer is the most common neoplasm for women in the western world and is associated with more female deaths than any other neoplasm except for lung cancer [1; 2]. Surgery is the primary treatment for most breast cancers, followed by radiation therapy and/or systemic adjuvant chemotherapy [3;4] In locally advanced or inflammatory breast cancers (as defined below), neoadjuvant chemotherapy is employed to shrink tumors and improve local control of disease prior to surgery, after which additional rounds of chemotherapy are administered, possibly also involving sequential or concurrent radiation therapy [5-7]. Two popular classes of drugs used in the treatment of breast cancer are the anthracyclines (typically doxorubicin or epiuribicin) and the taxanes (paclitaxel or docetaxel) [8]. Anthracyclines disrupt the uncoiling of DNA by topoisomerase 2 (topo 2) [9], intercalate between DNA strands [10], and cause DNA lesions [11]. Taxanes, on the other hand, block the depolymerization of microtubules [12], resulting in an arrest of the cell cycle in mitosis and the subsequent induction of apoptosis [13;14]. Other drugs commonly used in chemotherapy regimens to treat breast cancer in both the adjuvant and neoadjuvant settings including 5-Fluorouacil and cyclophosphamide [15]. Receptor targeting agents that block pathways associated with promotion of breast tumor cell growth, the estrogen receptor (ER) [16] and EGF receptor HER2 [17], are also used in chemotherapy treatment regimens to prevent tumor recurrence post-treatment. Such agents include the ER antagonist tamoxifen, the aromatase inhibitors exemestane and anastrozole, and the HER2 antagonist trastuzumab.

Although treatments have improved both survival and progression-free survival for early and metastatic breast cancer patients [18-20], those with locally advanced breast cancer (LABC) have significantly poorer treatment outcome [21]. LABC is traditionally defined as stage IIB (T3N0) and Stage IIIA/B from the TMN classification.

Clinically these tumors are greater than 5 cm in size and/or extend beyond the breast tissue into the surrounding skin or muscle, with or without matted axillary lymph nodes (N2), internal mammary nodes (N3) or ipsilateral supraclavicular lymph node involvement [22]. LABC represents approximately 10-15% of all breast cancer cases, and the survival is estimated at 30-42% at 5 years [23] a significant portion of whom will be living with metastatic disease. However, a small subset of women who receive neoadjuvant chemotherapy and achieve a pathologic complete response (pCR), (defined as no microscopic residual invasive breast cancer following neo-adjuvant treatment) have a vastly improved 5 year disease free survival rate of 87% [24] and 5 year overall survival rates of 89% [25] and 90% [26]. As such, pCR rates have become the commonly accepted surrogate measure for favorable long-term outcomes in trials involving neoadjuvant treatment, particularly since this is the only subgroup for which this value can be measured. The correlation between improved survival from locally advanced breast cancer and pCR has been identified in other studies, mainly using anthracyclines [27;28]. However, the use of pCR in assessing the efficacy or benefit from chemotherapy is of limited value, since this can only be done post-treatment and since patients with ER+/Her2− tumors exhibit substantially lower pCR rates for a variety of chemotherapy regimens involving cytotoxic drugs than patients with ER−/Her2− tumors (reviewed in [29]).

Despite their ability to reduce tumor size as assessed by palpation and imaging techniques [30], it is becoming increasingly apparent that by pCR criteria, primary systemic therapy with cytotoxic drugs increases disease free and overall survival in only a small a minority of breast cancer patients [31-33]. Since most breast cancer patients experience severe short-term and long-term side effects from chemotherapy [33-35] (whether or not treatment enhances survival benefit), there has long been a search for an effective intermediate endpoint for assessing chemotherapy response prior to or during treatment of breast cancer [36-38]. Given current evidence that switching regimens in nonresponders early in therapy can increase pCR rates and survival [39;40], the need for a test to reliably identify nonresponders to chemotherapy is becoming increasingly urgent. If this test (or another) can also accurately identify patients with chemotherapy-responsive tumors, then this would provide reassurance to patients with such tumors that the chosen treatment regimen is working. Validating such tools for use in the management of patients by chemotherapy would involve the use of adequate archived samples from a completed prospective clinical trial, preanalytical and analytical reproducibility of the test, the focus on a single classifier (ideally), and additional validation of tool efficacy through one or more similar studies involving an independent population [41].

It was reported that epirubicin/docetaxel treatment of locally advanced breast cancer patients in the MA.22 clinical trial reduced tumor RNA integrity and that low midtreatment tumor RNA integrity was associated with a pathologic complete response (pCR) post-treatment [Breast Cancer Res. Treat. 119:347-356; WO2009/03029, filed Sep. 5, 2008 herein incorporated by reference in its entirety].

A novel method for detection of chemotherapy-dependent loss of RNA integrity, the RNA disruption assay (RDA), has since been developed, which can stratify RNA disruption into 3 zones, where zone 1 represents drug effect inadequate to obtain a pCR, an intermediate zone (zone 2), and zone 3, which had the vast majority of pCRs [described in PCT/CA2013/000408 filed Apr. 24, 2013, ASSAYS, METHODS AND APPARATUS FOR ASSESSING RNA DISRUPTION herein incorporated by reference in its entirety].

In all evaluable MA.22 patients (n=85), the effect of chemotherapy on tumor RNA disruption and the relationship between RNA disruption on patient response and survival has now been assessed.

RNA was isolated from 2-3 tumor biopsies/patient prior to and after 3 (Schedule A) or 4 (Schedule B) cycles of chemotherapy at 3- or 2-weekly intervals, respectively. RNA quality was assessed on an Agilent 2100 Bioanalyzer and RNA disruption quantified using RDA. In this example RDA was calculated using the ratio of (Intermediate Area+LowC Area)/(28S+18S Areas).

Chemotherapy treatment significantly reduced maximum tumor RNA content by 2.1-fold and increased maximum tumour RNA disruption by 3.4-fold ($p<0.01$ for both observations by Sign test). Moreover, RNA disruption was associated with increased overall survival, with 2.9-fold more living patients in RDA zone 3 than in zone 1. Disease-free survival (DFS) was also significantly greater (by 23 months) for zone 3 patients than zone 1 patients [$p=0.0096$ by Mann Whitney (MWW) Test]. An RDI of 1361 was seen for a sample (the DFS for said patient was 83.2 months). A difference in DFS was even greater for HR+ patients, where patients with a zone 3 level of RNA disruption had 29.1 months greater DES than equivalent patients in zone 1 (0.0088). None of the ER+ patients exhibited a pCR. Moreover, the above differences in overall survival and DFS were not observed when RDA was performed on pre-treatment biopsies.

Chemotherapy exposure reduced maximum tumor RNA content from 197±24 ng/μl (mean±standard error) pre-treatment to 94.0±12.8 ng/μl mid-treatment, with maximum tumor RDI values increasing from 26.0±5.8 to 88.1±19.1 ($p<0.01$ for both observations by Sign test). At the time of assessment, there were similar numbers of deceased patients across tumor RDA zones 1, 2, and 3 mid-treatment (7, 8, and 9 patients, respectively). In contrast, there were 2.9-fold more living patients with tumors in RDA zone 3 (29) than in zone 1 (11). Disease-free survival (DFS) was significantly greater (by 23 months) for zone 3 patients (56.9±5.6 months) compared to zone 1 patients (33.9±6.4 months) ($p=0.0091$ by Mann Whitney Wilcoxon Test for this and all subsequent statistical tests). Living patients with tumor RDA values in zone 3 exhibited 24.5 months greater DFS than living patients with tumors in zone 1 (68.2±5.5 months versus 43.7±8.6 months, respectively; $p=0.011$). Given their high frequency within the patient population, greater DFS (an additional 29.1 months) could be seen for patients with estrogen receptor positive (ER+) tumors in zone 3 (61.0±7.0 months) compared to patients with similar tumors in zone 1 (31.9±7.6 months; $p=0.0066$). Living patients with ER+ tumors in zone 3 had even greater DFS (+41.9 months) compared to living patients with ER+ tumors in zone 1 (73.3±5.6 months versus 31.4±7.6 months, respectively; $p=0.00074$). There were also 2.5-fold more living patients with ER+ tumor RDA values in zone 3 (17) than in zone 1 (7). None of the above significant differences were observed when pre-treatment tumor RDI values or pre-treatment patient characteristics were assessed.

In living HR+ patients, the difference in survival was found to be 42 months, and for all living patients, the difference is 24 months.

Irrespective of breast tumor receptor subtype, chemotherapy-dependent RNA disruption mid-treatment was typically higher in patients that achieved a pCR post-treatment than for patients that did not. Taken together, the findings suggest that tumor RNA disruption measurements during treatment will be highly useful to predict response and survival for patients with locally advanced breast cancer, including patients with ER+ tumors.

In this study, evidence that an assay based on the ability of chemotherapy agents to induce tumor ribosomal RNA (rRNA) degradation (the RNA disruption assay) may be an effective tool for use in response guided neoadjuvant chemotherapy in breast cancer. This assay was developed from observations made in a clinical trial (MA.22) by the NCIC Clinical Trials Group [42]. In this study where the assay was first performed, total RNA was isolated from image guided tumor core biopsies taken from 50 locally advanced breast cancer patients prior to, during, and after treatment with concurrent epirubicin/docetaxel chemotherapy at various dose levels and dosing schedules. The RNA preparations from all biopsies were then resolved by capillary electrophoresis on an Agilent 2100 Bioanalyzer and RNA quality expressed as an RNA integrity number or RIN generated by the Bioanalyzer [43] (see Materials and Methods). A RIN value of 10 represented maximum RNA integrity, while a RIN value of zero represented completed degraded RNA. Using this approach, it was observed that for some patients, tumor RIN values strongly decreased in response to treatment in a dose-dependent manner. Low posttreatment tumor RIN values were strongly associated with post-treatment pathologic complete response, suggesting that tumor RNA degradation was associated with tumor cell destruction [42]. However, unlike tumor extent (tumor cellularity) at mid treatment, low mid-treatment RNA integrity values were associated with the achievement of pathologic complete response post-treatment [42]. These findings suggested that RNA disruption may actually precede tumor cell destruction and that tumor RIN measurements during treatment may be able to identify which patients will exhibit a pCR post-treatment and receive a survival benefit from chemotherapy treatment.

The RIN algorithm was designed specifically to quantify the degree of autolytic degradation occurring within a given RNA sample [43]. This degradation is often due to external factors affecting the quality of RNA from tissues, including poor tissue vascularization, improper sample handling, or delays in the immersing of samples into RNA stabilization agents. However, the RIN algorithm is not particularly effective in quantifying chemotherapy-dependent degradation of RNA, which results in RNA peaks in the electropherogram, which are distinct from those created by RNA autolytic degradation. Moreover, samples with highly contrasting RNA banding patterns often have similar RIN values. To compensate for these deficiencies, a proprietary algorithm that more accurately quantifies chemotherapy-dependent changes within the RNA electropherogram was designed (described in PCT/CA2013/000408 filed Apr. 24, 2013, ASSAYS, METHODS AND APPARATUS FOR ASSESSING RNA DISRUPTION herein incorporated by reference in its entirety). The term chemotherapy-dependent "RNA disruption" was coined and the assay is referred to as the RNA disruption assay or RDA. The algorithm computes the degree of RNA disruption as an RNA disruption index (RDI), where the magnitude of RDI is directly proportional to the degree of RNA disruption. In the current study, the relationship between tumor RDI values mid-treatment and patient response or survival post epirubicin/docetaxel chemotherapy in the MA.22 clinical trial was assessed. Moreover, with the completion of the MA.22 clinical trial, the number of patients assessed increased from the original 50 patients to 85. The study also examined for the first time, whether chemotherapy-dependent RNA disruption occurs across multiple subtypes of locally advanced breast cancer.

Materials and Methods

The CAN-NCIC-MA22 Clinical Trial Protocol

The CAN-NCIC-MA22 phase I/phase II clinical trial (ClinicalTrials.gov identifier NCT00066443) sought to determine the optimal dosing regimens for the administration of docetaxel/epirubicin combination chemotherapy in women with locally advanced or inflammatory breast cancer. Various doses of epirubicin and docetaxel were administered to patients in either a standard q 3 weekly (Schedule A) or dose dense q 2 weekly (Schedule B) regimen. Pegfilgrastim support was also provided to patients to combat neutropenia induced by the regimen. Doses for the q 3 weekly regimen were 75 mg/m2 IV of docetaxel and 75, 90, 105, or 120 mg/m2 IV of epirubicin (with 6 mg pegfilgrastim per cycle on day 2). Doses for both docetaxel and epirubicin in the q 2 weekly regimen were 50, 60, and 70 mg/m2 IV (with identical pegfilgrastim support).

The primary goal of the phase I portion of the MA.22 clinical trial was to determine the maximum tolerated dose (MTD) for locally advanced breast cancer patients under each dosing regimen, while the phase II portion evaluated response rates and toxicities at the MTD for both regimens. In the phase II portions of the trial, response to chemotherapy at both dosing schedules was evaluated by determining the clinical and pathological response rates and the duration of response at the recommended phase II doses.

Only chemotherapy-naïve women with no evidence of metastatic disease were eligible to enroll in the trial. Patients were allocated to the various phases and dosing regimens of the trial without randomization. In phase I, only a single patient was allocated at a time during dose escalation, in order to identify dose-limiting toxicities and to identify the maximally tolerated dose for the q 3 weekly and q 2 weekly regimens.

Measures of Clinical Response

Clinical response to treatment was assessed upon the completion of treatment, where a complete clinical response represented the absence of disease by palpation posttreatment.

Patients that by caliper measurements exhibited a decrease in tumor volume by greater than 50% were considered partial responders to treatment, while patients whose tumors decreased in size by less than 50% were considered to have stable disease. If tumors increased in size upon completion of treatment, such patients were deems to have progressive disease. If the patient exhibited the complete absence of disease at the microscopic level post-treatment by the pathologist associated with the trial, then she was found to exhibit a pathologic complete response (pCR) to treatment.

Obtainment of Image-Guided Needle Core Biopsies from Breast Cancer Patients

The size and location of the suspicious lesion was documented using the linear array L12-5 transducer of the Philips ATL HDI 5000 SonoCT ultrasound system (Bothell, Wash.). After the skin was cleansed with antiseptic, the skin and breast tissue near the lesion were infiltrated with 1% lidocaine local anaesthetic and a skin nick was made with a scalpel. Under ultrasound guidance with aseptic technique, six tissue samples were obtained through the same incision using a 14 gauge needle mounted on an automated spring-loaded device. Three samples were sent in formalin for analysis by the pathology department and an additional three samples were flash frozen and stored in liquid nitrogen for total RNA analysis. This procedure was performed three times per patient—at baseline, after 3 cycles and after 6 cycles of therapy.

Tissue Disruption and Homogenization and RNA Isolation of MA22 Biopsy Samples:

To disrupt and break up cells in needle core biopsies, the frozen biopsies were placed immediately into 0.5 ml of RLT buffer (component of Qiagen Laboratories RNeasy RNA isolation kit, Cat #74106) in an Eppendorf tube without thawing. A sterile pellet pestle was placed onto the end of a Coreless™ pellet pestle gun (both from Cosmo Bio Co. Tokyo, Japan). The biopsies were then homogenized 5 minutes at room temperature to completely lyse the tissue. In some instances, particularly after treatment, samples contained significant amounts of connective tissue, which required more extensive homogenization, but did not prevent successful RNA isolation. The lysate was then passed at least 5 times through a 20-gauge needle (0.9 mm diameter) fitted to an RNase-free syringe to shear associated genomic DNA. Total RNA was then isolated from the homogenate using Qiagen RNeasy mini kits (Cat #74106, Qiagen Laboratories, Mississauga, ON). To do this, the sample was made free of any particulate matter by centrifugation in a microfuge at maximum speed for 3 minutes, with retention of the supernatant. An equal volume of 70% ethanol was added to and mixed with the cleared lysate. The sample, including any precipitate that may have formed, was then added to an RNeasy spin column placed in a 2 ml collection tube (supplied). The sample was centrigued for 15 s at 8000×g, discarding the flowthrough.

Seven hundred 700 µl Buffer RW1 was added to the RNeasy spin column, after which the sample was washed twice in the same buffer. Bound RNA was then eluted from the column using 35·l of RNA-free water.

Assessment of RNA Quality and Quantification of Extent of RNA Degradation

RNA quality was assessed by applying 1·l of each of the above preparations onto Caliper™ RNA nanochips (Caliper Technologies, Hopkinton, Mass.) and resolving the various component RNAs by capillary electrophoresis on an Agilent 2100 Bioanalyzer as described in the manufacturer's protocol (http://www.chem.agilent.com/en-US/Search/Library/_layouts/Agilent/PublicationSummary.aspx?whid=46787&liid=1273). RNA standards of known mass and molecular weight were also run on the chip to determine the relative quantities of the various RNA peaks within the RNA electropherogram.

Quantification of the Degree of RNA Disruption in Tissue Biopsies in Response to Chemotherapy The various RNAs and RNA degradation products in the electropherogram were quantified using a proprietary algorithm and the degree of departure from the normal total RNA banding pattern expressed as an RNA disruption index (RDI).

Assessment of the Relationship Between Tumor RNA Concentration and/or Tumor RDI Values and Clinical Response The relationship between pre- and mid-treatment tumor RDI values (classified into various RDI zones) or tumor RNA concentration values and various measures of clinical response post-treatment were then assessed using various statistical tests. RDI zones capable of differentiating between levels of clinical response (pCR, non-pCR and mixed outcome) were computed and the ability of the lowest RDI zone to reliably identify the largest percentage of nonresponders to treatment (lack of pCR) assessed. Receiver Operating Characteristic (ROC) curves [44] were then established to determine the specificity and sensitivity at which mid-treatment RDA values could predict post-treatment clinical response. The negative predictive value (NPV) and positive predictive value (PPV) of the test for predicting response to treatment, including confidence limits, were also computed as described [44].

Assessment of Expression of Various Cell Surface Receptors in Patient Biopsies

The expression of various cell surface receptors in 82 of MA.22 patient biopsies [including the estrogen receptor (ER), progesterone receptor (PR), and Her2/Neu receptor (HER2)] were assessed by immunohistochemical microscopy prior to therapy as described previously [42]. The degree of RNA disruption in various tumors (classified by their receptor status) was then assessed in order to determine the frequency of RNA disruption within the various tumor subtypes.

Results

RDI as an Effective Measure of Chemotherapy-Dependent RNA Degradation

As shown in FIG. 1, highly intact RNA preparations have very low RDI values and high RIN values. Similarly, highly degraded RNA preparations have very high RDI values and low RNA integrity values. As the RDI value for an RNA sample increases, there is a progressively greater departure from the normal RNA banding pattern. Interestingly, in some instances, there is significant discordance between the two RNA quality metrics. For example, samples 9, 10, and 12 of FIG. 1 have very similar RIN values (2.1, 2.6, and 2.4 respectively), but have very different RNA banding patterns. Sample 9 has clear bands representing the 28S and 18S rRNAs, while samples 10 and 12 do not. Yet the RIN values for samples 10 and 12 are greater than sample 9. In contrast, the RDI values for samples 9 through 12 increase from 20.1 to 103. Thus, there is a clear discordance between these two RNA quality measures for tumors undergoing chemotherapy treatment. RDI is used as a measure of RNA quality during chemotherapy.

RDI as a Tool to Monitor Response to Chemotherapy in Breast Cancer Patients

In the initial analysis of 50 patients from the NCIC-CTG-MA.22 clinical trial, it was observed that low mid-treatment tumor RIN values were significantly associated with the achievement of a pathologic complete response (pCR) to epirubicin/docetaxel chemotherapy in patients with locally advanced breast cancer (absence of invasive or non-invasive disease in the breast and axilla post-treatment). Such an association was not observed for biopsies taken from these patients prior to treatment [42]. With the completion of the clinical trial, whether tumor RDI values or RNA concentration values changed during treatment and whether pre- or mid-treatment tumor RDA or RNA concentration values could be used to assess response to chemotherapy was determined.

As illustrated in Table 1, the mean tumor biopsy RNA concentration for all assessed patients was significantly reduced from 197±24.2 ng/µl prior to chemotherapy (84 patients assessed) to 94.0±12.8 ng/µl mid-way through chemotherapy (85 patients) ($p<0.01$ by Sign test). (All values are reported as mean±standard error, unless otherwise specified.) A highly significant reduction in mean tumor RNA concentration is observed.

RNA concentration reduction was observed for both Schedule A and Schedule B patients. This suggested that chemotherapy treatment either suppressed tumor RNA synthesis and/or stimulated tumor RNA degradation. In contrast, there was no significant differences [by the Mann Whitney Wilcoxon (MWW) test] in the mean pre-treatment RNA concentrations between the 8 patients that exhibited a pCR post-treatment and the 76 patients that did not (pCR nonresponders). Similarly, there were no significant differences (by MWW test) in tumor RNA concentration between the tumors of pCR responders and non-responders mid-treatment (see Table 1). Eight of 85 patients that completed the trial with follow-up exhibited a pCR, for a pCR response rate of 9.4%.

This is below the expected 15% response rate (based on a recent meta analysis of several neoadjuvant chemotherapy trials [39] and may reflect the high proportion of ER+ tumors in the population (see below).

The maximum tumor RNA disruption index (RDI) for all patients was significantly higher (by about 3.4-fold) for patients during treatment than prior to treatment ($p<0.01$ by Sign test), with mean maximum RDI values of 88.1±19.1 and 26.0±5.8, respectively. While pre-treatment maximum RDI values were not significantly different between pCR responders and non-responders (84 patients assessed; p=0.5574 by MWW test), mean mid-treatment maximum RDI values were substantially different between these two populations, with mean RDI values of 176±59.9 and 79.0±20.0, respectively (85 patients assessed; p=0.0049 by MWW test).

Chemotherapy treatment increased maximum tumor RDI values by 5.8-fold in pCR responders, compared to only 3.1-fold in pCR non-responders. The effects of treatment in both of these classes of patients were highly significant, with p values of P=0.0049 for max RDI higher in pCR Responders than pCR non-Responders, by the MWW test (Table 1). Taken together, the above findings indicate that epirubicin/doccetaxel chemotherapy reduces both the quantity and quality of tumor RNA in patients with locally advanced breast cancer and that chemotherapyresponsive tumors that exhibit a pCR post-treatment have more disrupted RNA than patients that do not. Also chemotherapy responsive tumours which have disrupted RNA have increased disease free survival time.

The above-described differences in RNA concentration and RNA disruption between pre-treatment and mid-treatment biopsies or between pCR responders and non-responders (many statistically significant) need not necessarily be useful as a chemotherapy response biomarker to manage chemotherapy treatment on an individual patient basis. Thus the ability of tumor RDI or RNA concentration values pre-treatment or mid-treatment to effectively distinguish between patients that exhibited a pCR post-treatment (pCR responders) versus those that did not was assessed. To aid in this analysis, RDI values (determined by RDA) were grouped into various zones (zone 1: ≥0 and ≤10; zone 2: >10 and ≤35; zone 3: >35). The distribution of tumor RDI values amongst pCR responders and responders was determined. As shown in Table 2 and FIG. 2A, the vast majority of tumors (58 of 84 or 69%) had pre-treatment maximum RDI values within zone 1, the zone exhibiting the least RNA disruption. This indicated that a large majority of pre-treatment tumors had very good RNA quality. However, there were 14 tumors (16.7%) prior to treatment that exhibited RDI values in zone 3, representing the poorest RNA quality, respectively. This may have been due to improper sample handling or may represent the true tumor RNA quality when the biopsy was taken from the patient. Pre-treatment, pCR responders also had tumors with RDI values predominantly within zone 1 (5 of 8 tumors), with only one tumor having an RDI value in zone 3. Thus, pre-treatment tumor RDA values could not be used to differentiate between pCR responders and nonresponders (as pCR responding and non-responding tumors have maximum RDI values predominantly in the same range. In contrast to the above findings where 69% of pre-treatment biopsies resided in RDA zone 1, only 17 of 85 patients (20%) had mid-treatment tumor RDI values in zone 1, with 38 or 44.7% in zone 3). This represents, upon treatment, a 3.4-fold reduction in the number of biopsies in zone 1 and a 2.7-fold increase in the number of biopsies in zone 3. The number of biopsies in zone 2 increased about 2.5-fold upon treatment.

Figure 2:
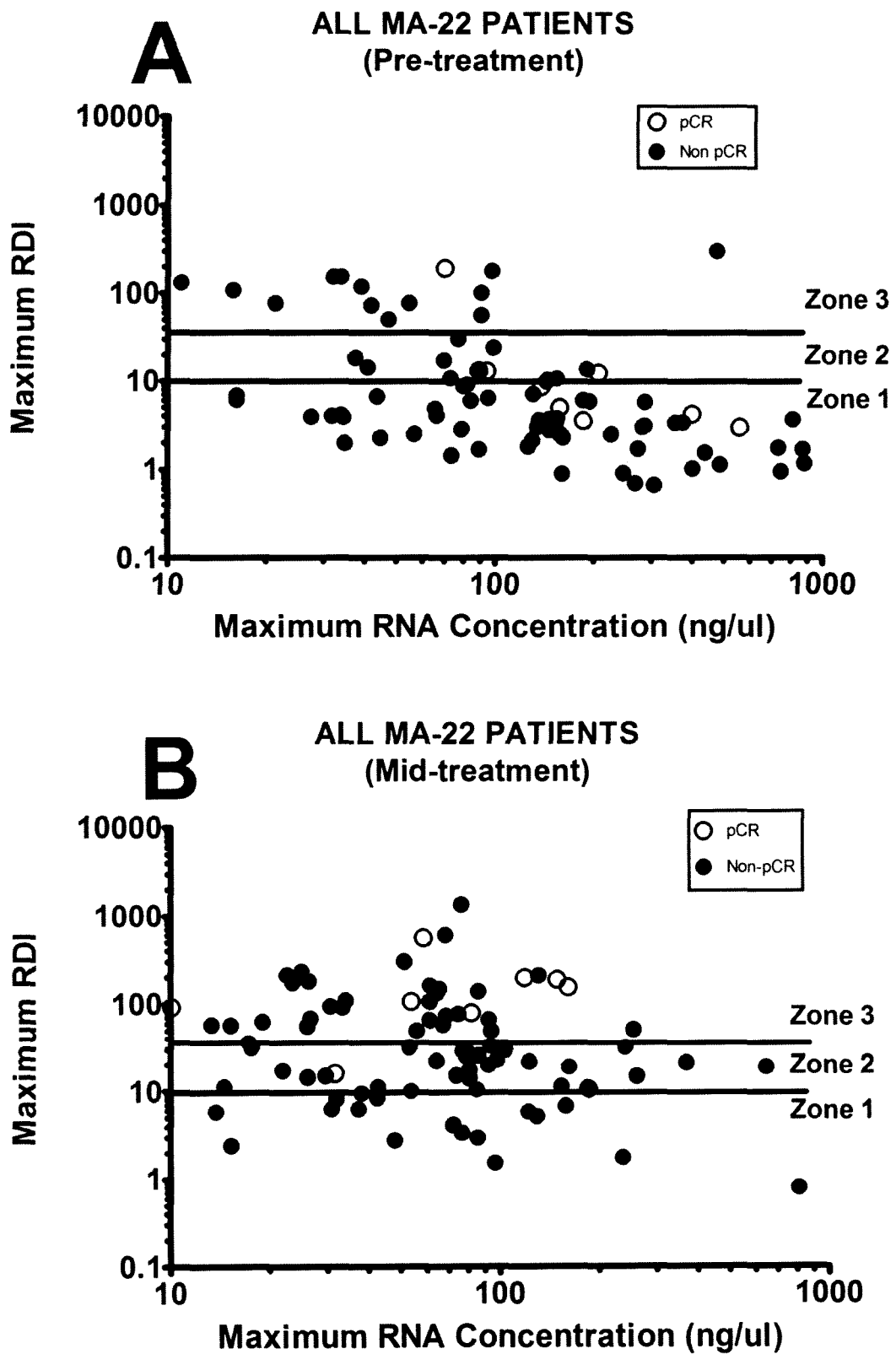
FIG. 2: Effects of epirubicin/docetaxel treatment on RNA concentration and on RNA quality (as expressed using the RNA disruption index (RDI) for 85 MA.22 patients. Patients that achieved a pathologic complete response (pCR) post-treatment are indicated in open circles and those that did not achieve a pCR are depicted with closed circles. A) Pre-treatment values are plotted. B) Mid-treatment values are plotted.

Thus, there is a clear shift in the tumor population towards increasing RDA zones upon treatment. Seven of 8 pCR responders (87.5%) had tumors in RDA zone 3 midtreatment, with the remaining 1 case in zone 2. No pCR responders had mid-treatment tumors that resided in zone 1. In viewing the data in graphical form that also plotted tumor RNA concentrations (FIG. 2), it was clear that mid-treatment biopsies of pCR responders clustered to the highest RDA zone, while pre-treatment biopsies of pCR responders clustered mainly to zone 1. While the mid-treatment biopsy RNA content spanned across a wide range of concentrations (generally in the 10 to 200 ng/μl range of both responders and nonresponders), this variable helped to further segregate the PCR responders from the nonresponders (no PCRs). pCR responders clustered to the top (high RDI) and often to the left (low RNA content) of plots of tumor RDI versus tumor RNA concentration (FIG. 2B).

Table 2 also describes the extent of clinical response to epirubicin/docetaxel chemotherapy in MA.22 patients (as examined by ultrasonography). Four patients exhibited no response to treatment (either stable disease or disease progression posttreatment).

The vast majority of patients (64 of 85 or 75%) exhibited a partial response to treatment (reduction of tumor size by >50%) and seventeen patients (20%) exhibited a complete clinical response (lack of detection of tumor by palpation post-treatment).

Only 8 patients (9.4%) achieved a pCR. Since only the achievement of a pCR in patients has been correlated with a survival benefit post-chemotherapy [45], it appears that that the assessment of clinical response, clearly over-estimates the number of true responders to chemotherapy. Only 4 of 85 patients (4.7%) were deemed clinical nonresponders to chemotherapy. In contrast, RDA suggested significant variability in the degree of clinical response amongst MA.22 patients. As shown in Table 2, 17 patients (20%) had tumors exhibiting very little RNA disruption mid-treatment (RDI zone 1), suggesting a lack of response to treatment. An additional 30 patients had tumors with RDIs in zone 2 (partial response), while 38 patients had RDIs in zone 3 (strong response). In terms of pCR responders, 7 had tumors in RDA zone 3 and 1 in zone 2.

In terms of clinical response for such pCR responders, 6 had a complete clinical response, 2 had a partial response, and none had no response. Thus, there appeared to be a better association between the occurrence of a pCR and a high RDI value than between the occurrence of complete clinical response and high RDI values. The higher number of patients in zone 1 using RDA (20%) compared to clinical response measurements by palpation (4.7%) suggests that RDA is suited to identifying non-responders to treatment. RDA identifies a larger number of patients who have increased DFS compared with pCR.

Sensitivity and Specificity of the RDA Assay to Identify Non-Responders to Treatment (Lack of pCR)

Figure 3:
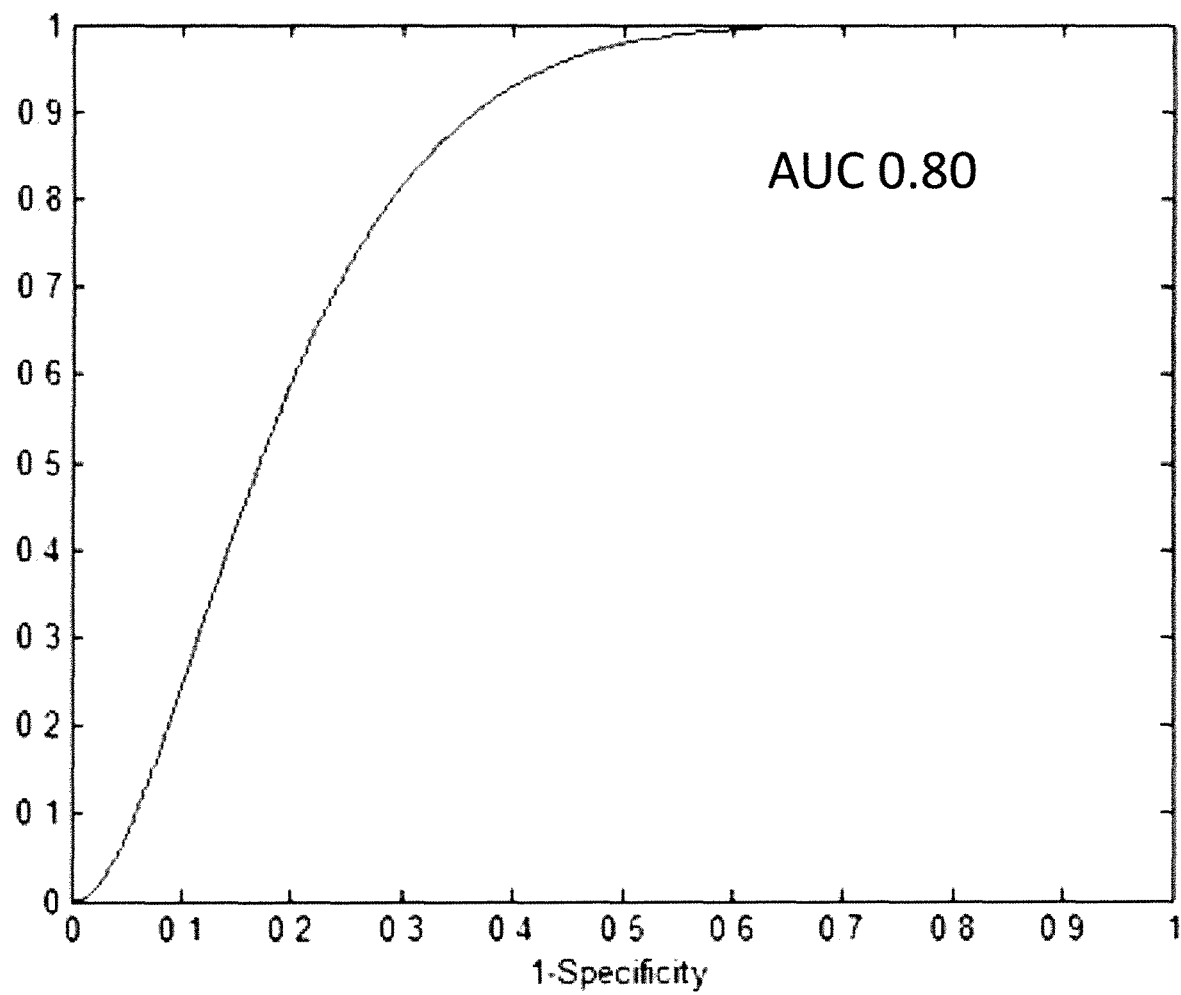
FIG. 3: Receiver Operator Characteristics (ROC) curve for RDA (for parameters (intermediate area+low C)/(28S+18S)) in terms of its ability mid-treatment to identify patients that will not achieve a pathologic complete response (pCR) post-treatment.

A Receiver Operator Characteristics (ROC) curve was constructed (as described in materials and methods) to assess the utility of RDA to effectively differentiate between pCR responders and pCR non-responders. When applied to patients in the MA.22 clinical trial after the 3rd or 4th cycle of chemotherapy, RDA had an AUC of 0.81 (FIG. 3) and could make the following predictions. Of the 85 patients with available tumor RDA and clinical response data, 17 or 20% of patients had tumor RDA values in zone 1 and were therefore predicted to be pCR non-responders (FIG. 2B). Receiver Operating Characteristic (ROC) analysis further showed that RDA can reliably identify 22% of pCR non-responders with a negative predictive value of 0.99 with a 95% confidence limit of 0.95-1.0 and a false negative rate of 7%. Of patients achieving a pCR, RDA predicted that 87% of them had an increased chance of responding. This prediction had a positive predictive value of 0.22, suggesting the test is not highly accurate in positively predicting pCR clinical response.

Ability of RDA to Identify pCR Responders Across Tumor Subtypes

Figure 4:
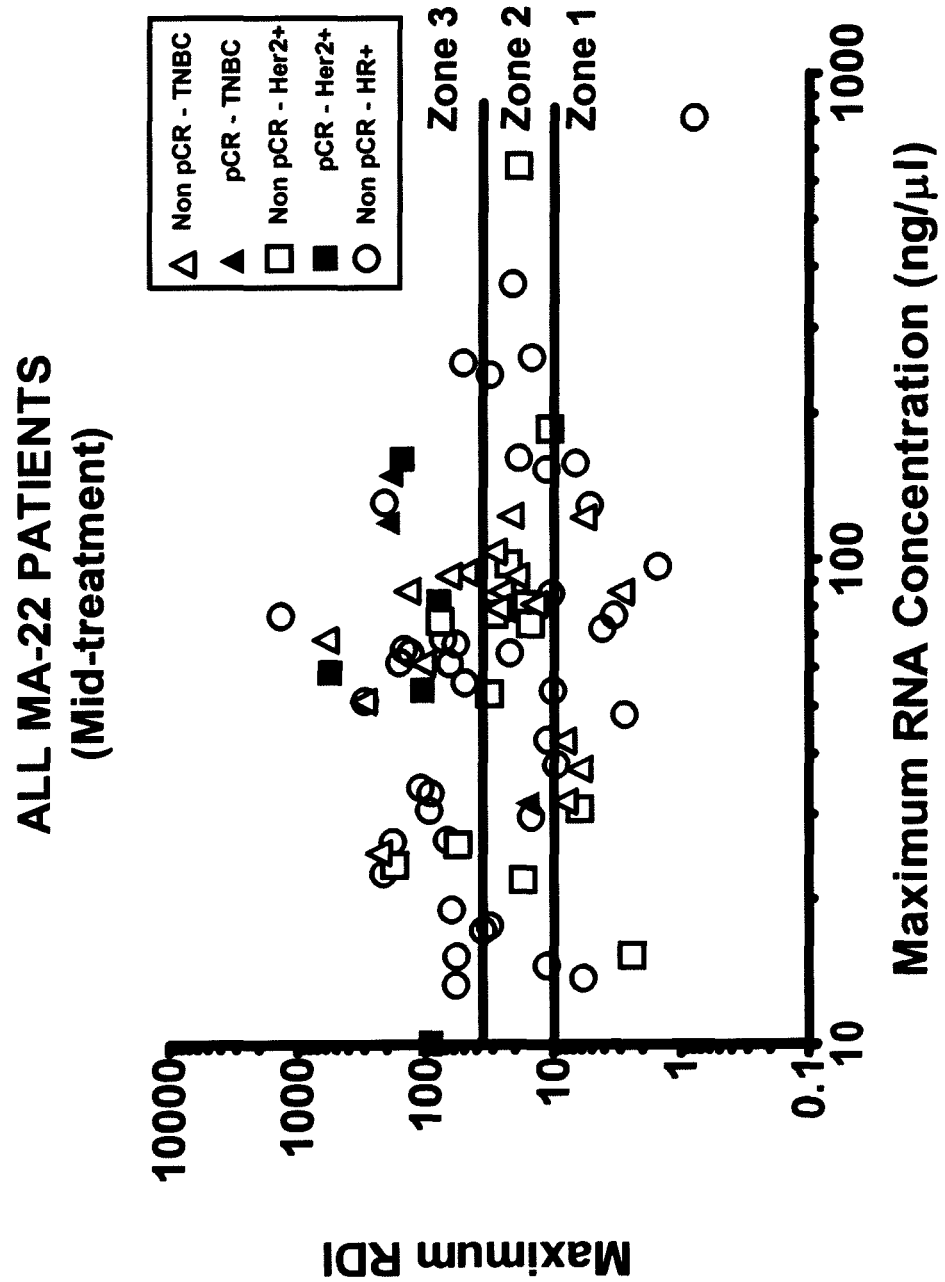
FIG. 4: Effects of epirubicin/docetaxel treatment on RNA concentration and on RNA quality (as expressed using the RNA disruption index (RDI) for 85 MA.22 patients, where patients are divided into groups depending upon their expression of the estrogen receptor (ER), and the human epidermal growth factor receptor 2 (Her2). Those patients that lacked expression of ER and Her2 are listed as "triple negative" (Trip. Neg.), providing they also lacked appreciable expression of the progesterone receptor (PR). Patients that achieved a pathologic complete response (pCR) post-treatment are indicated in closed symbols and those that did not achieve a pCR are depicted with open symbols.

The 82 MA.22 patients for which estrogen receptor (ER), progesterone receptor (PR) and Her2 receptor (Her2) expression status were known were classified as either pCR responders or non-responders (no pCR). As shown in FIG. 4, of 12 patients that were Her2+, but ER– and PR–/+, 4 exhibited pCRs for a 33.3% response rate. All four of the pCR responders were in zone 3. Of non-responders, 2 were in zone 1, 4 were in zone 2, and two were in zone 3. Of 20 patients that did not express any of the three receptors (triple negative), 3 were pCR responders and 17 were nonresponders (for a 15% response rate). Of these triple negative responders, 2 were in zone 3 and 1 in zone 2. Of the 17 nonresponders, 7 were in zone 1, 6 were in zone 2, and 3 were in zone 3. Of 6 patients expressing both the ER and Her2 receptors, but PR–/+, 1 was a pCR responder and 5 were not (for a 16.6% response rate). Interestingly, of 44 patients expressing the ER but not Her2, none were pCR responders, consistent with previously reported findings that patients with these tumor subtypes only rarely achieve a pCR [29]. Two major conclusions can be derived from these findings: Compared to nonresponders, pCR responders across all subtypes were clustered in regions of higher RNA disruption and generally of lower RNA content. In addition, RNA disruption was observed in all tumor subtypes that exhibited pCRs and was not restricted to only certain breast tumor subtypes.

Relationship Between the Extent of Tumor RNA Disruption Overall or Disease-Free Survival In the MA.22 clinical trial, patients were regularly assessed in order to determine if and when specific adverse effects were observed (including death) and to note the period of disease-free survival (DFS) post-treatment. Interestingly, as shown in Table 4, there were similar numbers of deceased patients across tumor RDA zones 1, 2, and 3 mid-treatment (7, 8, and 9 patients, respectively). In contrast, there were 2.9-fold more living patients with tumors in RDA zone 3 (29) than in zone 1 (10).

Figure 5:
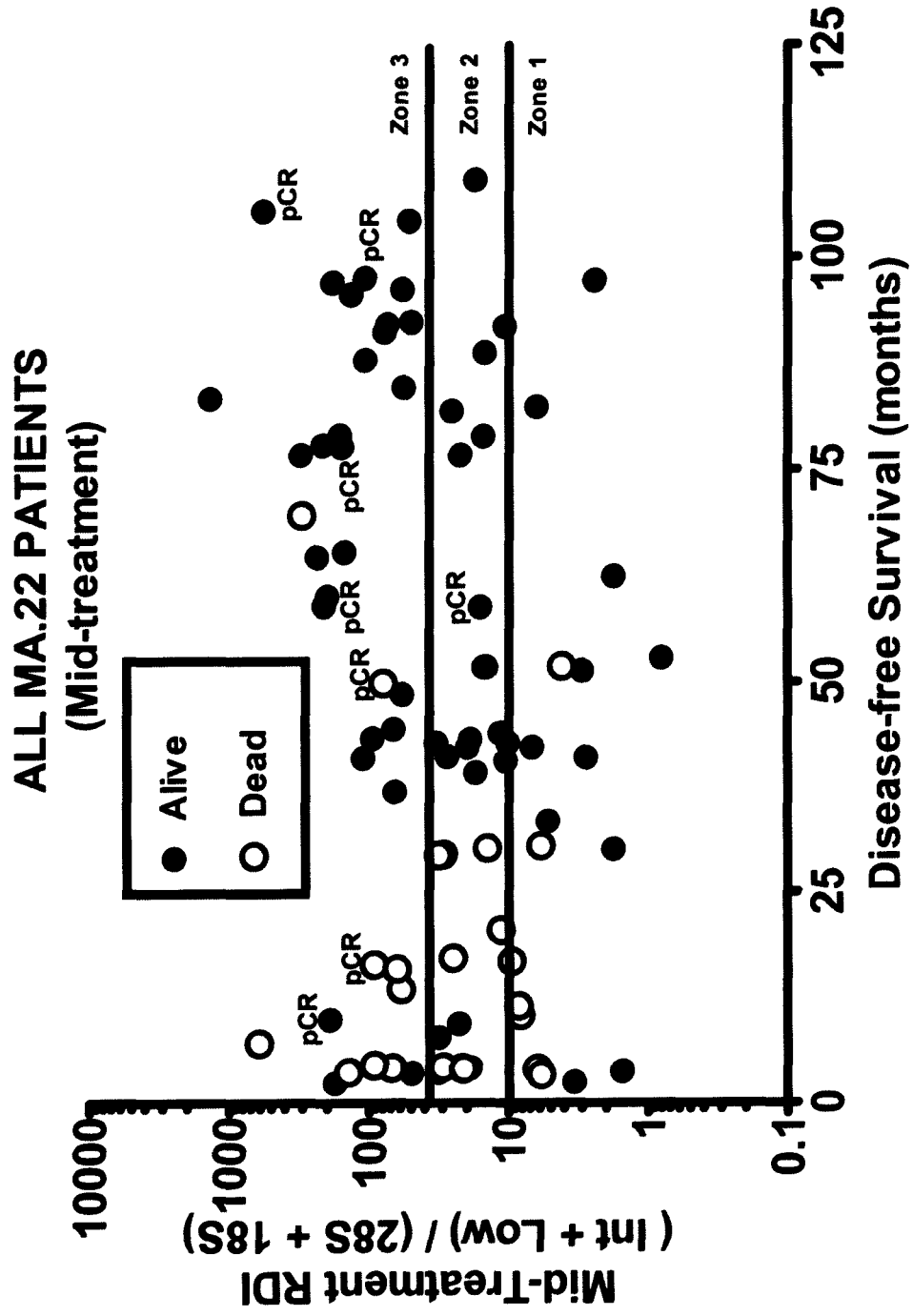
FIG. 5 is a graph illustrating relationship between disease-free survival and the mid-treatment tumour RNA disruption index (RDI) for all MA.22 patients. Patients that were alive at the time of assessment are depicted in solid circles, while deceased patients are depicted in open circles. Patients that achieved a pathologic complete response (pCR) post-treatment are also indicated. The zone 1, zone 2, and zone 3 levels of RNA disruption are indicated.

The mean DFS for all MA.22 patients was 46.6±3.5 years, with considerably greater DFS for living patients (57.5±3.9 months) than deceased ones (18.8±3.6 months). DFS was 54.5±5.8 months for Schedule A patients (n=43) and 38.5±3.7 months for Schedule B patients (n=42). Patients in Schedule B were recruited after Schedule A and have had less time for follow-up. Disease-free survival (DFS) was significantly greater (by 23 months) for zone 3 patients (56.9±5.6 months) compared to zone 1 patients (33.9±6.4 months; p=0.0091 by MWW test). Even without the establishment of RDA zones, a plot of patient RDI values and their respective DFS values (FIG. 5), clearly shows a trend towards increasing disease free survival in patients whose tumors exhibited increasing RNA disruption, in particular for patients that did not exhibit early disease progression (DFS less than 25 months). Living patients with tumor RDA values in zone 3 exhibited 24.5 months greater DFS than living patients with tumors in zone 1 (68.2±5.5 months versus 43.7±8.6 months, respectively; p=0.015 by MWW test) (see Table 4).

Given their high frequency within the patient population, it was also able to conclude that greater DFS (an additional 29.1 months) could be seen for patients with estrogen receptor positive (ER+) tumors in zone 3 (61.0±7.0 months) compared to patients with similar tumors in zone 1 (31.9±7.6 months; p=0.0066 by MWW test).

Living patients with ER+ tumors in zone 3 had even greater DFS (+41.9 months) compared to living patients with ER+ tumors in zone 1 (73.3±5.6 months versus 31.4±7.6 months, respectively; p=0.00074 by MWW test) (see FIG. 8B). There were also 2.5-fold more living patients with ER+ tumor RDA values in zone 3 (17) than in zone 1 (7) (see FIG. 8A). None of the above significant differences were observed when pretreatment tumor RDI values or pre-treatment patient characteristics were assessed.

Interestingly, Table 4 shows that the DFS for patients in Zone 3 is 57 months—very similar to those achieving a pCR (59 months). However, 38 patients (45%) enjoyed chemotherapy DFS benefit, as assessed by RDA, whereas only 8 patients (9%) could be identified by pCR. The table identifies 17 patients (20%) in RDA zone 1 (nonresponders with a DFS of 33 months), some of whom would likely benefit from an alternate treatment regimen.

Discussion

While either a reduction in tumor size as measured by palpation or MRI (partial clinical response) or the complete absence of tumor detection by these methods (complete clinical response) are common in advanced breast cancer patients after chemotherapy, such responses are typically short-lived, with continued presence of disease post-treatment [46]. However, if a pathologic complete response (pCR; complete eradication of all invasive and non-invasive tumor cells in the breast and axilla) is observed post-treatment, such patients typically have a considerably longer duration of progression-free and overall survival [39]. However, about 20% of pCR responders die within 100 months of treatment [39]. Moreover, a clear majority of breast cancer patients do not achieve a pCR after chemotherapy [46-48]. A recent meta-analysis of several studies places the pCR rate for standard neadjuvant chemotherapy regimens at only 15% [39]. This is also consistent with a prior meta-analysis of 28 clinical trials, which reported a mean pCR rate for various nontrastuzumab-based chemotherapy regimens at 16.4±1.3% [33]. It is also worth noting that the SWOG-8814 clinical trial of ER+ patients reported in a 10 year follow-up study that only 8% of patients received an overall survival benefit from CAF-T/tamoxifen chemotherapy compared to patients administered tamoxifen alone [33]. Therefore, pCR as an intermediate endpoint can be applied to a small fraction of neoadjuvant chemotherapy patients and may underestimate the effects of chemotherapy on enhancement of survival, particularly for ER+ patients. Such patients may strongly benefit from alternative response biomarkers to pCR, as recently suggested by von Minckwitz et al. [40].

Most patients, nevertheless, experience significant toxicities from adjuvant or neoajuvant chemotherapy, which may include neutropenia, emesis, anemia, thrombocytopenia, neuropathy, heart damage, shortness of breath, severe fatigue, premature death, and infertility [34;49-51].

Consequently, there is an unmet need for a test(s) to help the oncologist identify (prior to or early in chemotherapy administration) which patients are likely to receive a survival benefit from anthracycline- and/or taxane-based chemotherapy regimens and which will not. Using such a test, non-responders could be spared the toxicities associated with the ineffective regimen, and moved quickly to other potentially more beneficial treatments, including surgery, radiation therapy, or other chemotherapy regimens. Substantial health care dollars would also be saved by dramatically reducing the costs associated with the administration of ineffective chemotherapy drugs and the treatment of chemotherapy-related toxicities in patients.

Classification of breast tumors into specific subtypes prior to treatment has been successful in identifying populations of tumors that are more likely to respond to adjuvant or neoadjuvant chemotherapy (typically the HER2+ and triple negative tumor subtypes) [39;46]. However, while these predictive biomarkers provide useful information to evaluate risk of treatment failure in breast cancer patients, it does not provide essential information to accurately predict which patients within a particular subtype will receive a survival benefit from chemotherapy. pCRs can still be achieved in patients with less chemo-responsive subtypes (albeit rarely); consequently, one cannot forgo neoadjuvant chemotherapy for such patients. On the other hand, even for patients with the most chemoresponsive tumor subtype (HER2), there is only a 50/50 chance (approximately) that the patient with experience a pCR post-treatment [52].

Given these findings, there has been no effective approach to date to definitively predict which patients will respond well to neoadjuvant chemotherapy. Similarly, imaging approaches to monitor tumor drug response during treatment appear unable to reliably predict which patients will receive a survival benefit from chemotherapy. MRI scans can assess changes in tumor size during treatment, but cannot determine whether the tumor of reduced size is viable. Reductions in 18F-deoxy-glucose (FDG) uptake by tumors (as measured by positron emission tomography) often correlate with the achievement of a pCR in patients [53-55], but the sensitivity of this approach is only 23% in common lesions that are less than 10 mm [56] and in well-differentiated or slowly growing tumors that have lower rates of glucose metabolism [57;58]. While the achievement of pCR is the most widely accepted indicator to chemotherapy response, pCRs can only be ascertained post-chemotherapy and therefore cannot be used to guide chemotherapy response for the individual patient during therapy. In addition, pCRs are seldom achieved for patients with ER+ tumors [33;59;60].

An association is described herein between increased tumor RNA disruption mid-treatment and increased DFS MA.22 patients with mid-treatment tumor RDI values in zone 3 had almost 23 months greater DFS than patients with midtreatment tumor RDI values in zone 1 (Table 4). ER+ patients in the MA.22 clinical trial with mid-treatment tumor RDI values in zone 3 had even greater DFS (an extra 29.1 months) compared to equivalent patients in zone 1 (Table 4). In addition, at the time of the analysis, there were almost 3-fold more living patients that had tumor RDI values in zone three than deceased patients with tumor RDI values greater DFS than patients that had mid-treatment tumor RDI chemothervalues in zone 1. Taken together, the above findings on the relationship between elevated tumor RNA disruption and both the increased incidence of a pCR and increased overall or disease-free survival suggests that RDA is highly useful indicator of clinical response to neoadjuvant chemotherapy. Moreover, evidence that patients with a zone 3 level of RNA disruption have similar DFS as patients that achieve a pCR is provided. Patients with ER+ tumours have almost identical DFS as patients that achieve a pCR. The data thus suggests that RDA demonstrates a clinical benefit from chemotherapy for patients with ER+ tumours, even though none of these patients achieved a pCR. In addition, RDA identified almost 5 times the number of non-responding patients with low DFS than clinical response measurements. Midtreatment RDA tests could enable the oncologist to reliably assess a patient's risk of treatment failure, whereby patients with tumor RDI levels in zone 1 during treatment would be deemed unlikely to manifest a pathologic complete response and/or an enhanced DFS from treatment. Moreover, the patient would be expected to be at higher risk of both disease recurrence and death. These assessments, unlike current predictive biomarkers, would be based on an individual tumor's "real time" response to chemotherapy during treatment. As stated previously, current pre-treatment biomarkers, at best, can indicate that a particular patient has a 50% chance of achieving a pCR post-treatment, with no prediction of duration of DFS. This may be helpful for guiding whether to continue chemotherapy or move on to surgery, radiation therapy, or another drug regimen.

Interestingly, patients varied significantly in terms of the extent of their disease-free survival (ranging from 2.4 to 108.9 months). Even the achievement a pCR post-treatment (which has been correlated with prolonged survival [27;28]) did not consistently result in a higher duration of disease-free survival, with two pCR responders have a disease-free survival of <20 months. This is consistent with a variety of other studies that show about 20% of pCR responders die within 100 months of treatment [39]. Why would some patients experiencing a pCR post-treatment exhibit low disease-free survival, such that an additional indicator of drug-response would be an added asset? The first possibility is that pathologic response after chemotherapy is typically assessed using several sections of the post-treatment lesion, but not the entire lesion. Hence, regions of focal disease (cancerous tissues) may have remained posttreatment and missed by the pathologist. Alternatively, the low disease-free survival seen in some MA.22 patients could have been the result of remaining tumor cells and/or tissues distant from the breast and axilla. Supporting this view, it has been shown that the presence of occult cytokeratin-positive metastatic cells in bone marrow is an independent prognostic indicator of the risk of death in patients with stage I, II, or III breast cancer [61]. Such cells may have been present in MA.22 patients that exhibited low disease-free survival, including pCR recipients that had no evidence of disease in the breast and axilla post-treatment.

Table 5 shows mid-treatment tumour RNA disruption and its relationship to MA.22 patient overall survival, disease-free survival (DFS), and pathologic complete response post-treatment. The level of RNA disruption was divided into three zones, where zone 1 (RDI≥0 and ≤10) is the lowest level of RNA disruption, zone 2 (RDA>10 and ≤35) is an intermediate level of RNA disruption, and zone 3 (RDI>35) is a high level of RNA disruption. The number of patients alive with disease (AWD) across the RNA disruption zones was also noted.

Tables 4 and 6 indicates DFS by RDA zone. RDA Zone1-2 Cutoff selected for NPV>0.99 for pCR; RDA Zone 2-3 Cut-off was includes 1 pCR in Zone 2 and 7/8 pCRs in Zone 3. RDA identifies individuals with increased DFS. Furthermore, RDA test results are obtained early during therapy so as to assist "Response Guided Therapy".

Tables 4 and 7 shows DFS in zone 3 patients by tumour subtype. In RDA zone 3 DFS is comparable between patients that show pCR and patients that do not show pCR, irrespective of subtype.

Example 2

The development of metastatic disease is the major cause of death in patients with breast cancer [62]. Metastasizing breast cancer cells disseminate to lymph nodes, peripheral blood, bone marrow and/or other distant sites, in the course of the disease. Metastatic spread often occurs at early stages of the disease: about 30-40% of patients, in fact, with apparently a localized disease, may present occult metastasis, which will be responsible for the disease progression [61, 63].

Recent preclinical and clinical studies have suggested that bone provides a permissive niche to tumour cell growth, and targeting the interactions within the bone milieu may represent an important strategy to suppress tumour development [64]. Although the precise molecular mechanisms underlying this process remain to be elucidated, it is now increasingly being recognized that the unique characteristics of the bone niche provide homing signals to cancer cells, and create a microenvironment conducive for the cancer cells to colonize. Concomitantly, cancer cells release several regulatory factors that result in abnormal bone destruction and/or formation [65]. This bidirectional interaction between the cancer cells and bone microenvironment results in the creation of a "vicious cycle" that increases bone destruction known as bone metastases, ultimately resulting also in establishment/development of cancer micrometastases.

Thus, targeting the pre-metastatic niche, and manipulation of its regulatory mechanisms of indwelling cells may prove highly advantageous in ameliorating the progression of micrometastases and impact on the cancer patients outcome [676].

Bisphosphonates (BP)s have been widely used for the prevention and management of skeletal related event (SRE)s in patients with osteolytic/osteoblastic metastasis. An increasing body of evidence supports their direct and indirect anticancer actions both in vitro and in vivo (reviewed by Clezardin 7). BP as zoledronic acid (ZA) was found to inhibit tumor cell growth, induce tumor cell apoptosis, and synergize with chemotherapy and radiotherapy in vitro [698]. Also in vivo, bisphosphonates induced inhibition of cancer cell proliferation, induction of apoptosis inhibition of angiogenesis, inhibition of tumor migration, invasion, and metastasis; reduction in disseminated tumor cells (DTCs); stimulation of immune surveillance; and suppression of bone-derived growth factors [69-754].

However, the clinical evidence of the BPs anti-tumour effect is still under evaluation. Recent data suggest that the addition of ZA to oncologic therapies improves disease response rate and also outcomes in premenopausal women with early breast cancer [75]; the neoadjuvant subgroup analysis of the AZURE trial showed a significant increase in pCRs in patients treated with ZA and the ABCSG-12 and Z/Zo-FAST have shown a disease-free survival benefit with ZA in women receiving adjuvant endocrine therapy [75, 76]. These experimental and clinical findings carry important clinical implications not only for the treatment of bone metastases but also to reduce the probability of tumor progression [77]. They suggest that BPs should be used early in the clinical management of cancers to positively impact on patients' survival.

However, the concomitant administration of an active anti-neoplastic treatment is a confounding factor to evaluate the real antitumor effect of ZA.

In order to elucidate this issue, a prospective study was performed to investigate the in vivo role of ZA, administered alone in a "biological window therapy" opportunity in two different settings: Group 1 of breast cancer patients with locally advanced breast cancer and Group 2 of "bone only" metastatic breast cancer patients at their first relapse. The anti-tumor action of ZA was evaluated by analyzing proliferation/angiogenesis/death-rate as markers of tumor growth in Group 1 and Circulating Tumor Cell (CTC) number (total and M30+ve) along with soluble markers of cell death as marker of tumor dissemination in Group 2.

Material and Methods
Patients' Characteristics

Thirty-three patients with locally advanced breast cancer (Group 1) and twenty patients at their first relapse with bone metastasis only (Group 2) were considered eligible for the study. They had a histologically confirmed solid neoplasm in Group 1 and presence of only bone metastases in Group 2 evaluated with 18FDG-PET/CT or CT scan identification and radiographic confirmation of bone metastases. Patients' characteristics are shown in Table 8.

Figure 9:
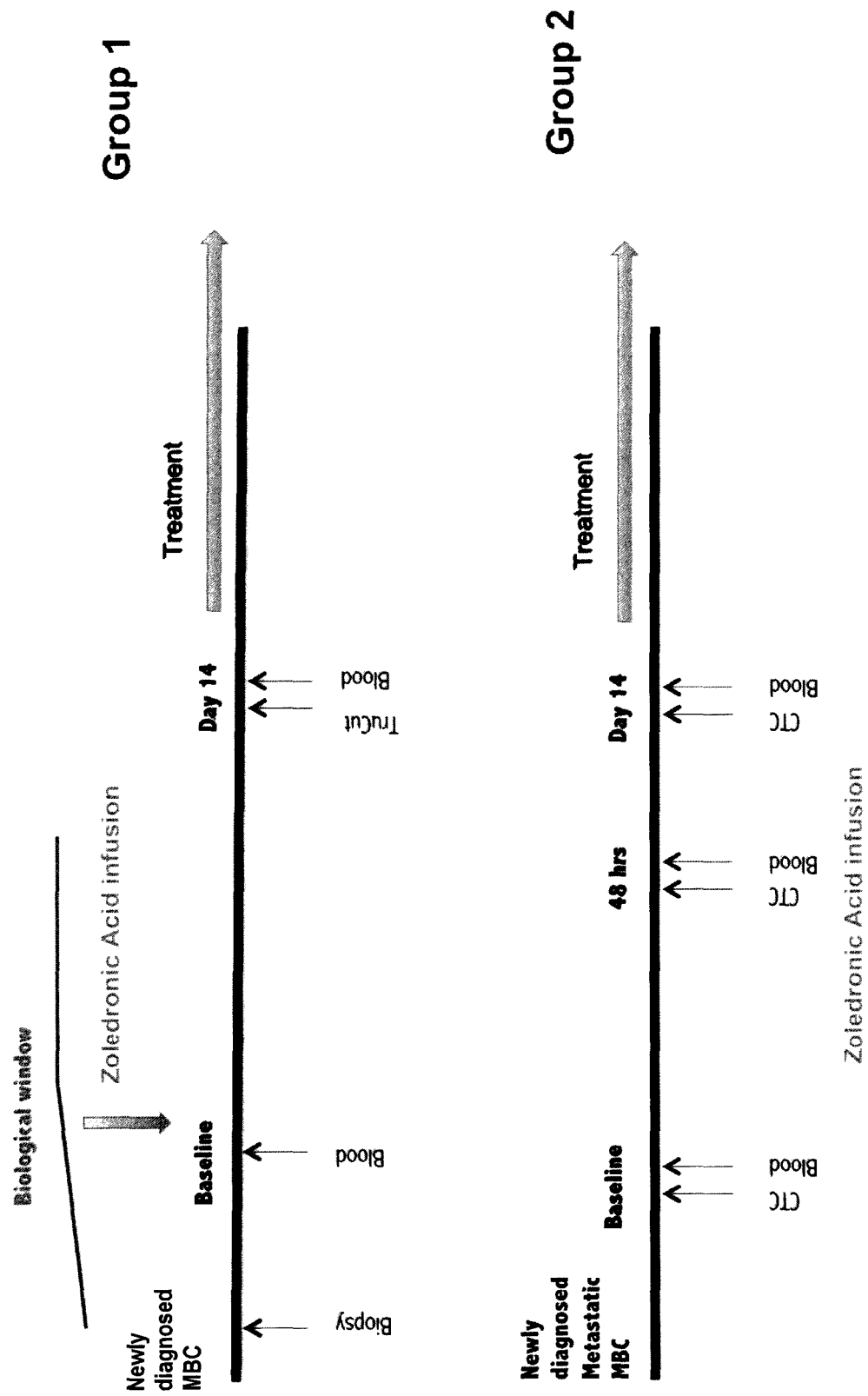
FIG. 9: Diagram of the "biological window opportunity"

Enrolled patients received 4 mg single dose of ZA (Zometa®, Novartis, Milan, Italy) before starting any treatment (biological window of 14 days) (FIG. 9). Markers of tumor proliferation/death were tested immunohistochemically and at ATP and RNA level in tumour specimens obtained before and after ZA administration in those patients with locally advanced breast cancer (Group 1) and the count of circulating tumour cells (CTCs) by CellSearch System along with serological markers as marker of tumor dissemination were carried out in metastatic patients (Group 2).

All patients were required to have at study inclusion a baseline Eastern Cooperative Oncology Group (ECOG) performance status<2, a neutrophil count>1.5×109/liter, a platelet count>100×109/liter, normal hepatic and renal function as determined by serum creatinine<1.5 times the upper limit of normal and creatinine clearance>60 ml/minute and no acute or chronic infections or inflammatory diseases. Patients were considered ineligible for accrual when they had reported fever (body temperature>38.0° C.) during the last week before study entry or had received any radiotherapy, chemotherapy, immunotherapy, or growth factors during the last 4 weeks before study accrual. Any chemotherapy or hormone therapy were excluded during the "biological window" opportunity treatment (2 weeks). Patients recently (<1 week) or simultaneously treated with steroids were considered ineligible for the study. Patients were excluded if they had previously been treated with BPs for the current disease or for previous non neoplastic diseases. During the study period no patient received daily calcium and vitamin D supplementation. All patients received ZA on an out-patients basis and provided written informed consent prior to screening. The institutional review board approved this prospective study (CE Approval EUDRACT number 2007-001526-27).

Treatment Schedule

Patients received a single dose of 4 mg diluted in 100 ml saline, intravenously, in about 15 mins of ZA without any other active concomitant treatments (i.e chemotherapy or endocrine therapy) (Groups 1 and 2). In patients with locally advanced disease, the biological evaluations were performed at baseline on the diagnostic biopsy and repeated after 14 days from ZA administration on a second tru-cut biopsy (Group 1) whereas in patients with bone metastatic disease, CTCs counts along with serological markers were performed before ZA administration, at 48 hours and at 14 days after treatment (Group 2) (FIG. 9).

Immunohistochemistry

Immunohistochemical evaluation was performed on formalin-fixed paraffin-embedded tumor samples obtained at diagnosis and at 14th days on tru-cut. ER, PgR, overexpression of HER2 and Ki67, CD31 with p53 and bcl-2 staining were performed at the Pathology Unit of the Azienda Ospedaliera-Istituti Ospitalieri of Cremona (Italy). The immunohistochemical methodology is fully described elsewhere [79]. The Caspase 3 immunohistochemistry was performed at the Pathology Unit of Peter MacCallum Cancer Centre (Australia); the used methodology followed that reported by others evaluating protein expression in breast tumours [79].

ATP

ATP content was assayed as previously described [80] using a luminescence assay system (ATPlite, PerkinElmer) according to manufacturing instructions. Briefly, frozen tumor biopsies were minced and homogenized in ice-cold lysis solution provided with the kit using a homogenizer. Membranes and cellular debris were eliminated by centrifuging at 12,000×g for 10 min at 4° C. Protein concentrations were determined by DC protein-assay (Bio-Rad Laboratories). Equal amounts of tissue proteins from each sample (30 µg/50 µl of lysis solution) were incubated with 50 µl of luciferine/luciferase substrate solution and analyzed for ATP content by using a Luminescence Counter (Enspire, PerkinElmer). ATP concentrations were calculated on the basis of an ATP standard-curve and expressed as pmol/mg protein.

RNA Disruption Index (RDI)

Tumour samples were shipped in a RNA preservative to Rna Diagnostics (Sudbury, Canada) where they were subsectioned to reduce the amount of tissue for RNA isolation based on gross pathology. RNA was then isolated using the Qiagen miRNeasy kit from each portion of the tumour and the RNA analysed using an Agilent Bioanalyzer 2100. Data from the resulting RNA electropherograms were analysed using proprietary algorithms and an RNA Disruption Index (RDI) value was established for each RNA isolate. Mean RDI values were calculated for each tumour sample.

Circulating Tumor Cells (CTCs) Assay

The enumeration of CTC in whole blood was done by the CellSearch System according to manufacturers instruction as described by Cristofanilli et al. [81]. The identification and count of CTCs was performed using the CellSearch Analyzer, a semi-automated fluorescence-based microscopy system that permits computer-generated reconstruction of cellular images. The criteria used are round or oval morphology, a DAPI positivity, positivity for cytokeratin and negative staining for CD45. Results are expressed as number of cells/7.5 ml of blood. Quality control was maintained via the CellSearch CTC Control Kit used to standardize reagents, instruments, and operator technique.

To quantify the fraction of apoptotic CTC, M30-positive CTC were detected integrating CTC assay with a specific mAb (M30 PEVIVA AB, Bromma, Sweden), recognizing the M30 neoepitope of cytokeratin 18 (CK18), analyzed with the fourth filter of the CellSearch System; results were expressed as the total number of CTC and M30-positive CTC per 7.5 mL of blood as described elsewhere [82].

M30/M65 Apoptosense Assay

Blood samples were collected from patients at the same time-point as indicated for Group 2 into the K2EDTA anticoagulant tubes, and then centrifuged at 1,500 g for 10 min to obtain plasma. Levels of M30 and M65 were measured in blood samples drawn at 8 am before starting ZA administration and thereafter at 48 hours and at 14 days after the initial treatment (FIG. 9).

M30 and M65 measurements were tested in triplicate accordingly to the manufacturers' instructions (PEVIVA AB, Bromma, Sweden) as previously described in detail [83].

Statistical Analysis

Changes in Ki-67 labelling indices, CD31, p53, bcl-2, caspase 3 expression, CTCs counts, M65 and M30 expression over time were tested with the Wilcoxon signed rank test. Relationships were examined using the Spearman's rank correlation. All tests were performed two-sided and p values <0.05 were considered statistically significant. Statistics on ATP and RDA values were done with paired t-test. All analyses were performed with STATA software system (version 12.1, Taxas, USA: www.stata.com).

Results

Patients' Characteristics and Treatment Tolerability

Thirty-three patients with locally advanced breast cancer (Group 1) and twenty-one patients at their first relapse with bone metastasis only (Group 2), were considered eligible for the study. Baseline characteristics of the enrolled patients are summarized in Table 8.

ZA administration was well tolerated. Patients were evaluated by physical examination, and blood samples were obtained for laboratory analysis. Mean serum creatinine level did not vary with treatment. ZA administration did not lead significant difference on the levels of bone-turnover markers, as calcium, PTH, BALP and VIT-D3(1-25). No patient developed osteonecrosis of the jaw or other significant adverse events.

Markers of Tumor Proliferation

Figure 10:
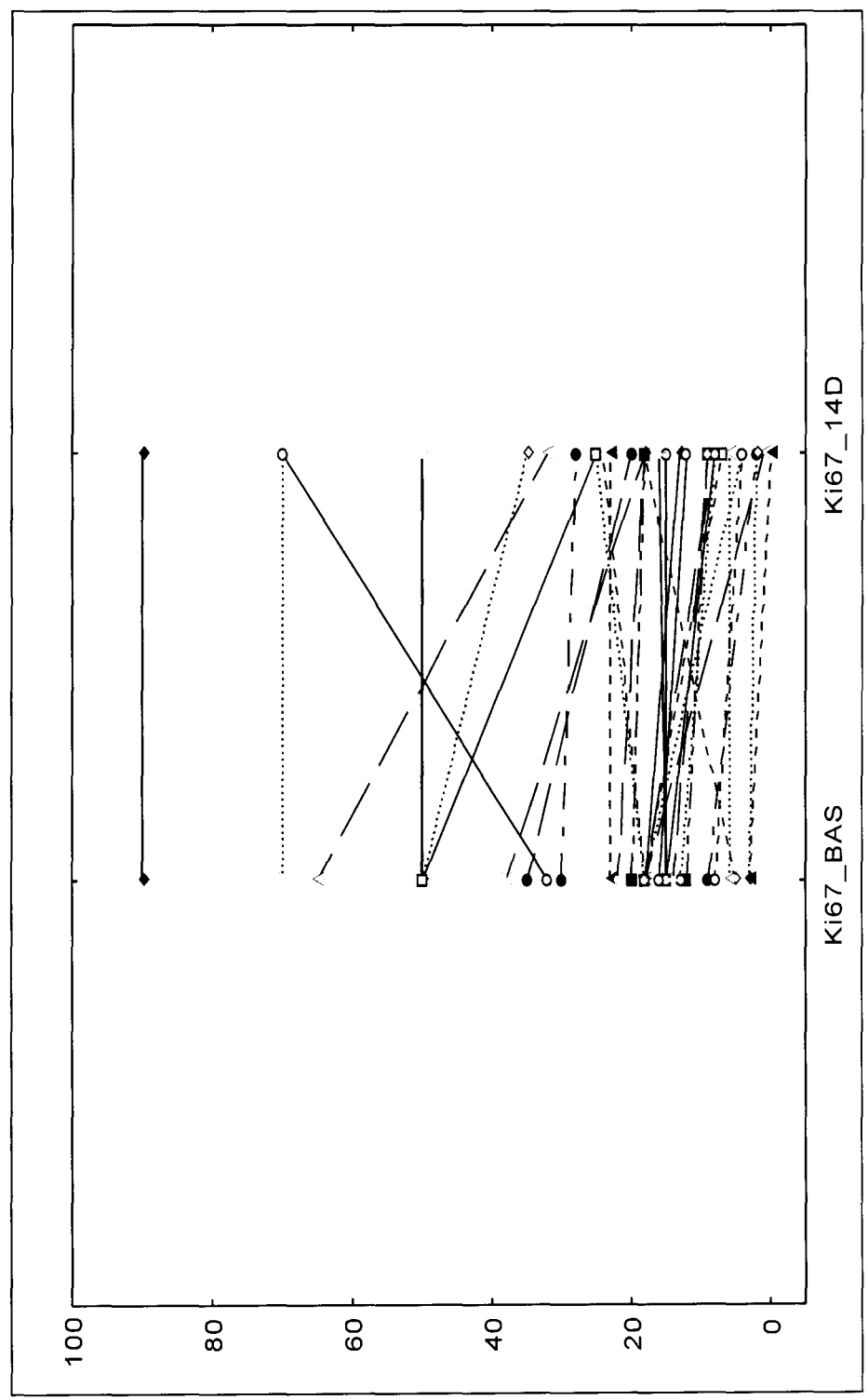
FIG. 10: Changes in Ki-67 (A) and CD31 (B) expression for patients at baseline and post-treatment histology according to treatment received. The large majority of patients randomized receiving ZA showed a suppression of Ki-67 and CD31 expression

In Group 1, no clinical variation in tumour size was detected after treatment with ZA. The median Ki67 basal value (18%; range: 3-90) showed a significant decrease after 14 days of ZA infusion (16%; range: 0-90) ($p=0.0032$); 22 (66.6%) patients had a decrease, 6 (18.2%) an increase and 5 (15.2%) a stable in Ki67 expression under treatment, respectively. FIG. 10 shows the absolute changes of Ki67 expression in each of the 33 evaluated patients. Moreover, the median of CD31 basal expression (27%; range 10-53) showed a significant reduction in expression after treatment (16%; range 9-39) ($p=0.0001$), FIG. 11.

Figure 11:
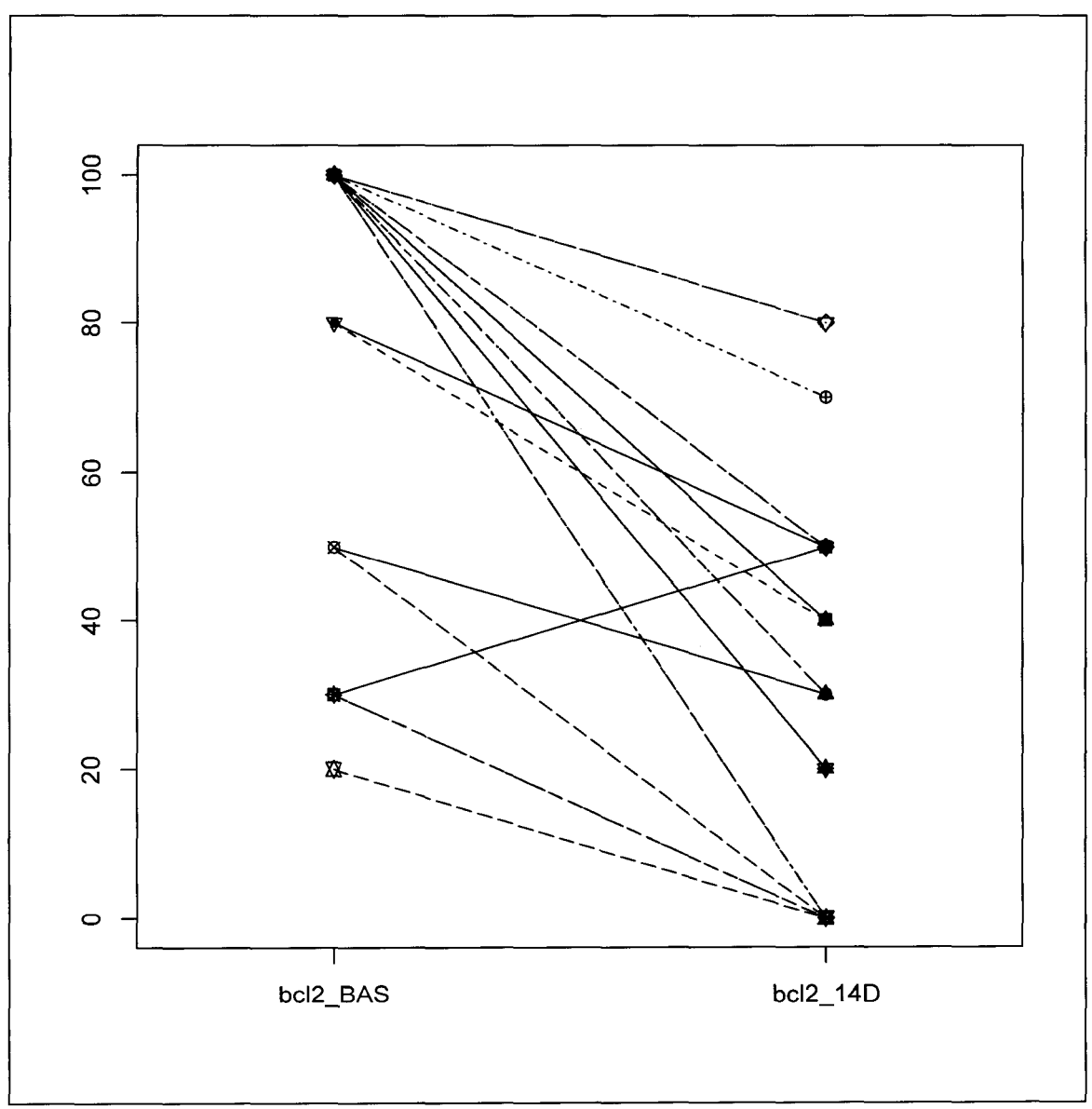
FIG. 11: Changes in bcl-2 and p53 expression for patients at baseline and post-treatment histology according to treatment received. The large majority of patients randomized receiving ZA showed a decrease of bcl-2 expression (A) without changes of p53 expression (B)
Figure 11:
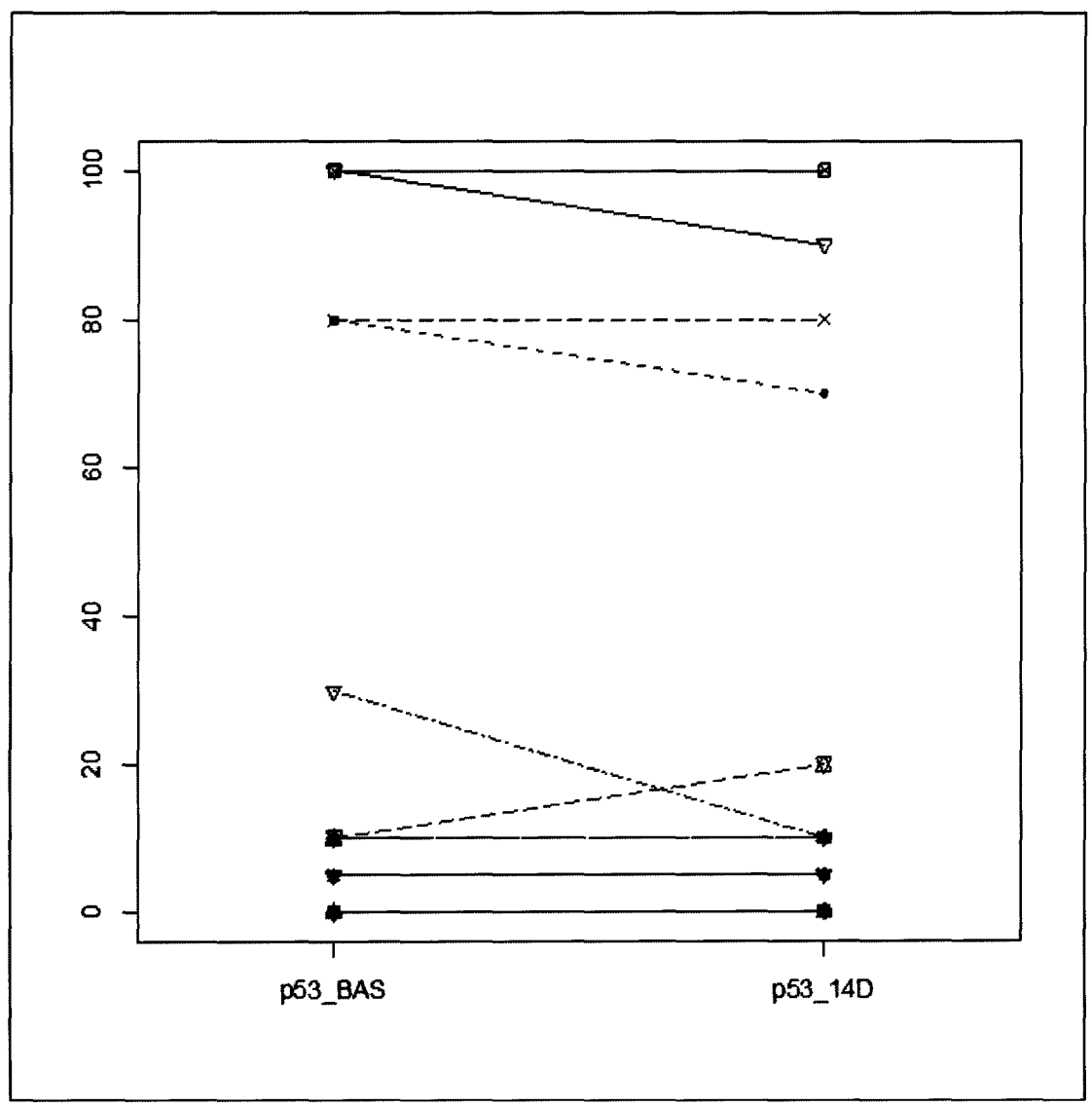

With regards to the markers of apoptosis, no changes in caspase 3 expression before and after treatment were detected; on the counterpart the effect on p53 and bcl-2 expression was also analysed. p53 and bcl-2 data at baseline and after 14 days were available for 31 patients. p53 expression was not affected ($p=0.3094$) by the treatment, being unchanged in 27 specimens (87.1%), increased in 1 (3.2%) and decreased in 3 (9.7%). In contrast, bcl-2 expression showed a statistically significant decrease ($p<0.00001$) from baseline (100%; range: 20-100) to the 14 days (40%; range 0-80), being decreased in 30 specimens (96.8%), and increased in only 1 (3.2%) (FIG. 11).

Figure 12:
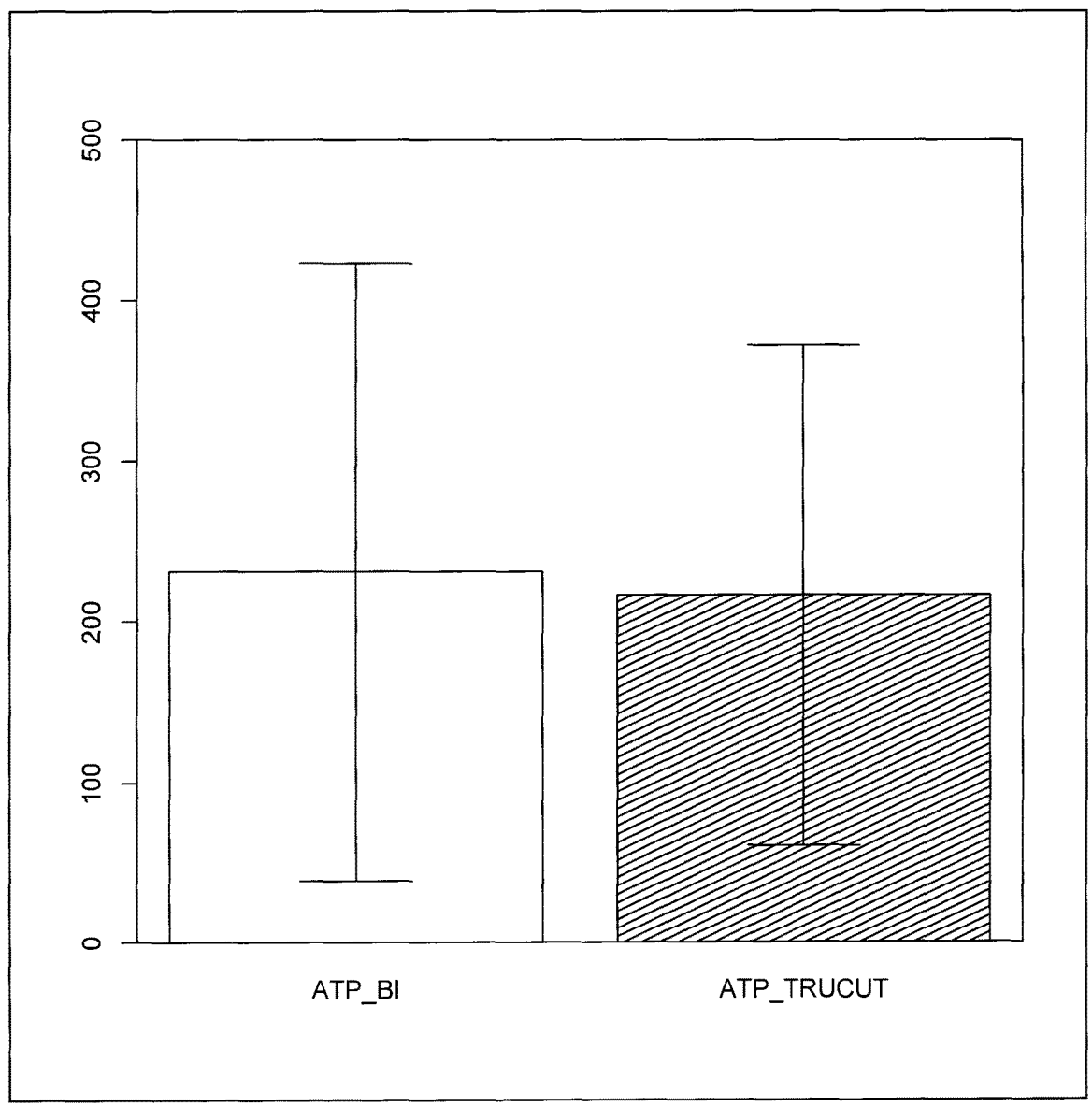
FIG. 12: Median values of ATP levels in the tumor specimens at baseline and after 14 days of administration of ZA

As shown in FIG. 12, in 24 analysed matched-pairs samples, the average of ATP value was 230.93 pmol/mg protein at the incisional biopsy and 216.57 pmol/mg protein at the tru-cut after administration of ZA, respectively, indicating a slightly increase of antitumor activity of ZA detected by the reduction of tumour energy in primary breast cancer. However, the difference between the two groups was not significant ($p=0.79$).

Figure 13:
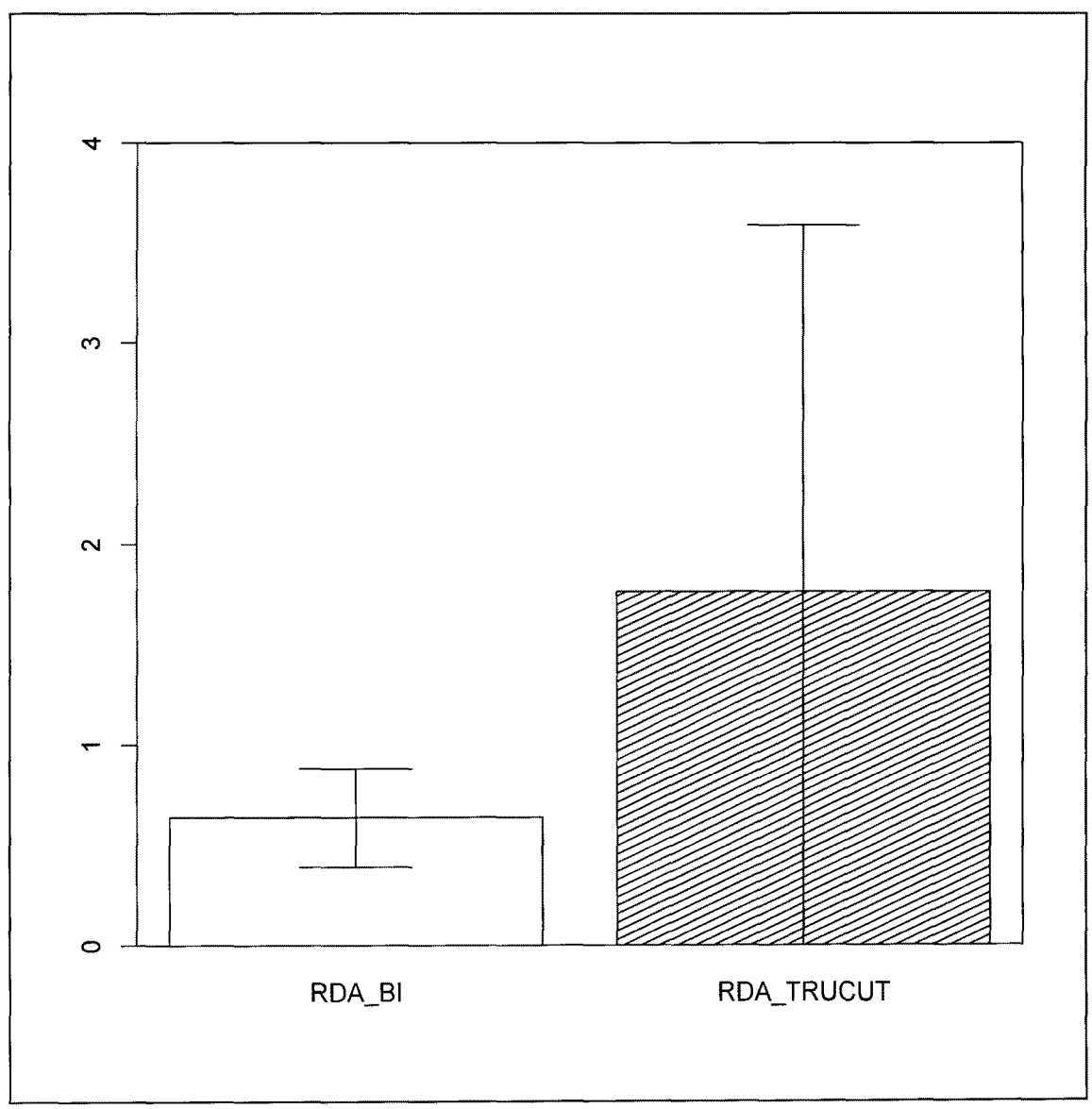
FIG. 13: Median values of RDI levels in the tumor specimens before (baseline) and after (14 days) administration of ZA (p<0.0076)

Also, in 14 matched-pairs samples, analysing the RNA Disruption Index (RDI) induced by the treatment it was noticed that the single administration of ZA induced a significant increase ($p<0.0076$) of RDI levels after treatment (baseline: 0.63; range 0.29-0.95; 14 days: 1.21; range 0.53-7.51) suggesting an alteration of RNA integrity by the bisphosphonate (FIG. 13). Of note, there was no correlation of Ki 67 with RNA Disruption.

Marker of Tumor Dissemination

Figure 14:
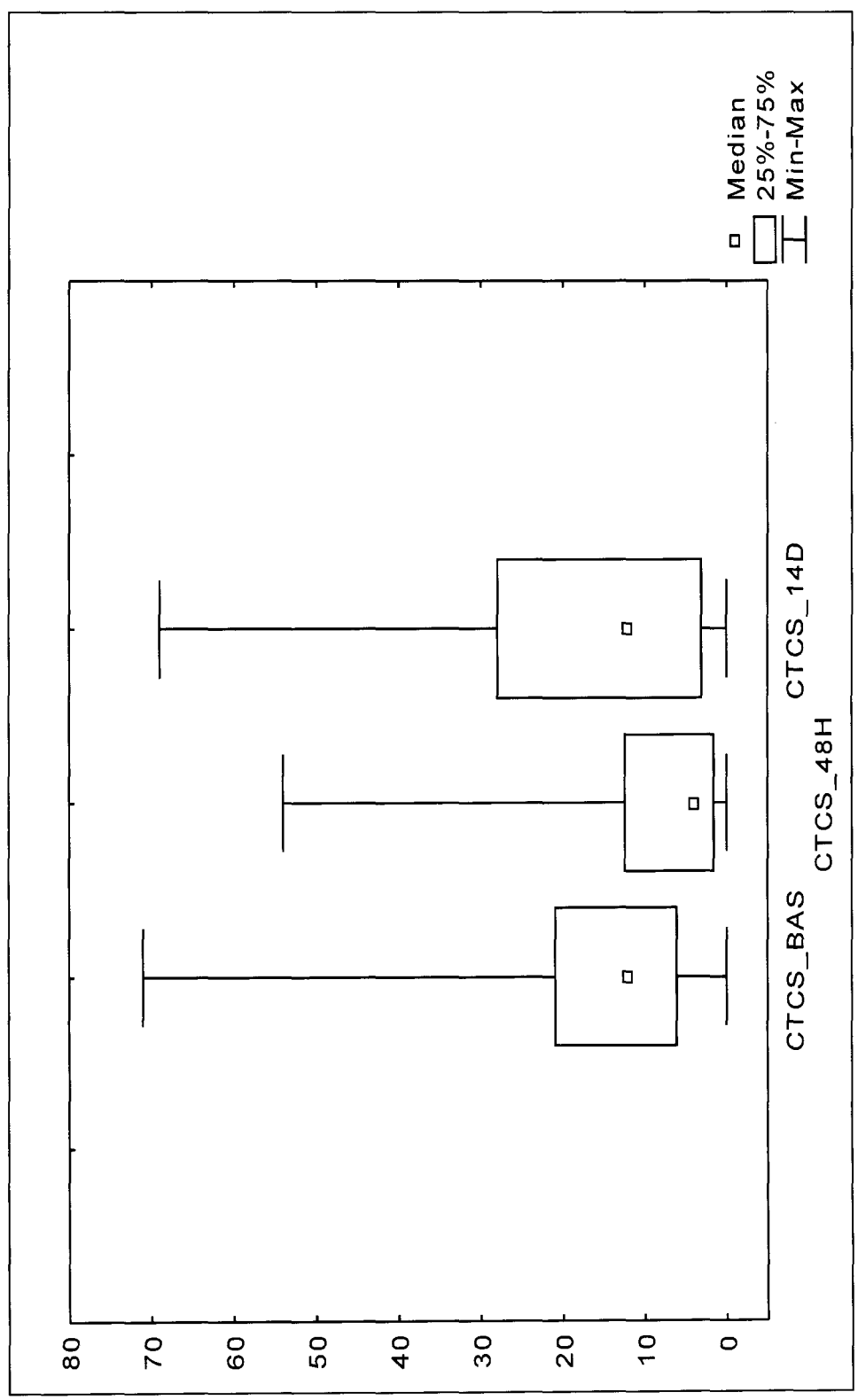
FIG. 14: Changes in CTCs at baseline, at 48 hours and at 14 days after ZA administration. A) Alive CTCs; the number of CTCs decrease after treatment (p=0.0012) at 48 hours; the effect still present after 14 days (p=0.012) B) Apoptotic CTCs/M30+ve; the number of CTC/M30+ve increase after treatment (p=0.018) at 14 days
Figure 14:
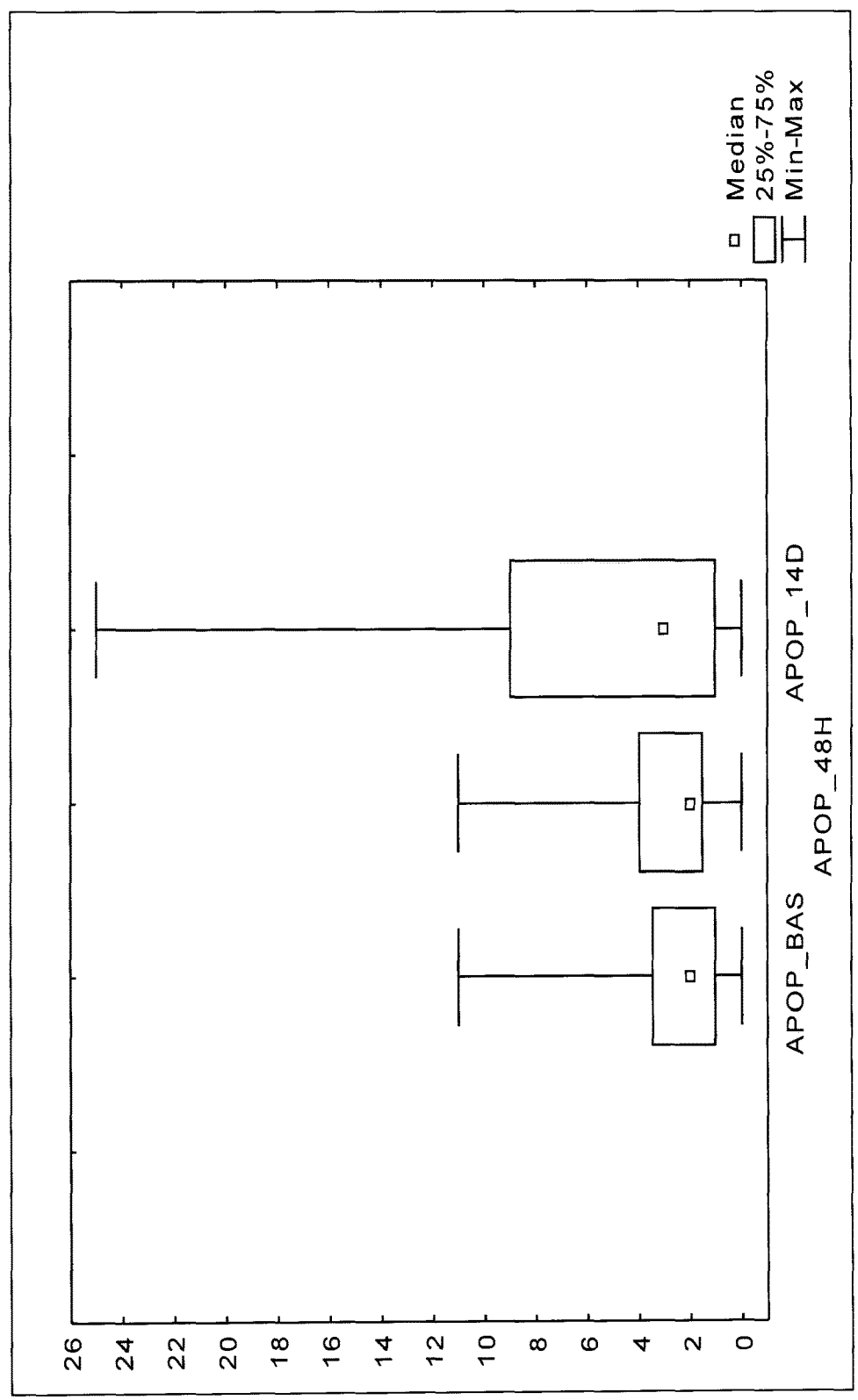

The effects on median alive circulating CTC levels tested at 0, 2 and 14 days after the first ZA infusion were observed. The median CTC basal value (12 cells/7.5 ml of blood; range: 0-71) showed an early statistically significant ($p=0.0012$) decrease already 48 hours after the first ZA infusion (4 cells/7.5 ml of blood; range: 0-54) (FIG. 14 A). No differences were noted between baseline and 14 days ($p=0.6574$)

With regards to the apoptotic CTCs/M30+ve, the median of basal CTC/M30+ve value (2 cells/7.5 ml of blood; range: 0-11) showed an increase level after treatment: at 14 days (3 cells/7.5 ml of blood; range: 0-25) ($p=0.018$) (FIG. 14B): no significant changes at 48 hours (2 cells/7.5 ml of blood; range: 0-11) ($p=0.7065$) were observed. Significant increase of CTC/M30+ve cells were noted between 48 hrs and 14 days ($p<0.019$)

Figure 15:
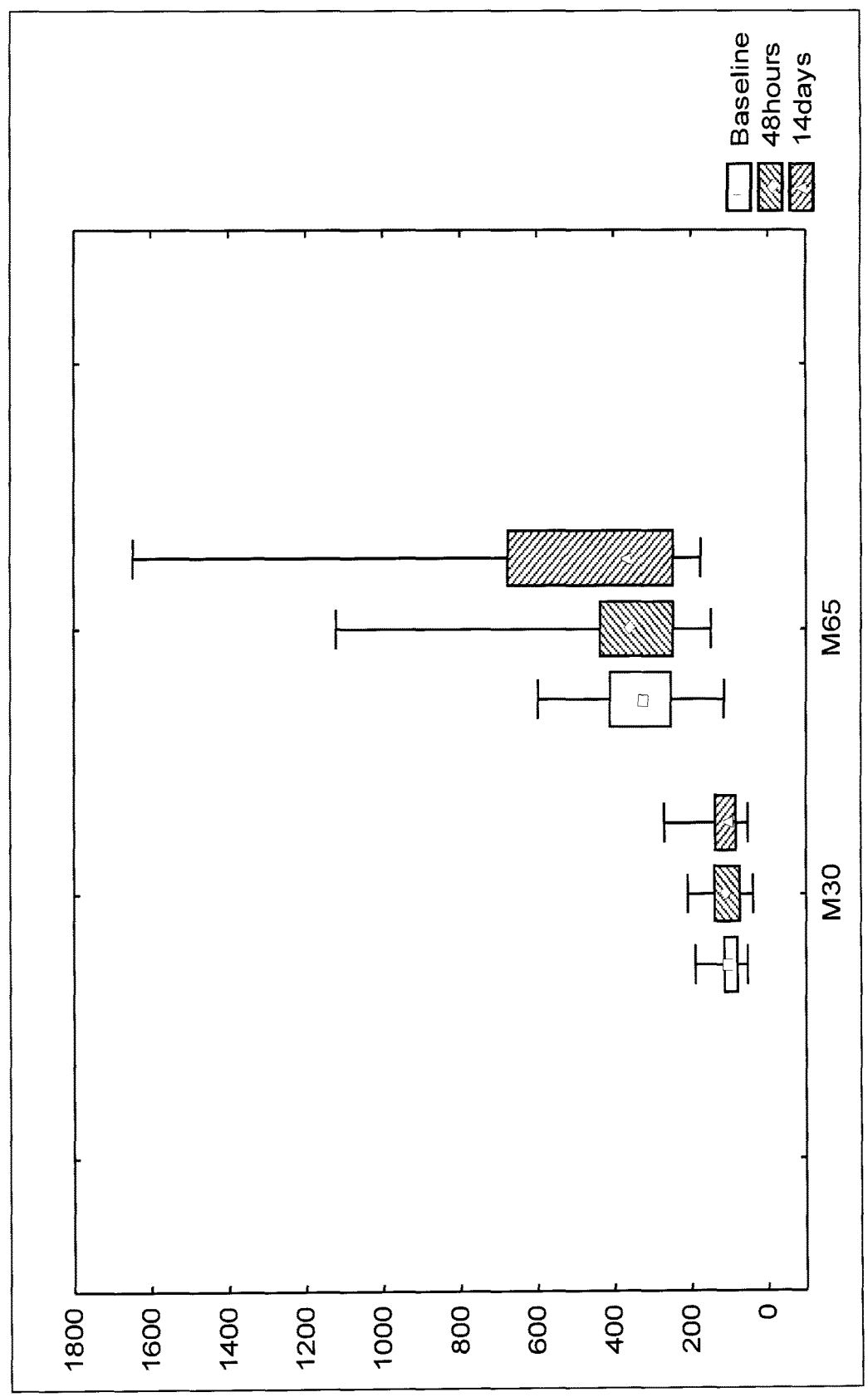
FIG. 15: Changes in M30 and M65 levels at baseline, at 48 hours and at 14 days after zoledronic acid administration. No changes of M30 were detected; M65 levels were statistically significant higher after drug administration when compared to the baseline (p<0.039).

The M30 is a biomarker assay for the quantitative determination of caspase-cleaved cytokeratin 18 (CK18) released from apoptotic carcinoma cells into blood and may estimate the tumour response to the treatment. Total CK18 (cleaved and non cleaved) is detected by M65. The levels of M30 and M65 were determined on blood samples of metastatic breast cancer patients (Group 2) collected at baseline, at 48 hours and at 14 days after ZA administration at the same time point of CTCs evaluation to assess apoptosis and cell death induced by the treatment. In Group 2, no statistically significant change in serum M30 level was observed before and after ZA treatment (p=0.9811) or at 48 hours after administration (p=0.2461). M65 levels were statistically significant higher after drug administration (14 days) when compared to the baseline (370.69 U/L versus 335.3 U/L; range 174.2-1646.5 versus 113.7-596.4; p=0.039). A non-significant increase was detected after 48 hours from infusion (p=0.1128). Serum M30 and M65 levels during ZA treatment are summarized in FIG. 15.

Discussion

Zoledronic acid (ZA) is now the standard treatment in clinical routine in the management of patients with metastatic bone disease in preventing SRE [84] and evidence from its antitumor activity suggest a role in the adjuvant treatment of breast cancer in order to improve the disease free survival [77]. Recent papers showed the capacity of ZA to improve chemotherapy activity inducing a higher rate of pCR in neoadjuvant setting [75] and, in postmenopausal, to induce a consistent improvement in both DFS and OS [85, 86]. In spite of these data, a possible anti-proliferative/anti-tumor activity of ZA is still a matter of investigation as the published studies in clinical setting are always based on the combination of ZA with chemotherapy. If a trend for a higher proportion of patients treated with the combination achieving pCR compared with chemotherapy (CT) alone led to the antitumor hypothesis of ZA in vivo, the molecular mechanisms behind this synergy remain to be established. Winter at al [87] have tried to explain the phenomenon analysing the role of ZA on cell growth index (increased apoptosis and reduced proliferation) which did not show a significant changes between the two groups (chemotherapy+ZA arm and chemotherapy alone arm). An early greater reduction in serum VEGF was noted with the combination compared with CT only. Preclinical studies have shown sequence-dependent synergy between chemotherapy agents and ZA including an increased tumor cell apoptosis, reduced tumor proliferation, and inhibition of tumor vascularization as an antitumor effects [70]. In clinical setting the reproducibility of the data is still difficult maybe due to the difficulty of designing a proper trial to investigate these topics, or to the interaction of tumor microenvironment with the administered treatments, or to the presence of CT in combination with ZA which could cover the real biological effect of the BP.

In order to understand the pure anti-tumor activity of ZA along with the possible implicated molecular mechanisms in breast cancer patients the study investigated the biologic effects of ZA in neo-adjuvant setting and in bone only" metastatic breast cancer at their first relapse administered alone in a "biological window therapy" opportunity.

In neoadjuvant setting, ZA exerts an antitumor activity showing a significant reduction of Ki67 after 14 days. These data are aligned with the early reduction of proliferation induced by hormone therapy or CT suggesting a real effect of BP on proliferating tumour cells[88]. ZA also showed a concomitant reduction of the proliferation of endothelial cells, evaluated by immunohistochemical staining (CD31) confirming in breast cancer patients its anti-angiogenic activity already showed in vitro [89].

This possible effect of ZA is of potential clinical significance, as studies have correlated high expression or changes of Ki67 and/or CD31 with disease progression or poor survival [90, 91] [78]. Focusing of apoptosis-related markers, the study showed a significant ZA-induced decrease in bcl-2 expression and in p53 and caspase 3 expression after 14 days. This induction of apoptosis includes the activation of the intrinsic mitochondrial pathway leading to a release of cytochrome c into the cytosol where it triggers a number of apoptotic events, including the activation of AIF (Apoptosis Inducing Factor) or caspase 9 which in turn activates caspase 3 and caspase 7 [92] [93]. The un-changed expression of caspase 3 induced by the treatment may suggest that the apoptosis event could be dependent on AIF which exits through the mitochondrial membrane, enters the cytosol, and finally ends up in the cell nucleus where it signals the cell to condense its chromosomes and fragment its DNA molecules in order to prepare for cell death [94]. In the study, p53 expression was also not affected by the treatment suggesting that ZA could exert cytotoxic effects against p53-mutant cancer cells similar to those against the wt-p53 parental cells [95], demonstrating for the first time in vivo that ZA-induced apoptosis does not involve the p53 signaling cascade.

Nutrient and metabolic molecules as intracellular amino acid and adenosine triphosphate (ATP) availability are crucial for cell-life and their absence leads to cell-death. WThe intracellular content of ATP was measured as a possible surrogate marker of anti-tumor activity of ZA. The data showed only a slightly reduction in ATP level at the tumor level induced by a single shot of ZA. However, they are aligned with Fehm T et al's report [96]. They have investigated the anti-proliferative effect of ZA in freshly ex vivo resected human breast specimens and compared it to the effect of commonly used chemotherapeutic regimen, such as FEC and TAC using ATP luminescence assay. The results revealed that ZA was at least equal or even superior in its anti-tumoral effect (seen as a reduction of ATP level in the tumor) when compared to both combined regimens [96].

Knowing that with a larger sample-size the magnitude of the detected ZA effects on ATP levels should be more pronounced, however, the data altogether showed that ZA induced tumor cell apoptosis via mitochondrial pathway associated via a reduction in ATP levels.

The antitumor effect of ZA was seen also at RNA level. The ribosomal RNA (rRNA) is usually very highly conserved: intact rRNA is necessary for full ribosome function and cell survival. However, abnormal rRNA peaks, termed "RNA Disruption", were identified and are generally absent in pre-therapy samples [97, 98]. If RNA Disruption affects only a portion of cells or if the RNA disruption is subcritical, tumour cells can survive with compromised function. When rRNA structure is sufficiently disrupted the cell can no longer make proteins and other substances necessary for cell division. If rRNA disruption is more extensive, the cell cannot maintain its basic functions leading to subsequent cell death. The study showed a significant increase of rRNA disruption after treatment indicating decreased rRNA integrity induced by the administered treatment. These data enforce the previous results related to the antitumor effect of ZA.

Circulating tumor cells (CTCs) are a biomarker for prognosis and predictor for therapeutic response and represent a liquid biopsy useful for monitoring the activity of the administered treatments or for selection of personalized treatments [99]. This approach was used in patients at their first relapse with bone metastasis only to understand the anti-tumor effect of ZA on CTCs. A significant reduction was detected after 48 hours only with a slight increase till the 14 days. Concomitantly a significant increase of apoptotic circulating tumor cells marked with M30 (as described before [82]) after 14 days was observed. These data are in agreement with the reports on ZA based-treatment, which showed a reduction of disseminated tumor cells (DTCs) in the bone marrow of patients with breast cancer [100, 101]. ZA showed a decrease in tumor cell proliferation as it occurs under chemotherapy, as early as 24 to 48 hours [102] [101]. The early reduction of alive CTCs/increased of M30+ve CTCs could be explained by the pharmacokinetic of ZA. ZA plasma disposition is multiphasic: half-lifes of 0.2 and 1.4 hours represent an early rapid decline of peak concentrations from the end of infusion to <1% of Cmax at 24 h post-dose during which ZA shows its activity, and half-lifes of 39 and 4526 hours describe subsequent phases of very low concentrations between days 2 and 28 post-dose [103]. Elimination occurs almost exclusively by the kidney. Within 24 hours after ZA administration, up to 41% of the dose infused is excreted unmetabolized in the urine, suggesting that 60% of the dose is retained in the skeleton or in fat tissue. Bone remodeling processes or fat tissue will slowly release retained ZA back into the systemic circulation where it could exert its activity before being excreted [104].

M30 and M65 are biomarker of apoptosis and they are increasingly used for the evaluation of responses to anti-cancer drugs in several tumor types [105]. In the series M30 did not show a significant changes neither in an early phase nor in a late phase under ZA administration. This data is aligned with the late increase of M30+ve CTCS, suggesting that the induction of apoptosis by ZA is a slow process.

Although deregulated control of apoptosis has been suggested to contribute to tumor development and progression in most cancers, increased levels of M65 might indicate that predominant cell death might be caused by necrosis rather than apoptosis in this setting. It has been proven that cells undergo necrosis instead of apoptosis due to insufficient production of ATP [106] and in the series ZA was able to reduce the tumoral ATP level after treatment. In the present study, M30 levels were not statistically modified by the treatment; in contrast, serum M65 levels were associated with significant increase. Increase of cell death, especially necrotic cell death, might be reflecting the ZA activity on the most aggressive behaviour of cancer cells; on the counterpart the induction of apoptosis by ZA is confined to the less aggressive cancer cells. These data, taken together, support the hypothesis that ZA is able to modulate the tumor dissemination reducing the alive CTCs and increasing the apoptotic counterpart, mirroring what found on tumor tissue exposed to ZA in the same biological window treatment.

In conclusion the changes in the analysed biomarkers suggest a critical role of zoledronic acid in anti-tumor proliferation and anti-tumor dissemination maybe due to relevant interactions between ZA, tumor biology and bone microenvironment. The data strongly support the use of ZA in combination to oncological treatments in breast cancer patients in order to achieve a better outcome.

Example 3

As there is now evidence that switching non responders to primary systemic therapy can enhance survival in some breast cancer patients, the need for an intermediate endpoint that can guide treatment response is needed. Recently, chemotherapy drugs have been shown to induce RNA disruption in tumour cells, leading to subsequent tumour cell death.

RNA Disruption in tumour cells was quantitated from RNA electrophoresis and expressed as a RNA Disruption Index (RDI). To develop a RNA Disruption Assay (RDA), RDI, and pCRs from the NCIC-CTG MA.22 breast cancer clinical trial were used as an index study. Patients were stratified into Zone 1, pCR non-responders, Zone 2, intermediate response and Zone 3 including most pCR responders.

As well, to determine early response, RNA Disruption was examined by RDI effect in 85 breast cancers after 15 days exposure to either Trastuzumab, or Zoledronic Acid, or Letrozole+Cyclophosphamide±Sorafenib therapy.

RDA stratified 23 of 85 patients in Zone 1 as pCR non responders, 24 patients in zone 2, an intermediate zone and 38 patients in Zone 3, likely responders. In the early response studies, after 15 days exposure to chemotherapy, RNA Disruption as measured by RDI elevation could be detected in 3/12 trastuzumab, 8/15 zoledronic acid, 4/29 Letrozole+Cyclophosphamide, and 5/23 Letrozole+Cyclophosphamide+Sorafenib patients.

RNA Disruption Assay is a novel intermediate endpoint that has promise for clinical utility early in response guided primary systemic therapy.

It is well recognized that primary systemic therapy results in an increase in disease free survival only in a minority of breast cancer patients[31,32], even though most tumours shrink with treatment as assessed by palpation and imaging techniques[30]. Because all chemotherapy patients experience severe side effects whether or not treatment has enhanced survival benefit, the search for an effective intermediate endpoint for drug response in primary systemic therapy of breast cancer has been a long sought goal.[36-38] As there is evidence that switching therapy of nonresponders early in therapy enhances pCR and survival, the need for a test to identify chemotherapy nonresponders early in chemotherapy is increasingly urgent.[39]

An ideal intermediate endpoint would be able to stratify patients for disease free survival or overall survival sufficiently early in therapy to be useful for decision making where the endpoint indicates that the patient is not responding or inadequately responding to therapy. Of course, an endpoint that also indicates with high probability that the patient is responding to therapy would have high reassurance value for both patients and their physicians. Validating such an endpoint using archived samples by strict level of evidence criteria is recognized as a formidable task[41]. These criteria include: adequate archived samples from a completed prospective clinical trial, preanalytical and analytical reproducibility, focus on a single classifier, and clinical validation through one or more similar studies involving an independent population.[41]

An assay for measuring RNA disruption has been developed and is a more accurate predictor of chemotherapy effect, both positive and negative, than the Agilent or Bio-Rad RNA Quality RIN indices because their algorithms were designed primarily to assess the degree of RNA autolytic degradation.

RNA Disruption and Chemotherapy

RNA is a major component of the cell representing about 1% of cell content. About 85% of the cell's RNA is in ribosomes. Each ribosome contains 4 RNA molecules, 5S, 5.8 s, 18S, 28S, collectively termed ribosomal RNA (rRNA), which are visualized as the only distinct peaks in normal RNA electrophoresis. rRNA is usually very highly conserved although rRNA disorders known as ribosomopathies are now recognized[107]. Intact rRNA is necessary for full ribosome function and cell survival. By studying the RNA electrophoretic patterns of mid treatment tumour RNA samples, abnormal rRNA peaks were identified which were termed "RNA Disruption". These peaks were generally absent in pre therapy samples and were very distinct from the peaks in the fast region associated with RNA autolytic degradation[43] and RNA cleavage peaks described with apoptosis[97,98]. If RNA Disruption affects only a portion of cells or if the RNA disruption is subcritical, tumour cells can survive with compromised function. When rRNA structure is sufficiently disrupted the cell can no longer make proteins and other substances necessary for cell division. If rRNA disruption is more extensive, the cell cannot maintain its basic functions and the cell dies. These graded effects of RNA Disruption have been shown experimentally by using increasing doses of docetaxel in tumour cell culture. In cell culture, chemotherapy drugs are known to alter rRNA metabolism[108] and ribosome biogenesis at levels of rRNA transcription as well as early or late rRNA processing[109]. Further, Fimognari et al[110] detected RNA damage as aberrant patterns in RNA electropherograms derived from cell cultures exposed to doxorubicin and other agents. Copois et al[111] observed compromised RNA quality in human colon cancer tissues previously exposed to chemotherapy in vivo and developed a RNA Quality Scale (RQS) in which one component included abnormal rRNA electrophoretic peaks between 28S and 18S RNA peaks.

RNA Disruption Assay Development

Figure 35:
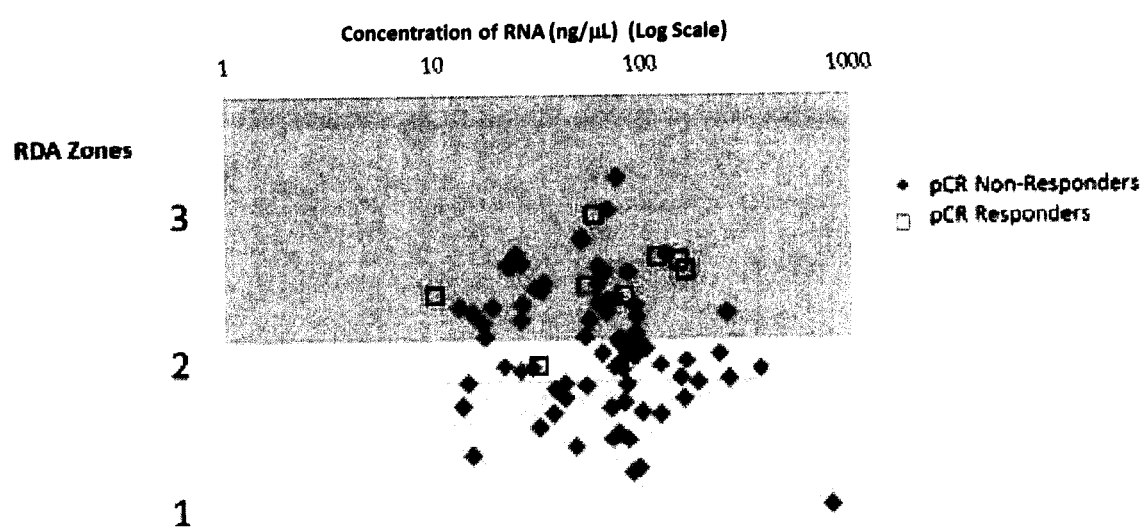
FIG. 35 is a table that demonstrates the distribution of MA.22 patients in the RDA zones.

Methods to quantify the disrupted RNA in each sample and to express the results as a RNA Disruption Index (RDI) were developed. RDI data from 85 MA.22 patients who completed the trial were stratified into 3 clinical zones based on their mid-treatment RDI and subsequent pCR response. pCR was defined strictly as no residual tumour in either the breast or axillary regional nodes. A priori, a Zone 1, Zone 2 cut off with Negative Predictive Value (NPV) for pCR >0.99 (RDI=10) was established. Below this cut off level, the chance of achieving pCR is <1%. Zone 3 was established above the Zone 2, 3 cut off level with a Positive Predictive Value for pCR of >2 (RDI=35). FIG. 35 demonstrates the distribution of MA.22 patients in the RDA zones. RDA, vertical axis is plotted on a log scale as is the horizontal axis, RNA concentration. Zone 3 incorporated 7 of 8 pCRs and Zone 2 incorporated 1 pCR observed. RDA showed 23 patients (27%) distributed in Zone 1, 24 patients, Zone 2 (28%) and 38 patients in Zone 3 (45%). RDA can be measured accurately over 3 orders of RNA concentration magnitude 10-1000 ng/ul with limit of detection <10 ng/ul. Hr+ve, Her2+ve and Triple Negative breast cancer subtypes were present in all 3 zones. Specifically, midtreatment RDI did not correlate with tumor shrinkage as observed clinically or by imaging performed before and during therapy.

Early Response Studies

For a response intermediate endpoint to be maximally effective, it is desirable that the endpoint demonstrate its effect early in chemotherapy, preferably within the first two weeks of starting therapy. Preliminary data has been obtained in biologic window of opportunity trials for 5 agents, Trastuzumab, zoledronic Acid, Letrozole+Cyclophosphamide and Letazole+Cyclophosphamide+Sorafenib in breast cancer T2-4, N 0-1, M0 after 15 days exposure, with control biopsies pre-therapy (Table 9B). The Limit of Detection for RDI s RDI=0.3. RDI=1.5, 5 times the Level of Detection, was used as a provisional baseline cut off between nonresponders and responders. Most striking, by this conservative criteria, 8 of 15 patients exposed to zoledronic acid; 4 in the Letrozole-cyclophosphamide group, 5 in the Letrazole+Cyclophosphamide+Sorafenib and 3 in the Trastuzumab group showed elevated RDI. RDI did not correlate with tumour response as observed by clinical PET or MRI.

Discussion pCR is well recognized as the best intermediate endpoint to predict disease free survival. However, pCR has severe limitations which limit its utility for response guided therapy, including its availability only after therapy, and pCR response in <10% of hormone receptor positive (HR+ve) patients[31,59,60]. Like pCR, RDI is a direct marker of drug effect to incapacitate tumour cells but RDI can be measured before cell death. For zone 3 patients, RDA may have predictive power not only for patients achieving pCR but for the entire patient population irrespective of subtypes. In zone 1, RDA predicts strongly those patients who are not responding to therapy and in Zone 2, those patients responding insufficiently to therapy.

These results suggest that measuring enhanced survival particularly in HR+ve patients, may provide a better measure of drug effect on DFS.

While the early response studies are preliminary, the results indicate that in some tumours, RDI elevation can be detected as early as two weeks after start of metronomic therapy. Further, for each of the drug regimens studied but especially for zoledronic acid, there is direct indication in human breast cancer that RNA Disruption has broader specificities than just anthracyclines and taxanes as previously demonstrated in the MA.22 study.

The search for an effective intermediate endpoint useful for guiding therapeutic response has encompassed imaging, molecular and histochemical markers but up to the present, none has proved more accurate than pCR. _RDA can stratify the portion of the patient population that will not subsequently develop pCR.] Further, RDA can be applied to the entire patient population early during therapy at a time where treatment changes can be considered for non-responders. Experimentally, RNA Disruption has been shown to be a mechanism which results in subsequent death of cancer cells. Presently, RDA appears to be a most promising intermediate endpoint in development for response guided primary systemic therapy of breast cancer.

Example 4

Chemotherapy-dependent changes in tumour RNA integrity result in distinct changes to the tumour RNA banding pattern (termed "RNA disruption", which have been found to be distinct from that observed upon autolytic RNA degradation). RNA electrophoretic changes have been previously observed in vitro in response to a variety of apoptosis-inducing agents 112,97, 113]. An in vitro model of RNA disruption by anti-cancer agents was established in order to better understand the cellular and biochemical mechanisms associated with this phenomenon and its relation, if any, to apoptosis.

Methods:

Various cell lines were treated with anti-cancer agents and the effects of these treatments on the cellular RNA banding pattern, Annexin V-FITC binding to cells, cellular DNA content, poly ADP ribose polymerase (PARP) cleavage, and cell proliferation in the absence of drug post-treatment were assessed. The effect of an inhibitor of effector caspases (Q-DEVD-Oph) on RNA disruption by specific chemotherapy agents was also examined.

Results:

The A2780 ovarian tumour cell line was particularly adept at manifesting RNA disruption in culture in response to a wide variety of anti-cancer agents (alone or in combination), including paclitaxel, docetaxel, epirubicin, carboplatin, and radiation therapy. Alterations in the RNA banding pattern were both dose- and time-dependent and were similar for some classes or types of anti-cancer agents, but not others. Upon achieving a specific level of RNA disruption by chemotherapy drugs, cells were no longer able to replicate in culture, even in drug-free culture medium. RNA disruption by the chemotherapy agent docetaxel was found to be temporally associated with apoptosis induction in cells, as exhibited by the ability of the drug to: a) enhance Annexin V-FITC binding to cells, b) generate cells containing a sub-G1 level of DNA content, and c) induce the cleavage of poly ADP ribose polymerase (PARP). However, no DNA laddering was observed and cells appeared to retain their membrane integrity, as seen by the lack of propiclium iodide staining after drug-treatment. Interestingly, it was observed that docetaxel activated cellular caspase activity and that the caspase inhibitor Q-DEVD-Oph significantly reduced RNA disruption, as seen through reduced levels of aberrant rRNA bands and increased levels of 28S and 18S rRNA bands.

Discussion and Conclusions:

An in vitro model of RNA disruption by chemotherapy agents is described. RNA disruption by some anti-cancer agents can be temporally correlated with the activation of apoptotic pathways and RNA disruption can be associated with activation of cellular caspases. However, RNA cleavage by apoptosis-inducing agents has been shown to occur in the absence of apoptosis [98] and apoptosis can occur without RNA disruption [114]. Moreover, it is known that caspases regulate cell cycle progression (independently of their role in apoptosis regulation) and that the caspase-inhibitor Q-DEVD-Cho can induce late stage mitotic arrest [115]. It remains unclear whether apoptosis induction is important for chemotherapy-induced RNA disruption.

Example 5

The media used in these experiments contained 5% FBS; 50% media is media diluted in PBS (1:1).

RNA was isolated from a core biopsy of a MCF-7 tumour xenograft that has been kept at room temperature in saline for 24 hours where autolytic degradation takes place and separated using an Agilent 2100 Bioanalyzer.

RNA was isolated from ovarian cancer cell line A2780 cells which had been treated with 10 µM docetaxel in 50% media or 20 µM epirubicin, each in 50% media. Cells were treated with the chemotherapeutic for 24 hours at 37° C. Isolated RNA was separated by microcapillary electrophoresis using the Agilent 2100 Bioanalyzer.

FIGS. 16-18 show electropherogram traces of the MCF-7 tumour RNA kept at room temperature with saline resulting autolytic RNA degradation (FIG. 16) and A2780 tumour cell RNA treated with chemotherapy drugs docetaxel and epirubicin (FIG. 17 and FIG. 18 respectively).

Xenograft tumour kept in saline for 24 hours shows a large peak of small fragments at approximately the 26 second mark of the trace (FIG. 16). There is also a loss of area of the 28S peak. Cancer cells treated with chemotherapeutic drugs show a different pattern of RNA disruption. For example, FIG. 17 which shows human ovarian cancer cell line A2780 treated with chemotherapeutic docetaxel, shows an intermediate peak and a peak adjacent to the 18S peak. FIG. 18 shows A2780 cells treated with chemotherapeutic epirubicin. The electropherogram shows intermediate bands between the 18S and 28S peaks. In addition, the location of the detected 28S and 18S peaks are shifted relative to the 18S and 28S peaks compared to intact RNA and autocatalytic RNA degradation.

Figure 23A:
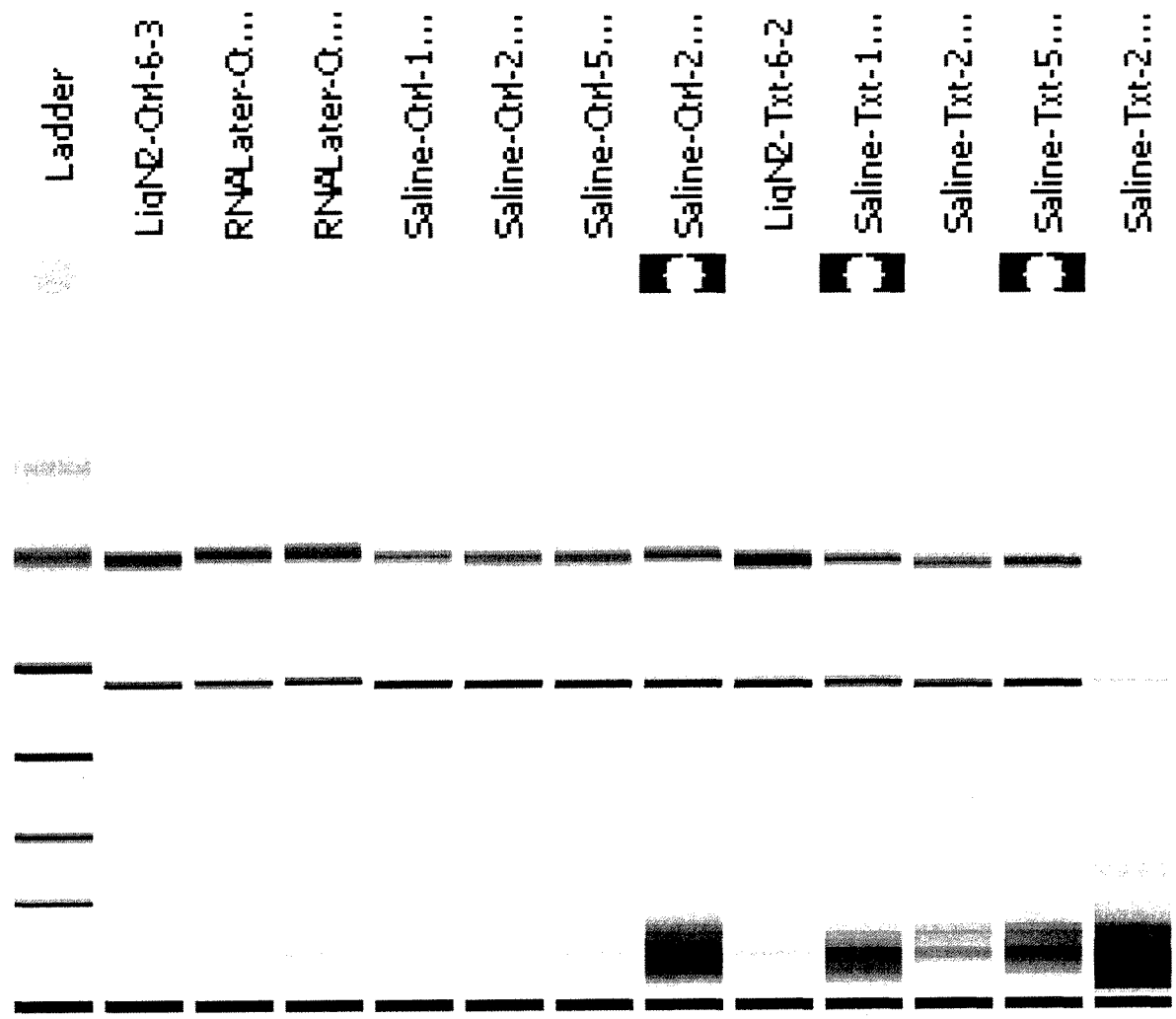
FIG. 23A is an image of a gel of electrophoretically separated xenograft tumour RNA samples.

RNA isolated from xenograft tumours stored in liquid nitrogen, RNALater™ solution or left in saline for 1 h, 2 h, 5 h and 24 h to induce autocatalytic degradation was analyzed by measuring an RNA Integrity Number (RIN) using Agilent 2100 Bioanalyzer. FIGS. 23B-23M shows that the 28S and 18S peaks are not misidentified by this software in RNA samples with autolytic degradation (samples 4-7 and 9-12 of FIG. 23A). Circles above the gel lanes indicate that an RIN number could be calculated (FIG. 23A). Circles encapsulated by squares indicate samples for which an RIN number could not be calculated. Control samples were untreated xenograft tumours (1-7). Treated samples (8-12) were given docetaxel.

Example 6

The MA22 RNA electropherogram data was examined to determine which components of the electropherogram best correlated with clinical response. It became evident that the Agilent Bioanalyzer software misidentified either the 28S peak or the 18S peak on electropherograms in >20% of the samples. In these samples, a small portion of the tip of a peak was identified as the whole peak. The Agilent 2100 Bioanalyzer software (Agilent Expert) (Mueller 2004; Vespucci 2005) was able to correctly identify the 28S and 18S peaks on electropherograms of intact RNA which are identifiable by eye. However, in samples with disrupted RNA, electropherogram peaks were misidentified by Agilent RIN software although the correct peaks remained in appropriate locations visually on the electropherogram. The Agilent method which generates RIN values, hereafter referred to as the RIN algorithm, was based on RNA samples which were either intact or had undergone complete autolytic degradation and had few "partially degraded" samples (Schroeder, Mueller et al. 2006).

Accordingly, methods were used to determine an RDA score herein, as described with respect to FIGS. 20A and 20B, which are different from the methods used to calculate RIN. The output RDA scores were subjected to Receiver Operating Characteristic (ROC) analysis to generate an ROC curve from which the Area under the Curve (AUC) was calculated (Hurley 2011). The ROC curve was then used to determine the utility in discriminating Responders from Non-Responders using certain features of the electropherogram (as measured by a pathological complete response post-treatment).

Assessment of RNA quality and concentration using an Agilent 2100 BioAnalyzer with Agilent RNA 6000 Nano kits and Caliper Technology's RNA Nanochips: The procedure used for assessing the quantity and integrity (also referred to as RNA quality) of the above RNA preparations involved capillary electrophoresis on an Agilent 2100 Bioanalyzer (Agilent Technologies, Mississauga, ON) using a protocol described in detail in the Agilent RNA 6000 Nano Kit Guide available on the Agilent Technologies website (Aqilent Publication Part Number: G2938-90035).

The protocol document includes a detailed description on setting up the assay equipment, preparing and running the RNA Nanochips, and analysis of the capillary electrophoretic data using the Agilent 21000 Bioanalyzer and its associated "Expert software". The document includes "Essential Measurement Practices" to be followed. RNA 6000 "Nanochips" and associated solutions are obtained in RNA 6000 Nano kits that can be purchased from Agilent Technologies (Mississauga, ON). RNA Nanochips are manufactured by Caliper Life Sciences (Hopkinton, Mass.). The sizes of the rRNAs, and the concentration of RNA in a given sample are determined by extrapolation from a standard curve of reference RNAs provided in the RNA 6000

NANO kits. Data from the Bioanalyzer runs were stored as PDF and XAD files. The Agilent 2100 Expert software was used to obtain all data from the capillary electrophoresis runs, including the size of RNAs and the RNA integrity/quality and quantity for a given RNA preparation. Raw data from each electropherogram was then exported from the XAD files into EXCEL files which contain the raw electropherogram data at time intervals of 0.05 s.

Peak Identification Code

Based on the methods described herein, the current error rate for peak misidentification is 3% for chemotherapy treated samples.

Results of Area and Ratio Calculations

The error rate for the correct identification of 28S and 18S peaks fell from 25% to 3% using the described method. Included as errors were 28S and 18S peaks that were merged into the "intermediate banding" region resulting in small values for the area under the peak. Including only the mid-identification of the 28S and 18S peaks in electropherograms in which the RNA ran aberrantly gave an error rate of 1%. All ratio values of "0" were eliminated using this method and samples that were assigned RIN values of N/A by the Agilent Bioanalyzer were then quantifiable.

TABLE 10

Error Types within MA22 Electropherograms
Type of Error

Peak before 28S
All peaks shifted
Large amount of lower banding with absence of 18S and 28S
Large intermediate peak with absence of 28S and 18S
Large intermediate peak with merged 28S and 18S Samples used to assess RDA were taken after the third cycle of chemotherapy. The analysis of pre-therapy samples found that RNA integrity/quality and quantity were generally high and could not discriminate between Responders and non-Responders. In vitro studies and treatment of tumours in xenograft mouse models suggest that assessment of RNA disruption could demonstrate an effect as early as after the first cycle of chemotherapy.

The ratio of 28S:18S was calculated based on new area values. In intact RNA the accepted maximum value of 28S:18S is 2.0 (Sambrook, Fritsch, & Maniatis, 1989). This ratio has been shown to change in aging (Mori, Mizuno et al. 1978) (Payao, Smith, Winter, & Bertolucci, 1998), in diseases such as Alzheimer's (da Silva, Payao, Borsatto, Bertolucci, & Smith, 2000) and atherosclerosis (Martinet, De Meyer, Herman, & Kockx, 2004).

Previous work has indicated that during autolytic RNA degradation the height of the 28S peak decreases more rapidly than the height of the 18S peak (Schroeder, et al., 2006). However, in chemotherapy disrupted RNA, this ratio can decrease indicative of a preferential loss of 28S and was also found to increase indicating an increased rate of fragmentation of the 18S peak compared with the 28S peak. This ratio may be useful to discriminate between intact and chemotherapy disrupted RNA but would require two cutoff values such that values greater than approximately 2.5 or less than approximately 1.3 are indicative of chemotherapy disrupted RNA. An increased ratio is not typically found with autolytic degradation.

Abnormal 28S:18S ratios have been found in other systems such as connective tissue and tumour tissue (Skrypina et al. 2003) as well as in pure spermatozoal fractions in which 28S depletion results in a significantly lower ratio (median 0.11) than that described for somatic cells (Cappallo-Obermann, Schulze et al. 2011). It has been suggested that this loss in 28S is due to preferential cleavage within GC-rich regions (Johnson, Sendler, Lalancette, Hauser, Diamond, & Krawetz, 2011).

Figure 21A:
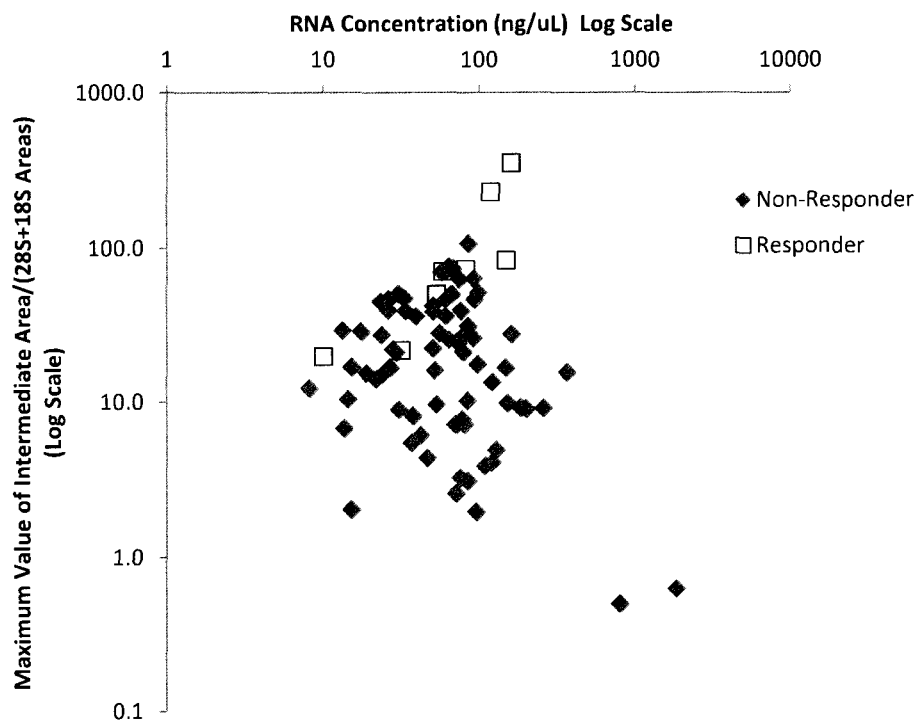
FIG. 21A is a log-log graph of the feature of log (Maximum Intermediate/(28S+18S)) versus log RNA concentration.

The area of the intermediate banding region was measured and ratios calculated to normalize to the total area (i.e. intermediate/total area) and to determine how the area of intermediate banding region compares with the area of the 28S and 18S peaks (i.e. intermediate/(28S+18S)). The area in the low banding region (below the 18S peak) was also calculated. Other ratios were also calculated including intermediate/28S, intermediate/18S, (low+intermediate)/(28S+18S) and low banding region/total area. Minimum and maximum ratios were determined for several electropherograms of samples that were taken at the same time and graphed against concentration, an example of which is shown in FIG. 21A. Accordingly, if a feature uses the term maximum or minimum then this means that a ratio was calculated for each electropherogram dataset and then the maximum or minimum of these ratios was calculated as the case may be.

In the ratios of the features that follow below, the term "intermediate" means the area in the intermediate region, the term "28S" means the area of the 28S peak, the term "18S" means the area of the 18S peak, the term "low banding" means the area of the low banding region and the term "total area" means the sum of the areas of the low banding region, the 18S peak, the intermediate region and the 28S peak. The term concentration (for the graphs in FIGS. 21A-21D and FIGS. 21F-21K) means the concentration of the RNA in the samples from which the electropherogram was generated. In the cases where the maximum or minimum was taken of a ratio, the concentration used in the plot was that of the electropherogram dataset that had the maximum or minimum value for the ratio.

Figure 21B:
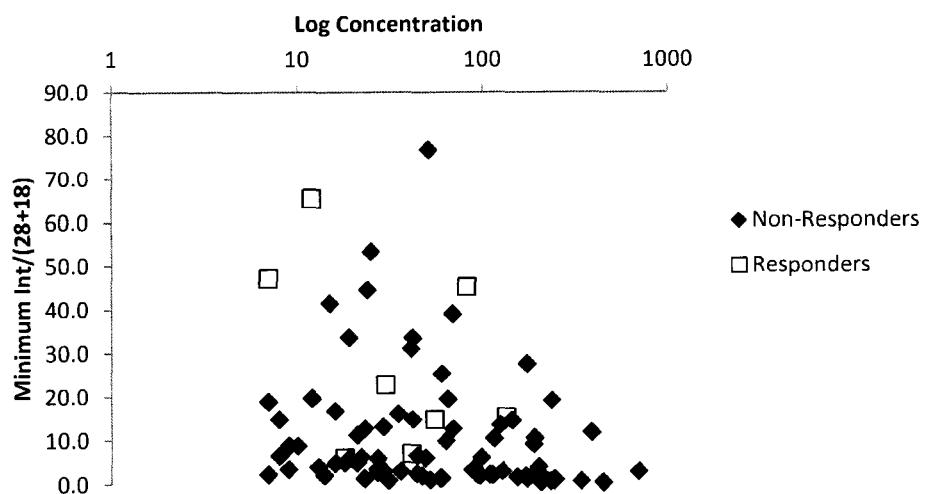
FIG. 21B is a semi-log graph of the feature of Minimum Intermediate/(28S+18S) versus log RNA concentration for a sample study.

The AUC value for the feature of maximum intermediate/(28S+18S) was 0.81 and the AUC value for the ratio of minimum intermediate/(28+18) was 0.75 indicating that both of these ratios are able to discriminate between Responders and Non-Responders. The AUC was the area under the ROC curve. The ROC curve was obtained by applying thresholds to the RDA score that was generated based on the indicated feature. A log-log graph of the first combination of features versus log concentration is shown in FIG. 21A and a semi-log graph of the second combination of features versus log concentration is shown in FIG. 21B.

Figure 21C:
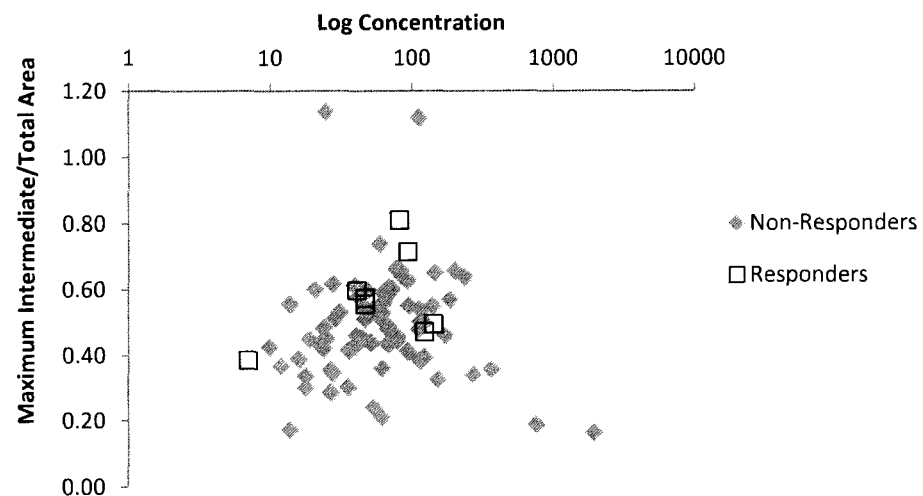
FIG. 21C is a semi-log graph of the feature of Maximum Intermediate/Total Area versus log RNA concentration for a sample study.

The AUC value for the feature of maximum intermediate/total area was 0.71 and the AUC value for the ratio of minimum intermediate/total area the AUC was 0.56. A semi-log graph of the feature of maximum intermediate/total area versus log concentration is shown in FIG. 21C.

Figure 21D:
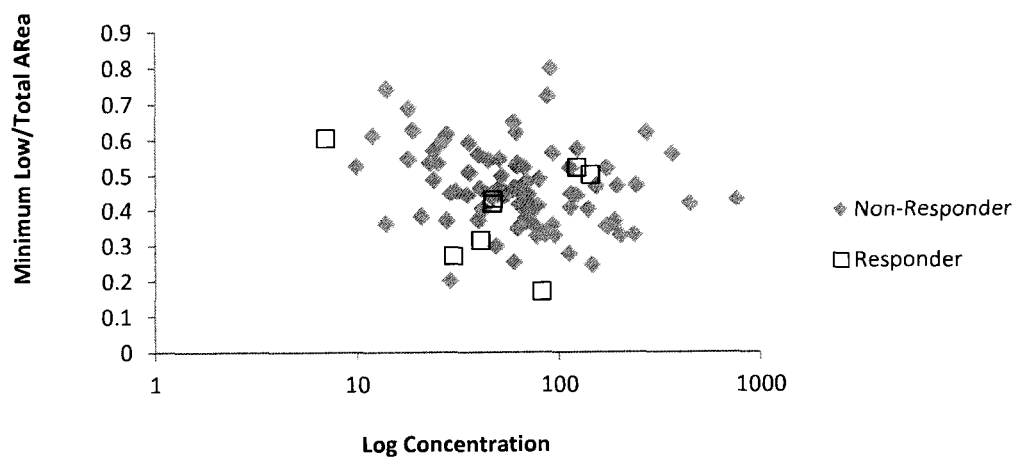
FIG. 21D is a semi-log graph of the feature of Minimum Value Low Banding/Total Area versus log RNA concentration for a sample study.
Figure 21E:
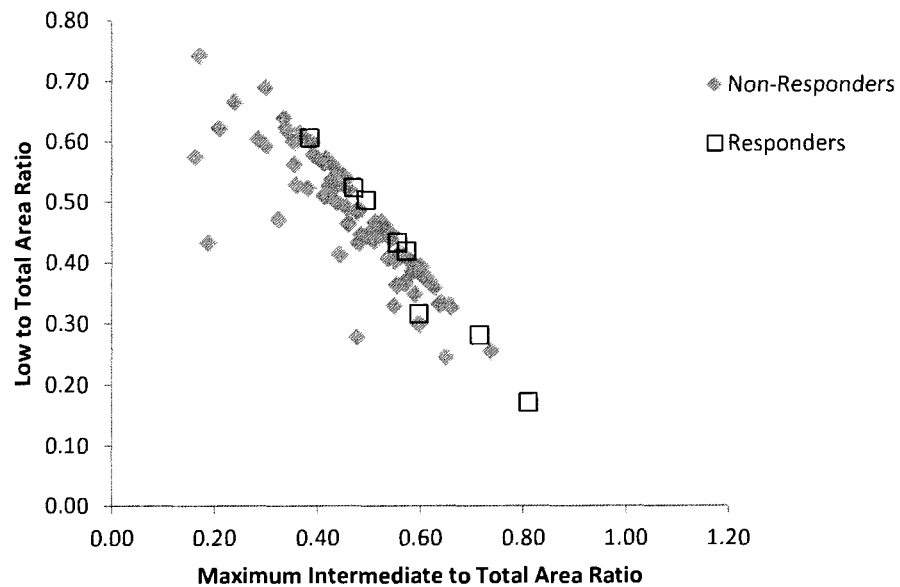
FIG. 21E is a graph of the feature Low to Total Area ratio versus Maximum Intermediate to Total Area ratio for a sample study.

The AUC value for the feature of minimum Low Banding/Total Area was 0.63; however the AUC value for the feature of maximum Low Banding/Total Area value was 0.50. A semi-log graph of the feature of minimum low banding/total area versus log concentration is shown in FIG. 21D. The feature of low banding/Total area may be a useful feature in combination with other components as shown in FIG. 21E.

Figure 21F:
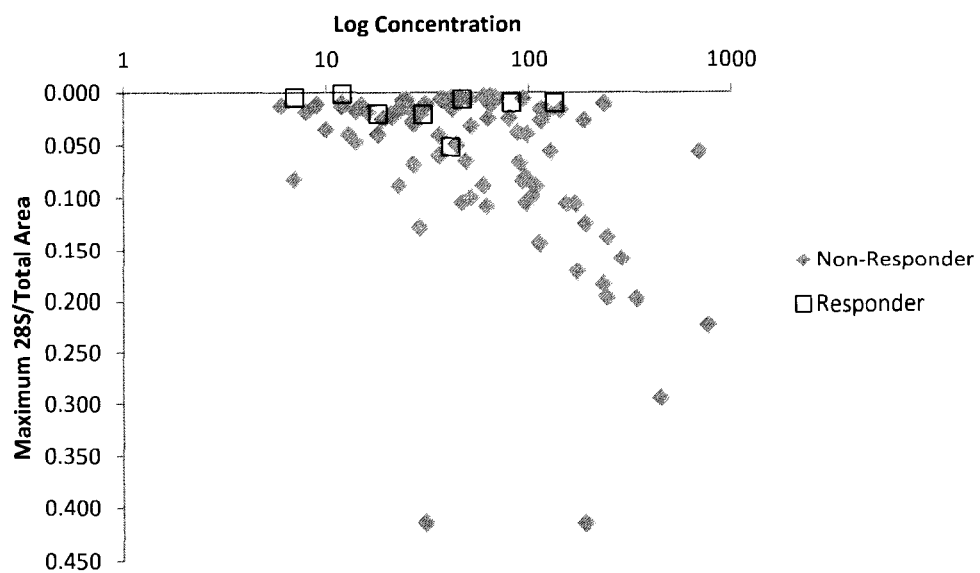
FIG. 21F is a semi-log graph of the feature of Maximum 28S/Total Area versus log RNA concentration for a sample study.
Figure 21G:
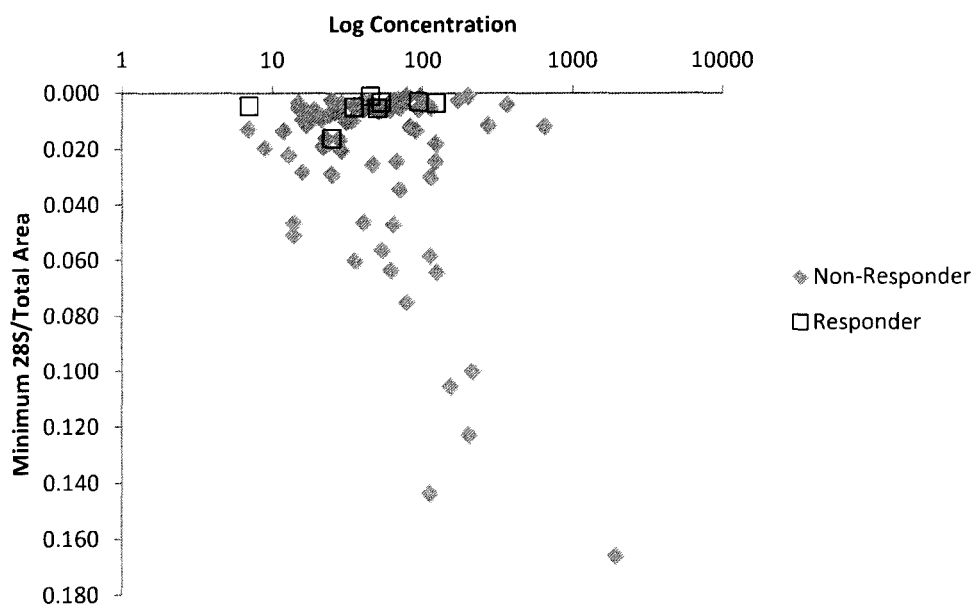
FIG. 21G is a semi-log graph of the feature of Minimum 28S/Total Area versus log RNA concentration for a sample study.
Figure 21H:
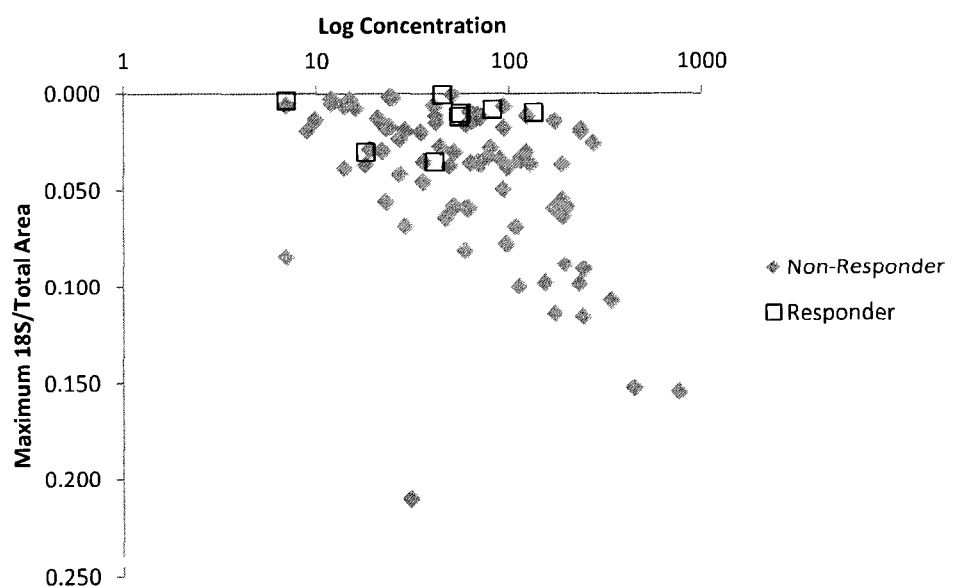
FIG. 21H is a semi-log graph of the feature of Maximum 18S/Total Area versus log RNA concentration for a sample study.
Figure 21I:
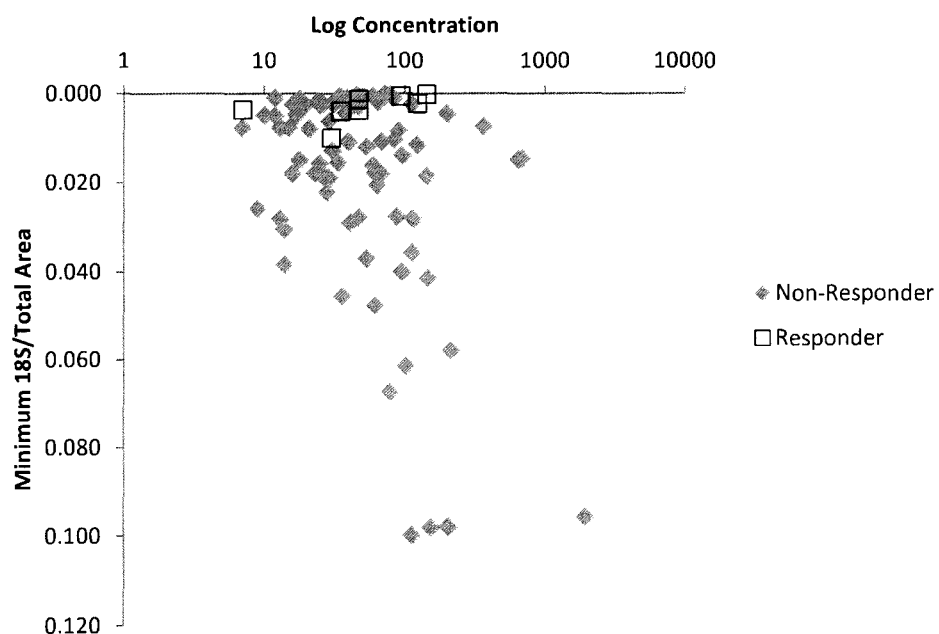
FIG. 21I is a semi-log graph of the feature of Minimum 18S/Total Area versus log RNA concentration for a sample study.

Ratios were also generated for the area of the 28S peak over (i.e. with respect to or divided by) total area (28S/total area) and the area of the 18S peak over total area (18S/total area). The features of maximum and minimum ratios of 28S/total area were graphed against log concentration on semi-log graphs as shown in FIGS. 21F-21G, respectively. The features of maximum and minimum ratios of 18S/total area were graphed against log concentration on semi-log graphs as shown in FIGS. 21H-21I, respectively.

The AUC value for the feature of maximum 28S/Total Area was 0.69. The AUC value for the feature of minimum 28S/Total Area was 0.62. The AUC value for the feature of maximum 18S/Total Area was 0.76. The AUC value for the feature of minimum 18S/Total Area was 0.68. This suggests that these features may be useful components to separate Responders from Non-Responders.

Figure 21J:
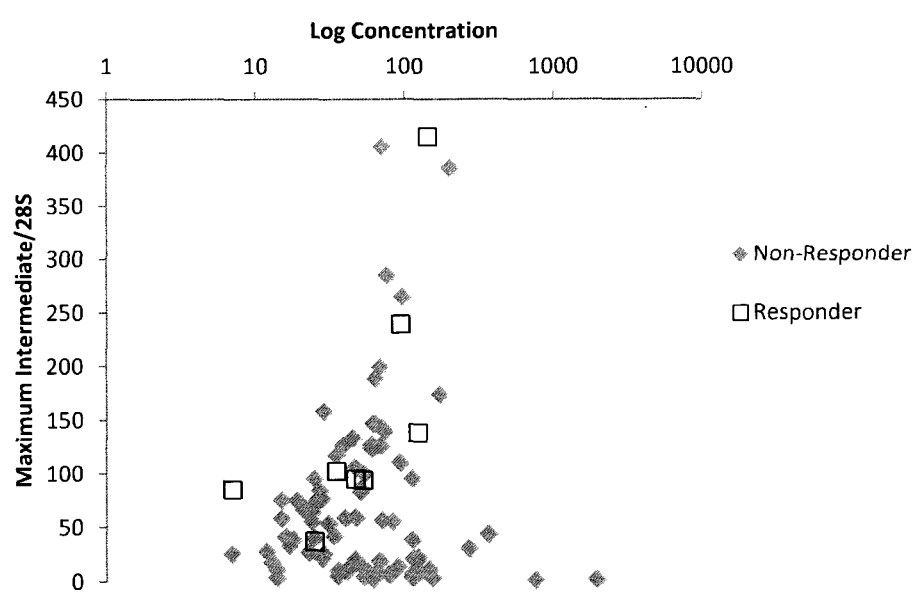
FIG. 21J is a semi-log graph of the feature of Maximum Intermediate/28S versus log RNA concentration for a sample study.
Figure 21K:
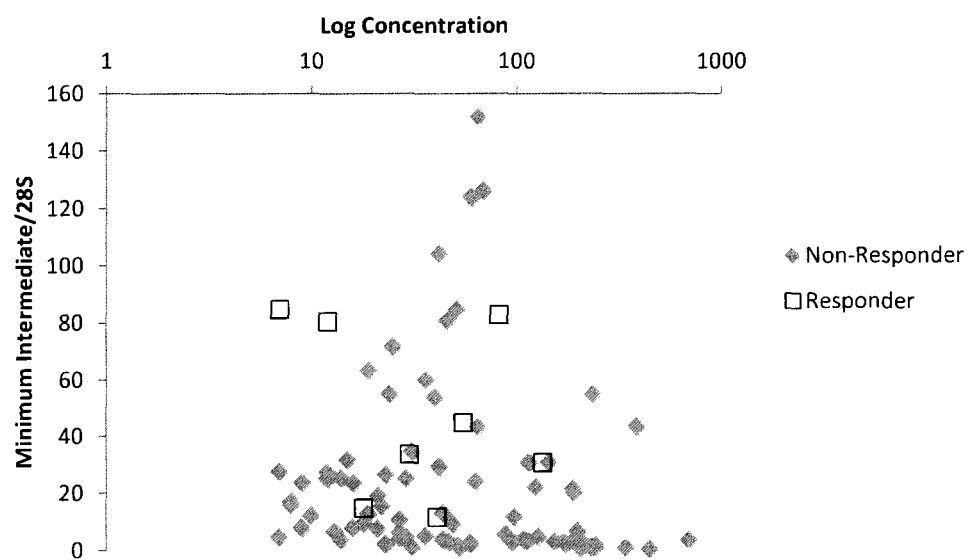
FIG. 21K is a semi-log graph of the feature of Minimum Intermediate/28S versus log RNA concentration for a sample study.

The features of maximum and minimum ratios of Intermediate/28S are shown in FIGS. 21J-21K.

The 18S and 28S peak widths were calculated for the MA22 dataset and assessed for their ability to discriminate between Responders and Non-Responders. The accuracy (e.g. (the number of data whose true labels equal to their predicted labels)/(the total number of data)) as determined by linear discriminant analysis of using this combination of features to generate the RDA score was 0.6 and had an AUC of 0.67.

RNA Disruption Vs RNA Autolytic Degradation

Distinguishing between the fragmentation effect of drugs and autolytic degradation may be possible using A) changes in electropherogram graphical baseline (i.e. measure of the base between the peaks), B) appearance of low molecular weight banding, C) low RNA concentration and/or D) measuring loss of 28S compared with 18S peaks.

Discussion

As reported herein the electropherograms of autolytic RNA degradation can differ from chemotherapy induced RNA disruption. Existing tools for analyzing RNA degradation have not been directed to assessing non-autolytic degradation. Accurate analysis of the RNA electropherograms is key to determining the extent of disruption in tumour RNA samples that have been treated with chemotherapy. The disclosed peak identification method provides the ability to fully analyze an increased number of samples since samples that were previously marked an RIN of N/A by the Agilent Bioanalyzer were assessed and area values generated using the methods described herein. Features associated with rRNA disruption by chemotherapy are listed in TABLE 11.

TABLE 11

Features Associated with rRNA Disruption by Chemotherapy

| Feature | Effect |
|---|---|
| 28S peak | Loss of area, peak height, peak width |
| 18S peak | Loss of area, peak height, peak width |
| 28S:18S ratio | Increase or decrease |
| Intermediate banding | Area, peak height, discrete banding? |
| Low banding | Area, peak height, discrete banding |

The maximum ratio of 28S to 18S has been commonly assigned the value of 2.0; and a fall in this ratio has been ascribed to degradation (e.g. less than 1.8). In the study of Example 6, it was found that in samples with disrupted RNA, the 28S:18S ratio either decreased, or in some cases increased. In both cases, strong intermediate banding was present. The extent of fragmentation of the 28S differed from the fragmentation occurring in the 18S rRNA.

The intermediate banding region appears to be an important component in the RNA electropherogram when determining the extent of fragmentation of RNA (e.g. RNA disruption). The appearance of banding in the intermediate region along with 28S and/or 18S bands that make up smaller proportions of the total area indicate a disruption of RNA.

Example 7

The need for a prognostic biomarker to assess long term breast cancer chemotherapy efficacy is well established. The RNA Disruption Assay (RDA) is a novel prognostic test for women undergoing neoadjuvant chemotherapy that enables assessment of drug efficacy during treatment. RDA was developed from the findings of a clinical trial for women with locally advanced breast cancer (CAN-NCIC-CTG MA.22). Varying doses of docetaxel and epirubicin were given at two weekly (dose dense) or three weekly intervals. Tumours were biopsied in duplicate at 3 time points; pre-therapy, mid-therapy and post-therapy. Trial endpoints included clinical response, pathological complete response (pCR), disease-free survival and overall survival.

Methods:

RDA is based on analysis of RNA electropherograms generated to assess RNA integrity/quality. At mid-therapy, patients with tumours responding to treatment exhibited a dramatic reduction in RNA quality (RNA disruption). A method to provide an RDA score was then developed by combining various features of the electropherogram to discriminate between those patients who subsequently exhibited pCR and those that did not. This method generates an RDA score that indicates the degree of RNA disruption. A high RDA score is associated with subsequent pCR, while a low RDA score indicates that patients are unlikely to receive long term chemotherapy benefit. For this example, the RDA score was based on the maximum value for the ratio of the area of the intermediate region to the sum or the areas of the 28S and 18S peaks (i.e. intermediate/(28S+18S)).

Figure 22A:
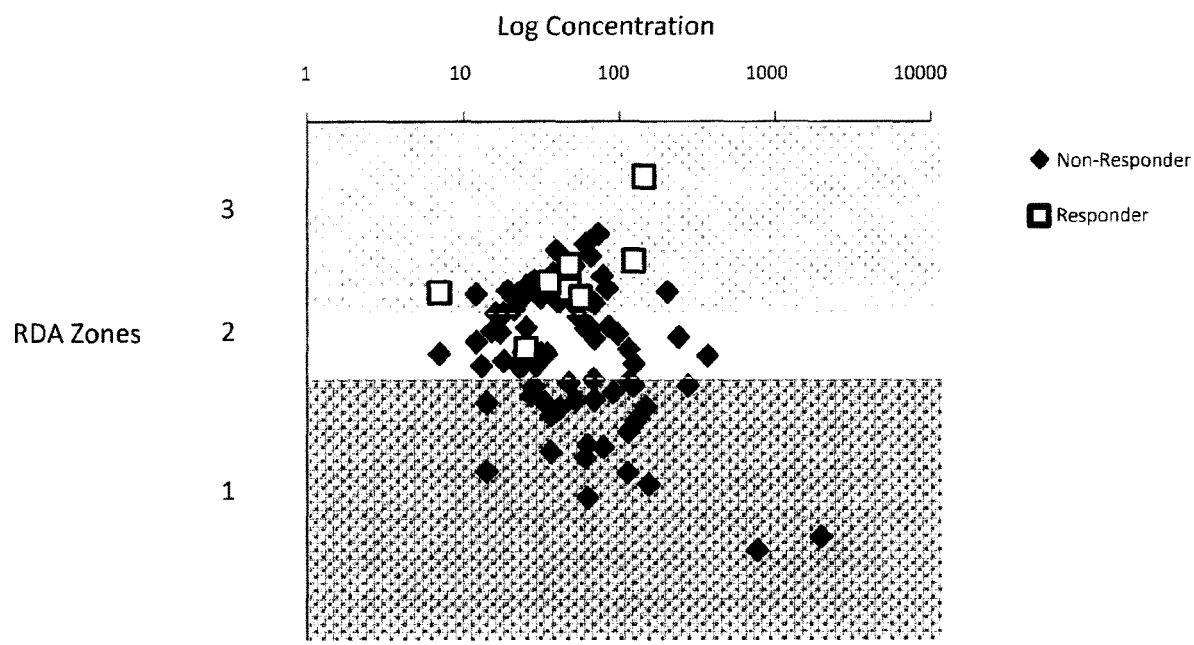
FIG. 22A is a graph of patient distribution in RDA zones.
Figure 22B:
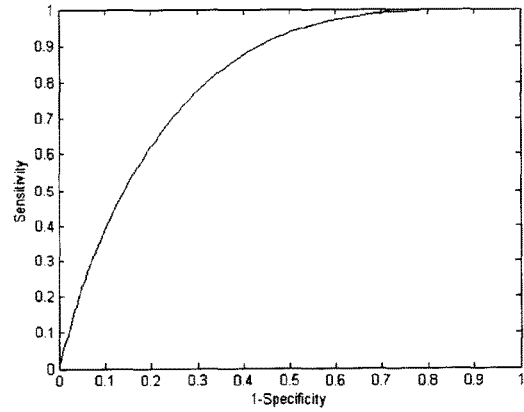
FIG. 22B is an ROC curve corresponding to FIG. 21A.

Results:

When applied to patients in the MA.22 study (partial patient details available in Parissenti et al. 2010 and PCT/CA2008/001561; 35 additional patients have been analyzed for a total of 85 patients and in some cases 3 samples per subject were analyzed; PPV AND NPV numbers described herein are based on the full data set) after the $3^{rd}$ or $4^{th}$ cycle of chemotherapy, the RDA score (e.g. based on the ratio of the Intermediate Area/(28S+18S Areas)) made the following predictions. Of the 85 patients studied, it predicted 32% to be non-responders. This prediction had a negative predictive value of 0.99 with a 95% confidence limit of 0.98-1.0 and a false negative rate of 2%. Of patients achieving pCR, RDA predicted 87% of having an increased chance of responding. This prediction had a positive predictive value of 0.19 reflecting that some patients had a drug effect but did not achieve a pCR. FIG. 22A illustrates the RDA Zones and identified responders and non-responders and FIG. 22B illustrates the ROC curve. The number of responders is also tabulated below in TABLE 12.

For example, selecting a threshold of 10.2 for the RDA score, the negative prediction value for mid treatment responders is 0.99. This means that a tumour sample having an RDA of >10, for example, can be predicted to be non-responsive to the chemotherapy treatment with greater than 99% confidence.

The average standard deviation for samples measured in triplicate and using RDI based on the ratio of Intermediate Area/(28S+18S Areas) was 41. This was for mid-therapy samples and is expected as tumours can be highly heterogeneous.

TABLE 12

MA22 Patient Response

| Clinical Response | Complete Pathologic Response pCR | | RDA |
|---|---|---|---|
| Complete 17 patients | 6 Patients | 7 Patients | Zone 3 25 Patients No pCR 7 pCR |
| Partial: 64 Patients | 2 Patients | 1 Patient | Zone 2 25 Patients No pCR 1 pCR |
| No response: 4 Patients | | | Zone 1 27 Patients No pCR |

Conclusions:

Use of RDA in clinical practice will enable identification of patients unlikely to respond to breast cancer chemotherapy. Patients with an RDA score that indicates no long term chemotherapy benefit can then avoid the toxic side-effects of chemotherapy and can be switched to an alternate treatment, which may provide a better clinical outcome as well as health care cost savings.

Example 8

The methods and assays described herein can be used for assessing the benefit of changing therapy for non-responders. Changing chemotherapy protocols midstream on the basis of patient response may result in improved overall survival as well as improved disease free survival rates.

Predicting ultimate response rapidly, for example, after one or two cycles of a chemotherapy treatment, could provide useful information for maximizing clinical benefit and/or minimizing toxicity.

To assess this, patients are treated with one or more different chemotherapy drugs. Core biopsies are taken from the patients at one or more times of before, during and/or after treatment. The biopsies are analyzed using an RNA disruption/degradation assay. Responders and non-responders predicted based on the RDA assay are identified. Non-responders are randomized into two or more groups. For example, subjects can be maintained on their same treatment or receive adjuvant or other treatment (e.g. e.g. adjuvant, different drug or other therapy such as surgery or radiation). Outcomes for the predicted "non-responder" groups are compared to assess accuracy of prediction and to assess whether altering treatment (e.g. adjuvant, different drug or other therapy such as surgery or radiation) results in improved outcome.

Additional markers can be analyzed pre, mid and/or post treatment.

Example 9

Subjects with ER/PR+/HER2− negative and triple negative tumours are assigned a therapy based on, for example, molecular profiling. For example, an arm could receive neo-adjuvant hormonal treatment and a second arm neo-adjuvant chemotherapy A.

Responders and non-responders are predicted using an RNA disruption assay method. Non-responders can be randomized to receive different or additional treatment. For example, non-responders in the first arm would either continue on the hormonal treatment or receive chemotherapy or hormonal therapy plus an adjuvant therapy; and non-responders in the second arm would either continue to receive chemotherapy A or receive chemotherapy B and/or surgery. The outcomes such as disease free survival for all patients and also patients switching therapy would be compared to patients continuing therapy.

Example 10

Cells were plated and treated with docetaxel concentrations ranging from 0.001-40 µM for 24 to 72 hours to assess the effect on cell number, RNA content, and integrity (measured using a Bioanalyzer 2100 from Agilent Technologies, Inc.).

A2780 cells were treated for up to 72 hours with docetaxel at 0.005 uM and 0.2 uM. Cell counts were measured at each time-point. Cell numbers remained constant for concentrations of docetaxel greater than or equal to 0.005 uM (FIG. 24A). The use of the asterix (*) in FIGS. 24A and 24B refers to whether the differences between the drug-treated samples and the drug-free control are considered statistically significant (in a two-way ANOVA with Bonferroni post test to determine significance).

A2780 cells treated for up to 72 hours with docetaxel at 0.005 uM and 0.2 uM, were analyzed for the amount of RNA per cell. RNA was isolated and electophoretically separated using an Agilent Bioanalyzer. The amount of RNA per cell was calculated and shown to increase in a time-dependent and dose-dependent manner. The results are shown in FIG. 24B.

A Recovery Assay was next carried out to determine if A2780 cells could recover (grow in drug-free medium) after treatment with various concentrations of docetaxel for various lengths of time. A2780 cells were treated with 0.2 uM docetaxel for up to 72 hours and then washed and replated in drug-free media. No resumption of cell proliferation was seen under these conditions (FIG. 24C). Recovery was not possible when cells were exposed to 200 nM docetaxel even for a brief (24 hour) time period. A much lower concentration of docetaxel (5 nM) permitted cell recovery, but only when the incubation period was 48 hours or less. Interestingly, when one considers the effect of docetaxel dose and time on cellular RDI values (FIG. 24 Hb), the data suggests that cells can tolerate a level of RNA disruption, above which they become non-viable (e.g. 1.3 or greater).

Electrophoretic separation of A2780 cell RNA from cells treated with docetaxel for 24 hours at concentrations ranging from 0 to 40 uM, demonstrate the appearance of bands in the intermediate region and the low banding region. RNA was isolated and electrophoretically separated on an Agilent Bioanalyzer. As shown in FIG. 24D bands appeared just below the 28S (e.g. intermediate) and 18S bands (e.g. low banding region) at 0.005 uM and peaked at 0.2 uM.

Traces of the electropherograms also illustrate that the banding which appears just below the 28S and 18S peaks at a concentration of 0.005 uM and peaks at a concentration of 0.2 uM (FIG. 24E).

Figure 24F:
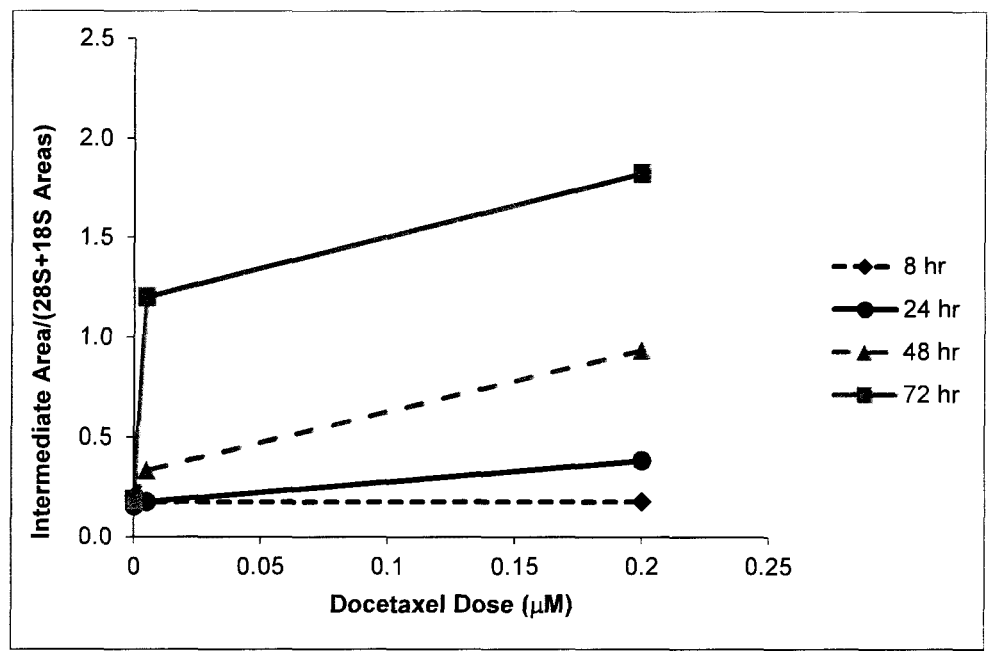
FIG. 24F is a graph of the intermediate area/(28S+18S) calculated from the trace of FIG. 24E.
Figure 24G:
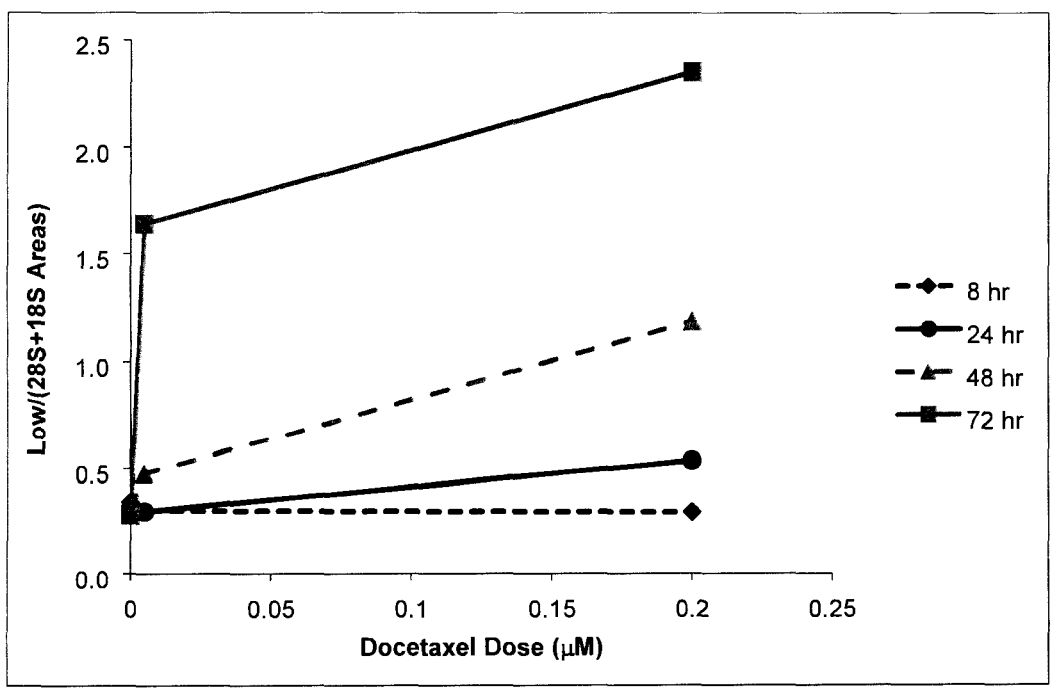
FIG. 24G is a graph of the Low Area/(28S+18S) calculated from the trace of FIG. 24E.

It should be noted that the RDI values shown in FIGS. 24F and 24G were determined using the methods 200 and 300 although method 400 could be used instead of method 300.

Analysis using RDA was performed. FIG. 24F is a plot of the measure of Intermediate/(28S+18S) for A2780 cells treated with docetaxel concentrations of 0.005 uM and 0.2 uM for 24 to 72 hours. Each value represents a single sample. Two replicate experiments had similar results. The graph demonstrates that the ratio of the Intermediate/(28S+ 18S) increases dramatically with time. Similarly, a graph of the ratio of Low banding area/(28S+18S) demonstrates this ratio also increases with time (FIG. 24G). As before each value represents a single sample. Two replicate experiments had similar results.

Figure 24H:
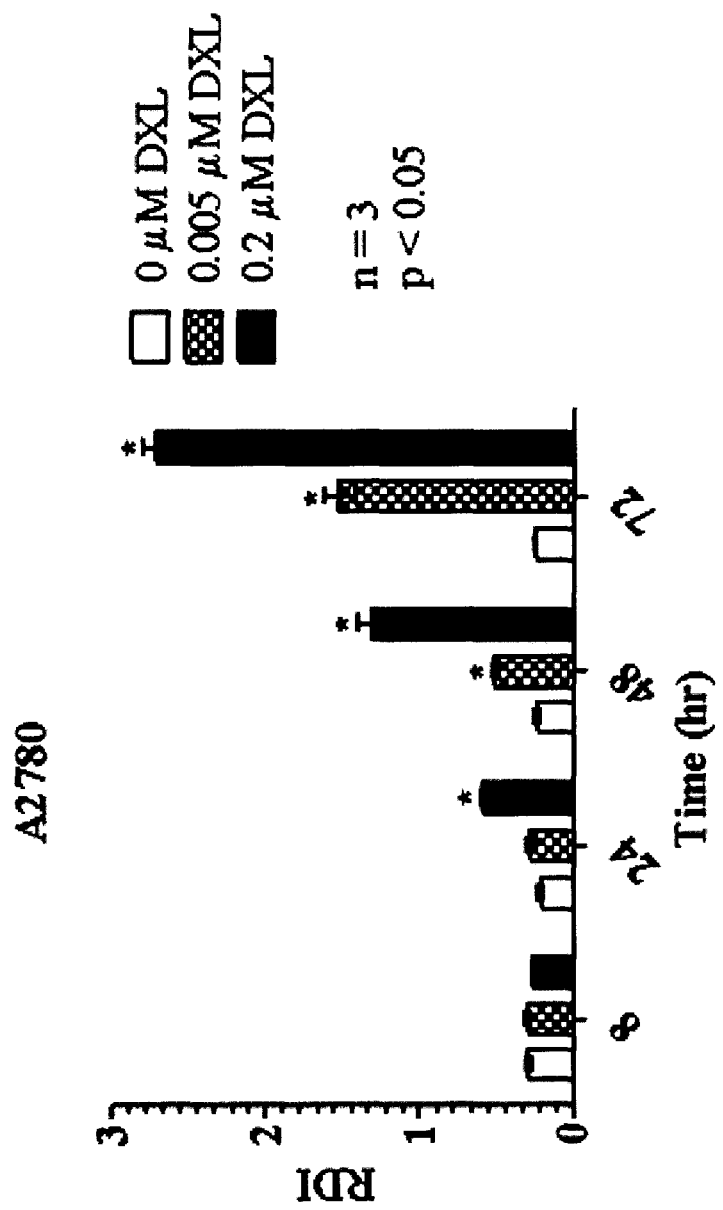
FIG. 24H is an image (a) of a gel of electrophoretically separated A2780 ovarian cancer cell RNA samples of cells treated with different concentrations of docetaxel for different time periods and a graph (b) of the RDI values for samples separated in (a).

A time course experiment was conducted in A2780 cells. Cells were treated for up to 72 hours with docetaxel at 0.005 uM and 0.2 uM. RNA was isolated and run on an Agilent Bioanalyzer. FIG. 24H demonstrates that banding appears below the 28S and 18S bands at all time-points. FIG. 24H a) demonstrates time- and dose-dependent changes in the RNA banding pattern for A2780 cells treated with docetaxel. FIG. 24 H b) provides the RDI values for the same samples and shows a similar time- and dose-dependent increase in RDI values.

A docetaxel A2780 resistant cell line was made as described in Li et al., Int. J. Mol. Med 2004 14(20): 257-264.

A time course experiment was conducted. Sensitive parental and docetaxel resistant A2780 cells were treated with docetaxel for 24 hours. RNA was isolated and run on an Agilent Bioanalyzer.

Figure 24I:
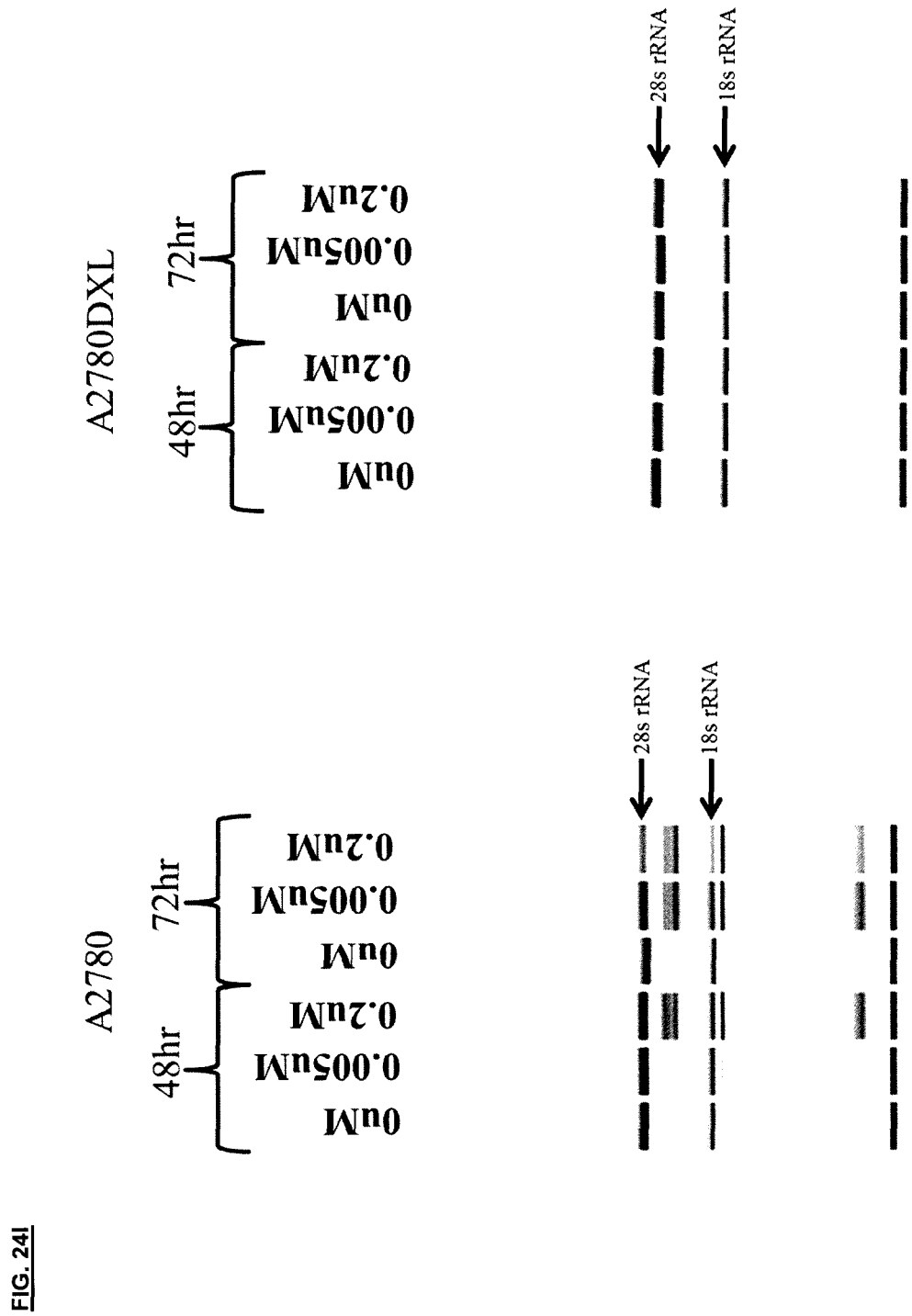
FIG. 24I is a series of images of gels of electrophoretically separated A2780 sensitive and resistant cell RNA samples.

As shown in FIG. 24I, banding appears below the 28S and 18S bands at 0.005 uM in sensitive cells. However, no banding is evident in resistant cells.

The effect of a caspase inhibitor on RNA integrity changes was next assessed. Cells were treated with or without docetaxel at a concentration of 0.2 uM in the presence or absence of the caspase inhibitor Q-DEVD-OPH (Biovision Laboratories) at a concentration of 10 uM.

Figure 24J:
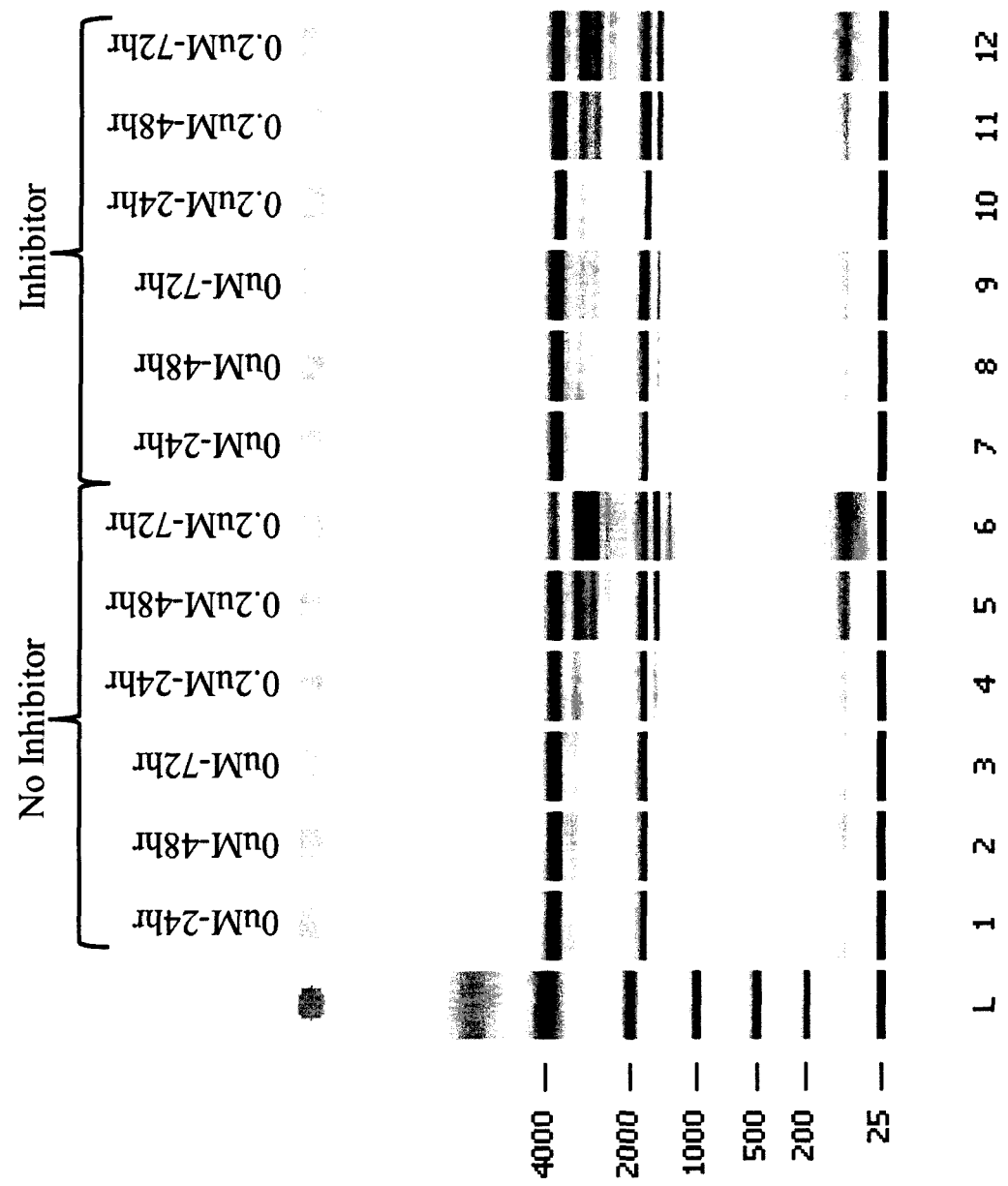
FIG. 24J is an image of a gel of electrophoretically separated A2780 ovarian cancer cell RNA samples treated with different concentrations of docetaxel for different time periods in the presence or absence of caspase inhibitor.

RNA was isolated and run on an Agilent Bioanalyzer and the banding pattern is shown in FIG. 24J. The inhibitor reduces the loss of 28S and 18S bands at 72 hr. Bands below the 28S and 18S bands are detectable in the presence and absence of the caspase inhibitor.

Although cell number remained constant for concentrations ≥0.005 uM docetaxel, withdrawal of the drug did not result in resumption of cell proliferation. RNA content increased per cell (p<0.05) while RIN did not change significantly in this range. However, novel discrete bands appeared in the rRNA banding pattern at 0.005 μM, peaking at 0.2 μM docetaxel, just below the 28s and 18s rRNA bands. In contrast, docetaxel-resistant A2780DXL cells did not display similar changes upon treatment, indicating that changes in tumor cell RNA content and integrity could be used to monitor response to chemotherapy agents.

Example 11

A2780 ovarian cancer cells were treated with radiation of 2 to 10 Gray using a Gulmay RS320 Irradiation System and subsequently harvested after 24, 48 and 72 hr. RNA was isolated and run on an Agilent Bioanalyzer. Analysis of the electropherogram demonstrated that an increase in the ratio Intermediate Area/(28S+18S Areas) at 72 hours is detectable in radiation treated cells (FIG. 25A). For example, cells treated at 10 Gray for 72 hours show RNA disruption in the intermediate region and the low banding region, but not much difference in the area of the electropherogram where the autolysis peak resides. FIG. 25B shows A2780 cells treated with 5 Gy for 24 hrs (lane A), 5 Gy for 48 hrs (lane B), 5 Gy for 72 hrs (lane C), 10 Gy for 24 hrs (lane D), 10Gy for 48 hrs (lane E) and 10 Gy for 72 hrs (lane F). RNA disruption is evident at 72 hrs at both dose levels.

Example 12

Methods

Administration of the FEC-D Regimen with Concurrent Radiation

Thirty two patients with stage III non-metastatic, non-inflammatory locally advanced breast cancer were treated with neoadjuvant 5-Fluoro-uracil, Epirubicin, and Cyclophosphamide (FEC also referred to as CEF) q3 weekly for 4 cycles followed by weekly Docetaxel (35 mg/m$^2$) concurrently with regional radiation (45 Gy with 16 Gy boost in 25 & 5 fractions) for 6 weeks followed by an additional 3 weeks of docetaxel chemotherapy without radiation. This was followed by a modified radical mastectomy. Patient and tumour characteristics were recorded at baseline and following treatment and clinical response and treatment-related toxicities noted. Image guided serial 14 gauge tumour core biopsies were taken from the patients pre-, mid- and post-treatment, and 1 mm$^3$ sections were immediately taken from the biopsies, immersed in RNAlater™, and stored frozen. MID treatment is after FEC but before docetaxel with concurrent radiation therapy.

Isolation of RNA from Tumour Core Biopsies

RNA was isolated from image-guided tumour core biopsies of patients pre-, mid-, and post-treatment using Qiagen miRNeasy® Mini kits, following a modification of the protocol published on the manufacturer's website, http://www1.qiagen.com/literature/handbooks/literature.aspx?id=1000291. Biopsies were cut into several sections for various assays, with the section used for RNA integrity analysis placed in RNAlater. The biopsies in RNAlater were immediately dropped in 0.5 ml of RLT buffer containing 13-ME (10 μl into 1 ml) in a 1.5 ml tube. The biopsies in RLT buffer were homogenized with a Coreless motor homogenizer for 5 min (from the Kontes Glass Company). The lysate was then passaged at least 5 times through a 20-gauge needle (0.9 mm diameter) fitted to an RNase-free syringe. The sample was then centrifuged at high speed in a refrigerated microfuge at 4° C. for 3 minutes, with transfer of the supernatant to a new tube. One volume (500 μl) of 70% ethanol was then added to the supernatant and the sample was mixed well by repeated pipetting. If some lysate was lost during homogenization, then the volume of ethanol was adjusted accordingly. Visible precipitates formed after the addition of ethanol in some samples did not affect the RNA isolation procedure. A maximum of 700 μl of the sample, including any precipitate, was added to a Qiagen® mini column and placed in a 2 ml collection tube. The column was centrifuged for 15 s at ≥8000×g (≥10,000 rpm) and the flow-through discarded. The remainder of the sample was then added to the column and the column centrifuged again. From this point forward, the column was then washed twice in RPE buffer and dried by centrifugation as per the manufacturer's protocol. The RNA was then eluted from the column in 30 μl of RNase-free water and the elute reapplied and eluted from the column to increase the yield and concentration of the RNA obtained.

Assessment of RNA Quality Using an Aqilent 2100 Bioanalyzer

The above RNA samples were applied to RNA 6000 Nano Lapchips™ (purchased from Agilent Biotechnologies, Inc.) and subjected to capillary electrophoresis using an Agilent® 2100 Bioanalyzer.

Further details of the study and clinical results are provided Cancer Res 2012; 72(24 Suppl): Abstract nr P1-14-13.

Results

RNA isolated from patient tumour samples after radiation was run on an Agilent Bioanalyzer. Analysis of the electropherogram demonstrated an increase in the ratio Intermediate Area/(28S+18S Areas) in two patients that had a pathological complete response (FIG. 26a).

Analysis of the electropherogram also demonstrated an increase in the ratio Low Area/(28S+18S Areas) in two patients that had a pathological complete response (FIG. 26b).

Example 13

Another method can be used for peak identification and generally comprises determining a standard sample (i.e. a normal sample) for a plurality of samples, for example such as the samples provided on a platform such as an RNA chip and the 28S and 18S peaks, as well as other features of interest, are identified by comparing the retention times for each sample to the standard sample. For example, when the standard sample is determined the method then generally comprises determining which samples require adjustment (e.g. forming an adjustment group), determining the standard retention time for the platform, adjusting samples in the adjusting group based on the standard retention time, determining peaks using the standard retention time and calculating one or more features of the peaks and nearby regions (as shown by the examples given in the discussion of FIG. 20A). By identifying a "standard" or "normal" sample for each platform, (for example, when multiple test samples are run simultaneously, as in the case of when an Agilent Bioanalyser chip platform can run 12 samples per chip, for example), the 28S and 18S peaks can more readily be determined by comparing the retention times of each sample to those of the "standard" sample of the chip platform. This then allows for a normalization for the samples that are collected at the same time using the same means. Further details on this method are provided in Example 10 and FIG. 27A which provides a flowchart of an example embodiment to implement the aforementioned method of peak identification and feature calculation.

Figure 27B:
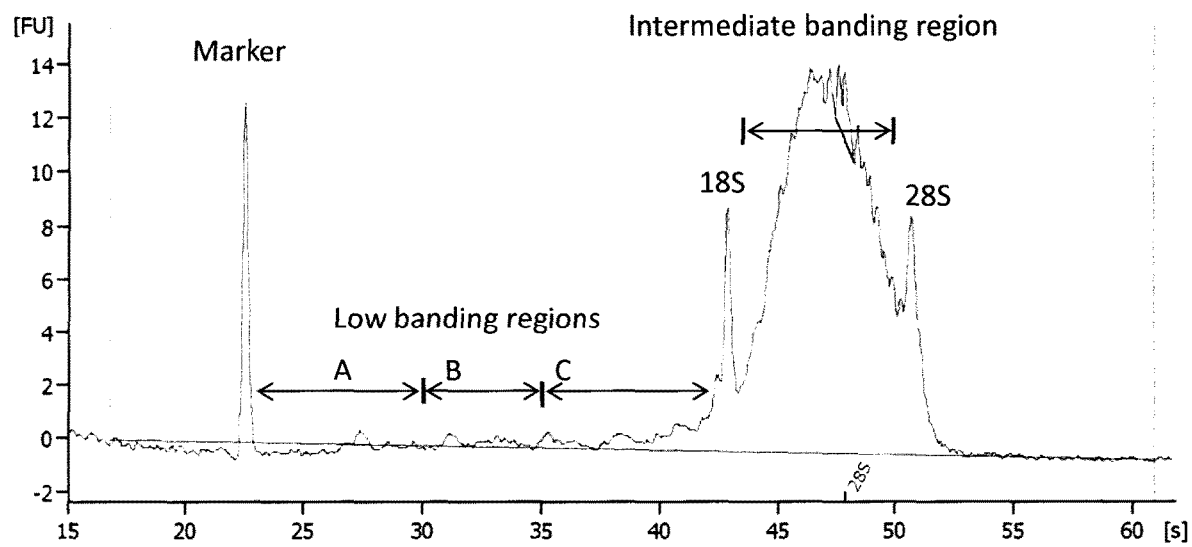
FIG. 27B is a graph of an example electropherogram in which the 18S peak, the 28S peak, the intermediate banding region, the low C banding region, the low B banding region, the low A banding region and the marker region are defined.

Additional features have also been identified as can be seen in FIG. 27B in which the low banding region is trisected into several regions including the low A banding region, the low B banding region and the low C banding region.

Example 14

Modified Method Using the Agilent Bioanalyzer

Referring now to FIG. 27A, shown therein is an example of an alternative embodiment of a method 400 for determining peaks and calculating features for electropherogram datasets. The method 400 generally involves identifying a standard sample or normal sample for a plurality of electropherogram datasets obtained from samples on a common analysis platform, such as an RNA chip for example, and then using the standard sample to adjust the location of peaks for the electropherograms for the samples that are determined to require adjustment and are therefore contained within an adjustment group. The plurality of electropherogram datasets are generated using samples that are analyzed using the same platform such as an RNA chip, for example. It has been found that the peak retention times are different for different RNA chips (e.g. different platforms). It has been found that the method 400 allows for the more accurate assessment of the 18S peak and the 28S peak in samples that are highly fragmented.

At 402, the method 400 determines a range for the peaks of interest. This range may be initialized to a default setting and then shifted if required. For example, for the 18S and 28S peaks, the default ranges can be initially set to [39.5 s, 44.95 s] and [45.05 s, 53.5 s]. On a scale of 0 to 100, the range for the 18S region is [45.85, 61.25], and that for the 28S region is [61.6, 85.75]. These ranges can then be shifted under certain conditions, such as, but not limited to the case when the marker region is not at its expected location. For example, these ranges may be shifted if the time of the marker, which is the time associated with the first peak that is a dye-only peak meaning that it does not contain any RNA but rather indicates the start of the run for the gel, is not at about 22.5 seconds. For these samples, a shift factor is calculated according to equation 1:

$$rngshft = \text{marker time} - 22.5 \qquad (1)$$

where marker time is the start time of the marker. The range for the 18S region is then shifted up according to [39.5+rngshft×1.5, 44.95+rngshft×1.5] and the range of the for the 28S region is shifted up according to [45.05+rngshft×2.5, 53.5+rngshft×2.5].

Figure 27C:
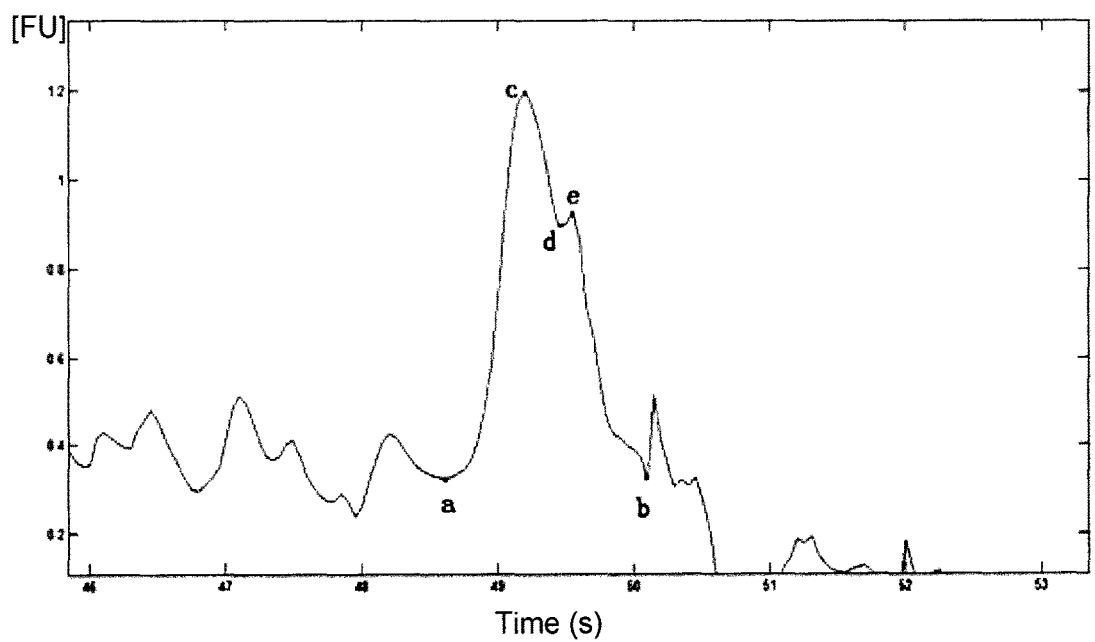
FIG. 27C is a graph showing how a peak is determined using the method of FIG. 27A.

Referring now to FIG. 27C, shown therein is a graph of an example peak which is now used to illustrate some aspects of how peaks are defined using method 400. FIG. 27C shows a plot of a general peak with one sub-peak with the x-axis being time in seconds and the y axis being is the value [FU].

It should be noted that a real-valued function t defined as a non-linear line is said to have a local (i.e. a relative) maximum point at the time point x*, if there exists some ε>0 such that f(x*)≥f(x) when |x−x*|<249 . The value of the local maximum point does not have to be larger than the value of all the other points but rather it just needs to be the largest value within a local range. The function f has a global (i.e. absolute) maximum point at x*, if f(x*)≥f(x) for all x. A global maximum point must have the largest value. A function can have more than one local maximum point, but only one global maximum point. In a similar way, there is also a local minimum point and a global minimum point.

The whole peak region is defined from time a to time b. The time point a is the starting point of the peak and the time point b is the ending point. The global minimum point in the range [a, b] is either a or b. The peak point is defined as the global maximum point, i.e. c. The peak height is defined as the value of the highest point, i.e. the value of c. The peak width is defined as (ending time−starting time), i.e. b-a. The peak area is defined as the area above the x-axis and under the curve from time point x=a to x=b. The local maximum point e is a sub-peak point. The 18S and 28S peaks can have more than one sub-peak. The local minimum point d is the sub-peak low.

At 404, the peaks are located by first searching for all possible peak candidates in the two identifying ranges. This involves searching for local maximums surrounded by local minima on either side. Each part of the electropherogram within the range which has these criteria is designated as a "peak candidate". The height difference of each possible peak candidate is then calculated. The height difference of a peak candidate is defined as the difference of the highest peak value and the average lowest peak values. The lowest peak values that are averaged are the starting point and ending point of the peak at the starting time and the ending time for each peak and any sub-peak low values (i.e. local minima) are not included. The two peak candidates with the largest height differences can be chosen as the 18S and 28S. The 18S peak or the 28S peak may have the higher value. Once the 18S peak and the 28S peak are correctly identified, the desired features can then be calculated such as, but not limited to, the width, the height and the area of the 18S and 28S peaks, the intermediate area, the low C banding region area, etc. The sub peak is included in the area calculation or the width calculation and it has no impact on the height (because it is always smaller). The values for these features can be calculated now since they will not change for some of the samples. In an alternative embodiment, the values for these features may be calculated for all samples after the samples requiring adjusting have been adjusted.

It should be noted that with method 400, there are two cases when the peak is allowed to have more than one maximum value. First, if the width of a peak is less than 0.15 seconds, this peak is considered as a sub-peak of its adjacent peak. Secondly, if the difference between the starting value and the ending value of a peak is too large, this peak is considered as a sub-peak of its adjacent peak. The difference is considered to be too large when the height of the sub-peak (i.e. the value at time point e minus the value at time point b in FIG. 27C) divided by the difference between the local maximum and local minimum (i.e. the value at time point e minus the value at time point d in FIG. 27C) is larger than a threshold value, such as, but not limited to, 5, for example, then it is too large. In general it has been found that one or two peaks may be associated with the 18S peak and the 28S peak using method 400.

Furthermore, in method 400, there is no restriction based on the width of the 18S peak and the 28S peak when determining the 18S peak and the 28S peak locations. Also, in method 400, there is no restriction based on the distance between the 18S peak and the 28S peak when determining the 18S peak and the 28S peak locations.

At 406, the standard sample for the plurality of samples is determined. The standard sample may be defined to be the sample having the smallest standard score in the plurality of samples wherein the standard score is defined equation 2.

$$\text{standard score} = \frac{\text{intermediate area} + \text{lower } b \text{ area} + \text{lower } e \text{ area}}{18S \text{ peak area} + 28S \text{ peak area}} \quad (2)$$

At 408, the retention time of the standard sample is compared with the retention time of the other samples. The retention time is examined for both the 28S and 18S peaks. Those samples whose retention time is not around the retention time of the standard sample will be assigned to an adjustment group, and the rest of the samples will be assigned to a standard group. A threshold value can be used to assess this (i.e. the retention time not "being around") such as, but not limited to, 0.5 seconds. Accordingly, if the difference between the retention time of both the 18S peak and the 28S peak for a sample is off by more than 0.5 seconds compared to the same peaks of the standard sample, then the sample is put into the adjustment group and requires adjusting.

At 410, the standard retention time for the 18S peak and the 28S peak is chosen based on the samples in the standard group. For example, the standard retention time may be chosen as the median of the retention time of the samples in the standard group. In alternative embodiments, other statistical measures may be used such as, but not limited to, the mean or some variations on the mean.

At 412, the 18S and 28S peaks for each sample in the adjustment group are determined by locating the peaks that are around the standard retention times determined in act 410 (i.e. the times of the 18S and 28S peaks determined from the standard samples). For example, using the samples that are in the standard group, and hence represent the most intact RNA, the median value of the retention time for the 28S and the 18S is identified. Each sample in the adjustment group is then examined to find the peaks that appear at that retention time. However, the actual retention time of the 28S and 18S peaks may not be identical to the those of the standard sample as the peak may not have its highest point at the same exact retention time. In this case if the peak area still includes the "standard retention time", this peak is designated as the 18S peak or the 28S peak even though the maximum value of the peak does not occur exactly at the same retention time. All measurements (width, height, area) are then taken based on this peak. Other regions of interest can also be determined once the 18S and 28S peaks are located such as, but not limited to, the low C banding region and the intermediate region, for example.

At 414, the features of interest that are used in determining the RDA score or RDI are then calculated for all of the samples.

An RDI score may be calculated for each sample on the RNA chip including the "control" sample, which may be defined as the sample on the RNA chip that is the closest to "intact RNA".

In one embodiment, the combination of features is a ratio of the low C banding region area to the sum of the 18S peak area and the 28S peak area, which can be represented by the expression "low C/(18S+28S)". Method 300 can also be used with this combination of features.

It should be noted that the method 400 can also operate if there are two samples on the RNA chip in which one of the samples is a positive control sample of intact RNA, which in fact is run on every chip, and the other sample can be the sample for which an RDA or an RDI value is obtained. Alternatively, the second sample may also be an analyzing sample which may be useful under certain circumstances.

Accordingly, at least one embodiment described herein comprises obtaining two electropherogram datasets corresponding to a test sample and a control sample, the test sample being a unique biological sample comprising cellular RNA optionally at a time point before, during or after the treatment requiring analysis and the control sample being another unique biological sample or a positive control sample of intact RNA or approximately intact RNA; placing the electropherogram of the test sample into an adjustment group and placing the electropherogram of the control sample into a standard group; identifying normal characteristics representative of a normal sample from the standard group; determining locations of peaks for the electropherogram in the adjustment group and adjusting the location of the peaks based on the normal characteristics; and determining values for features from the adjusted electropherogram and optionally the electropherogram from the standard group when the control sample is another unique biological sample requiring analysis.

Example 15

The Boundaries of the Low A, Low B, and Low C Banding Regions

The boundaries were set based on the location of discrete sets of peaks within the Low region, which is the region between the marker region and the 18S region (i.e. 18S band). The Low A banding region may be defined as the range between the marker region and 30.0 s. The Low B banding region may be defined as the range between 30.0 s and 35.0 s. The Low C banding region may be defined as the range between 35.0 s and the 18S region.

Linear Discriminant Analysis was used to identify features that are most predictive in the MA22 data set. Combinations of two or three features were found to improve prediction performance and many combinations listed in TABLES 16 to 17 were very close in their ability to predict responders. All peak measurements, area measurements, and width measurements for various features (i.e. 28S, 18S, intermediate, Low C) used in this analysis were normalized to the entire area. The entire area is defined to be the sum of the areas of the low banding region, the 18S region, the intermediate region and the 28S region which represents the total amount of RNA present in the analyzed sample.

Example 16

The methods 200 and 400 of were used to assess the MA22 trial dataset in a similar fashion as for the use of methods 200 and 300 in Example 2. RNA isolated from mid-therapy tumour samples was analyzed using an Agilent Bioanalyzer. The result was that the misidentification of the 28S peak in the chemotherapy treated samples fell to 0.3% using the method 400 (see TABLE 13).

TABLE 13

Error Rates and Types in MA22 Dataset

| Reason | Rate |
| --- | --- |
| Inadequate Sample | 9.6% of samples |
| Aberrant Run - baseline or marker issue | 1.9% of samples |
| Mis-identification of 28S and 18S peak | 0.3% of samples |

Figure 28:
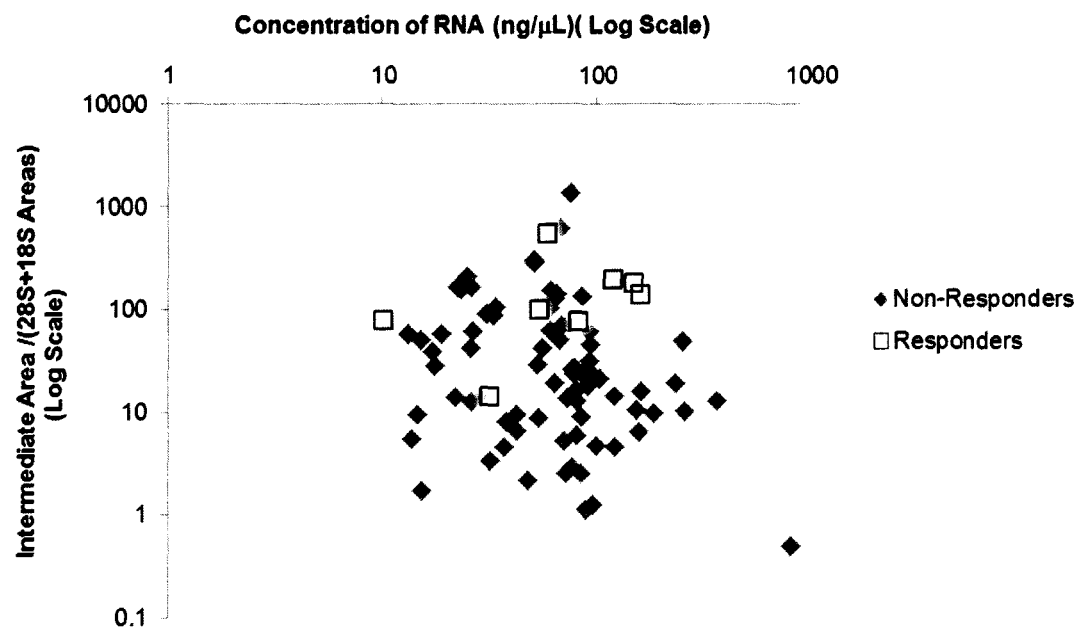
FIG. 28 is a log-log graph of the feature of log (Intermediate/(28S+18S)) versus log RNA concentration for a sample study using the modified peak identification method.
Figure 29A:
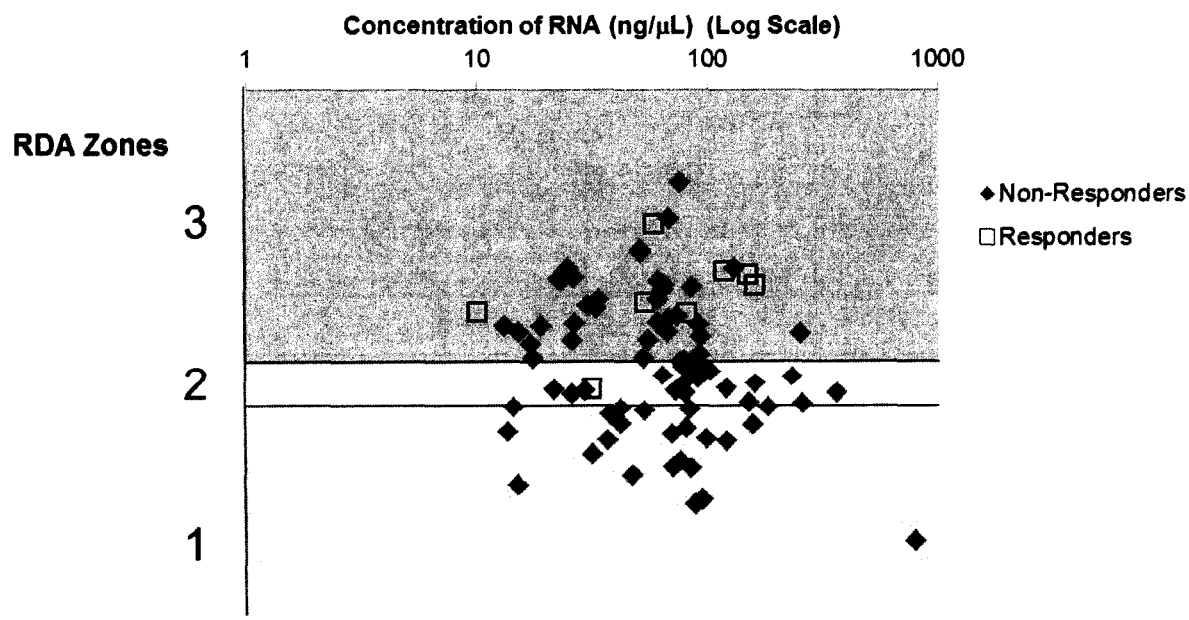
FIG. 29A is a graph of patient distribution in RDA zones using the modified peak identification method.
Figure 29B:
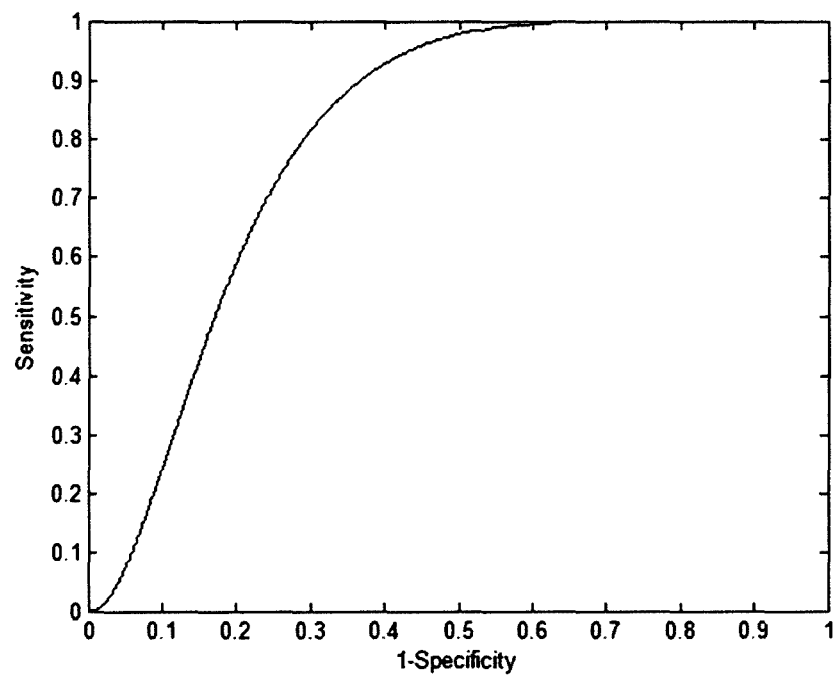
FIG. 29B is an ROC curve corresponding to FIG. 29A.

The ratio of the intermediate area to the sum of the 28S and 18S areas was generated for mid-therapy tumour samples and plotted versus concentration on a log-log graph. In particular, the maximum ratio value for each patient was graphed (FIG. 28). RDA zones were established based on clinical criteria. In this example, the clinical criteria was a negative predictive value for the threshold value between zone 1 and 2 at 0.98 or 0.99. For zones 2 and 3, the clinical criteria were chosen to be the best PPV value possible while including most of the responders in zone 3. The maximum RDA for each patient was graphed vs. log concentration on a semi-log chart and is shown in FIG. 29A for the various RDA zones. FIG. 29B shows the Receiver Operating Characteristic (Sensitivity vs. 1-Specificity) curve for Maximum value of the ratio of the Intermediate area/(18S+2S). The Area under the curve (AUC) was about 0.8.

Figure 29C:
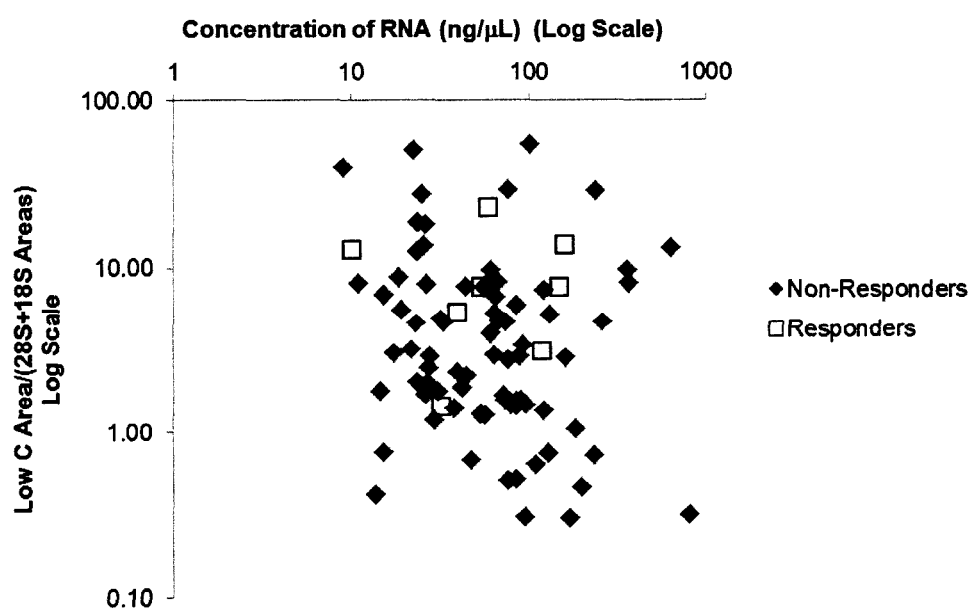
FIG. 29C is a log-log graph of the feature of log (low C/(28S+18S)) versus log RNA concentration for a sample study using the modified peak identification method.

A ratio of the Low C banding region area to the sum of the 28S and 18S areas was also generated. The maximum value for this ratio for each patient was plotted vs. RNA sample concentration (for the sample that had the maximum ratio) on a log-log plot and is shown in FIG. 29C.

Figure 29D:
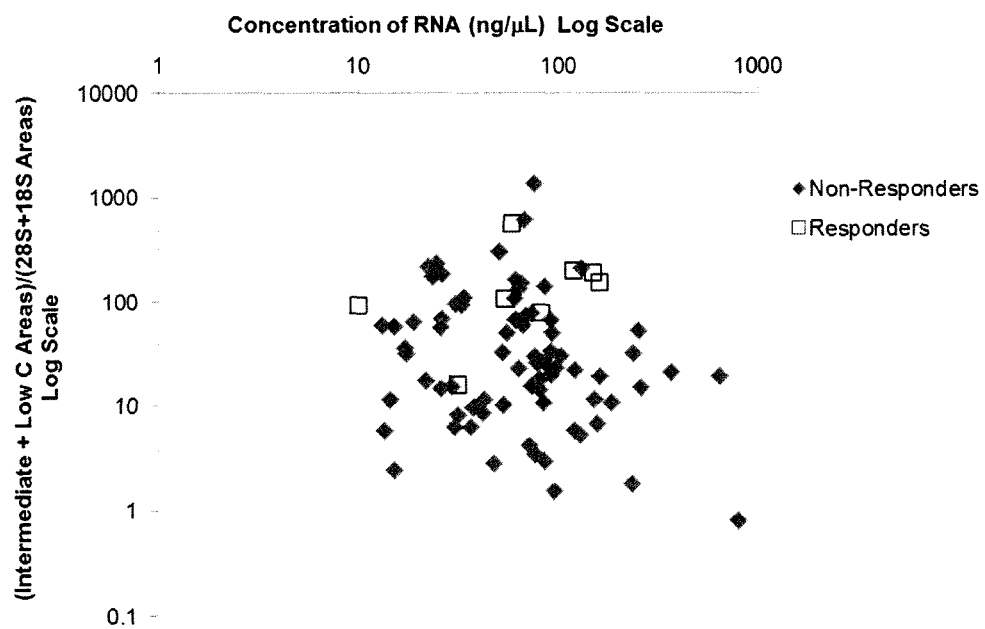
FIG. 29D is a log-log graph of the feature of log (Intermediate+low C)/(28S+18S) versus log RNA concentration for a sample study using the modified peak identification method.

A ratio of the sum of the intermediate area and the Low C banding region area to the sum of the 28S and 18S areas was also generated. The maximum value for this ratio for each patient was plotted vs. RNA sample concentration (for the sample that had the maximum ratio) and is shown in FIG. 29D.

Other ratios were also calculated and then Linear Discriminant Analysis (LDA) was used to identify the features that were most predictive for the MA22 data set. The details for the application of the LDA are discussed in Example 13 below. In general, combinations of two or three features were found to provide superior prediction performance but most of the combinations listed in TABLES 17 and 18 below were found to be close in their ability to predict responders vs. non-responders.

TABLE 14 identifies features associated with RNA disruption by Chemotherapy determined while using method 400.

TABLE 14

Features Associated with rRNA Disruption by Chemotherapy identified using Linear Discriminant analysis

| Feature | Effect |
| --- | --- |
| 28S peak | Loss of area, peak height, peak width |
| 18S peak | Loss of area, peak height, peak width |
| Intermediate region | Area, discrete banding |
| Low C region | Area, discrete banding |
| Concentration | Decrease |
| Ratio of 28S to 18S | Increase or decrease |

When the methods 100 and 400 were applied to patients in the MA.22 study (patient details available in Parissenti et al. 2010 and PCT patent application No. PCT/CA2008/001561) after the $3^{rd}$ or $4^{th}$ cycle of chemotherapy, the RDA score was used to predict that, out of the 85 patients that were studied, 27% were non-responders. This prediction had a negative predictive value of 0.99 with a 95% confidence limit of 0.95-1.0. Of patients achieving pCR, the RDA score predicted 87% of these patients as having an increased chance of responding. This prediction had a positive predictive value of 0.22 reflecting that some patients had a drug effect but did not achieve a pCR. FIG. 29A illustrates the RDA Zones and identified responders and non-responders and FIG. 29B illustrates the ROC curve. The number of responders is also tabulated below in TABLE 15.

TABLE 15

MA22 Patient Response

| Clinical Response | Complete Pathologic Response | | RDA |
| --- | --- | --- | --- |
| | pCR | | |
| Complete 17 patients | 6 patients | 7 patients | Zone 3 38 patients 31 No pCR 7 pCR |
| Partial 64 patients | 2 patient | 1 patient | Zone 2 24 patients 23 No pCR 1 pCR |
| No response 4 patients | | | Zone 1 23 patients No pCR |

Example 17

The Area Under Curve (AUC) is an important measure of accuracy for a detection or prediction technique as is known to those skilled in the art. Accordingly, the AUC was used to determine which features and which combinations of features are useful for predicting responders or non-responders to a particular treatment based on samples taken at a certain time point in the treatment regimen. For example, such samples include patient samples that exhibit RNA changes in response to an inducer such as chemotherapy or radiation therapy. Linear Discriminant Analysis was also used (one of the most commonly used classification methods) with different thresholds to assess different features to determine which features or combination of features had the best predictive or discriminative ability. LDA was used when two or three sets of combinations were plotted against one another on two dimensional or three dimensional plots respectively as is shown in TABLES 17 and 18 and this is referred to as two dimensional feature sets and three dimensional feature sets respectively.

TABLE 16 provides the AUC values when a one dimensional feature set comprising single features was assessed on the MA22 dataset using the methods 100 and 400. In this case the values for the various one dimensional single features were calculated and compared to various threshold values to discriminate between responders and non-responders (i.e. the threshold values were scalar values).

TABLE 16

AUC for one dimensional feature set analysis on the MA22 dataset

| Features | AUC |
|---|---|
| 18S peak area | 0.7706 |
| 28S peak area | 0.7500 |
| 18S peak height | 0.7184 |
| 28S peak height | 0.7848 |
| 18S peak width | 0.4509 |
| 28S peak width | 0.6266 |
| Intermediate region area | 0.7041 |
| Low C banding region area | 0.7041 |
| Low B banding region area | 0.6978 |
| Concentration | 0.5316 |

When a one dimensional feature set, in which only a single feature is used, is used to discriminate between responders and non-responders, the 18S peak area, the 28S peak area and the 28S peak height were found to have the best performance; while the features of 18S peak height, intermediate area, low C area and low B area had the second best performance. However, the features of 18S peak width, 28S peak width and concentration may also carry some useful prediction information.

Accordingly, in one embodiment, the single feature may be the 18S peak area in the 18S region. This can be represented by the expressions "18S" or "18S peak area".

In one embodiment, the single feature may be the 28S peak area in the 28S region. This can be represented by the expressions "28S" or "28S peak area".

In one embodiment, the single feature may be the 18S peak height in the 18S region. This can be represented by the expression "18S peak height".

In one embodiment, the single feature may be the 28S peak height in the 28S region. This can be represented by the expression "28S peak height".

In one embodiment, the single feature may be intermediate area. This can be represented by the expressions "Intermediate" or "Intermediate area".

In one embodiment, the single feature may be low C banding region area. This can be represented by the expression "low C area" or "low C".

In one embodiment, the single feature may be low B banding region area. This can be represented by the expression "low B area" or "low B".

TABLE 17 provides the AUC values when two dimensional feature sets, comprising at least one feature in each feature set, was assessed on the MA22 dataset using the methods 100 and 400. In this case, the values for the various two dimensional feature sets were calculated and compared to various two dimensional threshold zones to discriminate between responders and non-responders (i.e. the threshold zones are defined by lines).

TABLE 17

AUC for two feature analysis on the MA22 dataset

| Combination of Features | AUC |
|---|---|
| 18S peak area vs. 28S peak area | 0.7722 |
| 18S peak height vs. 28S peak height | 0.7769 |
| (18S peak area + 28S peak area) vs. intermediate area | 0.7587 |
| (18S peak area + 28S peak area) vs. low B banding region area | 0.7745 |
| (18S peak area + 28S peak area) vs. low C banding region area | 0.7951 |
| (18S peak area + 28S peak area) vs. (18S peak width + 28S peak width) | 0.7935 |
| (18S peak area + 28S peak area) vs. concentration | 0.7832 |
| (18S peak height + 28S peak height) vs. intermediate area | 0.7508 |
| (18S peak height + 28S peak height) vs. low C banding region area | 0.784 |
| (18S peak height + 28S peak height) vs. (18S peak area + 28S peak area) | 0.7927 |
| (18S peak height + 28S peak height) vs. (18S peak width + 28S peak width) | 0.7698 |
| (18S peak height + 28S peak height) vs. concentration | 0.7714 |

When a two dimensional feature set was used to do the discrimination between responders and non-responders, it was found that the peak areas and peak heights are useful for discrimination. Accordingly, better discrimination results can be obtained when combining them with other features. From TABLE 17, the two dimensional feature sets of (18S peak area+28S peak area) and low C banding region area, (18S peak area+28S peak area) and (18S peak width+28S peak width), and (18S peak height+28S peak height) and (18S peak area+28S peak area) were found to have the best AUC results. Other combinations listed in Table 17 may also be useful.

Accordingly, in one embodiment, the two dimensional feature sets are used in a two dimensional plot using two orthogonal variables representing each feature set to graph an RDA coordinate that is used to discriminate responders from non-responders. One of the variables is defined by a first feature set and the other variable is defined by a second feature set. These variables may be combined using LDA or QDA as will be described with respect to FIGS. 30A-30D. The first variable comprises the 18S peak area and the second variable comprises the 28S peak area. This can be represented by the expression "18S area vs. 28S area" or "18S vs. 28S".

In another embodiment, the first variable comprises the 18S peak height and the second variable comprises the 28S peak height. This can be represented by the expression "18S peak height vs. 28S peak height".

In another alternative embodiment, the first variable comprises the sum of the 28S peak area and the 18S peak area and the second variable comprises the low C banding region area. This can be represented by the expression "(28S+18S) vs. low C".

In another alternative embodiment, the first variable comprises the sum of the 28S peak area and the 18S peak area and the second variable comprises the low B banding region area. This can be represented by the expression "(28S+18S) vs. low B".

In another alternative embodiment, the first variable comprises the sum of the 18S peak area and the 28S peak area and the second variable comprises the sum of the 18S and 28S peak widths. This can be represented by the expression "(18S+28S) vs. (18S peak width+28S peak width)".

In another alternative embodiment, the first variable comprises the sum of the 28S and 18S peak heights and the second variable comprises the sum of the 28S peak area and the 18S peak area. This can be represented by the expression "(28S peak height+18S peak height) vs. (28S+18S)".

In another alternative embodiment, first variable comprises the sum of the 18S peak area and the 28S peak area and the second variable comprises the intermediate area. This can be represented by the expression "(18S+28S) vs. (intermediate)".

In another embodiment, the first variable comprises the sum of the 18S peak area and the 28S peak area and the second variable comprises the RNA concentration of the sample. This can be represented by the expression "(18S+28S) vs. (concentration)".

In another embodiment, the first variable comprises the sum of the 18S peak height and the 28S peak height and the second variable comprises the RNA concentration of the sample. This can be represented by the expression "(18S peak height+28S peak height) vs. (concentration)".

It should be noted that concentration may be used as a feature in two-feature analysis as it has been found to show good discriminative ability when combined with some other features. The concentration is the RNA concentration in the sample which may be determined using various techniques. For example, in embodiments where the electropherogram is produced by a system like the Bioagilent system, the RNA concentration can be determined using measurements obtainable from the electropherogram. In an example, RNA concentration may be determined by comparing to a known quantity of a known standard such as the marker or ladder. For example the amount of the RNA in a standard or ladder band is divided by the area under the curve for the entire marker. The Total Area of each sample may then be multiplied by this value to give a RNA concentration for each sample.

In another embodiment, the first variable comprises the sum of the 18S and 28S peak heights and the second variable comprises the intermediate area. This can be represented by the expression "(18S peak height+28S peak height) vs. (intermediate)".

In another embodiment, the first variable comprises the sum of the 18S and 28S peak heights and the second variable comprises the low C banding region area. This can be represented by the expression "(18S peak height+28S peak height) vs. low C".

In another embodiment, the first variable comprises the sum of the 18S and 28S peak widths and the second variable comprises the sum of 18S peak area and the 28S peak area, which can be represented by the expression "(18S peak width+28S peak width) vs. (18S+28S)".

TABLE 18 provides the AUC values when three dimensional features sets, comprising at least one feature in each feature set, was assessed on the MA22 dataset using the methods 100 and 400. In this case, the values for the various three dimensional feature sets were calculated and compared to various three dimensional threshold zones to discriminate between responders and non-responders (i.e. the threshold zones were defined by planes).

TABLE 18

AUC for three feature analysis on the MA22 dataset

| Combinations of Features | AUC |
| --- | --- |
| (18S peak area + 28S peak area) vs. (18S peak height + 28S peak height) vs. low C banding region area | 0.7864 |
| (18S peak area + 28S peak area) vs. (18S peak height + 28S peak height) vs. (18S peak width + 28S peak width) | 0.7761 |
| (18S peak area + 28S peak area) vs. (18S peak height + 28S peak height) vs. intermediate area | 0.7445 |
| (18S peak area + 28S peak area) vs. (18S peak width + 28S peak width)vs. low C banding region area | 0.8141 |

The three dimensional feature sets were selected for analysis based on the best two dimensional feature set combinations. The three dimensional feature set where the first feature comprises (18S peak area+28S peak area), the second feature set comprises (18S peak width+28S peak width) and the third feature set comprises lower c area was found to have the highest AUC based on the sample study. It has also been found that using three dimensional feature sets increases the spread in the data which makes it easier to discriminate between responders and non-responders.

Accordingly, in one embodiment, the three dimensional feature sets are used in a three dimensional plot using three orthogonal variables representing each feature set to graph an RDA coordinate that is used to discriminate responders from non-responders. One of the variables is defined by a first feature set, another variable is defined by a second feature set and the third variable is defined by a third feature set. These variables may be combined using LDA or QDA as will be described with respect to FIGS. 30A-30D. The first variable comprises the sum of the 18S peak area and the 28S peak area and is associated with a first axis. The second variable comprises the sum of the 18S peak height and the 28S peak height and is associated with a second axis. The third variable comprises the low C banding area and is associated with a third axis. This can be represented by the expression "(18S+28S) vs. (18S peak height+28S peak height) vs. low C banding area".

In another embodiment, the first variable comprises the sum of the 18S peak area and the 28S peak area and is associated with a first axis. The second variable comprises the sum of the 18S peak height and the 28S peak height and is associated with a second axis. The third variable comprises the sum of the 18S peak width and the 28S peak width and is associated with a third axis. This can be represented by the expression "(18S+28S) vs. (18S peak height+28S peak height) vs. (18S peak width+28S peak width)".

In another embodiment, the first variable comprises the sum of the 18S peak area and the 28S peak area and is associated with a first axis. The second variable comprises the sum of the 18S peak height and the 28S peak height and is associated with a second axis. The third variable comprises the intermediate area and is associated with a third axis. This can be represented by the expression "(18S+28S) vs. (18S peak height+28S peak height) vs. intermediate area".

In another embodiment, the first variable comprises the sum of the 18S peak area and the 28S peak area and is associated with a first axis. The second variable comprises the sum of the 18S peak width and the 28S peak width and is associated with a second axis. The third variable comprises the low C band area and is associated with a third axis. This can be represented by the expression "(18S+28S) vs. (18S peak width+28S peak width) vs. low C band area".

Example 18

The following example describes how a selection threshold is determined for a dataset for a selected set of features comprising the combination of features (18S peak area+28S peak area) and (18S peak width+28S peak width), which is showed herein for illustrative purposes only. This procedure can be repeated with other features or combinations of features. It should be noted that the feature sets that are used with LDA or QDA have been normalized with respect to the total area which is the area of the low banding region, the 18S region, the intermediate region and the 28S region.

Figure 30A:
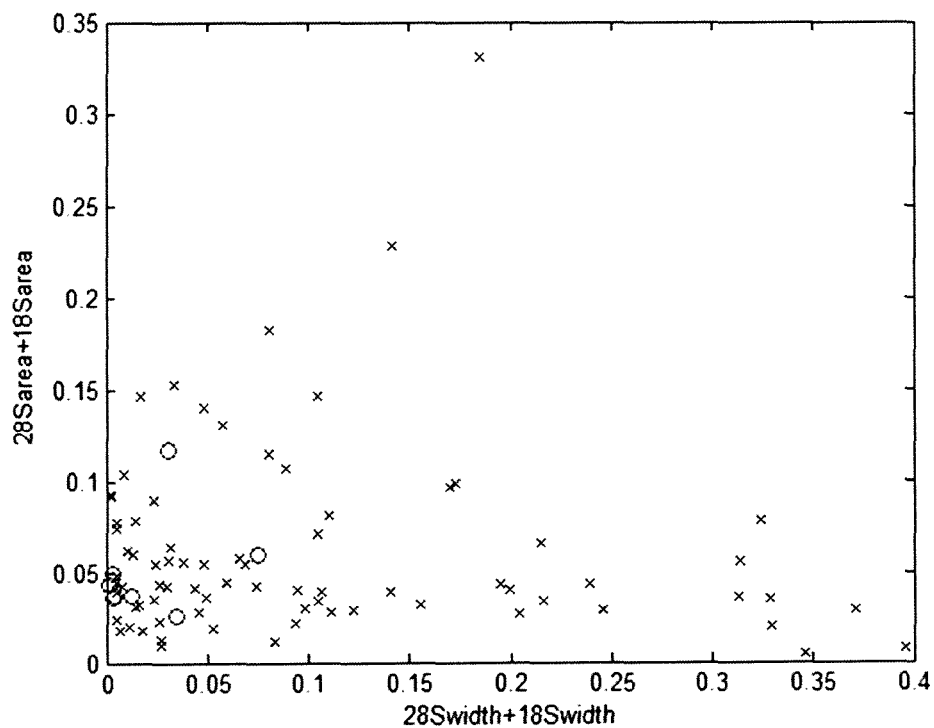
FIG. 30A is a graph of the feature of (28S peak width+18S peak width) versus (28S+18S) for a sample study using the modified peak identification method.

Referring now to FIG. 30A, a first variable representing the 18S peak area+28S peak area was plotted along the x-axis and a second variable representing the 18S peak width+28S peak width was plotted along the y-axis for different patients from the MA22 study. The circles 'o' represent responders and the crosses 'x' represent non-responders in FIG. 30A.

For each threshold value, LDA, which is a classification method, was used to generate values for coefficients that can be used with the first and second variables and the threshold value to define a line that can be used to divide the samples into two groups (i.e. responders and non-responders). This line satisfies equation 3:

$$a \times (18S \text{ peak area} + 28S \text{ peak area}) + b \times (18S \text{ peak width} + 28S \text{ peak width}) - \text{threshold} = 0 \quad (3)$$

where a and b are the coefficient values determined by LDA.

It should be noted that in general, equation 3 can be rewritten as equation 4:

$$y = kx + b \quad (4)$$

in which a feature or a combination of features are used for the variables x and y. In this example, x is (18S area+28S area) and y is (18S width+28S width). The parameter k is the slope of the line which is determined by LDA. The parameter b is the intercept of the line which is the intersection point of the y axis and the line.

Figure 30B:
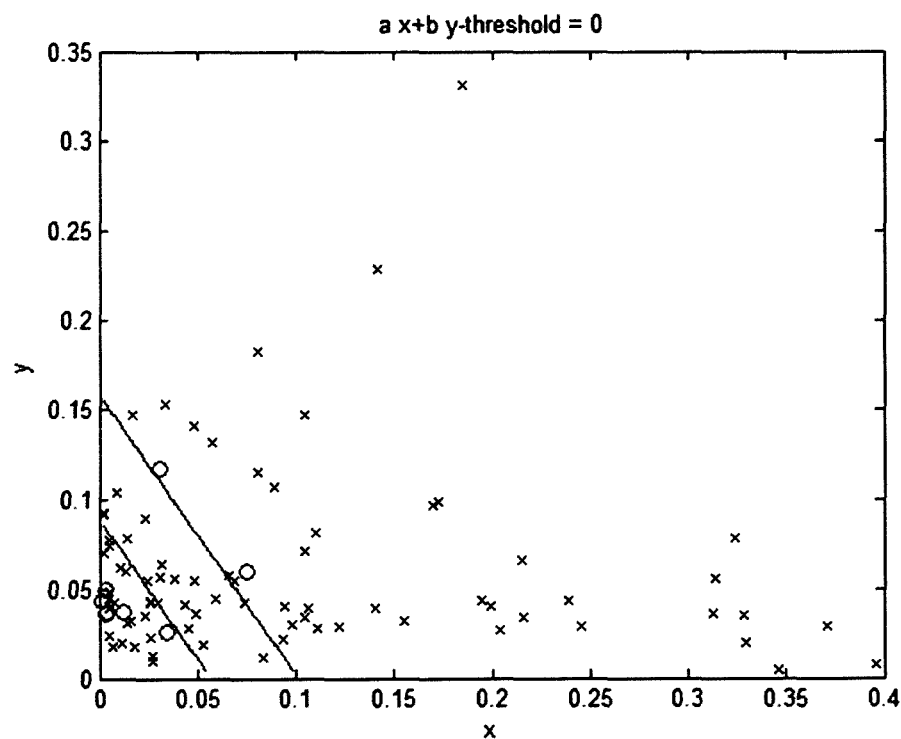
FIG. 30B is the graph of FIG. 30A further comprising Linear Discriminant Analysis (LDA) determined partition lines.

Multiple lines can be determined using multiple threshold values (each threshold value is associated with a line) and these lines can be used to create zones in a plot of the two variables. For example, two lines can be determined for two different threshold values to divide the patients into three zones with two lines. This can be done such that the lines are parallel to one another as is shown in FIG. 30B. The slope of the lines is determined by the LDA and it depends on the actual data samples as well as the combination of features that is used for the different variables.

In order to determine the threshold values, many different threshold values are assessed in terms of one or more predictive or detective measures. For example, for each threshold value, LDA can be used to generate the line and then the samples in the resulting zones can be assessed to determine at least one of the sensitivity, specificity, negative predictive value, positive predictive value, false negative rate and false positive rate associated with the threshold value. The threshold value is then selected based on the one that has the best discriminative or predictive values. For example, the threshold values can be assessed on which threshold value has the best positive predictive value and the negative predictive value.

For each patient, using the two features that are selected as the x and y variable as well as the slope that is determined by LDA analysis, the equation 3 can be used to determine a particular intercept for the patient can be used as the LDA score for the patient.

Figure 30C:
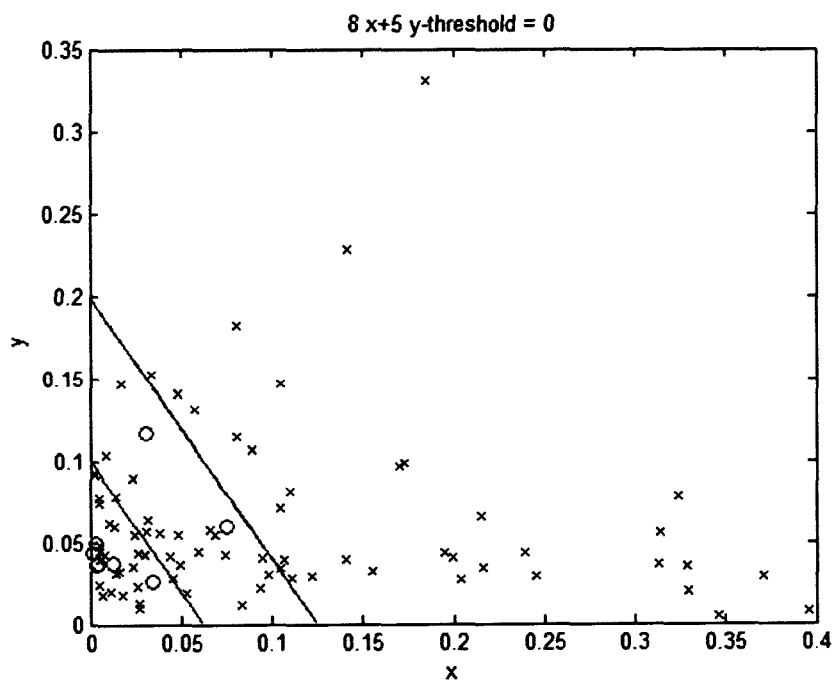
FIG. 30C is the graph of FIG. 30A further comprising another example pair of LDA determined partition lines.

For example, assume 0.1 and 0.2 are selected as the y-intercept to define the zone-partitions. The patients can then be divided into three zones as shown in FIG. 30C. The uppermost line is given by the equation y=−1.6x+0.2 (or 8x+5y=1) and the lowermost line is given by the equation y=−1.6x+0.1 (or 8x+5y=0.5). The x-axis and y-axis variables are (18S peak area+28S peak area) and (18S peak width+28S peak width), respectively.

The region underneath the lowermost line, above the x axis and to the right of the y axis defines zone 1 in which there are 29 patients, 6 of which are responders. The region between the uppermost and lowermost lines and to the right of the y axis defines zone 2 in which there are 22 patients, 2 of which are responders. The region above the uppermost line and to the right of the y-axis define zone 3 in which there are 34 patients, all of which are non-responders.

Example 19

In an alternative embodiment, rather than using LDA to determine RDA zones as was done in FIGS. 30B and 30C, Quadratic Discriminant Analysis (QDA) can be used to determine partitions for the zones that can be used for prediction. With different thresholds, QDA gives different curves to divide the samples into various groups. For example, using two threshold values two groups, satisfying the following equation 5:

$$c_1 \times (18S \text{ peak area} + 28S \text{ peak area})^2 + c_3 \times (18S \text{ peak width} + 28S \text{ peak width})^2 - c_2 \times (18S \text{ peak area} + 28S \text{ peak area}) \times (18S \text{ peak width} + 28S \text{ peak width}) - a_1 \times (18S \text{ peak area} + 28S \text{ peak area}) + b_1 \times (18S \text{ peak width} + 28S \text{ peak width}) - \text{threshold} = 0 \quad (5)$$

where a first variable represents the feature 18S peak area+ 28S peak area and a second variable represents the feature 18S peak width+28S peak width and the parameters $a_1$, $b_1$, $c_1$, $c_2$ and $c_3$ are determined by QDA.

Figure 30D:
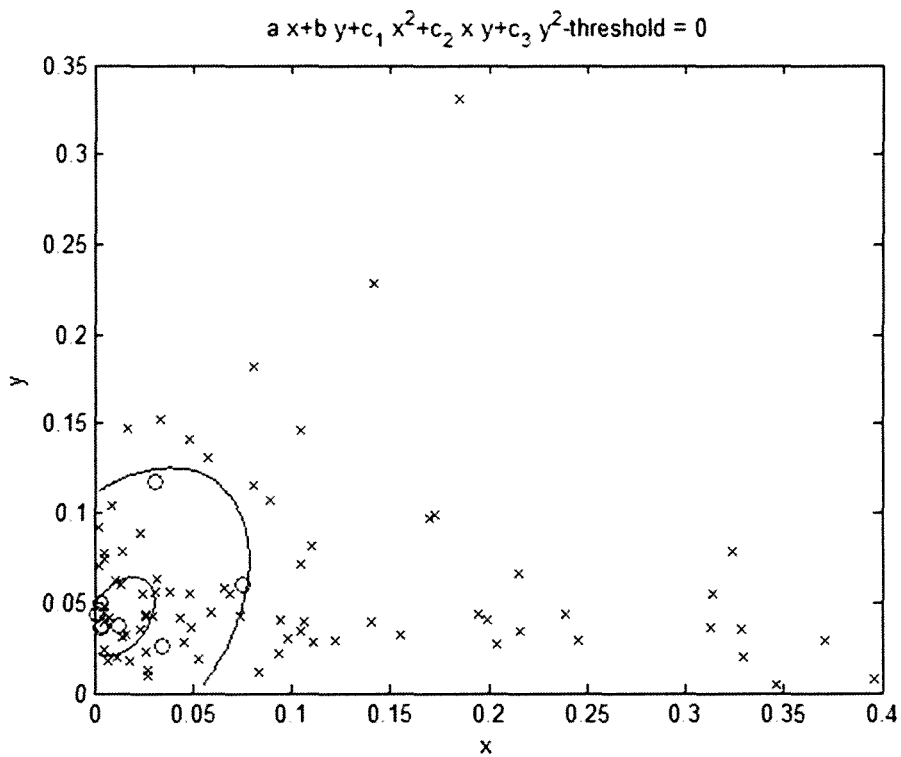
FIG. 30D is the graph of FIG. 30A further comprising Quadratic Discriminant Analysis (QDA) determined partition lines.

Equation 4 can be used with two thresholds to generate two concentric curves that: can divide the patients into three zones as shown in FIG. 30D. Once again, the circles 'o' represent responders, and the crosses 'x' represent non-responders. The appropriate threshold values can be determined as was explained previously using LDA, namely that for several threshold values the predictive measures of sensitivity, specificity, negative predictive value, positive predictive value, false negative rate and false positive rate can be calculated for each threshold. The desired threshold values can then be selected which result in the best predictive values.

For combinations of three features, the same analysis can be used to determine the RDA zones using either LDA or QDA.

It should be noted that in alternative embodiments, other techniques may be used to determine the RDA zones. For example, other machine learning methods may be used to do the prediction where there is a larger dataset such as, but not limited to, Support Vector Machine (SVM), Neural Networks, and the k-nearest neighbors algorithm (kNN).

Example 20

The RNA Disruption index (RDI) is the output of an RDA assay described herein, for example a value corresponding to a ratio of at least some of the various combinations of features described herein or the result of LDA or quadratic discriminant analysis of at least two of the feature sets described herein. The cutoff point between zone 2 and zone 3 may be chosen to maximize the PPV such that most of the responders from the MA22 dataset would be located in zone 3. For example, the RDI ranges used based on the study samples are about: 0.3 to 10 (zone 1), 10.1 to 35 (zone 2) and greater than 35.1 (zone 3). There may be other zones in other situations. For example, the fragmented RNA can be determined by the sum of the intermediate region area and the low C region area. This index can be used to compare samples for the extent of RNA disruption, for example for research purposes. Clinical zones can be established which capture a range of RDI values wherein the clinical zones are defined by cutoff points (e.g. between zone 1 and 2 and between zone 2 and 3). For example the cutoff point between zone 1 and zone 2 can be set to correspond to a RDI value that gives an NPV of 0.99.

Example 21

The data described in Example 6 was reanalyzed using the peak identification method 400 described in Example 10.

Plots of the combination of features Intermediate Area/ (28S+18S) and Low C Area/(28S+18S) were generated using the method 400 although method 300 may also be used.

The ratio of Low C Area/(28S+18S) was plotted against docetaxel dose. Little change was seen at 8 hr, 24 hr, or 48 hr. However, after 72 hr, a dramatic increase in the sample. Two replicate experiments had similar results.

Figure 31A:
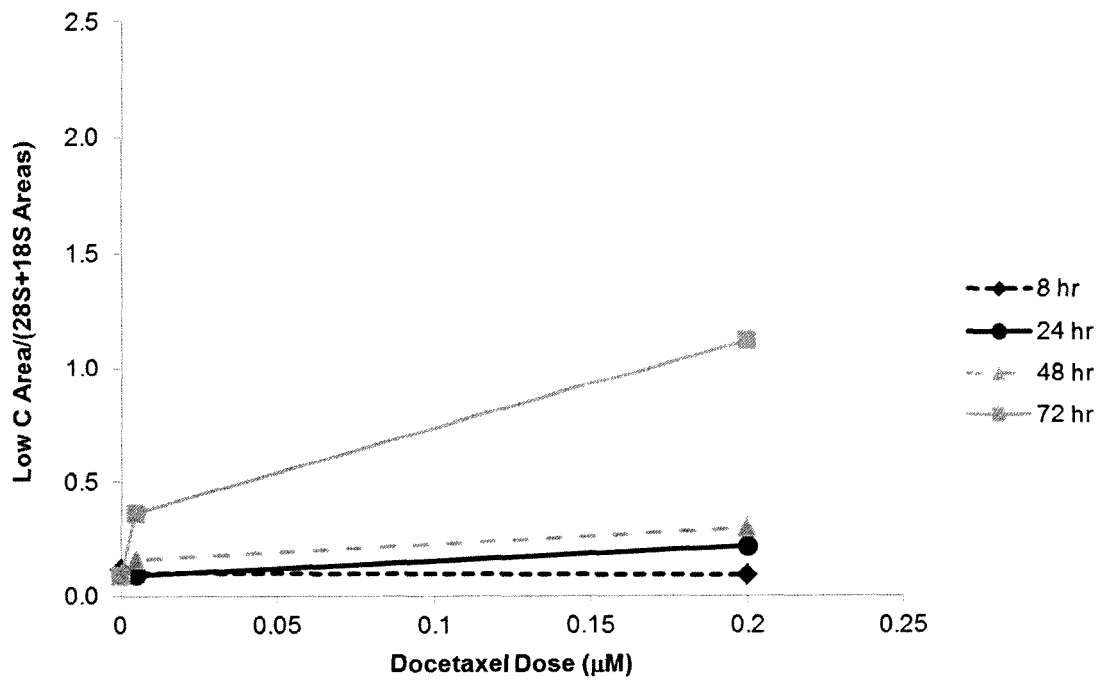
FIG. 31A is a graph of the feature low C/(28S+18S) versus docetaxel dose for an in vitro study using the modified peak identification method.
Figure 31B:
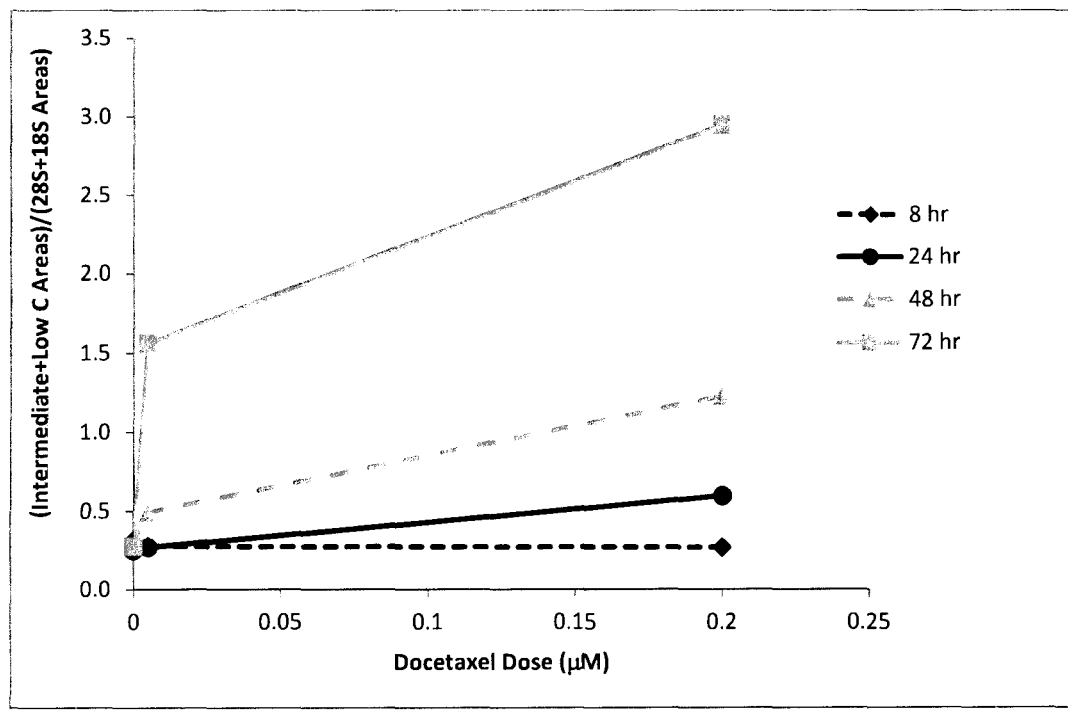
FIG. 31B is a graph of the feature (Intermediate+low C)/(28S+18S) versus docetaxel dose for an in vitro study using the modified peak identification method.

The maximum of the ratio (Intermediate Area+Low C Area)/(28S+18S) was plotted against docetaxel dose and the results are shown in FIG. 31B. Each value represents a single sample. Two replicate experiments had similar results.

Example 22

Figure 32A:
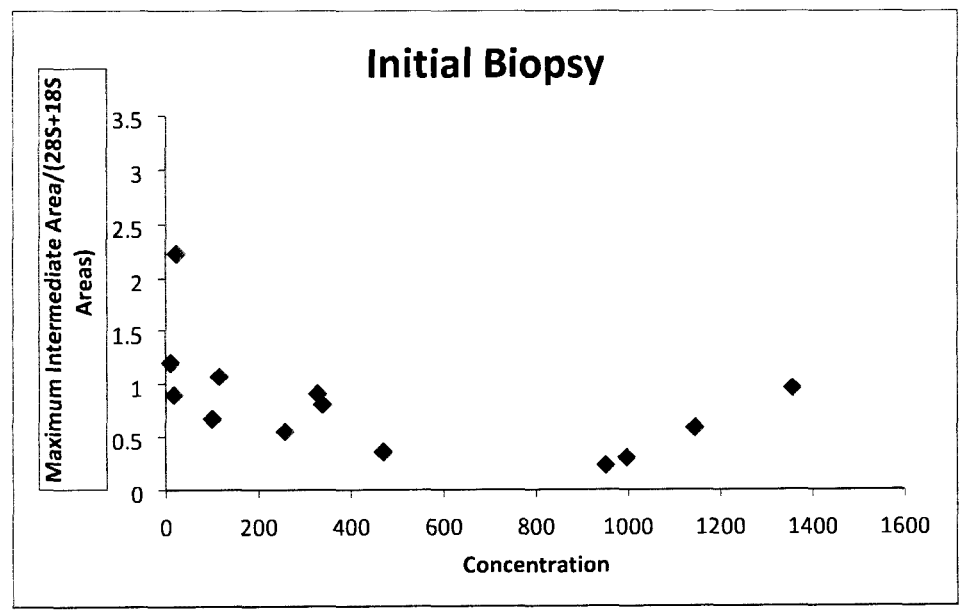
FIG. 32A is a graph of the feature Maximum Intermediate/(28S+18S) versus RNA concentration for a sample study for patients undergoing neo-adjuvant therapy with Trastuzumab.
Figure 32B:
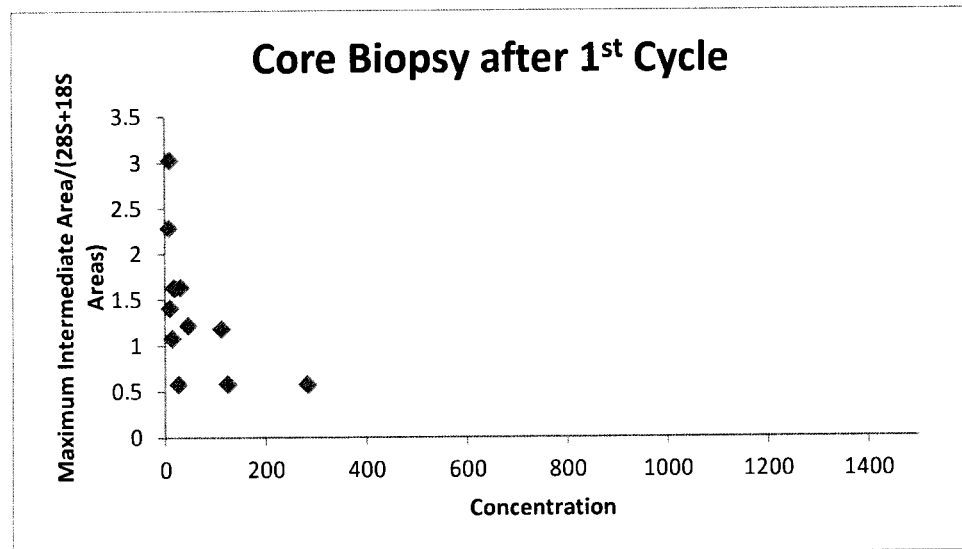
FIG. 32B is a graph of the feature Maximum Intermediate/(28S+18S) versus RNA concentration for a sample study for patients undergoing neo-adjuvant therapy with Trastuzumab.

Biopsy samples before and after a treatment dose were obtained from patients undergoing neo-adjuvant therapy with Trastuzumab. RNA was isolated and analyzed using the Agilent Bioanalyzer. Electropherograms were analyzed using the methods 100 and 400 and the maximal RDI score was graphed for each tumour sample at each time-point. The RDI values are increased in some patients after the first cycle of Trastuzumab (FIG. 32A and FIG. 32B).

Figure 32C:
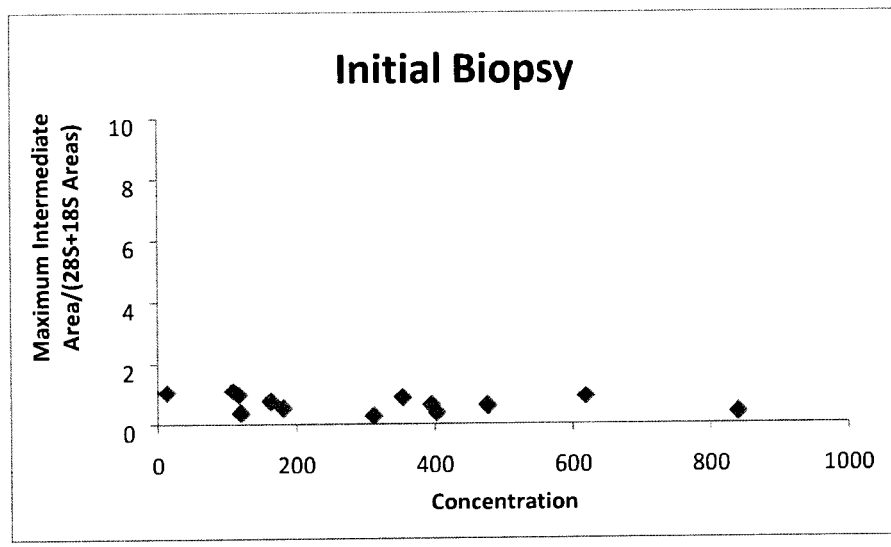
FIG. 32C is a graph of the feature Maximum Intermediate/(28S+18S) versus RNA concentration for a sample study for patients undergoing neo-adjuvant therapy with Zometa.
Figure 32D:
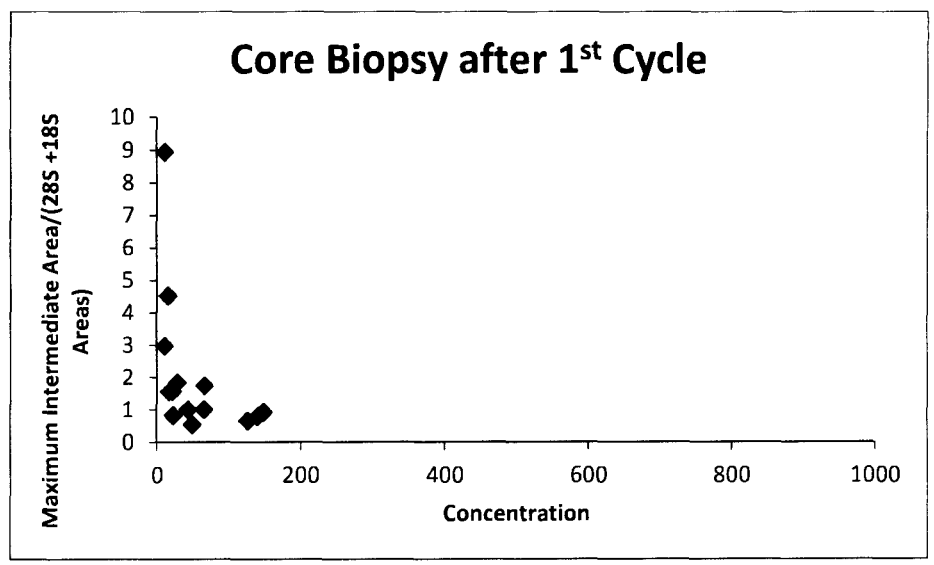
FIG. 32D is a graph of the feature Maximum Intermediate/(28S+18S) versus RNA concentration for a sample study for patients undergoing neo-adjuvant therapy with Zometa.
Figure 33A:
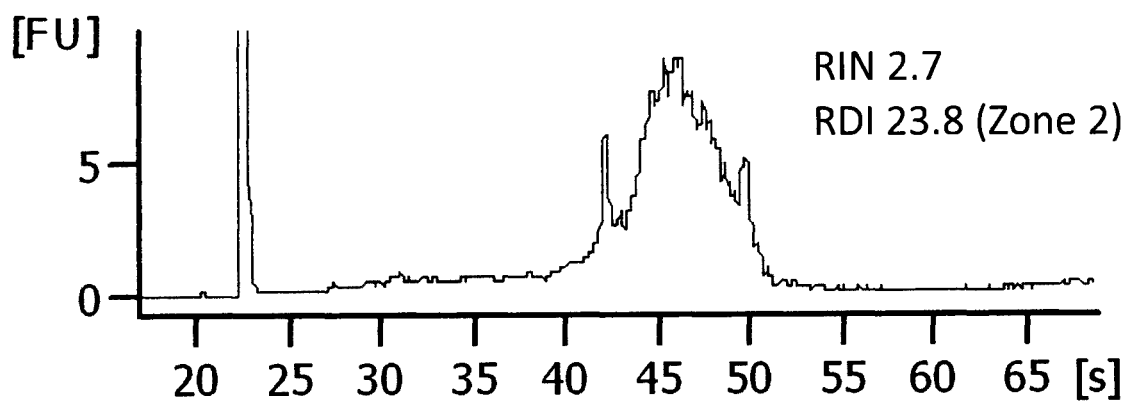
FIGS. 33A-33F are a series of illustrations of electropherogram traces with the calculated RIN and RDI values for each.
Figure 33B:
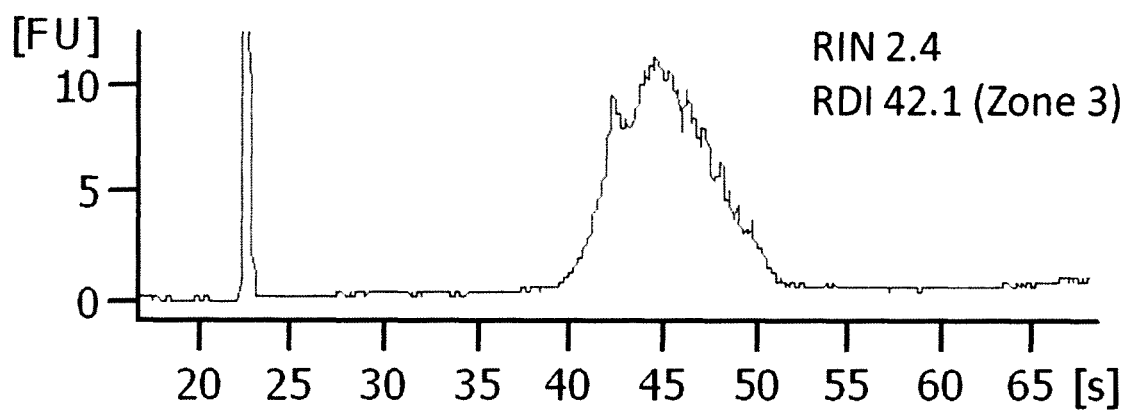
Figure 33C:
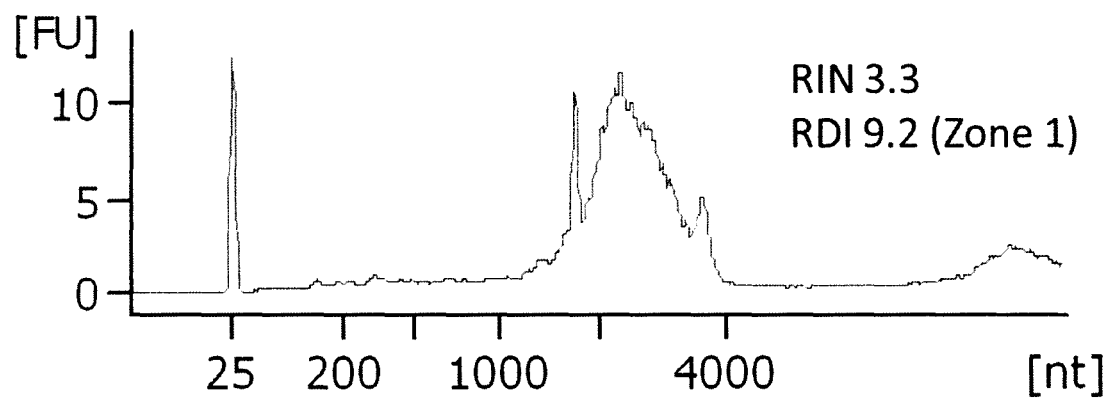
Figure 33D:
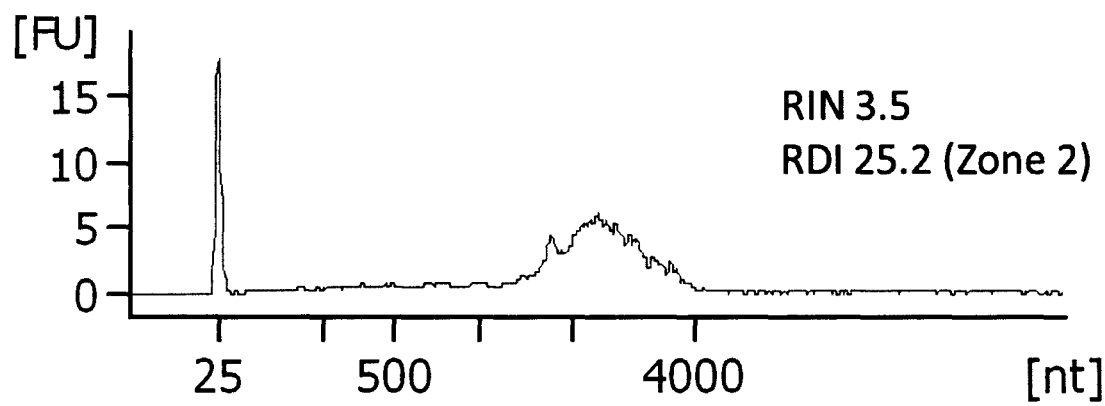
Figure 33E:
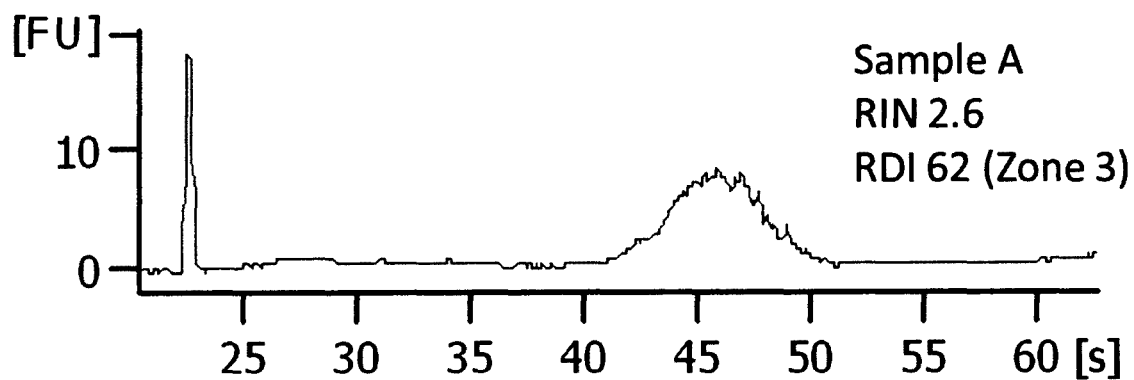
Figure 33F:
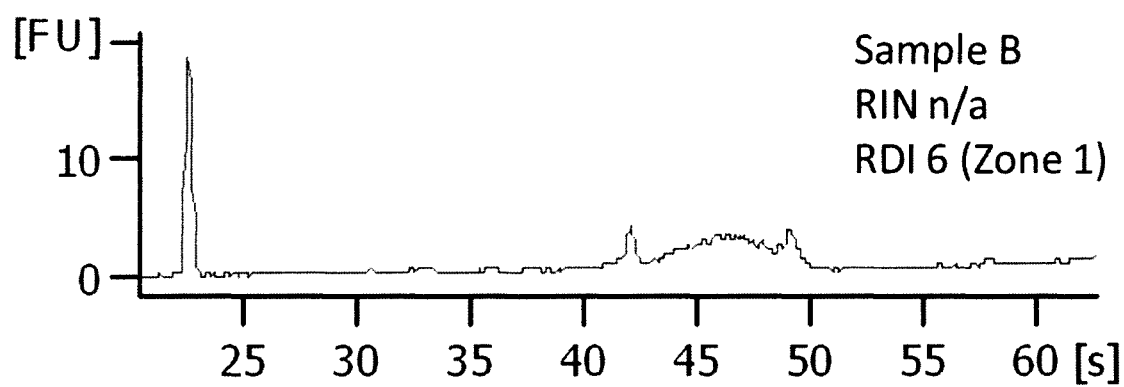

Biopsy samples were obtained from patients undergoing neo-adjuvant therapy with Zometa. RNA was isolated and analyzed using the Agilent Bioanalyzer. Electropherograms were analyzed using the methods 100 and 400 and the maximal RDI score was graphed for each tumour sample at each time-point. The RDI values are increased in some patients after the first cycle of Zometa (FIG. 32C and FIG. 32D).

Example 23

FIGS. 33A-33F show several samples where the RIN algorithm gives a low RIN or "n/a" whereas the RDI score, determined as described herein, is better able to differentiate these samples. The electropherograms of FIGS. 33A-33F were taken from mid-therapy MA22 data. FIGS. 33A-33F also show that RIN values can be the same in electropherograms which demonstrate different patterns whereas the RDI score appears to be able to differentiate between these electropherograms. The RDI was calculated using the ratio or feature combination Intermediate Area/(28S+18S Areas).

FIG. 1 compares RIN to RDI in mid-therapy MA22 samples. When the RNA is intact, both the RIN and RDI scores are accurate. However, once the RNA becomes fragmented, for example due to drug exposure, the RDI is a better measure. The feature combination that was used for the RDI determination was Intermediate Area/(28S+18S).

Example 24

The need for biomarkers to accurately assess long term breast cancer chemotherapy efficacy is well established and is particularly needed for triple negative breast cancer (TNBC). To date, most in vitro diagnostic tests offered have been limited to hormone receptor positive patients. The RNA Disruption Assay (RDA), described herein, is a novel prognostic test for patients undergoing neoadjuvant chemotherapy that enables assessment of drug efficacy during treatment. RDA was developed in association with the CAN-NCIC-CTG MA.22 clinical trial for women with locally advanced breast cancer. Varying doses of docetaxel and epirubicin were given at two weekly (close dense) or three weekly intervals. Tumours were biopsied in duplicate at three time points: pre-therapy, mid-therapy and post-therapy. Trial endpoints included clinical response, pathological complete response (pCR), disease-free survival and overall survival.

RDA is based on RNA electropherogram analysis generated to assess RNA quality as measured by the extent of ribosomal RNA (rRNA) disruption, mid-therapy. rRNA Disruption is quantified by a method described herein for example as described in FIGS. 20A and 20B or 27A and then stratified into an RNA Disruption Assay (RDA) score with 3 zones corresponding to the degree of RNA disruption. An RDA score in Zone 3 is associated with an increased likelihood of subsequent pathological complete response, an RDA score in Zone 2 is associated with an increased likelihood of at least partial response, and an RDA score in Zone 1 indicates that patients are very unlikely to receive long term chemotherapy benefit, NPV>0.98, for example.

When applied to the MA.22 study after the $3^{rd}$ or $4^{th}$ cycle of chemotherapy, 34 of 85 patients (40%) had tumours with RDA scores in zone 1.

Subsequently, it has been demonstrated in tumour cell lines that rRNA disruption leads directly to subsequent tumour cell death and that the extent of rRNA disruption is cell line type, dose, and time dependent.

Methods

Paraffin-embedded, formalin-fixed tumours from 82 MA.22 patients were subtyped by immunohistochemistry for estrogen receptor (ER), progesterone receptor (PR) and Her2/neu (Her2) expression status pre-therapy.

RDA, clinical response data and pCR occurrence data were obtained for each patient and matched to the tumour expression status for the above receptors. The feature combination that was used for the RDA determination was Intermediate Area/(28S+18S). The TNBC patients' tumours were then assessed for RNA disruption (RDA zones 1, 2 or 3) and compared to similar data for receptor positive patients. A similar comparison was made classifying patients by clinical response (e.g. no response/stable disease, partial response, or complete clinical response).

Results

Both Triple Negative Breast Cancer (TNBC) patients and receptor positive patients had tumours in each of the three RDA zones and in each of the clinical response categories. The pCR response rates were 3 of 21 (14% response rate) for TNBC patients, 0 of 43 (0% response rate) for ER+, Her2-ve patients, 1 of 6 (17% response rate) for ER+, Her2+ patients, and 4 of 12 (33% response rate) for Her2+ patients. Six of eight pCR responders were in RDA Zone 3 and two were in RDA Zone 2. Clinically, 6 of 8 pCR responders had a complete response, and two had partial responses. For the three TNBC clinical non responders who had stable disease, the RDA scores were in RDA Zone 3 for one patient, RDA Zone 2 for the second patient and RDA Zone 1 for the third. Seven of 18 non-responder TNBC patients were in RDA Zone 1. However, clinically, five of these patients had a partial response, one had a complete response and one had stable disease. Two of the three TNBC pCR responders showed an RDA score in RDA Zone 3 but clinically one had a partial response. For other subtypes, 12 of 44 ER+, Her2-ve patients were in RDA Zone 1; 3 of 6 Er+ve, Her2+ve patients were in RDA Zone 1; 2 of 12 Her2+ve patients were in RDA zone 1. Using pCR and non pCR as definitive criteria, RDA was equally predictive with clinical response for prediction of complete response but was much superior for prediction of pCR non-response.

In both TNBC and other subtypes of locally advanced breast cancer, RDA can identify pCR non-responders much better than clinical response. Currently, based on this study, RDA can identify approximately 33% of TNBC patients as non-responders compared to approximately 28% for ER+ve Her2-ve patients. These results indicate that RDA, as a test for response guided therapy, can identify a subpopulation of non-responding TNBC patients who can be considered for alternate therapy.

Example 25

One major obstacle to the successful destruction of tumors using chemotherapy drugs is the presence of intrinsic or acquired resistance to anti-cancer agents. Assessed herein is whether chemotherapy-dependent alterations in tumor RNA quantity and integrity could also be demonstrated in vitro using the A2780 ovarian cancer cell line. An equal number of cells were plated and treated with various docetaxel concentrations to determine the effect of the drug on cell division, cellular RNA content, and RNA integrity. At low docetaxel concentrations, RNA content increased per cell, likely due to increased rRNA production prior to a cell cycle arrest at mitosis. However, at higher docetaxel concentrations (≥0.1 µM), dose and time-dependent reductions in cell number and cell RIN values were observed while the RDI based on the feature combination of Intermediate Area/(28S+18S) increased, which coincided with dramatic changes in the RNA banding pattern (i.e. RNA disruption). This included the formation of novel discrete bands distinct from the 28S and 18S rRNA bands. In contrast, treating docetaxel-resistant A2780DXL cells with docetaxel did not result in RNA disruption or changes in cellular RNA content. These findings support the view that chemotherapy dependent changes in tumor cell RNA content and integrity (as measured using the RNA disruption assay or RDA technique described herein) could effectively be used to monitor cellular response to chemotherapy agents and to differentiate between drug-sensitive and drug-resistant tumor cells in vitro and in vivo.

Example 26

Figure 34A:
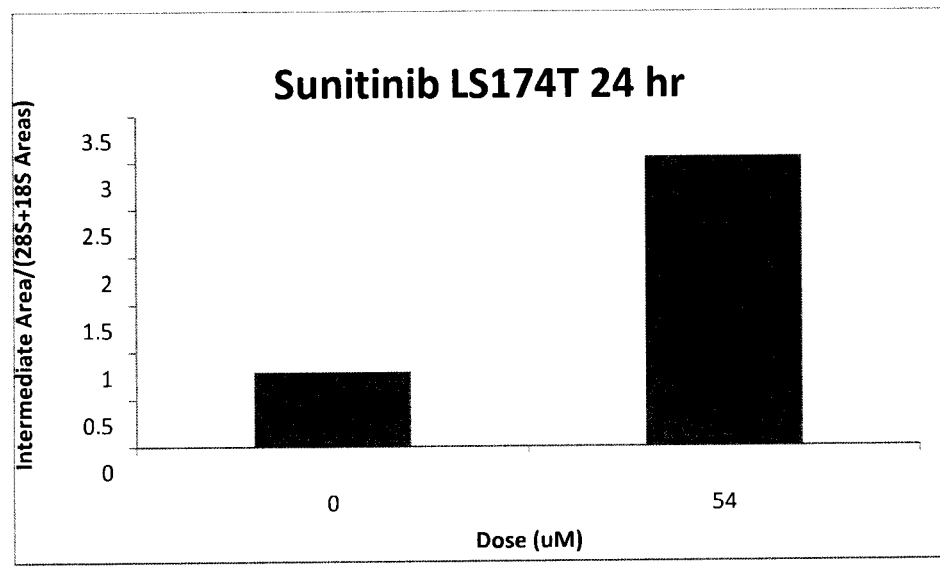
FIG. 34A is a graph of the feature Intermediate Area/(28S+18S Areas) for colon adenocarcinoma cells incubated with Sunitinib.

Colon adenocarcinoma cells LS174T were incubated with Sunitinib, a receptor tyrosine kinase inhibitor. RNA was isolated from the cells and analyzed using an Agilent Bioanalyzer. RNA Disruption is evident at 24 hr at 54 mM (see FIG. 34A).

Figure 34B:
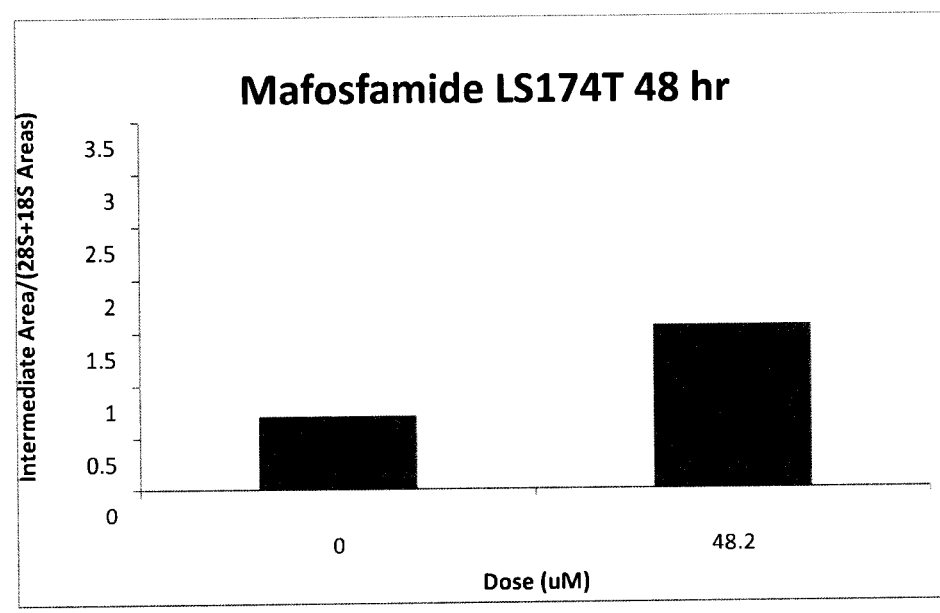
FIG. 34B is a graph of the feature Intermediate Area/(28S+18S Areas) for colon adenocarcinoma cells incubated with Mafosfamide.

Colon adenocarcinoma cells LS174T were incubated with Mafosfamide, a DNA cross-linking agent. RNA was isolated from the cells and analyzed using an Agilent Bioanalyzer. RNA Disruption is evident at 48 hr at 48.2 mM (see FIG. 34B).

Figure 34C:
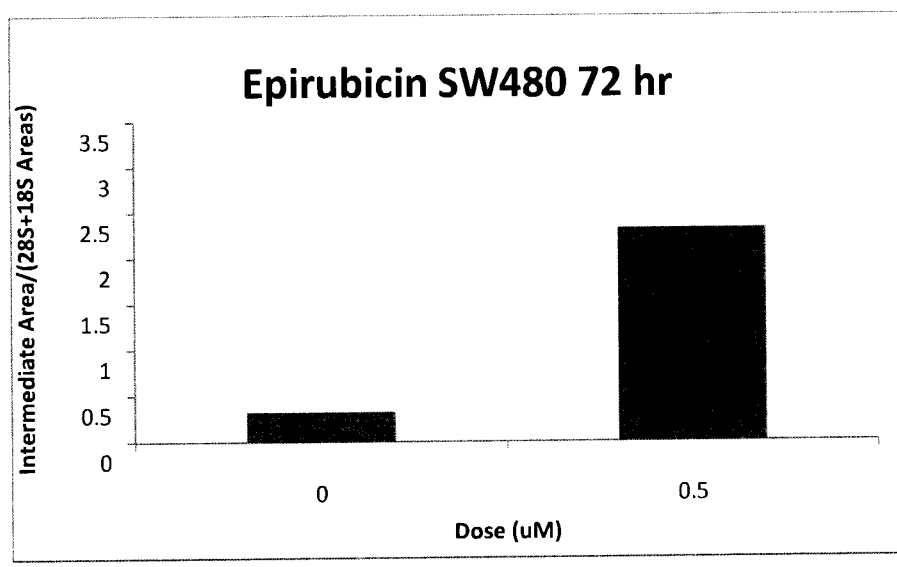
FIG. 34C is a graph of the feature Intermediate Area/(28S+18S Areas) for colon adenocarcinoma cells incubated with Epirubicin.

Colon adenocarcinoma cells SW480 were incubated with Epirubicin, a DNA synthesis inhibitor. RNA was isolated from the cells and analyzed using an Agilent Bioanalyzer. RNA Disruption is evident at 72 hr at 0.5 mM (see FIG. 34C).

It should be noted that either method 300 or method 400 can be used in determining the values for the combinations of features or the feature sets used in LDA and QDA analysis.

Example 27

CaOV3 ovarian tumour cell line and Jurkat leukemia cell line were assessed for RNA disruption. These cell lines also show RNA disruption. The CaOV3 ovarian tumour cell line and Jurkat leukemia cell line were also assessed for their ability to exhibit docetaxel-induced RNA disruption. RNA disruption was also observed in these cell lines, although the abnormal peaks generated in the electropherogram by docetaxel were distinct in these additional cell lines. Similar to A2780 ovarian tumour cells, the extent of RNA disruption in these additional cell lines varied (depending upon the chemotherapy drug administered and the duration of drug exposure). Taken together, these data suggest that multiple cell lines can be used to screen for agents that induce RNA disruption. It would be expected that the degree of RNA disruption observed in screening for RNA disruptive agents will be dependent upon the cell line used, the capacity of agents to induce RNA disruption, and the incubation time.

Example 28

A high throughput robotic assay to quantify RNA disruption in cells or tumours (the RNA disruption assay or RDA) is described. Cell lines exhibit RNA disruption in vitro, the sensitivity, resistance, and cross-resistance of such cells to specific chemotherapy drugs (as measured by RDA) is comparable to that determined in the standard clonogenic assay. Viability studies after drug treatment reveal that cells can only tolerate a determinable level of rRNA degradation, above which cells become non-viable. Agents that induce extensive rRNA disruption commit cells to cell death. As described above, it is shown in clinical trial (MA.22) that extensive tumour RNA disruption is associated with complete tumour destruction post-treatment (pathologic complete response or pCR) and that high tumour RNA disruption mid-treatment predicts strongly enhanced disease-free survival post-treatment. These findings suggest that RDA can identify agents that reliably induce tumour death in vitro and in vivo. These agents are expected may also promote increased patient survival.

Drug sensitivity assays will be used to monitor the effects of various classes of anti-cancer agents (with or without chemosensitizers) on ovarian tumour and Jurkat lymphoma cells. Drugs to be tested included the taxane paclitaxel, the platinating agent cisplatin, the anthracycline epirubicin, the podophyllotoxin etoposide, and tumour necrosis factor alpha, which causes growth arrest in MCF-7 cells, but cells remain viable.

RDA like clonogenic assays can be used to identify drugs that are cytotoxic (FIG. 24C iv). The ability of RDA to distinguish between drug-sensitive A2780 ovarian tumour cells (closed circles) and docetaxel-resistant A2780DXL ovarian tumour cells (open circles) in terms of the ability to induce RNA disruption (as measured using the RNA disruption index or RDI). The cell lines have widely differing sensitivity to docetaxel in a clonogenic assay, with IC50 values differing by over three orders of magnitude. (The IC50 represented the concentration of docetaxel at which 50% of colony formation is suppressed.) Similarly, RNA disruption varied over at least three orders of magnitude for the two cell lines. Moreover, high RNA disruption is observed at concentrations where the maximum response to drug in a clonogenic assay is reached (the IC100, where no surviving colonies are detected).

Drug sensitivity will be assessed using RDI and other assays including for example MTT, SRB, and trypan blue exclusion assays, assays that measure DNA replication, or kits that measure Ki-67 immunostaining, and Annexin V/PI staining. The ability of RDA to identify agents that induce RNA disruption in cell lines of highly varying cell doubling times (19 to 100 hours), including wildtype and drug-resistant ovarian cancer cell lines (A2780, OVCAR-3, CAOV3, IGROV-1) and wildtype lymphoma cell lines (Jurkat, U-H01, SP53, and MC116) will be tested.

The ability of the chemotherapy agents listed above to permit the generation of surviving drug-resistant clones of the above-listed ovarian and lymphoma cell lines will be assessed.

Example 29

Chemotherapy induced RNA disruption is seen in tumour cells in culture as described herein. For example RNA concentration of a model in vitro cell line A2780 is 1220 ng/microliter and has an RDI of 0.23 prior to drug treatment. As shown in FIG. 24C Docetaxel treatment at 0.2 micromolar results in a RNA concentration decrease to about 359 ng/microliter and a RDI of 3.09 (72 hrs).

Docetaxel resistant cells have been made and have an IC50 of about 650 nM (parental A2780 cells have an IC50 of about 1.1. nm). RDI can be plotted. Agents can be tested to see what agents potentiate and/or restore (e.g. in resistant cells) docetaxel sensitivity.

FIG. 24C v) shows that potentiators of docetaxel can be identified. The a\Ability of RDA to detect potentiators of docetaxel (Dxl) sensitivity. We have well established that drug-sensitive A2780CC cells (dark bars) should strong docetaxel-dependent RNA disruption, as measured by the RNA disruption index or RDI. In contrast, docetaxel-resistant A2780DXL cells (bars with horizontal lines) do not show docetaxel-induced RNA disruption. We have also established in a clonogenic assay that Cyclosporine A (CycA) restores sensitivity to docetaxel in A2780DXL cells by inhibiting the function of drug transporters in these cells that promote docetaxel efflux. Interestingly, CycA also restored docetaxel's ability to induce RNA disruption, almost back to that observed in drug-sensitive A2780CC cells. Thus, RDA may be used to screen for potentiators of chemotherapy drug cytotoxicity.

Compared to clonogenic assays, RDI has one or more advantages, it is sensitive, is relatively low labour, has a short duration, can be automated, is quantitative and/or can distinguish between arrested and dead cells.

In patient samples RDA predicts long term survival. Candidates that have an increased RDI using an an in vitro cell model, for example an increase of at least 2 fold, at least 2.2 fold, at least 2.4 fold, at least 2.8 fold, at least 3 fold or greater are further tested.

TABLE 1

|  | Pre-Treatment | | | Mid-Treatment | | |
| --- | --- | --- | --- | --- | --- | --- |
|  | Non-pCR | pCR | All Patients | Non-pCR | pCR | All Patients |
| No. of Patients Assessed | 76 | 8 | 84 | 77 | 8 | 85 |
| Mean RNA Conc. (ng/µl) | 193 ± 26.1 | 226 ± 59.3 | 197 ± 24.2 | 94.9 ± 14.1 | 83.0 ± 19.4 | 94.0 ± 12.8 |
| Mean Max RDI | 25.6 ± 6.0 | 30.4 ± 23.3 | 26.0 ± 5.8 | 79.0 ± 20.0 | 176 ± 59.9 | 88.1 ± 19.1 |

TABLE 2

The number of patients exhibiting various measures of clinical response and various degrees of RNA disruption (zones) pre- and mid-treatment by epirubicin/docetaxel chemotherapy. The degree of RNA disruption was expressed in three zones, where zone 1 (RDI ≥0 and ≤10) is the lowest level of RNA disruption, zone 2 (RDA >10 and ≤35) is an intermediate level of RNA disruption, and zone 3 (RDI >35) is a high level of RNA disruption.

| Patient Clinical Response | pCRs by Extent of Clinical Response | pCRs by RDA Zone Mid-treatment | Maximum Tumour RDI Mid-treatment | pCRs by RDA Zone Pre-treatment | Maximum Tumour RDI Pre-treatment |
| --- | --- | --- | --- | --- | --- |
| Complete: 17 | Complete: 6 | Zone 3: 7 | Zone 3: 38 | Zone 3: 1 | Zone 3: 14 |
| Partial: 64 | Partial: 2 | Zone 2: 1 | Zone 2: 30 | Zone 2: 2 | Zone 2: 12 |
| No Response (SD/PD): 4 | No response: 0 | Zone 1: 0 | Zone 1: 17 | Zone 1: 5 | Zone 1: 58 |

TABLE 3

Relationship between the extent of clinical response to epirubicin/docetaxel chemotherapy for MA.22 patients and the degree of tumor RNA disruption mid-treatment, where zone 1 (RDI ≥0 and ≤10) is the lowest level of RNA disruption, zone 2 (RDA >10 and ≤35) is an intermediate level of RNA disruption, and zone 3 (RDI >35) is a high level of RNA disruption.

| RDA Zone | pCR | CR | PR | SD |
| --- | --- | --- | --- | --- |
| Zone 1 | 0 (0%) | 1 (5.9%) | 14 (21.9%) | 2 (50%) |
| Zone 2 | 1 (12.5%) | 7 (41.2%) | 22 (34.4%) | 1 (25%) |
| Zone 3 | 7 (87.5%) | 9 (52.9%) | 28 (43.8%) | 1 (25%) |

TABLE 4

| Category of MA.22 Patients | DFS in months (mean ± S.E.), n (number of patients) | | | | Significance of Difference in DFS Between Zone 3 and Zone 1 |
| --- | --- | --- | --- | --- | --- |
|  | RDA Zone 1 | RDA Zone 2 | RDA Zone 3 | pCR Responders |  |
| ALL | 33.9 ± 6.4, 18 | 41.0 ± 5.5, 29 | 56.9 ± 5.6, 38 | 59.4 ± 12, 8 | p = 0.0091 |
| ALL (Living*) | 43.7 ± 8.6, 11 | 49.6 ± 6.5, 21 | 68.2 ± 5.5, 29 | 68.1 ± 14, 6 | p = 0.011 |
| ALL (Deceased) | 18.4 ± 6.6, 7 | 17.5 ± 4.2, 8 | 20.5 ± 7.7, 9 | 33.1 ± 17, 2 | N.S.[1] |
| HR | 31.9 ± 5.8, 10 | 38.5 ± 8.5, 11 | 61.0 ± 7.0, 21 | n/a, 0 | p = 0.0066 |
| HR+ (Living*) | 31.4 ± 7.6, 7 | 44.3 ± 9.2, 9 | 73.3 ± 5.6, 17 | n/a, 0 | p = 0.00074 |
| HR+ (Deceased) | 33.1 ± 10, 3 | 12.3 ± 8.2, 2 | 21.5 ± 12, 5 | n/a, 0 | N.S. |

*Includes disease-free patients and patients alive with relapse

TABLE 5

Mid-treatment tumour RNA disruption and its relationship to MA.22 patient overall survival, disease-free survival (DFS), and pathologic complete response post-treatment. The level of RNA disruption was divided into three zones, where zone 1 (RDI ≥ 0 and ≤ 10) is the lowest level of RNA disruption, zone 2 (RDA > 10 and ≤ 35) is an intermediate level of RNA disruption, and zone 3 (RDI > 35) is a high level of RNA disruption. The number of patients alive with disease (AWD) across the RNA disruption zones was also noted.

| Patients | RDA Zone 1 | | RDA Zone 2 | | RDA Zone 3 | | pCR | |
| --- | --- | --- | --- | --- | --- | --- | --- | --- |
|  | n (%) | DFS (months) | n (%) | DFS (months) | n (%) | DFS (months) | n (%) | DFS (months) |
| ALL | 17 (20%) | 33.3 ± 6.8 | 30 (35%) | 41.1 ± 5.3 | 38 (45%) | 56.9 ± 5.8 | 8 (9%) | 59.4 ± 12 |
| Alive | 10 (12%) | 43.7 ± 9.5 | 22 (26%) | 49.7 ± 6.2 | 29 (34%) | 68.2 ± 5.5 | 6 (7%) | 68.1 ± 14 |

TABLE 5-continued

Mid-treatment tumour RNA disruption and its relationship to MA.22 patient overall survival, disease-free survival (DFS), and pathologic complete response post-treatment. The level of RNA disruption was divided into three zones, where zone 1 (RDI ≥ 0 and ≤ 10) is the lowest level of RNA disruption, zone 2 (RDA > 10 and ≤ 35) is an intermediate level of RNA disruption, and zone 3 (RDI > 35) is a high level of RNA disruption. The number of patients alive with disease (AWD) across the RNA disruption zones was also noted.

| Patients | RDA Zone 1 | | RDA Zone 2 | | RDA Zone 3 | | pCR | |
|---|---|---|---|---|---|---|---|---|
| | n (%) | DFS (months) | n (%) | DFS (months) | n (%) | DFS (months) | n (%) | DFS (months) |
| Dead | 7 (8%) | 18.4 ± 6.6 | 8 (9%) | 17.5 ± 4.2 | 9 (11%) | 20.5 ± 7.7 | 2 (2%) | 33.1 ± 16.7 |
| AWD | 2 (2%) | 3.2 ± 0.7 | 5 (6%) | 19.6 ± 8.5 | 3 (4%) | 22.8 ± 19.8 | 0 | n/a |

TABLE 6

Disease Free Survival (DFS) by RDA Zone

| Patients | RDA Zone 1 | | RDA Zone 2 | | RDA Zone 3 | | pCR | |
|---|---|---|---|---|---|---|---|---|
| | n | DFS (months) | n | DFS (months) | n | DFS (months) | n | DFS (months) |
| ALL | 17 | 33.3 ± 6.8 | 30 | 41.1 ± 5.3 | 38 | 56.9 ± 5.8 | 8 | 59.4 ± 12 |

Algorithm design:
RDA Zone 1, defined as pCR nonresponder, no pCR observed in Zone 1
RDA Zone 2, defined as pCR partial responder, 1 pCR observed in Zone 2
RDA Zone 3, defined to include most pCR responders, 7 pCRs observed in Zone 3
RDA Zone1-2 Cutoff was designed at NPV > 0.99 for pCR
RDA Zone 2-3 Cuttoff was designed to include 1 pCR in Zone 2 and 7/8 pCRs in Zone3

TABLE 7

DFS By subtype, RDA Zone 3

| Subtype | ALL | HR+ve* | Her2+ve** | TNBC*** |
|---|---|---|---|---|
| DFS months | | | | |
| DFS | 56.9 | 61.0 | 65.6 | 39.7 |
| (n) | (38) | (21) | (8) | (9) |
| DFS pCR +ve | 59.4 | | 69.3 | 34.9 |
| (n) | (7) | (0) | (5) | (2) |
| DFS, no pCR | 56.3 | 61.0 | 59.4 | 41.1 |
| (n) | (31) | (21) | (3) | (7) |

DFS = disease free Survival, months,
n = sum of patients,
*HR+ve = ER+PR−, ER+PR +, ER−PR+
**Her2+ or Her2+ER+,
***TNBC = Triple Negative Breast Cancer
In RDA Zone 3, DFS is comparable, pCR+ve or PCR−ve, irrespective of subtype

TABLE 8

Baseline characteristics of the patients in the Group 1 (Neoadjuvant setting) and Group 2 (Metastatic setting)

| CLINICAL PARAMETERS | GROUP 1 (n = 33) | GROUP 2 (n = 20) |
|---|---|---|
| Sex, n (%) | | |
| Female | 33 (100.0) | 20 (100) |
| Male | 0 | |
| Age, years (%) | | |
| Median | 47.8 | 70.1 |
| [range] | [34.6-69.2] | [40.1-81.8] |
| Mean ± SD | 49.4 ± 8.2 | 67.6 ± 11.2 |
| <65 | 31 (93.9) | 7 (35) |
| ≥65 | 2 (6.1) | 13 (65) |
| Menopausal status, n (%) | | |
| Pre- | 20 (60.6) | 1 (5) |
| Post- | 13 (39.4) | 19 (95) |
| Not known | 0 | 0 |
| Basal histotype, n (%) | | |
| IDC | 19 (57.6) | 15 (75) |
| ILC | 8 (24.2) | 3 (15) |
| Other | 5 (15.2) | 0 |
| Not known | 1 (3.0) | 2 (10) |
| Tumor grade, n (%) | | |
| 1 | 0 | 0 |
| 2 | 20 (60.6) | 5 (25) |
| 3 | 12 (36.4) | 12 (60) |
| Not known | 1 (3.0) | 3 (15) |
| ER status, n (%) | | |
| Positive | 29 (87.9) | 16 (80) |
| Negative | 4 (12.1) | 3 (15) |
| Not known | 0 | 1 (5) |
| PgR status, n (%) | | |
| Positive | 26 (78.8) | 8 (40) |
| Negative | 7 (21.2) | 11 (55) |
| Not known | 0 | 1 (5) |
| HER2 status, n (%) | | |
| Positive | 0 | 6 (30) |
| Negative | 33 (100.0) | 13 (65) |
| Not known | 0 | 1 (5) |
| Basal MIB-1 LI, % (%) | | |
| Median | 18 | 18 |
| [range] | [3-90] | [1-70] |
| Mean ± SD | 25.3 ± 20.6 | 24.2 ± 17.4 |
| <14 | 9 (27.3) | 4 (20) |
| ≥14 | 24 (72.7) | 15 (75) |
| Not Known | 0 | 1 (5) |

TABLE 9

RNA Disruption, 15 Days After Initiation of Therapy,

| Drug | Dose | Patients Total | Patients Responding* | RDI Range, Responding Patients |
|---|---|---|---|---|
| Trastuzumab | 6 mg/kg | 12 | 3 | 1.6-2.3 |
| zoledronic Acid | 4 mg | 15 | 8 | 1.8-8.9 |
| Letrozole + Cyclophosphamide metronomic dosage | 2.5 mg/day 50 mg/day | 29 | 4 | 1.9-2.7 |

TABLE 9-continued

RNA Disruption, 15 Days After Initiation of Therapy.

| Drug | Dose | Patients Total | Patients Responding* | RDI Range, Responding Patients |
|---|---|---|---|---|
| Letrozole + Cyclophosphamide + Sorafenib metronomic dosage | 2.5 mg/day 50 mg/day 400 mg bid | 23 | 5 | 2.0-3.5 |

*Patients with RDI above Baseline RDI = 1.5.
RDI = 1.5 is 5 times RDI, Level of Detection, RDI = 0.3

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

CITATIONS FOR REFERENCES REFERRED TO IN THE SPECIFICATION

[1] H. K. Weir, M. J. Thun, B. F. Hankey, L. A. Ries, H. L. Howe, P. A. Wingo, A. Jemal, E. Ward, R. N. Anderson, and B. K. Edwards, Annual report to the nation on the status of cancer, 1975-2000, featuring the uses of surveillance data for cancer prevention and control, J. Natl. Cancer Inst. 95 (2003) 1276-1299.

[2] S. Pecorelli, G. Favalli, L. Zigliani, and F. Odicino, Cancer in women, Int. J. Gynaecol. Obstet. 82 (2003) 369-379.

[3] G. Bonadonna and P. Valagussa, Primary chemotherapy in operable breast cancer, Semin. Oricol. 23 (1996) 464-474.

[4] Y. Belkacemi, J. Gligorov, M. P. Chauvet, P. G. Tsoutsou, H. Boussen, and C. Bourgier, [Radiotherapy and combined therapy in breast cancer: standards and innovations in the adjuvant setting], J. Gynecol. Obstet. Biol. Reprod. (Paris) 39 (2010) F63-F69.

[5] C. H. Yang and M. Cristofanilli, Systemic treatments for inflammatory breast cancer, Breast Dis. 22 (2005) 55-65.

[6] A. Rustogi, A. Budrukkar, K. Dinshaw, and R. Jalali, Management of locally advanced breast cancer: evolution and current practice, J. Cancer Res. Ther. 1 (2005) 21-30.

[7] K. Adamowicz, M. Marczewska, and J. Jassem, Combining systemic therapies with radiation in breast cancer, Cancer Treat. Rev. 35 (2009) 409-416.

[8] A. M. Parissenti, S. L. Hembruff, D. J. Villeneuve, Z. Veitch, B. Guo, and J. Eng, Gene expression profiles as biomarkers for the prediction of chemotherapy drug response in human tumour cells, Anticancer Drugs 18 (2007) 499-523.

[9] J. G. Zijlstra, S. de Jong, E. G. de Vries, and N. H. Mulder, Topoisomerases, new targets in cancer chemotherapy, Med. Oncol. Tumor Pharmacother. 7 (1990) 11-18.

[10] D. S. Richardson and S. A. Johnson, Anthracyclines in haematology: preclinical studies, toxicity and delivery systems, Blood Rev. 11 (1997) 201-223.

[11] G. Capranico, S. Tinelli, and F. Zunino, Formation, resealing and persistence of DNA breaks produced by 4-demethoxydaunorubicin in P388 leukemia cells, Chem. Biol. Interact. 72 (1989) 113-123.

[12] M. Chazard, B. Pellae-Cosset, F. Garet, J. A. Soares, B. Lucidi, Y. Lavail, and L. Lenaz, [Taxol (paclitaxel), first molecule of a new class of cytotoxic agents: taxanes], Bull. Cancer 81 (1994) 173-181

[13] M. Distefano, G. Scambia, C. Ferlini, C. Gaggini, R. De Vincenzo, A. Riva, E. Bombardelli, I. Ojima, A. Fattorossi, P. B. Panici, and S. Mancuso, Anti-proliferative activity of a new class of taxanes (14beta-hydroxy-10-deacetylbaccatin III derivatives) on multidrug-resistance-positive human cancer cells, Int. J. Cancer 72 (1997) 844-850.

[14] P. J. Moos and F. A. Fitzpatrick, Taxane-mediated gene induction is independent of microtubule stabilization: induction of transcription regulators and enzymes that modulate inflammation and apoptosis, Proc. Natl. Acad. Sci. U.S.A 95 (1998) 3896-3901.

[15] S. Ohnoa, M. Toi, K. Kuroi, S. Nakamura, H. Iwata, M. Kusama, N. Masuda, K. Yamazaki, K. Hisamatsu, Y. Sato, Y. Takatsuka, E. Shin, H. Kaise, M. Kurozumi, H. Tsuda, and F. Akiyama, Update results of FEC followed by docetaxel neoadjuvant trials for primary breast cancer, Biomed. Pharmacother. 59 Suppl 2 (2005) S323-S324.

[16] I. Obiorah and V. C. Jordan, Progress in endocrine approaches to the treatment and prevention of breast cancer, Maturitas 70 (2011) 315-321.

[17] D. Jelovac and A. C. Wolff, The adjuvant treatment of HER2-positive breast cancer, Curr. Treat. Options. Oncol. 13 (2012) 230-239.

[18] A. Dufresne, X. Pivot, C. Tournigand, T. Facchini, T. Alweeg, L. Chaigneau, and G. A. De, Maintenance hormonal treatment improves progression free survival after a first line chemotherapy in patients with metastatic breast cancer, Int. J. Med. Sci. 5 (2008) 100-105.

[19] T. Ferguson, N. Wilcken, R. Vagg, D. Ghersi, and A. K. Nowak, Taxanes for adjuvant treatment of early breast cancer, Cochrane. Database. Syst. Rev. (2007) CD004421.

[20] S. Gluck, The worldwide perspective in the adjuvant treatment of primary lymph node positive breast cancer, Breast Cancer 8 (2001) 321-328.

[21] R. Plagne, Breast tumours: a review of adjuvant chemotherapy trials, Drugs Exp. Clin. Res. 12 (1986) 135-142.

[22] G. N. Hortobagyi, A. U. Buzdar, E. A. Strom, F. C. Ames, and S. E. Singletary, Primary chemotherapy for early and advanced breast cancer, Cancer Lett. 90 (1995) 103-109.

[23] Canadian Cancer Society. Canadian Cancer Statistics. http://www.cancer.ca/vgn/images/portal/cit_86751114/10/34/614137951cw_library_WNTK_Bladder_Punjabi2005.pdf.2008. Ref Type: Electronic Citation

[24] H. M. Kuerer, L. A. Newman, T. L. Smith, F. C. Ames, K. K. Hunt, K. Dhingra, R. L. Theriault, G. Singh, S. M. Binkley, N. Sneige, T. A. Buchholz, M. I. Ross, M. D. McNeese, A. U. Buzdar, G. N. Hortobagyi, and S. E. Singletary, Clinical course of breast cancer patients with complete pathologic primary tumor and axillary lymph node response to doxorubicin-based neoadjuvant chemotherapy, J Clin. Oncol 17 (1999) 460-469.

[25] H. M. Kuerer, L. A. Newman, T. L. Smith, F. C. Ames, K. K. Hunt, K. Dhingra, R. L. Theriault, G. Singh, S. M. Binkley, N. Sneige, T. A. Buchholz, M. I. Ross, M. D.

McNeese, A. U. Buzdar, G. N. Hortobagyi, and S. E. Singletary, Clinical course of breast cancer patients with complete pathologic primary tumor and axillary lymph node response to doxorubicin-based neoadjuvant chemotherapy, J Clin. Oncol. 17 (1999) 460-469.

[26] S. C. Formenti, G. Dunnington, B. Uzieli, H. Lenz, S. Keren-Rosenberg, H. Silberman, D. Spicer, M. Denk, G. Leichman, S. Groshen, K. Watkins, F. Muggia, B. Florentine, M. Press, K. Danenberg, and P. Danenberg, Original p53 status predicts for pathological response in locally advanced breast cancer patients treated preoperatively with continuous infusion 5-fluorouracil and radiation therapy, Int. J Radiat. Oncol. Biol. Phys 39 (1997) 1059-1068.

[27] J. Specht and J. R. Gralow, Neoadjuvant chemotherapy for locally advanced breast cancer, Semin. Radiat. Oncol. 19 (2009) 222-228.

[28] S. Sinclair and S. M. Swain, Primary systemic chemotherapy for inflammatory breast cancer, Cancer 116 (2010) 2821-2828.

[29] I. Sachelarie, M. L. Grossbard, M. Chadha, S. Feldman, M. Ghesani, and R. H. Blum, Primary systemic therapy of breast cancer, Oncologist. 11 (2006) 574-589.

[30] R. Croshaw, H. Shapiro-Wright, E. Svensson, K. Erb, and T. Julian, Accuracy of clinical examination, digital mammogram, ultrasound, and MRI in determining post-neoadjuvant pathologic tumor response in operable breast cancer patients, Ann. Surg. Oncol. 18 (2011) 3160-3163.

[31] K. S. Albain, W. E. Barlow, S. Shak, G. N. Hortobagyi, R. B. Livingston, I. T. Yeh, P. Ravdin, R. Bugarini, F. L. Baehner, N. E. Davidson, G. W. Sledge, E. P. Winer, C. Hudis, J. N. Ingle, E. A. Perez, K. I. Pritchard, L. Shepherd, J. R. Gralow, C. Yoshizawa, D. C. Allred, C. K. Osborne, and D. F. Hayes, Prognostic and predictive value of the 21-gene recurrence score assay in postmenopausal women with node-positive, oestrogen-receptor-positive breast cancer on chemotherapy: a retrospective analysis of a randomised trial, Lancet Oncol. 11 (2010) 55-65.

[32] A. Goldhirsch, J. N. Ingle, R. D. Gelber, A. S. Coates, B. Thurlimann, and H. J. Senn, Thresholds for therapies: highlights of the St Gallen International Expert Consensus on the primary therapy of early breast cancer 2009, Ann. Oncol. 20 (2009) 1319-1329.

[33] K. S. Albain, W. E. Barlow, P. M. Ravdin, W. B. Farrar, G. V. Burton, S. J. Ketchel, C. D. Cobau, E. G. Levine, J. N. Ingle, K. I. Pritchard, A. S. Lichter, D. J. Schneider, M. D. Abeloff, I. C. Henderson, H. B. Muss, S. J. Green, D. Lew, R. B. Livingston, S. Martino, and C. K. Osborne, Adjuvant chemotherapy and timing of tamoxifen in postmenopausal patients with endocrine-responsive, node-positive breast cancer: a phase 3, open-label, randomised controlled trial, Lancet 374 (2009) 2055-2063.

[34] R. Ng, N. Better, and M. D. Green, Anticancer agents and cardiotoxicity, Semin. Oncol. 33 (2006) 2-14.

[35] J. Schwartz, S. M. Domchek, W. T. Hwang, and K. Fox, Evaluation of anemia, neutropenia and skin toxicities in standard or dose-dense doxorubicin/cyclophosphamide (AC)-paclitaxel or docetaxel adjuvant chemotherapy in breast cancer, Ann. Oncol. 16 (2005) 247-252.

[36] A. Berruti, D. Generali, V. Bertaglia, M. P. Brizzi, T. Mele, L. Dogliotti, P. Bruzzi, and A. Bottini, Intermediate endpoints of primary systemic therapy in breast cancer patients, J. Natl. Cancer Inst. Monogr 2011 (2011) 142-146.

[37] A. Goldhirsch, W. C. Wood, A. S. Coates, R. D. Gelber, B. Thurlimann, and H. J. Senn, Strategies for subtypes—dealing with the diversity of breast cancer: highlights of the St. Gallen International Expert Consensus on the Primary Therapy of Early Breast Cancer 2011, Ann. Oncol. 22 (2011) 1736-1747.

[38] M. Untch and M. G. von, Neoadjuvant chemotherapy: early response as a guide for further treatment: clinical, radiological, and biological, J. Natl. Cancer Inst. Monogr 2011 (2011) 138-141.

[39] G. von Minckwitz, M. Untch, J. U. Blohmer, S. D. Costa, H. Eidtmann, P. A. Fasching, B. Gerber, W. Eiermann, J. Hilfrich, J. Huober, C. Jackisch, M. Kaufmann, G. E. Konecny, C. Denkert, V. Nekljudova, K. Mehta, and S. Loibl, Definition and impact of pathologic complete response on prognosis after neoadjuvant chemotherapy in various intrinsic breast cancer subtypes, J. Clin. Oncol. 30 (2012) 1796-1804.

[40] G. von Minckwitz, J. U. Blohmer, S. D. Costa, C. Denkert, H. Eidtmann, W. Eiermann, B. Gerber, C. Hanusch, J. Hilfrich, J. Huober, C. Jackisch, M. Kaufmann, S. Kummel, S. Paepke, A. Schneeweiss, M. Untch, D. M. Zahm, K. Mehta, and S. Loibl, Response-Guided Neoadjuvant Chemotherapy for Breast Cancer, J. Clin. Oncol. (2013).

[41] R. M. Simon, S. Paik, and D. F. Hayes, Use of archived specimens in evaluation of prognostic and predictive biomarkers, J. Natl. Cancer Inst. 101 (2009) 1446-1452.

[42] A. M. Parissenti, J. A. Chapman, H. J. Kahn, B. Guo, L. Han, P. O'Brien, M. P. Clemons, R. Jong, R. Dent, B. Fitzgerald, K. I. Pritchard, L. E. Shepherd, and M. E. Trudeau, Association of low tumor RNA integrity with response to chemotherapy in breast cancer patients, Breast Cancer Res. Treat. 119 (2010) 347-356.

[43] A. Schroeder, O. Mueller, S. Stocker, R. Salowsky, M. Leiber, M. Gassmann, S. Lightfoot, W. Menzel, M. Granzow, and T. Ragg, The RIN: an RNA integrity number for assigning integrity values to RNA measurements, BMC. Mol. Biol. 7 (2006) 3.

[44] K. Hajian-Tilaki, Receiver Operating Characteristic (ROC) Curve Analysis for Medical Diagnostic Test Evaluation, Caspian. J. Intern. Med. 4 (2013) 627-635.

[45] H. M. Kuerer, L. A. Newman, T. L. Smith, F. C. Ames, K. K. Hunt, K. Dhingra, R. L. Theriault, G. Singh, S. M. Binkley, N. Sneige, T. A. Buchholz, M. I. Ross, M. D. McNeese, A. U. Buzdar, G. N. Hortobagyi, and S. E. Singletary, Clinical course of breast cancer patients with complete pathologic primary tumor and axillary lymph node response to doxorubicin-based neoadjuvant chemotherapy, J Clin. Oncol. 17 (1999) 460-469.

[46] V. Guarneri, K. Broglio, S. W. Kau, M. Cristofanilli, A. U. Buzdar, V. Valero, T. Buchholz, F. Meric, L. Middleton, G. N. Hortobagyi, and A. M. Gonzalez-Angulo, Prognostic value of pathologic complete response after primary chemotherapy in relation to hormone receptor status and other factors, J. Clin. Oncol. 24 (2006) 1037-1044.

[47] H. M. Kuerer, L. A. Newman, T. L. Smith, F. C. Ames, K. K. Hunt, K. Dhingra, R. L. Theriault, G. Singh, S. M. Binkley, N. Sneige, T. A. Buchholz, M. I. Ross, M. D. McNeese, A. U. Buzdar, G. N. Hortobagyi, and S. E. Singletary, Clinical course of breast cancer patients with complete pathologic primary tumor and axillary lymph node response to doxorubicin-based neoadjuvant chemotherapy, J Clin. Oncol. 17 (1999) 460-469.

[48] S. V. Liu, L. Melstrom, K. Yao, C. A. Russell, and S. F. Sener, Neoadjuvant therapy for breast cancer, J. Surg. Oncol. 101 (2010) 283-291.

[49] A. Hurria, M. T. Fleming, S. D. Baker, W. K. Kelly, K. Cutchall, K. Panageas, J. Caravelli, H. Yeung, M. G. Kris, J. Gomez, V. A. Miller, G. D'Andrea, H. I. Scher, L. Norton, and C. Hudis, Pharmacokinetics and toxicity of weekly docetaxel in older patients, Clin. Cancer Res. 12 (2006) 6100-6105.

[50] J. A. Sparano, M. Wang, S. Martino, V. Jones, E. A. Perez, T. Saphner, A. C. Wolff, G. W. Sledge, Jr., W. C. Wood, and N. E. Davidson, Weekly paclitaxel in the adjuvant treatment of breast cancer, N. Engl. J. Med. 358 (2008) 1663-1671.

[51] N. I. Marupudi, J. E. Han, K. W. Li, V. M. Renard, B. M. Tyler, and H. Brem, Paclitaxel: a review of adverse toxicities and novel delivery strategies, Expert. Opin. Drug Saf 6 (2007) 609-621.

[52] L. A. Carey, E. C. Dees, L. Sawyer, L. Gatti, D. T. Moore, F. Collichio, D. W. Ollila, C. I. Sartor, M. L. Graham, and C. M. Perou, The triple negative paradox: primary tumor chemosensitivity of breast cancer subtypes, Clin. Cancer Res. 13 (2007) 2329-2334.

[53] W. A. Weber, M. Schwaiger, and N. Avril, Quantitative assessment of tumor metabolism using FDG-PET imaging, Nucl. Med. Biol. 27 (2000) 683-687.

[54] S. J. Kim, S. K. Kim, E. S. Lee, J. Ro, and S. Kang, Predictive value of [18F]FDG PET for pathological response of breast cancer to neo-adjuvant chemotherapy, Ann. Oncol. 15 (2004) 1352-1357.

[55] G. M. McDermott, A. Welch, R. T. Staff, F. J. Gilbert, L. Schweiger, S. I. Semple, T. A. Smith, A. W. Hutcheon, I. D. Miller, I. C. Smith, and S. D. Heys, Monitoring primary breast cancer throughout chemotherapy using FDG-PET, Breast Cancer Res. Treat. 102 (2007) 75-84.

[56] R. Kumar, A. Chauhan, H. Zhuang, P. Chandra, M. Schnall, and A. Alavi, Standardized uptake values of normal breast tissue with 2-deoxy-2-[F-18]fluoro-D: glucose positron emission tomography: variations with age, breast density, and menopausal status, Mol. Imaging Biol. 8 (2006) 355-362.

[57] N. Avril, C. A. Rose, M. Schelling, J. Dose, W. Kuhn, S. Bense, W. Weber, S. Ziegler, H. Graeff, and M. Schwaiger, Breast imaging with positron emission tomography and fluorine-18 fluorodeoxyglucose: use and limitations, J. Clin. Oncol. 18 (2000) 3495-3502.

[58] H. S. Lim, W. Yoon, T. W. Chung, J. K. Kim, J. G. Park, H. K. Kang, H. S. Bom, and J. H. Yoon, FDG PET/CT for the detection and evaluation of breast diseases: usefulness and limitations, Radiographics 27 Suppl 1 (2007) S197-S213.

[59] V. Guarneri, E. Barbieri, and P. Conte, Biomarkers predicting clinical benefit: fact or fiction?, J. Natl. Cancer Inst. Monogr 2011 (2011) 63-66.

[60] A. Berruti, D. Generali, M. Kaufmann, L. Purtai, G. Curigliano, M. Aglietta, L. Gianni, W. R. Miller, M. Untch, C. Sotiriou, M. Daidone, P. Conte, D. Kennedy, G. Damia, P. Petronini, C. S. Di, P. Bruzzi, M. Dowsett, C. Desmedt, R. E. Mansel, L. Olivetti, C. Tondini, A. Sapino, P. Fenaroli, G. Tortora, H. Thorne, F. Bertolini, F. Ferrozzi, M. Danova, E. Tagliabue, A. E. de, A. Makris, M. Tampellini, G. Dontu, V. L. Van't, A. L. Harris, S. B. Fox, L. Dogliotti, and A. Bottini, International expert consensus on primary systemic therapy in the management of early breast cancer: highlights of the Fourth Symposium on Primary Systemic Therapy in the Management of Operable Breast Cancer, Cremona, Italy (2010), J. Natl. Cancer Inst. Monogr 2011 (2011) 147-151.

[61] S. Braun, K. Pantel, P. Muller, W. Janni, F. Hepp, C. R. Kentenich, S. Gastroph, A. Wischnik, T. Dimpfl, G. Kindermann, G. Riethmuller, and G. Schlimok, Cytokeratinpositive cells in the bone marrow and survival of patients with stage I, II, or III breast cancer, N. Engl. J. Med. 342 (2000) 525-533.

62. Manders K, van de Poll-Franse L V, Creemers G J, et al. Clinical management of women with metastatic breast cancer: a descriptive study according to age group. BMC Cancer 2006; 6:179.

63. Cristofanilli M. Circulating tumor cells, disease progression, and survival in metastatic breast cancer. Semin Oncol 2006; 33(3 Suppl 9):59-14.

64. Sceneay J, Smyth M J, Moller A. The pre-metastatic niche: finding common ground. Cancer Metastasis Rev 2013.

65. Kingsley L A, Fournier P G, Chirgwin J M, et al. Molecular biology of bone metastasis. Mol Cancer Ther 2007; 6(10):2609-17.

66. Zoccoli A, luliani M, Pantano F, et al. Premetastatic niche: ready for new therapeutic interventions? Expert Opin Ther Targets 2012; 16 Suppl 2:S119-29.

67. Clezardin P. Anti-tumour activity of zoledronic acid. Cancer Treat Rev 2005; 31 Suppl 3:1-8.

68. Gnant M, Clezardin P. Direct and indirect anticancer activity of bisphosphonates: a brief review of published literature. Cancer Treat Rev 2012; 38(5):407-15.

69. Neville-Webbe H L, Evans C A, Coleman R E, et al. Mechanisms of the synergistic interaction between the bisphosphonate zoledronic acid and the chemotherapy agent paclitaxel in breast cancer cells in vitro. Tumour Biol 2006; 27(2):92-103.

70. Ottewell P D, Monkkonen H, Jones M, et al. Antitumor effects of doxorubicin followed by zoledronic acid in a mouse model of breast cancer. J Natl Cancer Inst 2008; 100(16):1167-78.

71. Santini D, Vincenzi B, Dicuonzo G, et al. Zoledronic acid induces significant and long-lasting modifications of circulating angiogenic factors in cancer patients. Clin Cancer Res 2003; 9(8):2893-7.

72. Jagdev S P, Coleman R E, Shipman C M, et al. The bisphosphonate, zoledronic acid, induces apoptosis of breast cancer cells: evidence for synergy with paclitaxel. Br J Cancer 2001; 84(8):1126-34.

73. Kunzmann V, Bauer E, Feurle J, et al. Stimulation of gammadelta T cells by aminobisphosphonates and induction of antiplasma cell activity in multiple myeloma. Blood 2000; 96(2):384-92.

74. Aft R, Perez J R, Raje N, et al. Could targeting bone delay cancer progression? Potential mechanisms of action of bisphosphonates. Crit Rev Oncol Hematol 2012; 82(2): 233-48.

75. Coleman R E, Winter M C, Cameron D, et al. The effects of adding zoledronic acid to neoadjuvant chemotherapy on tumour response: exploratory evidence for direct anti-tumour activity in breast cancer. Br J Cancer 2010; 102(7):1099-105.

76. Gnant M, Mlineritsch B, Stoeger H, et al. Adjuvant endocrine therapy plus zoledronic acid in premenopausal women with early-stage breast cancer: 62-month follow-up from the ABCSG-12 randomised trial. Lancet Oncol 2011; 12(7):631-41.

77. Coleman R, Gnant M, Morgan G, et al. Effects of bone-targeted agents on cancer progression and mortality. J Natl Cancer Inst 2012; 104(14):1059-67.

78. Bottini A, Berruti A, Bersiga A, et al. Relationship between tumour shrinkage and reduction in Ki67 expression after primary chemotherapy in human breast cancer. Br J Cancer 2001; 85(8)1106-12.

79. Nakopoulou L, Alexandrou P, Stefanaki K, et al. Immunohistochemical expression of caspase-3 as an adverse indicator of the clinical outcome in human breast cancer. Pathobiology 2001; 69(5):266-73.
80. Fumarola C, La Monica S, Guidotti G G. Amino acid signaling through the mammalian target of rapamycin (mTOR) pathway: Role of glutamine and of cell shrinkage. J Cell Physiol 2005; 204(1):155-65.
81. Cristofanilli M, Budd G T, Ellis M J, et al. Circulating tumor cells, disease progression, and survival in metastatic breast cancer. N Engl J Med 2004; 351(8):781-91.
82. Rossi E, Basso U, Celadin R, et al. M30 neoepitope expression in epithelial cancer: quantification of apoptosis in circulating tumor cells by CellSearch analysis. Clin Cancer Res 2010; 16(21):5233-43.
83. Come P C, Come S E, Hawley C R, et al. Echocardiographic manifestations of carcinoid heart disease. J Clin Ultrasound 1982; 10(5):233-7.
84. Coleman R E, McCloskey E V. Bisphosphonates in oncology. Bone 2011; 49(1):71-6.
85. Coleman R E, Marshall H, Cameron D, et al. Breast-cancer adjuvant therapy with zoledronic acid. N Engl J Med 2011; 365(15):1396-405.
86. Gnant M, Mlineritsch B, Schippinger W, et al. Endocrine therapy plus zoledronic acid in premenopausal breast cancer. N Engl J Med 2009; 360(7):679-91.
87. Winter M C, Wilson C, Syddall S P, et al. Neoadjuvant chemotherapy with or without zoledronic acid in early breast cancer—a randomized biomarker pilot study. Clin Cancer Res 2013; 19(10):2755-65.
88. Dowsett M, Nielsen T O, A'Hern R, et al. Assessment of Ki67 in breast cancer: recommendations from the International Ki67 in Breast Cancer working group. J Natl Cancer Inst 2011; 103(22): 1656-64.
89. Ottewell P D, Woodward J K, Lefley D V, et al. Anticancer mechanisms of doxorubicin and zoledronic acid in breast cancer tumor growth in bone. Mol Cancer Ther 2009; 8(10):2821-32.
90. Yang S X, Steinberg S M, Nguyen D, et al. Gene expression profile and angiogenic marker correlates with response to neoadjuvant bevacizumab followed by bevacizumab plus chemotherapy in breast cancer. Clin Cancer Res 2008; 14(18):5893-9.
91. Gluz O, Wild P, Liedtke C, et al. Tumor angiogenesis as prognostic and predictive marker for chemotherapy dose-intensification efficacy in high-risk breast cancer patients within the WSG AM-01 trial. Breast Cancer Res Treat 2011; 126(3):643-51.
92. Brenner C, Grimm S. The permeability transition pore complex in cancer cell death. Oncogene 2006; 25(34): 4744-56.
93. Garrido C, Galluzzi L, Brunet M, et al. Mechanisms of cytochrome c release from mitochondria. Cell Death Differ 2006; 13(9):1423-33.
94. Cande C, Cohen I, Daugas E, et al. Apoptosis-inducing factor (AIF): a novel caspase-independent death effector released from mitochondria. Biochimie 2002; 84(2-3): 215-22.
95. Kuroda J, Kimura S, Segawa H, et al. p53-independent anti-tumor effects of the nitrogen-containing bisphosphonate zoledronic acid. Cancer Sci 2004; 95(2):186-92.
96. Fehm T, Zwirner M, Wallwiener D, et at Antitumor activity of zoledronic acid in primary breast cancer cells determined by the ATP tumor chemosensitivity assay. BMC Cancer 2012; 12:308.
97. Houge G, Robaye B, Eikhom T S, et al. Fine mapping of 28S rRNA sites specifically cleaved in cells undergoing apoptosis. Mol Cell Biol 1995; 15(4):2051-62.
98. King K L, Jewell C M, Bortner C D, et al. 28S ribosome degradation in lymphoid cell apoptosis: evidence for caspase and Bcl-2-dependent and -independent pathways. Cell Death Differ 2000; 7(10):994-1001.
99. Onstenk W, Gratama J W, Foekens J A, et al. Towards a personalized breast cancer treatment approach guided by circulating tumor cell (CTC) characteristics. Cancer Treat Rev 2013.
100. Solomayer E F, Gebauer G, Hirnle P, et al. Influence of zoledronic acid on disseminated tumor cells in primary breast cancer patients. Ann Oncol 2012; 23(9):2271-7.
101. Chang J, Ormerod M, Powles T J, et al. Apoptosis and proliferation as predictors of chemotherapy response in patients with breast carcinoma. Cancer 2000; 89(11): 2145-52.
102. Archer C D, Parton M, Smith I E, et al. Early changes in apoptosis and proliferation following primary chemotherapy for breast cancer. Br J Cancer 2003; 89(6):1035-41.
103. Lin J H. Bisphosphonates: a review of their pharmacokinetic properties. Bone 1996; 18(2):75-85.
104. Chen T, Berenson J, Vescio R, et al. Pharmacokinetics and pharmacodynamics of zoledronic acid in cancer patients with bone metastases. J Clin Pharmacol 2002; 42(11):1228-36.
105. Cummings J, Ward T H, LaCasse E, et al. Validation of pharmacodynamic assays to evaluate the clinical efficacy of an antisense compound (AEG 35156) targeted to the X-linked inhibitor of apoptosis protein XIAP. Br J Cancer 2005; 92(3):532-8.
106 Leist M, Single B, Naumann H, et al. Inhibition of mitochondrial ATP generation by nitric oxide switches apoptosis to necrosis. Exp Cell Res 1999; 249(2):396-403.
107. Narla A, Ebert B L. Ribosomopathies: human disorders of ribosome dysfunction. Blood 2010 Apr. 22; 115(16): 3196-205.
108. Greenhalgh D A, Parish J H. Effect of 5-fluorouracil combination therapy on RNA processing in human colonic carcinoma cells. British journal of cancer 1990 March; 61(3):415-9.
109. Burger K, Muhl B, Harasim T, Rohrmoser M, Malamoussi A, Orban M, et al. Chemotherapeutic drugs inhibit ribosome biogenesis at various levels. The Journal of biological chemistry 2010 Apr. 16; 285(16):12416-25.
110. Fimognari C, Sestili P, Lenzi M, Cantelli-Forti G, Hrelia P. Protective effect of creatine against RNA damage. Mutation research 2009 Nov. 2; 670(1-2):59-67.
111. Copois V, Bibeau F, Bascoul-Mollevi C, Salvetat N, Chalbos P, Bareil C, et al. Impact of RNA degradation on gene expression profiles: assessment of different methods to reliably determine RNA quality. Journal of biotechnology 2007 Jan. 20; 127(4):549-59.
112. Gjertsen, B T, Cressey, L I, Ruchaud, S, Houge, G, Lanotte, M and Doskeland, S O (1994) Multiple apoptotic death types triggered through activation of separate pathways by cAMP and inhibitors of protein phosphatases in one (IPC leukemia) cell line. *J. Cell Science* 107: 3363-3377
113 Degen, W G J, Pruijn, G J M, Raats, J M H and van Venrooij, W J (2000) Caspase-dependent cleavage of nucleic acids. *Cell Death Differ.* 7(7): 616-627
114 Crawford, D R, Lauzon, R J, Wang, Y, Mazurkiewicz, J E, Schools, G P, and Davies, K. J. A. (1997) 16S mitochondrial ribosomal degradation is associated with apoptosis. *Free Rad. Biol. Med.* 22(7): 1295-1300.

115 Swe, M and Sit, K H (2000) zVAD-fmk and DEVD-cho induced late mitotic arrest and apoptotic expressions. Apoptosis 5(1): 29-36.

116. Cortazar P et al. (2014) Pathological complete response and long-term clinical benefit in breast cancer: the CTNeoBC pooled analysisLancet Vol 384: 1-9.

117. Carey L, A. Commen (2014)t Lancet Vol 384:115-116.

The invention claimed is:

1. A method for response guided primary systemic therapy of a patient with breast cancer receiving a cancer treatment, the method comprising: determining if the patient is predicted to have: i) a favourable prediction of survival time or ii) an unfavourable prediction of survival time the method comprising;
   a) obtaining isolated RNA of a breast tumor tissue sample obtained from the patient after said patient has received one or more doses of a cancer treatment;
   b) separating the isolated RNA through a separation channel of a RNA chip suing an analytic microcapillary electrophoresis system wherein intercalating fluorescent dye binds the RNA and detecting the isolated RNA by detecting the fluorescent dye;
   c) measuring the amount of degraded RNA and intact RNA the measuring comprising; locating a dye-only peak, an 18S peak and a 28S peak and determining an intermediate region and a low C banding region, where the dye only peak is at about 22.5 seconds, the intermediate region is the region of the electropherogram between the located 18S and 28S peaks and the low C banding region is the region between 35 seconds and a start of the 18S peak; and
      determining values for the 28S peak area, an 18S peak area and at least one of an intermediate region area and a low C banding region area
   d) determining an RNA disruption assay (RDA) score for the tumor tissue sample, the RDA score comprising (1) a ratio of the intermediate area to a sum of the 28S peak area and the 18S peak area (2) a ratio of the low C banding region area to the sum of the 28S peak area and the 18S peak area; or (3) a ratio of the sum of the low C banding region area and the intermediate area to the sum of the 28S peak area and the 18S peak area;
   e) comparing said RDA score to one or more predetermined RNA disruption reference values determined from a plurality of samples from patients who responded with increased survival to the cancer regimen and non-responders;
   e) detecting that the RDA score determined for the tumour tissue sample is at least as high as the disruption reference value regimen indicating a favorable prediction and/or prognosis of survival time for said patient and continuing the cancer treatment; or
   detecting that the RDA score determined for the tumour tissue sample is lower than the disruption reference value indicates an unfavorable prediction and/or prognosis of survival time for said patient and changing the cancer treatment regimen, the changing selected from changing the dosage level and/or schedule the chemotherapeutic, adding a chemotherapeutic agent(s), biologic(s) to the treatment or changing to an alternate cancer drug therapy or surgery,
   optionally wherein the method further comprises measuring in the tumour tissue sample Annexin V-FITC binding, sub-G1 level of DNA content, cleavage of poly ADP ribose polymerase (PARP) and/or caspase activity.

2. The method of claim 1, wherein peaks are located by first locating possible peak candidates in the two identifying ranges, calculating height differences of each possible peak candidate, and defining the 18S and 28S peaks as the two largest peak candidates; optionally wherein a height difference of a given peak candidate is defined as a difference of a highest peak value and an average of lowest peak values for the given peak candidate where the low peak values that are averaged are a starting point and an ending point associated with the highest peak value.

3. The method of claim 1, wherein a plurality of electropherograms are separated into an adjustment group and a standard group and determining the standard sample from the plurality of electropherogram datasets where the standard sample has the smallest standard score defined by a ratio of a sum of intermediate area, lower B banding region area and lower C banding region area to a sum of 18S peak area and 28S peak area; optionally assigning a given electropherogram dataset to the adjustment group if retention times for at least one of the 18S and 28S peaks of the given sample differ by more than a certain time threshold to retention times of corresponding at least one of the 18S and 28S peaks of the standard sample.

4. The method of claim 1, wherein the shifted regions comprise a shifted 18S region in the range of 40.9 to 50.4 units and a shifted 28S region in the range of 58.1 to 69.5 units when a time axis of the at least one electropherogram dataset is converted to a scale of 0 to 100 units; optionally wherein if an 18S peak area in the shifted 18S region divided by total area multiplied by 100 is less than about 8 times a 28S peak area in the shifted 28S region divided by total area multiplied by 100, the shifted 18S region is defined to be the range of 42.8 to 51.4 units, the total area comprising the 18S peak area, the 28S peak area, intermediate banding region area and low banding region area; optionally wherein an 18S peak width is between 0.6 and 7.6 units; and/or wherein if a 28S peak area in the shifted 28S region divided by total area multiplied by 100 is less than about 8 times an 18S peak area in the shifted 18S region divided by total area multiplied by 100, the shifted 28S region is defined to be the range of 52.3 to 69.5 units, the total area comprising the 18S peak area, the 28S peak area, intermediate banding region area and low banding region area; optionally wherein a 28S peak width is between 0.8 and 10.5 units.

5. The method of claim 4, wherein an ending position of an 18S peak and a starting position of a 28S peak are less than 17.1 units apart.

6. The method of claim 1, wherein the RDA score is an RDI value determined by a RNA disruption assay, wherein the tumour tissue sample comprising cellular RNA is obtained from said patient after said patient has received one or more doses of the cancer treatment; and the method comprises determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and determining an RDA score based on a combination of the values of the features.

7. The method of claim 1, wherein the tumor tissue sample is obtained from the patient about midtreatment.

8. The method of claim 1, wherein the RDI value associated with a favourable prediction and/or prognosis is at least 10, at least 15, at least 20, at least 25, at least 30, at least 35, at least 40, at least 50, at least 60, at least 70, at least 80, at least 90, at least 100, at least 110, at least 120, at least 130, at least 140, at least 150, at least 160, or at least 170; and/or the RDI value is increased compared to a pretreatment RNA disruption reference value by at least 2 fold, at least 2.5 fold, at least 3 fold, at least 3.5 fold, at least 4 fold, at least 4.5 fold, at least 5 fold, at least 5.5 fold or at least 5.8 fold.

9. The method of claim 8, wherein the method further comprises comparing the RDA score to multiple thresholds, each threshold arranged to corresponding to an RDA zone boundary to determine effectiveness of the treatment, optionally wherein one of the thresholds corresponds to a selected negative predictive value (NPV) and defines a boundary between RDA zone 2 and RDA zone 3 and another of the threshold corresponds to a selected positive predictive value (PPV) and defines the boundary between a RDA zone 1 and RDA zone 2; optionally wherein the NPV is at least 0.98 and/or the PPV is at least 0.18, 0.19 or 0.20.

10. The method of claim 1, wherein two RNA disruption reference values are used to stratify patients into 3 zones, wherein zone 3 identifies patients having a favorable prediction and/or prognosis of survival time for said patient when said RDA score is higher than said predetermined RNA disruption reference value; zone 1 identifies patients with unfavorable prediction and/or prognosis of survival time for said patient when said RDA score is lower than said predetermined RNA disruption reference value; and zone 2 identifies patients with insufficient response and/or mixed survival prediction and/or prognosis.

11. The method of claim 1, wherein the method further comprises measuring RNA concentration of the tumor tissue sample.

12. The method of claim 1, wherein the cancer is breast cancer; optionally wherein the breast cancer is locally advanced breast cancer; and/or ER+/−, HER2+/−, and/or PR+/−breast cancer; optionally wherein the breast cancer is ER+.

13. The method of claim 1, wherein the survival time is disease-free survival (DFS) or overall survival; optionally wherein the DFS is increased by at least 5 months, at least 10 months, at least 15 months, at least 20 months, at least 25 months, at least 30 months, at least 35 months or at least at least 40 months.

14. The method of claim 1, wherein the cancer treatment the patient is receiving comprises a bisphosphonate, a monoclonal antibody that targets HER2/neu receptor, aromatase inhibitor and/or a TKI and/or wherein the tumor tissue sample is obtained from the patient after 2 days, 5 days, 10 days or 15 days after administration of a dose of the cancer treatment.

15. The method of claim 1, wherein the cancer treatment comprises a bisphosphonate; optionally zoledronic acid; a monoclonal antibody that targets HER2/neu receptor; optionally trastuzumab; an aromatase inhibitor; optionally letrozole; tyrosine kinase inhibitor (TKI); optionally sorafenib; combinations included said cancer treatment, optionally an aromatase inhibitor, optionally letrozole, in combination with cyclosphosphamide and/or sorafenib.

16. The method of claim 1, wherein the tumor tissue sample is obtained after administration of a dose of the cancer treatment; optionally wherein the tumor tissue sample is obtained from the patient after 2 days, 5 days, 10 days or 15 days after administration of a dose of the cancer treatment.

* * * * *